US011795461B2

(12) United States Patent
Ahlers et al.

(10) Patent No.: US 11,795,461 B2
(45) **Date of Patent: *Oct. 24, 2023**

(54) COMPOSITIONS AND METHODS FOR TREATING BETA-HEMOGLOBINOPATHIES

(71) Applicants: CSL Behring Gene Therapy, Inc., Pasadena, CA (US); CSL Gene Therapy Pty Ltd., Parkville (AU)

(72) Inventors: Jeffrey Ahlers, Winterville, NC (US); Jeffrey Bartlett, Columbus, OH (US); Chi-Lin Lee, Arcadia, CA (US); Gene-Errol Eugenio Ringpis, West Hollywood, CA (US); Geoffrey Phillip Symonds, Rose Bay (AU); Ming Yan, Encino, CA (US)

(73) Assignees: CSL Behring Gene Therapy, Inc., Pasadena, CA (US); CSL Gene Therapy Pty Ltd., Melbourne (AU)

( * ) Notice: Subject to any disclaimer, the term of this patent is extended or adjusted under 35 U.S.C. 154(b) by 206 days.

This patent is subject to a terminal disclaimer.

(21) Appl. No.: 17/177,947

(22) Filed: Feb. 17, 2021

(65) Prior Publication Data

US 2021/0348170 A1 Nov. 11, 2021

Related U.S. Application Data

(63) Continuation of application No. 16/037,726, filed on Jul. 17, 2018, now Pat. No. 10,961,537.

(60) Provisional application No. 62/533,719, filed on Jul. 18, 2017, provisional application No. 62/541,931, filed on Aug. 7, 2017, provisional application No. 62/653,913, filed on Apr. 6, 2018.

(51) Int. Cl.

| | |
|---|---|
| ***C07H 21/04*** | (2006.01) |
| ***C12N 15/113*** | (2010.01) |
| ***A61K 35/28*** | (2015.01) |
| ***C07K 14/805*** | (2006.01) |
| ***C12N 15/86*** | (2006.01) |
| ***C12N 9/10*** | (2006.01) |
| ***A61P 7/00*** | (2006.01) |

(52) U.S. Cl.

CPC .......... *C12N 15/1137* (2013.01); *A61K 35/28* (2013.01); *A61P 7/00* (2018.01); *C07K 14/805* (2013.01); *C12N 9/1077* (2013.01); *C12N 15/86* (2013.01); *C12Y 204/02008* (2013.01); *C12N 2310/122* (2013.01); *C12N 2310/14* (2013.01); *C12N 2310/20* (2017.05); *C12N 2310/531* (2013.01); *C12N 2330/51* (2013.01); *C12N 2740/15043* (2013.01); *C12N 2740/16043* (2013.01); *C12N 2830/008* (2013.01)

(58) Field of Classification Search

None

See application file for complete search history.

(56) References Cited

PUBLICATIONS

Quigg, Donald J. "Animals—Patentability." Journal of the Patent and Trademark Office Society, vol. 69, No. 6, Jun. 1987, pp. 328-328. HeinOnline.*

* cited by examiner

*Primary Examiner* — Kimberly Chong
(74) *Attorney, Agent, or Firm* — Charney IP Law LLC; Thomas M. Finetti

(57) ABSTRACT

The present disclosure provides expression vectors comprising at least two nucleic acid sequences, namely a nucleic acid sequence encoding an anti-HPRT RNAi, and a nucleic acid sequence encoding a gamma globin gene. In some embodiments, the viral vector is a self-inactivating lentiviral vector. In some embodiments, the gamma-globin gene is used to genetically correct sickle cell disease or β-thalassemia or to reduce symptoms thereof.

21 Claims, 54 Drawing Sheets

Specification includes a Sequence Listing.

De Novo Pathway of dTTP

MFE Secondary Structure -56.77 kcal/mol

Base-pair Probabilities
0 1 miRNA211-3G sh734, Secondary Structure MFE -30.9 kcal/mol sh734.1 MFE= -36.16 kcal/mol; Freq. 65.95 % shHPRT 211 MFE=-33.56 kcal/mol.; freq. 65.71 %.

shHPRT 616 MFE=-33.56 kcal/mol.; freq. 65.71 %.

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY = -58.6 03/01/17 21:49:52
miRNA 734 de novo
SEQ ID NO: 23

Agosh 734 RNA, SEQ ID NO: 58

7SK RNA Promoter Region -- Corresponding to Nucleotides 7 through 248 of SEQ ID NO: 32

LENGTH = 242 COMBINED P-VALUE = 1.52e-06 E-VALUE = 1.5e-06

DIAGRAM: 7- [+3] - [+2]-3-[+1]-17-[+1]-20-[+3]-50-[-1]-44-[-1]-15-[+2]-10

7sKM1 promoter mutation. 7sKM1 Oct binding site mutations in the distal sequence enhancer (DSE) (dashed blue boxes) and predicted TAL-1 and GATA-1 binding sites.

NM_000194.2 Homo sapiens hypoxanthine
phosphoribosyltransferase 1 (HPRT1), mRNA
SEQ ID NO: 59

1 ggcggggcct gcttctcctc agcttcaggc ggctgcgacg agccctcagg cgaacctctc
61 ggctttcccg cgcggcgccg cctcttgctg cgcctccgcc tcctcctctg ctccgccacc
121 ggcttcctcc tcctgagcag tcagcccgcg cgccggccgg ctccgttatg gcgacccgca
181 gccctggcgt cgtgattagt gatgatgaac caggttatga ccttgattta ttttgcatac
241 ctaatcatta tgctgaggat ttggaaaggg tgtttattcc tcatggacta attatggaca
301 ggactgaacg tcttgctcga gatgtgatga aggagatggg aggccatcac attgtagccc
361 tctgtgtgct caaggggggc tataaattct ttgctgacct gctggattac atcaaagcac
421 tgaatagaaa tagtgataga tccattccta tgactgtaga ttttatcaga ctgaagagct
481 attgtaatga ccagtcaaca ggggacataa aagtaattgg tggagatgat ctctcaactt
541 taactggaaa gaatgtcttg attgtggaag atataattga cactggcaaa acaatgcaga
601 ctttgctttc cttggtcagg cagtataatc caaagatggt caaggtcgca agcttgctgg
661 tgaaaaggac cccacgaagt gttggatata agccagactt tgttggattt gaaattccag
721 acaagtttgt tgtoggotot gcccttgoct ataatgaata cttcagggat ttgaatcatg
781 tttgtgtcat tagtgaaact ggaaaagcaa aatacaaagc ctaagatgag agttcaagtt
841 gagtttggaa acatctggag tcctattgac atcgccagta aaattatcaa tgttctagtt
901 ctgtggccat ctgcttagta gagctttttg catgtatctt ctaagaattt tatctgtttt
961 gtactttaga aatgtcagtt gctgcattcc taaactgttt atttgcacta tgagcctata
1021 gactatcagt tccctttggg cggattgttg tttaacttgt aaatgaaaaa attctcttaa
1081 accacagcac tattgagtga aacattgaac tcatatctgt aagaaataaa gagaagatat
1141 attagttttt taattggtat tttaattttt atatatgcag gaaagaatag aagtgattga
1201 atattgttaa ttataccacc gtgtgttaga aaagtaagaa gcagtcaatt ttcacatcaa
1261 agacagcatc taagaagttt tgttctgtcc tggaattatt ttagtagtgt ttcagtaatg
1321 ttgactgtat ttttccaactt gttcaaatta ttaccagtga atctttgtca gcagttccct
1381 tttaaatgca aatcaataaa ttcccaaaaa tttaaaaaaa aaaaaaaaaa aaaaa shHPRT734
5'- AGGATATGCCCTTGACTATtttgtccgacATAGTCAAGGGCATACCTTTTT - 3'

SEQ ID NO: 30

FIG. 37

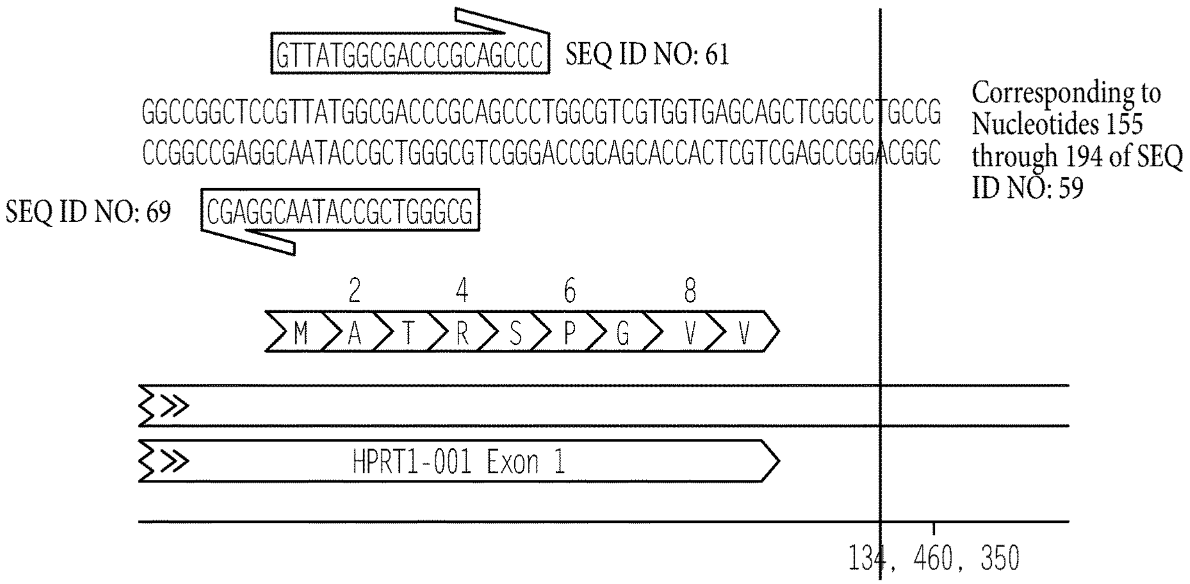

| Position | Strand | SequencePAM | Specificity Score | Efficiency Score | |
|---|---|---|---|---|---|
| 134460326 HPRT3 | 1 | GTTATGGCGACCCGCAGCCC TGG | 89 | 51 | SEQ ID NO: 61 |
| 134460307 HPRT4 | -1 | GCGGGTCGCCATAACGGAGC CGG | 98 | 50 | SEQ ID NO: 69 |

FIG. 38 sGbGm exons 1-3

CAGACACCATGGGTCATTTCACAGAGGAGGACAAGGCTACTATCACAAGCCTGTGGGACA
AGGTGAATGTGGAAGATGCTGGAGGAAAACCCTGGGAAGGCTCCTGGTTGTCTACC
CATGGACCCAGAGGTTCTTTGACAGCTTTGGCAACCTGTCCTCTGCCTCTGCCAT
CATGGGCAACCCCAAAGTCAAGGCACATGGCAAGAAGGTGCTGACTTCCTTGGGA
GATGCCATAAAGCACCTGGATGATCTCAAGGGCACCTTTGCCCAGCTGAGTGAAC
TGCACTGTGACAAGCTGCATGTGGATCCTGAGAACTTCAAGCTCCTGGGCAACGT
GCTGGTCACCGTGCTGGCCATTCACTTTGGCAAAGAATTCACCCCTGAGGTGCAG
GCTTCCTGGCAGAAGATGGTGACTGCAGTGGCCAGTGCCCTGTCCTCCAGATACC
ACTGAGCCTCTTGCCCATGATTCAGAGCTTTCAAGGATAGGCTTTATTCTGCAAG
CAATACAAATAATAAATCTATTCTGCTGAGAGATCAC

SEQ ID NO: 55

FIG. 39

Titration of γ-globin Expression Vectors

| Name | Average Titer (TU/mL) | Stdev |
|---|---|---|
| sGbG$^M$ | $1.90 \times 10^5$ | $5.72 \times 10^4$ |
| TL20c-sGbG$^M$ | $7.32 \times 10^5$ | $7.71 \times 10^4$ |
| Cal-H | $6.94 \times 10^5$ | $3.18 \times 10^5$ |

| Vectors | Day 0 | | | | Day 35 | | |
|---|---|---|---|---|---|---|---|
| | Dilution | %GFP+ | sh734/ %GFP+ | Rel.HPRT | %GFP+ | sh734/ %GFP+ | Rel.HPRT |
| Mock | Mock | 0.4 | | 1 | 0.7 | | 1 |
| TL20cw-UbC/GFP | 1024 | 10.4 | ND | 0.95 | 9.1 | N/A | N/A |
| TL20cw-7SK/sh734-UbC/GFP | 1024 | 8.3 | 3.03 | 1.19 | 99.6 | 21.06 | 0.087 |
| TL20cw-r7SK/sh734-UbC/GFP | 1024 | 8.2 | 4.49 | 0.71 | 95.4 | 27.48 | 0.070 |
| TL20cw-UbC/GFP-7SK/sh734 | 1024 | 12.4 | 0.87 | 0.94 | 59.6 | 6.98 | 0.223 |
| TL20cw-UbC/GFP-r7SK/sh734 | 1024 | 10.1 | 0.27 | 0.72 | 98 | 15.17 | 0.163 |

FIG. 49K

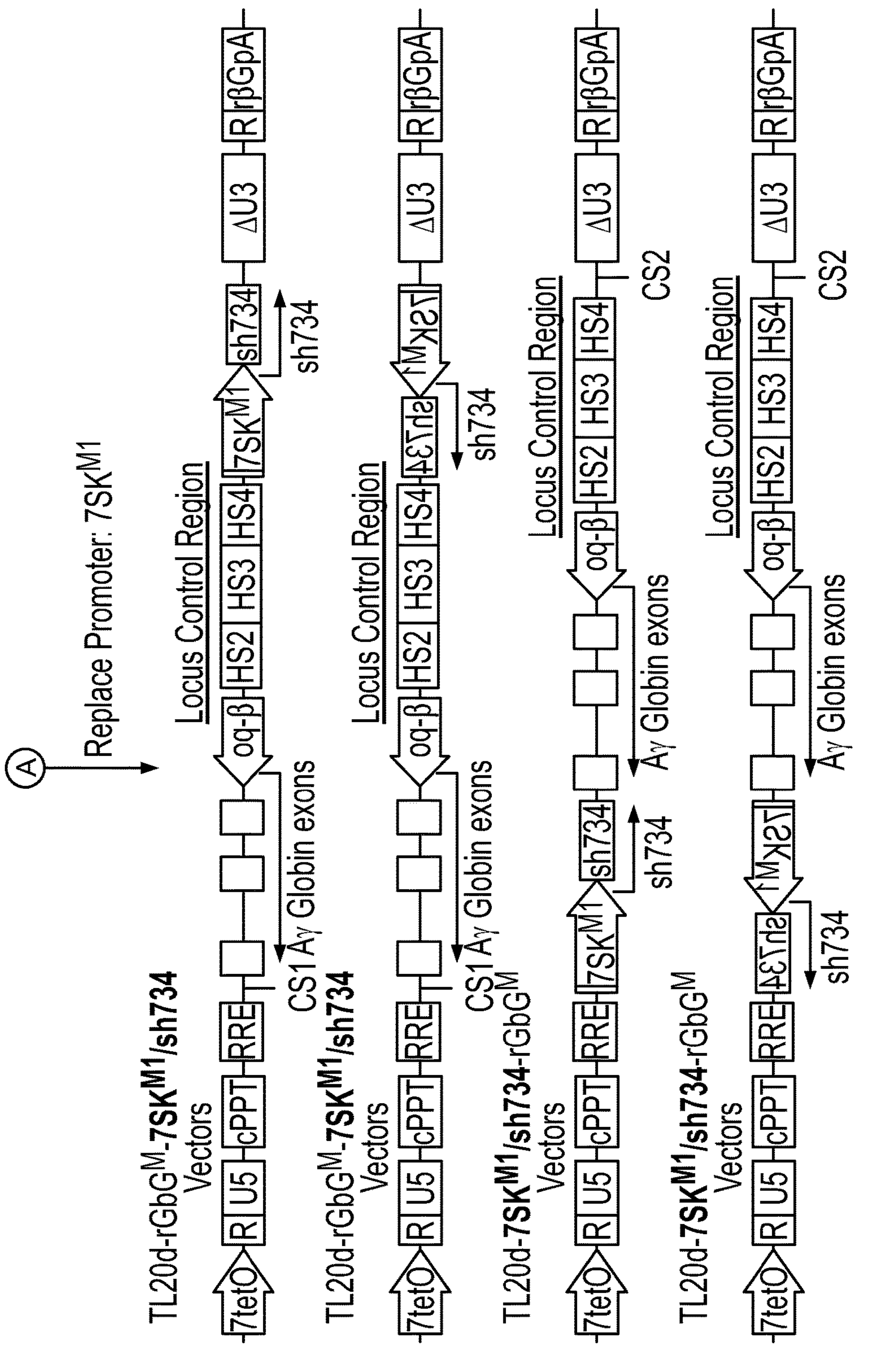
FIG. 53 (Cont..)

SEQUENCE LISTING

```
<160> NUMBER OF SEQ ID NOS: 69

<210> SEQ ID NO 1
<211> LENGTH: 46
<212> TYPE: DNA
<213> ORGANISM: Artificial Sequence
<220> FEATURE:
<223> OTHER INFORMATION: Synthetic: shRNA targeting an HPRT gene

<400> SEQUENCE: 1

aggatatgcc cttgactatt tgtccgacat agtcaagggc atatcc                46


<210> SEQ ID NO 2
<211> LENGTH: 46
<212> TYPE: DNA
<213> ORGANISM: Artificial Sequence
<220> FEATURE:
<223> OTHER INFORMATION: Synthetic: shRNA targeting an HPRT gene

<400> SEQUENCE: 2

tcctatacgg gaactgataa acaggctgta tcagttcccg tatagg                46


<210> SEQ ID NO 3
<211> LENGTH: 444
<212> TYPE: DNA
<213> ORGANISM: Artificial Sequence
<220> FEATURE:
<223> OTHER INFORMATION: Synthetic: sGbGm A gamma-globin translated
      sequence

<400> SEQUENCE: 3

atgggtcatt tcacagagga ggacaaggct actatcacaa gcctgtggga caaggtgaat      60

gtggaagatg ctggaggaga aaccctggga aggctcctgg ttgtctaccc atggacccag     120

aggttctttg acagctttgg caacctgtcc tctgcctctg ccatcatggg caaccccaaa     180
```

-continued

```
gtcaaggcac atggcaagaa ggtgctgact tccttgggag atgccataaa gcacctggat    240

gatctcaagg gcacctttgc ccagctgagt gaactgcact gtgacaagct gcatgtggat    300

cctgagaact tcaagctcct gggcaacgtg ctggtcaccg tgctggccat tcactttggc    360

aaagaattca cccctgaggt gcaggcttcc tggcagaaga tggtgactgc agtggccagt    420

gccctgtcct ccagatacca ctga                                           444
```

<210> SEQ ID NO 4
<211> LENGTH: 147
<212> TYPE: PRT
<213> ORGANISM: Artificial Sequence
<220> FEATURE:
<223> OTHER INFORMATION: Synthetic: sGbGM HGB1 amino acid sequece

<400> SEQUENCE: 4

```
Met Gly His Phe Thr Glu Glu Asp Lys Ala Thr Ile Thr Ser Leu Trp
1               5                   10                  15

Asp Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
    50                  55                  60

Gly Lys Lys Val Leu Thr Ser Leu Gly Asp Ala Ile Lys His Leu Asp
65                  70                  75                  80

Asp Leu Lys Gly Thr Phe Ala Gln Leu Ser Glu Leu His Cys Asp Lys
                85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Ala Val Ala Ser Ala Leu Ser Ser
    130                 135                 140

Arg Tyr His
145
```

<210> SEQ ID NO 5
<211> LENGTH: 12088
<212> TYPE: DNA
<213> ORGANISM: Artificial Sequence
<220> FEATURE:
<223> OTHER INFORMATION: Synthetic: TL20c-7SKM1/sh734-rGbGM

<400> SEQUENCE: 5

```
ggccgcctcg gccaaacagc ccttgagttt accactccct atcagtgata gagaaaagtg     60

aaagtcgagt ttaccactcc ctatcagtga tagagaaaag tgaaagtcga gtttaccact    120

ccctatcagt gatagagaaa agtgaaagtc gagtttacca ctccctatca gtgatagaga    180

aaagtgaaag tcgagtttac cagtccctat cagtgataga gaaaagtgaa agtcgagttt    240

accactccct atcagtgata gagaaaagtg aaagtcgagt ttaccactcc ctatcagtga    300

tagagaaaag tgaaagtcga gctcgccatg ggaggcgtgg cctgggcggg actggggagt    360

ggcgagccct cagatcctgc atataagcag ctgctttttg cctgtactgg gtctctctgg    420

ttagaccaga tctgagcctg ggagctctct ggctaactag ggaacccact gcttaagcct    480

caataaagct tgccttgagt gcttcaagta gtgtgtgccc gtctgttgtg tgactctggt    540

aactagagat ccctcagacc cttttagtca gtgtggaaaa tctctagcag tggcgcccga    600
```

```
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgct cgacgtgcag   2400
tcgggctact gccccaccca tagtaccggc attctggata gtgtcaaaac agccggaaat   2460
caagtccgtt tatctcaaac tttagcattt tgggaataaa tgatatttgc tatgctggtt   2520
aaattagatt ttagttaaat ttcctgctga agctctagta cgataagtaa cttgacctaa   2580
gtgtaaagtt gagatttcct tcaggtttat atagcttgtg cgccgcctgg gtacctcagg   2640
atatgccctt gactatttgt ccgacatagt caagggcata tcctttttta cgcgtgggga   2700
tcctctagag tcgagctcgc gaggatcatc accggtgcta gccggagcca gaagcaccat   2760
aagggacatg ataagggagc cagcagacct ctgatctctt cctgaatgct aatcttaaac   2820
atcctgagga agaatgggac ttccatttgg ggtgggccta tgatagggta ataagacagt   2880
agtgaatatc aagctacaaa aagccccctt tcaaattctt ctcagtccta actttttcata   2940
```

-continued

```
ctaagcccag tccttccaaa gcagactgtg aaagagtgat agttccggga gactagcacc   3000
ggctagccga gcttggaaca ctttcccttc attaagaacc atccttgcta ctcagctgca   3060
atcaatccag cccccaggtc ttcactgaac cttttcccat ctcttccaaa acatctgttt   3120
ctgagaagtc ctgtcctata gaggtctttc ttcccaccgg atttctccta caccatttac   3180
tcccacttgc agaactcccg tgtacaagtg tctttactgc ttttatttgc tcaacaaaat   3240
gcacatctca tataaaaata aatgaggagc atgcacacac cacaaacaca aacaggcatg   3300
cagaaataca catacacact tccctcaata taaacccttt gtggctcata tatttaaaaa   3360
gatgtaaaaa aaagagctga agaaaatcat gtgtgatctc tcagcagaat agatttatta   3420
tttgtattgc ttgcagaata aagcctatcc ttgaaagctc tgaatcatgg gcaagaggct   3480
cagtggtatc tggaggacag ggcactggcc actgcagtca ccatcttctg ccaggaagcc   3540
tgcacctcag gggtgaattc tttgccaaag tgaatggcca gcacggtgac cagcacgttg   3600
cccaggagct gtgggaggaa gataagaggt atgaacatga ttagcaaaag ggcctagctt   3660
ggactcagaa taatccagcc ttatcccaac cataaaataa aagcagaatg gtagctggat   3720
tgtagctgct attagcaata tgaaacctct tacatcagtt acaatttata tgcagaaata   3780
tttatatgca gaaatattgc tattgcctta acccagaaat tatcactgtt attctttaga   3840
atggtgcaaa gaggcatgat acattgtatc attattgccc tgaaagaaag agattaggga   3900
aagtattaga aataagataa acaaaaaagt atattaaaag aagaaagcat tttttaaaat   3960
tacaaatgca aaattaccct gatttggtca atatgtgtac cctgttactt ctccccttcc   4020
tatgacatga acttaaccat agaaaagaag gggaaagaaa acatcaaggg tcccatagac   4080
tcaccttgaa gttctcagga tccacatgca gcttgtcaca gtgcagttca ctcagctggg   4140
caaaggtgcc cttgagatca tccaggtgct ttatggcatc tcccaaggaa gtcagcacct   4200
tcttgccatg tgccttgact ttggggttgc ccatgatggc agaggcagag gacaggttgc   4260
caaagctgtc aaagaacctc tgggtccatg ggtagacaac caggagcctg tgagattgac   4320
aagaacagtt tgacagtcag aaggtgccac aaatcctgag aagcaacctg gacttttgcc   4380
aggcacaggg tccttccttc cctcccttgt cctggtcacc agagcctacc ttcccagggt   4440
ttctcctcca gcatcttcca cattcacctt gtcccacagg cttgtgatag tagccttgtc   4500
ctcctctgtg aaatgaccca tggtgtctgt ttgaggttgc tagtgaacac agttgtgtca   4560
gaagcaaatg taagcaatag atggctctgc cctgactttt atgcccagcc ctggctcctg   4620
ccctccctgc tcctgggagt agattggcca accctagggt gtggctccac agggtgaggt   4680
ctaagtgatg acagccgtac ctgtccttgg ctcttctggc actggcttag gagttggact   4740
tcaaaccctc agccctccct ctaagatata tctcttggcc ccataccatc agtacaaatt   4800
gctactaaaa acatcctcct ttgcaagtgt atttacgacg gtatcgatgt atgtgagcat   4860
gtgtcctcta acagcacagg ccttttgcca cctagctgtc caggggtgcc ttaaaatggc   4920
aaacaaggtt tgttttcttt tcctgttttc atgccttcct cttccatatc cttgtttcat   4980
attaatacat gtgtatagat cctaaaaatc tatacacatg tattaataaa gcctgattct   5040
gccgcttcta ggtatagagg ccacctgcaa gataaatatt tgattcacaa taactaatca   5100
ttctatggca attgataaca acaaatatat atatatatat atatatacgt atatgtgtat   5160
atatatatat atattcagga aataatatat tctagaatat gtcacattct gtctcaggca   5220
tccattttct ttatgatgcc gtttgaggtg gagttttagt caggtggtca gcttctcctt   5280
ttttttgcca tctgccctgt aagcatcctg ctggggaccc agataggagt catcactcta   5340
```

ggctgagaac atctgggcac acaccctaag cctcagcatg actcatcatg actcagcatt 5400
gctgtgcttg agccagaagg tttgcttaga aggttacaca gaaccagaag gcgggggtgg 5460
ggcactgacc ccgacagggg cctggccaga actgctcatg cttggactat gggaggtcac 5520
taatggagac acacagaaat gtaacaggaa ctaagggaat tccggtgccc tgcttaggag 5580
cttaatcttt aatgaaagct aagctttcat taaaaaaagt ctaaccagct gcattcgact 5640
ttgactgcag cagctggtta gaaggttcta ctggaggagg gtcccagccc attgctaaat 5700
taacatcagg ctctgagact ggcagtatat ctctaacagt ggttgatgct atcttctgga 5760
acttgcctgc tacattgaga ccactgaccc atacatagga agcccatagc tctgtcctga 5820
actgttaggc cactggtcca gagagtgtgc atctcctttg atcctcataa taaccctatg 5880
agatagacac aattattact cttactttat agatgatgat cctgaaaaca taggagtcaa 5940
ggcacttgcc cctagctggg ggtatagggg agcagtccca tgtagtagta gaatgaaaaa 6000
tgctgctatg ctgtgcctcc cccacctttc ccatgtctgc cctctactca tggtctatct 6060
ctcctggctc ctgggagtca tggactccac ccagcaccac caacctgacc taaccaccta 6120
tctgagcctg ccagcctata acccatctgg gccctgatag ctggtggcca gccctgaccc 6180
caccccaccc tccctggaac ctctgataga cacatctggc acaccagctc gcaaagtcac 6240
cgtgagggtc ttgtgtttgc tgagtcaaaa ttccttgaaa tccaagtcct tagagactcc 6300
tgctcccaaa tttacagtca tagacttctt catggctgtc tcctttatcc acagaatgat 6360
tcctttgctt cattgcccca tccatctgat cctcctcatc agtgcagcac agggcccatg 6420
agcagtagct gcagagtctc acataggtct ggcactgcct ctgacatgtc cgaccttagg 6480
caaatgcttg actcttctga gctcggatcc cttgagctca ggaggtcaag gctgcagtga 6540
gacatgatct tgccactgca ctccagcctg gacagcagag tgaaaccttg cctcacgaaa 6600
cagaatacaa aaacaaacaa acaaaaaact gctccgcaat gcgcttcctt gatgctctac 6660
cacataggtc tgggtacttt gtacacatta tctcattgct gttcataatt gttagattaa 6720
ttttgtaata ttgatattat tcctagaaag ctgaggcctc aagatgataa cttttatttt 6780
ctggacttgt aatagctttc tcttgtattc accatgttgt aactttctta gagtagtaac 6840
aatataaagt tattgtgagt ttttgcaaac acagcaaaca caacgaccca tatagacatt 6900
gatgtgaaat tgtctattgt caatttatgg gaaaacaagt atgtactttt tctactaagc 6960
cattgaaaca ggaataacag aacaagattg aaagaataca ttttccgaaa ttacttgagt 7020
attatacaaa gacaagcacg tggacctggg aggagggtta ttgtccatga ctggtgtgtg 7080
gagacaaatg caggtttata atagatggga tggcatctag cgcaatgact ttgccatcac 7140
ttttagagag ctcttggggg ccccagtaca caagagggga cgcagggtat atgtagacat 7200
ctcattcttt ttcttagtgt gagaataaga atagccatga cctgagttta tagacaatga 7260
gcccttttct ctctcccact cagcagctat gagatggctt gccctgcctc tctactaggc 7320
tgactcactc caaggcccag caatgggcag ggctctgtca gggctttgat agcactatct 7380
gcagagccag ggccgagaag gggtggactc cagagactct ccctcccatt cccgagcagg 7440
gtttgcttat ttatgcattt aaatgatata tttattttaa aagaaataac aggagactgc 7500
ccagccctgg ctgtgacatg gaaactatgt agaatatttt gggttccatt ttttttcct 7560
tctttcagtt agaggaaaag gggctcactg cacatacact agacagaaag tcaggagctt 7620
tgaatccaag cctgatcatt tccatgtcat actgagaaag tccccaccct tctctgagcc 7680

-continued

```
tcagtttctc tttttataag taggagtctg gagtaaatga tttccaatgg ctctcatttc   7740
aatacaaaat ttccgtttat taaatgcatg agcttccgtt actccaagac tgagaaggaa   7800
attgaacctg agactcattg actggcaaga tgtccccaga ggctctcatt cagcaataaa   7860
attctcacct tcacccaggc ccactagtgt cagatttgca tgcgttaacg cggccgcatc   7920
gatgccgtag tacctttaag accaatgact tacaaggcag ctgtagatct tagccacttt   7980
ttaaaagaaa aggggggact ggaagggcta attcactccc aaagaagaca agatccctgc   8040
aggcattcaa ggccaggctg gatgtggctc tgggcagcct gggctgctgg ttgatgaccc   8100
tgcacatagc agggggttgg atctggatga gcactgtgct cctttgcaac ccaggccgtt   8160
ctatgattct gtcattctaa atctctcttt cagcctaaag ctttttcccc gtatcccccc   8220
aggtgtctgc aggctcaaag agcagcgaga agcgttcaga ggaaagcgat cccgtgccac   8280
cttccccgtg cccgggctgt ccccgcacgc tgccggctcg ggatgcgggg gggagcgccg   8340
gaccggagcg gagccccggg cggctcgctg ctgcccccta gcgggggagg gacgtaatta   8400
catccctggg ggctttgggg gggggctgtc cccgtgagct ccccagatct gctttttgcc   8460
tgtactgggt ctctctggtt agaccagatc tgagcctggg agctctctgg ctaactaggg   8520
aacccactgc ttaagcctca ataaagcttc agctgctcga gctagcagat ctttttccct   8580
ctgccaaaaa ttatggggac atcatgaagc cccttgagca tctgacttct ggctaataaa   8640
ggaaatttat tttcattgca atagtgtgtt ggaatttttt gtgtctctca ctcggaagga   8700
catatgggag ggcaaatcat ttaaaacatc agaatgagta tttggtttag agtttggcaa   8760
catatgccca tatgctggct gccatgaaca aaggttggct ataaagaggt catcagtata   8820
tgaaacagcc ccctgctgtc cattccttat tccatagaaa agccttgact tgaggttaga   8880
tttttttat attttgtttt gtgttatttt tttctttaac atccctaaaa ttttccttac   8940
atgttttact agccagattt ttcctcctct cctgactact cccagtcata gctgtccctc   9000
ttctcttatg gagatccctc gacctgcagc ccaagcttgg cgtaatcatg gtcatagctg   9060
tttcctgtgt gaaattgtta tccgctcaca attccacaca acatacgagc cggaagcata   9120
aagtgtaaag cctggggtgc ctaatgagtg agctaactca cattaattgc gttgcgctca   9180
ctgcccgctt tccagtcggg aaacctgtcg tgccagcgga tccgcatctc aattagtcag   9240
caaccatagt cccgccccta actccgccca tcccgcccct aactccgccc agttccgccc   9300
attctccgcc ccatggctga ctaatttttt ttatttatgc agaggccgag gccgcctcgg   9360
cctctgagct attccagaag tagtgaggag gcttttttgg aggcctaggc ttttgcaaaa   9420
agctgtcgac tgcagaggcc tgcatgcaag cttggcgtaa tcatggtcat agctgtttcc   9480
tgtgtgaaat tgttatccgc tcacaattcc acacaacata cgagccggaa gcataaagtg   9540
taaagcctgg ggtgcctaat gagtgagcta actcacatta attgcgttgc gctcactgcc   9600
cgctttccag tcgggaaacc tgtcgtgcca gctgcattaa tgaatcggcc aacgcgcggg   9660
gagaggcggt ttgcgtattg ggcgctcttc cgcttcctcg ctcactgact cgctgcgctc   9720
ggtcgttcgg ctgcggcgag cggtatcagc tcactcaaag gcggtaatac ggttatccac   9780
agaatcaggg gataacgcag gaaagaacat gtgagcaaaa ggccagcaaa aggccaggaa   9840
ccgtaaaaag gccgcgttgc tggcgttttt ccataggctc cgcccccctg acgagcatca   9900
caaaaatcga cgctcaagtc agaggtggcg aaacccgaca ggactataaa gataccaggc   9960
gtttccccct ggaagctccc tcgtgcgctc tcctgttccg accctgccgc ttaccggata  10020
cctgtccgcc tttctccctt cgggaagcgt ggcgctttct catagctcac gctgtaggta  10080
```

tctcagttcg gtgtaggtcg ttcgctccaa gctgggctgt gtgcacgaac cccccgttca 10140
gcccgaccgc tgcgccttat ccggtaacta tcgtcttgag tccaacccgg taagacacga 10200
cttatcgcca ctggcagcag ccactggtaa caggattagc agagcgaggt atgtaggcgg 10260
tgctacagag ttcttgaagt ggtggcctaa ctacggctac actagaagaa cagtatttgg 10320
tatctgcgct ctgctgaagc cagttacctt cggaaaaaga gttggtagct cttgatccgg 10380
caaacaaacc accgctggta gcggtggttt ttttgtttgc aagcagcaga ttacgcgcag 10440
aaaaaaagga tctcaagaag atcctttgat cttttctacg gggtctgacg ctcagtggaa 10500
cgaaaactca cgttaaggga ttttggtcat gagattatca aaaaggatct tcacctagat 10560
ccttttaaat taaaaatgaa gttttaaatc aatctaaagt atatatgagt aaacttggtc 10620
tgacagttac caatgcttaa tcagtgaggc acctatctca gcgatctgtc tatttcgttc 10680
atccatagtt gcctgactcc ccgtcgtgta gataactacg atacgggagg gcttaccatc 10740
tggccccagt gctgcaatga taccgcgaga cccacgctca ccggctccag atttatcagc 10800
aataaaccag ccagccggaa gggccgagcg cagaagtggt cctgcaactt tatccgcctc 10860
catccagtct attaattgtt gccgggaagc tagagtaagt agttcgccag ttaatagttt 10920
gcgcaacgtt gttgccattg ctacaggcat cgtggtgtca cgctcgtcgt ttggtatggc 10980
ttcattcagc tccggttccc aacgatcaag gcgagttaca tgatccccca tgttgtgcaa 11040
aaaagcggtt agctccttcg gtcctccgat cgttgtcaga agtaagttgg ccgcagtgtt 11100
atcactcatg gttatggcag cactgcataa ttctcttact gtcatgccat ccgtaagatg 11160
cttttctgtg actggtgagt actcaaccaa gtcattctga gaatagtgta tgcggcgacc 11220
gagttgctct tgcccggcgt caatacggga taataccgcg ccacatagca gaactttaaa 11280
agtgctcatc attggaaaac gttcttcggg gcgaaaactc tcaaggatct taccgctgtt 11340
gagatccagt tcgatgtaac ccactcgtgc acccaactga tcttcagcat cttttacttt 11400
caccagcgtt tctgggtgag caaaaacagg aaggcaaaat gccgcaaaaa agggaataag 11460
ggcgacacgg aaatgttgaa tactcatact cttccttttt caatattatt gaagcattta 11520
tcagggttat tgtctcatga gcggatacat atttgaatgt atttagaaaa ataaacaaat 11580
aggggttccg cgcacatttc cccgaaaagt gccacctgac gtctaagaaa ccattattat 11640
catgacatta acctataaaa ataggcgtat cacgaggccc tttcgtctcg cgcgtttcgg 11700
tgatgacggt gaaaacctct gacacatgca gctcccggag acggtcacag cttgtctgta 11760
agcggatgcc gggagcagac aagcccgtca gggcgcgtca gcgggtgttg gcgggtgtcg 11820
gggctggctt aactatgcgg catcagagca gattgtactg agagtgcacc atatgcggtg 11880
tgaaataccg cacagatgcg taaggagaaa ataccgcatc aggcgccatt cgccattcag 11940
gctgcgcaac tgttgggaag ggcgatcggt gcgggcctct tcgctattac gccagctggc 12000
gaaaggggga tgtgctgcaa ggcgattaag ttgggtaacg ccagggtttt cccagtcacg 12060
acgttgtaaa acgacggcca gtgaattc 12088

<210> SEQ ID NO 6
<211> LENGTH: 12091
<212> TYPE: DNA
<213> ORGANISM: Artificial Sequence
<220> FEATURE:
<223> OTHER INFORMATION: Synthetic: TL20c-7SK/sh734-rGbGM

<400> SEQUENCE: 6

-continued

```
ggccgcctcg gccaaacagc ccttgagttt accactccct atcagtgata gagaaaagtg     60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgctttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgca tcgacgtgca   2400
```

-continued

```
gtatttagca tgccccaccc atctgcaagg cattctggat agtgtcaaaa cagccggaaa   2460
tcaagtccgt ttatctcaaa ctttagcatt ttgggaataa atgatatttg ctatgctggt   2520
taaattagat tttagttaaa tttcctgctg aagctctagt acgataagta acttgaccta   2580
agtgtaaagt tgagatttcc ttcaggttta tatagcttgt gcgccgcctg ggtacctcag   2640
gatatgccct tgactatttg tccgacatag tcaagggcat atcctttttt gtacgcgtgg   2700
ggatcctcta gagtcgagct cgcgaggatc atcaccggtg ctagccggag ccagaagcac   2760
cataagggac atgataaggg agccagcaga cctctgatct cttcctgaat gctaatctta   2820
aacatcctga ggaagaatgg gacttccatt tggggtgggc ctatgatagg gtaataagac   2880
agtagtgaat atcaagctac aaaaagcccc ctttcaaatt cttctcagtc ctaacttttc   2940
atactaagcc cagtccttcc aaagcagact gtgaaagagt gatagttccg ggagactagc   3000
accggctagc cgagcttgga acactttccc ttcattaaga accatccttg ctactcagct   3060
gcaatcaatc cagcccccag gtcttcactg aaccttttcc catctcttcc aaaacatctg   3120
tttctgagaa gtcctgtcct atagaggtct ttcttcccac cggatttctc ctacaccatt   3180
tactcccact tgcagaactc ccgtgtacaa gtgtctttac tgcttttatt tgctcaacaa   3240
aatgcacatc tcatataaaa ataaatgagg agcatgcaca caccacaaac acaaacaggc   3300
atgcagaaat acacatacac acttccctca atataaaccc tttgtggctc atatatttaa   3360
aaagatgtaa aaaaaagagc tgaagaaaat catgtgtgat ctctcagcag aatagattta   3420
ttatttgtat tgcttgcaga ataaagccta tccttgaaag ctctgaatca tgggcaagag   3480
gctcagtggt atctggagga cagggcactg gccactgcag tcaccatctt ctgccaggaa   3540
gcctgcacct caggggtgaa ttctttgcca aagtgaatgg ccagcacggt gaccagcacg   3600
ttgcccagga gctgtgggag gaagataaga ggtatgaaca tgattagcaa aagggcctag   3660
cttggactca gaataatcca gccttatccc aaccataaaa taaaagcaga atggtagctg   3720
gattgtagct gctattagca atatgaaacc tcttacatca gttacaattt atatgcagaa   3780
atatttatat gcagaaatat tgctattgcc ttaacccaga aattatcact gttattcttt   3840
agaatggtgc aaagaggcat gatacattgt atcattattg ccctgaaaga aagagattag   3900
ggaaagtatt agaaataaga taaacaaaaa agtatattaa aagaagaaag catttttttaa   3960
aattacaaat gcaaaattac cctgatttgg tcaatatgtg taccctgtta cttctcccct   4020
tcctatgaca tgaacttaac catagaaaag aaggggaaag aaaacatcaa gggtcccata   4080
gactcacctt gaagttctca ggatccacat gcagcttgtc acagtgcagt tcactcagct   4140
gggcaaaggt gcccttgaga tcatccaggt gctttatggc atctcccaag gaagtcagca   4200
ccttcttgcc atgtgccttg actttggggt tgcccatgat ggcagaggca gaggacaggt   4260
tgccaaagct gtcaaagaac ctctgggtcc atgggtagac aaccaggagc ctgtgagatt   4320
gacaagaaca gtttgacagt cagaaggtgc cacaaatcct gagaagcaac ctggactttt   4380
gccaggcaca gggtccttcc ttccctccct tgtcctggtc accagagcct accttcccag   4440
ggtttctcct ccagcatctt ccacattcac cttgtcccac aggcttgtga tagtagcctt   4500
gtcctcctct gtgaaatgac ccatggtgtc tgtttgaggt tgctagtgaa cacagttgtg   4560
tcagaagcaa atgtaagcaa tagatggctc tgccctgact tttatgccca gccctggctc   4620
ctgccctccc tgctcctggg agtagattgg ccaaccctag ggtgtggctc cacagggtga   4680
ggtctaagtg atgacagccg tacctgtcct tggctcttct ggcactggct taggagttgg   4740
```

```
acttcaaacc ctcagccctc cctctaagat atatctcttg gccccatacc atcagtacaa   4800
attgctacta aaaacatcct cctttgcaag tgtatttacg acggtatcga tgtatgtgag   4860
catgtgtcct ctaacagcac aggccttttg ccacctagct gtccaggggt gccttaaaat   4920
ggcaaacaag gtttgttttc ttttcctgtt ttcatgcctt cctcttccat atccttgttt   4980
catattaata catgtgtata gatcctaaaa atctatacac atgtattaat aaagcctgat   5040
tctgccgctt ctaggtatag aggccacctg caagataaat atttgattca caataactaa   5100
tcattctatg gcaattgata acaacaaata tatatatata tatatatata cgtatatgtg   5160
tatatatata tatatattca ggaaataata tattctagaa tatgtcacat tctgtctcag   5220
gcatccattt tctttatgat gccgtttgag gtggagtttt agtcaggtgg tcagcttctc   5280
cttttttttg ccatctgccc tgtaagcatc ctgctgggga cccagatagg agtcatcact   5340
ctaggctgag aacatctggg cacacaccct aagcctcagc atgactcatc atgactcagc   5400
attgctgtgc ttgagccaga aggtttgctt agaaggttac acagaaccag aaggcggggg   5460
tggggcactg accccgacag gggcctggcc agaactgctc atgcttggac tatgggaggt   5520
cactaatgga gacacacaga aatgtaacag gaactaaggg aattccggtg ccctgcttag   5580
gagcttaatc tttaatgaaa gctaagcttt cattaaaaaa agtctaacca gctgcattcg   5640
actttgactg cagcagctgg ttagaaggtt ctactggagg agggtcccag cccattgcta   5700
aattaacatc aggctctgag actggcagta tatctctaac agtggttgat gctatcttct   5760
ggaacttgcc tgctacattg agaccactga cccatacata ggaagcccat agctctgtcc   5820
tgaactgtta ggccactggt ccagagagtg tgcatctcct ttgatcctca taataaccct   5880
atgagataga cacaattatt actcttactt tatagatgat gatcctgaaa acataggagt   5940
caaggcactt gcccctagct gggggtatag gggagcagtc ccatgtagta gtagaatgaa   6000
aaatgctgct atgctgtgcc tcccccacct ttcccatgtc tgccctctac tcatggtcta   6060
tctctcctgg ctcctgggag tcatggactc cacccagcac caccaacctg acctaaccac   6120
ctatctgagc ctgccagcct ataacccatc tgggccctga tagctggtgg ccagccctga   6180
ccccacccca ccctccctgg aacctctgat agacacatct ggcacaccag ctcgcaaagt   6240
caccgtgagg gtcttgtgtt tgctgagtca aaattccttg aaatccaagt ccttagagac   6300
tcctgctccc aaatttacag tcatagactt cttcatggct gtctccttta tccacagaat   6360
gattcctttg cttcattgcc ccatccatct gatcctcctc atcagtgcag cacagggccc   6420
atgagcagta gctgcagagt ctcacatagg tctggcactg cctctgacat gtccgacctt   6480
aggcaaatgc ttgactcttc tgagctcgga tcccttgagc tcaggaggtc aaggctgcag   6540
tgagacatga tcttgccact gcactccagc ctggacagca gagtgaaacc ttgcctcacg   6600
aaacagaata caaaaacaaa caaacaaaaa actgctccgc aatgcgcttc cttgatgctc   6660
taccacatag gtctgggtac tttgtacaca ttatctcatt gctgttcata attgttagat   6720
taattttgta atattgatat tattcctaga aagctgaggc ctcaagatga taacttttat   6780
tttctggact tgtaatagct ttctcttgta ttcaccatgt tgtaactttc ttagagtagt   6840
aacaatataa agttattgtg agtttttgca aacacagcaa acacaacgac ccatatagac   6900
attgatgtga aattgtctat tgtcaattta tgggaaaaca agtatgtact ttttctacta   6960
agccattgaa acaggaataa cagaacaaga ttgaaagaat acattttccg aaattacttg   7020
agtattatac aaagacaagc acgtggacct gggaggaggg ttattgtcca tgactggtgt   7080
gtggagacaa atgcaggttt ataatagatg ggatggcatc tagcgcaatg actttgccat   7140
```

cacttttaga gagctcttgg gggccccagt acacaagagg ggacgcaggg tatatgtaga 7200
catctcattc tttttcttag tgtgagaata agaatagcca tgacctgagt ttatagacaa 7260
tgagcccttt tctctctccc actcagcagc tatgagatgg cttgccctgc ctctctacta 7320
ggctgactca ctccaaggcc cagcaatggg cagggctctg tcagggcttt gatagcacta 7380
tctgcagagc cagggccgag aaggggtgga ctccagagac tctccctccc attcccgagc 7440
agggtttgct tatttatgca tttaaatgat atatttattt taaaagaaat aacaggagac 7500
tgcccagccc tggctgtgac atggaaacta tgtagaatat tttgggttcc attttttttt 7560
ccttctttca gttagaggaa aaggggctca ctgcacatac actagacaga aagtcaggag 7620
ctttgaatcc aagcctgatc atttccatgt catactgaga aagtccccac ccttctctga 7680
gcctcagttt ctctttttat aagtaggagt ctggagtaaa tgatttccaa tggctctcat 7740
ttcaatacaa aatttccgtt tattaaatgc atgagcttcc gttactccaa gactgagaag 7800
gaaattgaac ctgagactca ttgactggca agatgtcccc agaggctctc attcagcaat 7860
aaaattctca ccttcaccca ggcccactag tgtcagattt gcatgcgtta acgcggccgc 7920
atcgatgccg tagtaccttt aagaccaatg acttacaagg cagctgtaga tcttagccac 7980
tttttaaaag aaaagggggg actggaaggg ctaattcact cccaaagaag acaagatccc 8040
tgcaggcatt caaggccagg ctggatgtgg ctctgggcag cctgggctgc tggttgatga 8100
ccctgcacat agcagggggt tggatctgga tgagcactgt gctcctttgc aacccaggcc 8160
gttctatgat tctgtcattc taaatctctc tttcagccta aagctttttc cccgtatccc 8220
cccaggtgtc tgcaggctca aagagcagcg agaagcgttc agaggaaagc gatcccgtgc 8280
caccttcccc gtgcccgggc tgtccccgca cgctgccggc tcggggatgc ggggggagcg 8340
ccggaccgga gcggagcccc gggcggctcg ctgctgcccc ctagcggggg agggacgtaa 8400
ttacatccct gggggctttg gggggggct gtccccgtga gctccccaga tctgcttttt 8460
gcctgtactg ggtctctctg gttagaccag atctgagcct gggagctctc tggctaacta 8520
gggaacccac tgcttaagcc tcaataaagc ttcagctgct cgagctagca gatctttttc 8580
cctctgccaa aaattatggg gacatcatga agccccttga gcatctgact tctggctaat 8640
aaaggaaatt tattttcatt gcaatagtgt gttggaattt tttgtgtctc tcactcggaa 8700
ggacatatgg gagggcaaat catttaaaac atcagaatga gtatttggtt tagagtttgg 8760
caacatatgc ccatatgctg gctgccatga acaaaggttg gctataaaga ggtcatcagt 8820
atatgaaaca gccccctgct gtccattcct tattccatag aaaagccttg acttgaggtt 8880
agattttttt tatattttgt tttgtgttat ttttttcttt aacatcccta aaattttcct 8940
tacatgtttt actagccaga tttttcctcc tctcctgact actcccagtc atagctgtcc 9000
ctcttctctt atggagatcc ctcgacctgc agcccaagct tggcgtaatc atggtcatag 9060
ctgtttcctg tgtgaaattg ttatccgctc acaattccac acaacatacg agccggaagc 9120
ataaagtgta aagcctgggg tgcctaatga gtgagctaac tcacattaat tgcgttgcgc 9180
tcactgcccg ctttccagtc gggaaacctg tcgtgccagc ggatccgcat ctcaattagt 9240
cagcaaccat agtcccgccc ctaactccgc ccatcccgcc cctaactccg cccagttccg 9300
cccattctcc gccccatggc tgactaattt tttttattta tgcagaggcc gaggccgcct 9360
cggcctctga gctattccag aagtagtgag gaggcttttt tggaggccta ggcttttgca 9420
aaaagctgtc gactgcagag gcctgcatgc aagcttggcg taatcatggt catagctgtt 9480

```
tcctgtgtga aattgttatc cgctcacaat tccacacaac atacgagccg gaagcataaa   9540
gtgtaaagcc tggggtgcct aatgagtgag ctaactcaca ttaattgcgt tgcgctcact   9600
gcccgctttc cagtcgggaa acctgtcgtg ccagctgcat taatgaatcg gccaacgcgc   9660
ggggagaggc ggtttgcgta ttgggcgctc ttccgcttcc tcgctcactg actcgctgcg   9720
ctcggtcgtt cggctgcggc gagcggtatc agctcactca aaggcggtaa tacggttatc   9780
cacagaatca ggggataacg caggaaagaa catgtgagca aaaggccagc aaaaggccag   9840
gaaccgtaaa aaggccgcgt tgctggcgtt tttccatagg ctccgccccc ctgacgagca   9900
tcacaaaaat cgacgctcaa gtcagaggtg gcgaaacccg acaggactat aaagatacca   9960
ggcgtttccc cctggaagct ccctcgtgcg ctctcctgtt ccgaccctgc cgcttaccgg  10020
atacctgtcc gcctttctcc cttcgggaag cgtggcgctt tctcatagct cacgctgtag  10080
gtatctcagt tcggtgtagg tcgttcgctc caagctgggc tgtgtgcacg aaccccccgt  10140
tcagcccgac cgctgcgcct tatccggtaa ctatcgtctt gagtccaacc cggtaagaca  10200
cgacttatcg ccactggcag cagccactgg taacaggatt agcagagcga ggtatgtagg  10260
cggtgctaca gagttcttga agtggtggcc taactacggc tacactagaa gaacagtatt  10320
tggtatctgc gctctgctga agccagttac cttcggaaaa agagttggta gctcttgatc  10380
cggcaaacaa accaccgctg gtagcggtgg tttttttgtt tgcaagcagc agattacgcg  10440
cagaaaaaaa ggatctcaag aagatccttt gatcttttct acggggtctg acgctcagtg  10500
gaacgaaaac tcacgttaag ggattttggt catgagatta tcaaaaagga tcttcaccta  10560
gatcctttta aattaaaaat gaagttttaa atcaatctaa agtatatatg agtaaacttg  10620
gtctgacagt taccaatgct taatcagtga ggcacctatc tcagcgatct gtctatttcg  10680
ttcatccata gttgcctgac tccccgtcgt gtagataact acgatacggg agggcttacc  10740
atctggcccc agtgctgcaa tgataccgcg agacccacgc tcaccggctc cagatttatc  10800
agcaataaac cagccagccg gaagggccga gcgcagaagt ggtcctgcaa ctttatccgc  10860
ctccatccag tctattaatt gttgccggga agctagagta agtagttcgc cagttaatag  10920
tttgcgcaac gttgttgcca ttgctacagg catcgtggtg tcacgctcgt cgtttggtat  10980
ggcttcattc agctccggtt cccaacgatc aaggcgagtt acatgatccc ccatgttgtg  11040
caaaaaagcg gttagctcct tcggtcctcc gatcgttgtc agaagtaagt tggccgcagt  11100
gttatcactc atggttatgg cagcactgca taattctctt actgtcatgc catccgtaag  11160
atgcttttct gtgactggtg agtactcaac caagtcattc tgagaatagt gtatgcggcg  11220
accgagttgc tcttgcccgg cgtcaatacg ggataatacc gcgccacata gcagaacttt  11280
aaaagtgctc atcattggaa aacgttcttc ggggcgaaaa ctctcaagga tcttaccgct  11340
gttgagatcc agttcgatgt aacccactcg tgcacccaac tgatcttcag catcttttac  11400
tttcaccagc gtttctgggt gagcaaaaac aggaaggcaa aatgccgcaa aaaagggaat  11460
aagggcgaca cggaaatgtt gaatactcat actcttcctt tttcaatatt attgaagcat  11520
ttatcagggt tattgtctca tgagcggata catatttgaa tgtatttaga aaaataaaca  11580
aataggggtt ccgcgcacat ttccccgaaa agtgccacct gacgtctaag aaaccattat  11640
tatcatgaca ttaacctata aaaataggcg tatcacgagg ccctttcgtc tcgcgcgttt  11700
cggtgatgac ggtgaaaacc tctgacacat gcagctcccg gagacggtca cagcttgtct  11760
gtaagcggat gccgggagca gacaagcccg tcagggcgcg tcagcgggtg ttggcgggtg  11820
tcggggctgg cttaactatg cggcatcaga gcagattgta ctgagagtgc accatatgcg  11880
```

```
gtgtgaaata ccgcacagat gcgtaaggag aaaataccgc atcaggcgcc attcgccatt  11940

caggctgcgc aactgttggg aagggcgatc ggtgcgggcc tcttcgctat tacgccagct  12000

ggcgaaaggg ggatgtgctg caaggcgatt aagttgggta acgccagggt tttcccagtc  12060

acgacgttgt aaaacgacgg ccagtgaatt c                                 12091
```

<210> SEQ ID NO 7
<211> LENGTH: 12088
<212> TYPE: DNA
<213> ORGANISM: Artificial Sequence
<220> FEATURE:
<223> OTHER INFORMATION: Synthetic: TL20c-r7SKM1/sh734-rGbGM

<400> SEQUENCE: 7

```
ggccgcctcg gccaaacagc ccttgagttt accactccct atcagtgata gagaaaagtg     60

aaagtcgagt ttaccactcc ctatcagtga tagagaaaag tgaaagtcga gtttaccact    120

ccctatcagt gatagagaaa agtgaaagtc gagtttacca ctccctatca gtgatagaga    180

aaagtgaaag tcgagtttac cagtccctat cagtgataga gaaaagtgaa agtcgagttt    240

accactccct atcagtgata gagaaaagtg aaagtcgagt ttaccactcc ctatcagtga    300

tagagaaaag tgaaagtcga gctcgccatg ggaggcgtgg cctgggcggg actggggagt    360

ggcgagccct cagatcctgc atataagcag ctgctttttg cctgtactgg gtctctctgg    420

ttagaccaga tctgagcctg ggagctctct ggctaactag ggaacccact gcttaagcct    480

caataaagct tgccttgagt gcttcaagta gtgtgtgccc gtctgttgtg tgactctggt    540

aactagagat ccctcagacc cttttagtca gtgtggaaaa tctctagcag tggcgcccga    600

acagggactt gaaagcgaaa gggaaaccag aggagctctc tcgacgcagg actcggcttg    660

ctgaagcgcg cacggcaaga ggcgaggggc ggcgactggt gagtacgcca aaaattttga    720

ctagcggagg ctagaaggag agagatgggt gcgagagcgt cagtattaag cgggggagaa    780

ttagatcgcg atgggaaaaa attcggttaa ggccaggggg aaagaaaaaa tataaattaa    840

aacatatagt atgggcaagc agggagctag aacgattcgc agttaatact ggcctgttag    900

aaacatcaga aggctgtaga caaatactgg gacagctaca accatccctt cagacaggat    960

cagaagaact tagatcatta tataatacag tagcaaccct ctattgtgtg catcaaagga   1020

tagagataaa agacaccaag gaagctttag acaagataga ggaagagcaa aacaaaagta   1080

agaaaaaagc acagcaagca gcaggatctt cagacctgga aattccctac aatccccaaa   1140

gtcaaggagt agtagaatct atgaataaag aattaaagaa aattatagga caggtaagag   1200

atcaggctga acatcttaag acagcagtac aaatggcagt attcatccac aattttaaaa   1260

gaaaaggggg gattgggggg tacagtgcag gggaaagaat agtagacata atagcaacag   1320

acatacaaac taaagaatta caaaaacaaa ttacaaaaat tcaaaatttt cgggtttatt   1380

acagggacag cagaaatcca ctttggaaag gaccagcaaa gctcctctgg aaaggtgaag   1440

gggcagtagt aatacaagat aatagtgaca taaaagtagt gccaagaaga aaagcaaaga   1500

tcattaggga ttatggaaaa cagatggcag gtgatgattg tgtggcaagt agacaggatg   1560

aggattagaa catggaaaag tttagtaaaa caccataagg aggagatatg agggacaatt   1620

ggagaagtga attatataaa tataaagtag taaaaattga accattagga gtagcaccca   1680

ccaaggcaaa gagaagagtg gtgcagagag aaaaaagagc agtgggaata ggagctttgt   1740

tccttgggtt cttgggagca gcaggaagca ctatgggcgc agcgtcaatg acgctgacgg   1800
```

-continued

```
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgca aaaaaggata   2400
tgcccttgac tatgtcggac aaatagtcaa gggcatatcc tgaggtaccc aggcggcgca   2460
caagctatat aaacctgaag gaaatctcaa ctttacactt aggtcaagtt acttatcgta   2520
ctagagcttc agcaggaaat ttaactaaaa tctaatttaa ccagcatagc aaatatcatt   2580
tattcccaaa atgctaaagt ttgagataaa cggacttgat ttccggctgt tttgacacta   2640
tccagaatgc cggtactatg ggtggggcag tagcccgact gcacgtcgaa cgcgtgggga   2700
tcctctagag tcgagctcgc gaggatcatc accggtgcta gccggagcca gaagcaccat   2760
aagggacatg ataagggagc cagcagacct ctgatctctt cctgaatgct aatcttaaac   2820
atcctgagga agaatgggac ttccatttgg ggtgggccta tgatagggta ataagacagt   2880
agtgaatatc aagctacaaa aagcccctt tcaaattctt ctcagtccta acttttcata   2940
ctaagcccag tccttccaaa gcagactgtg aaagagtgat agttccggga gactagcacc   3000
ggctagccga gcttggaaca ctttcccttc attaagaacc atccttgcta ctcagctgca   3060
atcaatccag cccccaggtc ttcactgaac cttttcccat ctcttccaaa acatctgttt   3120
ctgagaagtc ctgtcctata gaggtctttc ttcccaccgg atttctccta caccatttac   3180
tcccacttgc agaactcccg tgtacaagtg tctttactgc ttttatttgc tcaacaaaat   3240
gcacatctca tataaaaata aatgaggagc atgcacacac cacaaacaca aacaggcatg   3300
cagaaataca catacacact tccctcaata taaacccttt gtggctcata tatttaaaaa   3360
gatgtaaaaa aaagagctga agaaaatcat gtgtgatctc tcagcagaat agatttatta   3420
tttgtattgc ttgcagaata aagcctatcc ttgaaagctc tgaatcatgg gcaagaggct   3480
cagtggtatc tggaggacag ggcactggcc actgcagtca ccatcttctg ccaggaagcc   3540
tgcacctcag ggtgaattc tttgccaaag tgaatggcca gcacggtgac cagcacgttg   3600
cccaggagct gtgggaggaa gataagaggt atgaacatga ttagcaaaag ggcctagctt   3660
ggactcagaa taatccagcc ttatcccaac cataaaataa aagcagaatg gtagctggat   3720
tgtagctgct attagcaata tgaaacctct tacatcagtt acaatttata tgcagaaata   3780
tttatatgca gaaatattgc tattgcctta acccagaaat tatcactgtt attctttaga   3840
atggtgcaaa gaggcatgat acattgtatc attattgccc tgaaagaaag agattaggga   3900
aagtattaga aataagataa acaaaaaagt atattaaaag aagaaagcat tttttaaaat   3960
tacaaatgca aaattaccct gatttggtca atatgtgtac cctgttactt ctccccttcc   4020
tatgacatga acttaaccat agaaaagaag gggaaagaaa acatcaaggg tcccatagac   4080
tcaccttgaa gttctcagga tccacatgca gcttgtcaca gtgcagttca ctcagctggg   4140
caaaggtgcc cttgagatca tccaggtgct ttatggcatc tcccaaggaa gtcagcacct   4200
```

-continued

```
tcttgccatg tgccttgact ttggggttgc ccatgatggc agaggcagag gacaggttgc   4260
caaagctgtc aaagaacctc tgggtccatg ggtagacaac caggagcctg tgagattgac   4320
aagaacagtt tgacagtcag aaggtgccac aaatcctgag aagcaacctg gacttttgcc   4380
aggcacaggg tccttccttc cctcccttgt cctggtcacc agagcctacc ttcccagggt   4440
ttctcctcca gcatcttcca cattcacctt gtcccacagg cttgtgatag tagccttgtc   4500
ctcctctgtg aaatgaccca tggtgtctgt ttgaggttgc tagtgaacac agttgtgtca   4560
gaagcaaatg taagcaatag atggctctgc cctgactttt atgcccagcc ctggctcctg   4620
ccctccctgc tcctgggagt agattggcca accctagggt gtggctccac agggtgaggt   4680
ctaagtgatg acagccgtac ctgtccttgg ctcttctggc actggcttag gagttggact   4740
tcaaaccctc agccctccct ctaagatata tctcttggcc ccataccatc agtacaaatt   4800
gctactaaaa acatcctcct ttgcaagtgt atttacgacg gtatcgatgt atgtgagcat   4860
gtgtcctcta acagcacagg ccttttgcca cctagctgtc caggggtgcc ttaaaatggc   4920
aaacaaggtt tgttttcttt tcctgttttc atgccttcct cttccatatc cttgtttcat   4980
attaatacat gtgtatagat cctaaaaatc tatacacatg tattaataaa gcctgattct   5040
gccgcttcta ggtatagagg ccacctgcaa gataaatatt tgattcacaa taactaatca   5100
ttctatggca attgataaca acaaatatat atatatatat atatatacgt atatgtgtat   5160
atatatatat atattcagga aataatatat tctagaatat gtcacattct gtctcaggca   5220
tccattttct ttatgatgcc gtttgaggtg gagttttagt caggtggtca gcttctcctt   5280
tttttgcca tctgccctgt aagcatcctg ctggggaccc agataggagt catcactcta    5340
ggctgagaac atctgggcac acaccctaag cctcagcatg actcatcatg actcagcatt   5400
gctgtgcttg agccagaagg tttgcttaga aggttacaca gaaccagaag gcgggggtgg   5460
ggcactgacc ccgacagggg cctggccaga actgctcatg cttggactat gggaggtcac   5520
taatggagac acacagaaat gtaacaggaa ctaagggaat tccggtgccc tgcttaggag   5580
cttaatcttt aatgaaagct aagctttcat taaaaaaagt ctaaccagct gcattcgact   5640
ttgactgcag cagctggtta gaaggttcta ctggaggagg gtcccagccc attgctaaat   5700
taacatcagg ctctgagact ggcagtatat ctctaacagt ggttgatgct atcttctgga   5760
acttgcctgc tacattgaga ccactgaccc atacatagga agcccatagc tctgtcctga   5820
actgttaggc cactggtcca gagagtgtgc atctcctttg atcctcataa taaccctatg   5880
agatagacac aattattact cttactttat agatgatgat cctgaaaaca taggagtcaa   5940
ggcacttgcc cctagctggg ggtatagggg agcagtccca tgtagtagta gaatgaaaaa   6000
tgctgctatg ctgtgcctcc cccacctttc ccatgtctgc cctctactca tggtctatct   6060
ctcctggctc ctgggagtca tggactccac ccagcaccac caacctgacc taaccaccta   6120
tctgagcctg ccagcctata acccatctgg gccctgatag ctggtggcca gccctgaccc   6180
caccccaccc tccctggaac ctctgataga cacatctggc acaccagctc gcaaagtcac   6240
cgtgagggtc ttgtgtttgc tgagtcaaaa ttccttgaaa tccaagtcct tagagactcc   6300
tgctcccaaa tttacagtca tagacttctt catggctgtc tcctttatcc acagaatgat   6360
tcctttgctt cattgcccca tccatctgat cctcctcatc agtgcagcac agggcccatg   6420
agcagtagct gcagagtctc acataggtct ggcactgcct ctgacatgtc cgaccttagg   6480
caaatgcttg actcttctga gctcggatcc cttgagctca ggaggtcaag gctgcagtga   6540
```

-continued gacatgatct tgccactgca ctccagcctg gacagcagag tgaaaccttg cctcacgaaa 6600
cagaatacaa aaacaaacaa acaaaaaact gctccgcaat gcgcttcctt gatgctctac 6660
cacataggtc tgggtacttt gtacacatta tctcattgct gttcataatt gttagattaa 6720
ttttgtaata ttgatattat tcctagaaag ctgaggcctc aagatgataa cttttatttt 6780
ctggacttgt aatagctttc tcttgtattc accatgttgt aactttctta gagtagtaac 6840
aatataaagt tattgtgagt ttttgcaaac acagcaaaca caacgaccca tatagacatt 6900
gatgtgaaat tgtctattgt caatttatgg gaaaacaagt atgtactttt tctactaagc 6960
cattgaaaca ggaataacag aacaagattg aaagaataca ttttccgaaa ttacttgagt 7020
attatacaaa gacaagcacg tggacctggg aggagggtta ttgtccatga ctggtgtgtg 7080
gagacaaatg caggtttata atagatggga tggcatctag cgcaatgact ttgccatcac 7140
ttttagagag ctcttggggg ccccagtaca caagaggga cgcagggtat atgtagacat 7200
ctcattcttt ttcttagtgt gagaataaga atagccatga cctgagttta tagacaatga 7260
gcccttttct ctctcccact cagcagctat gagatggctt gccctgcctc tctactaggc 7320
tgactcactc caaggcccag caatgggcag ggctctgtca gggctttgat agcactatct 7380
gcagagccag ggccgagaag gggtggactc cagagactct ccctcccatt cccgagcagg 7440
gtttgcttat ttatgcattt aaatgatata tttattttaa aagaaataac aggagactgc 7500
ccagccctgg ctgtgacatg gaaactatgt agaatatttt gggttccatt ttttttttcct 7560
tctttcagtt agaggaaaag gggctcactg cacatacact agacagaaag tcaggagctt 7620
tgaatccaag cctgatcatt tccatgtcat actgagaaag tccccaccct tctctgagcc 7680
tcagtttctc tttttataag taggagtctg gagtaaatga tttccaatgg ctctcatttc 7740
aatacaaaat ttccgtttat taaatgcatg agcttccgtt actccaagac tgagaaggaa 7800
attgaacctg agactcattg actggcaaga tgtccccaga ggctctcatt cagcaataaa 7860
attctcacct tcacccaggc ccactagtgt cagatttgca tgcgttaacg cggccgcatc 7920
gatgccgtag tacctttaag accaatgact tacaaggcag ctgtagatct tagccacttt 7980
ttaaaagaaa aggggggact ggaagggcta attcactccc aaagaagaca agatccctgc 8040
aggcattcaa ggccaggctg gatgtggctc tgggcagcct gggctgctgg ttgatgaccc 8100
tgcacatagc agggggttgg atctggatga gcactgtgct cctttgcaac ccaggccgtt 8160
ctatgattct gtcattctaa atctctcttt cagcctaaag ctttttcccc gtatcccccc 8220
aggtgtctgc aggctcaaag agcagcgaga agcgttcaga ggaaagcgat cccgtgccac 8280
cttccccgtg cccgggctgt ccccgcacgc tgccggctcg gggatgcggg gggagcgccg 8340
gaccggagcg gagccccggg cggctcgctg ctgcccccta gcgggggagg gacgtaatta 8400
catccctggg ggctttgggg gggggctgtc cccgtgagct ccccagatct gctttttgcc 8460
tgtactgggt ctctctggtt agaccagatc tgagcctggg agctctctgg ctaactaggg 8520
aacccactgc ttaagcctca ataaagcttc agctgctcga gctagcagat ctttttccct 8580
ctgccaaaaa ttatggggac atcatgaagc cccttgagca tctgacttct ggctaataaa 8640
ggaaatttat tttcattgca atagtgtgtt ggaatttttt gtgtctctca ctcggaagga 8700
catatgggag ggcaaatcat ttaaaacatc agaatgagta tttggtttag agtttggcaa 8760
catatgccca tatgctggct gccatgaaca aaggttggct ataaagaggt catcagtata 8820
tgaaacagcc ccctgctgtc cattccttat tccatagaaa agccttgact tgaggttaga 8880
ttttttttat attttgtttt gtgttatttt tttctttaac atccctaaaa ttttccttac 8940
atgttttact agccagattt ttcctcctct cctgactact cccagtcata gctgtccctc 9000
ttctcttatg gagatccctc gacctgcagc ccaagcttgg cgtaatcatg gtcatagctg 9060
tttcctgtgt gaaattgtta tccgctcaca attccacaca acatacgagc cggaagcata 9120
aagtgtaaag cctggggtgc ctaatgagtg agctaactca cattaattgc gttgcgctca 9180
ctgcccgctt tccagtcggg aaacctgtcg tgccagcgga tccgcatctc aattagtcag 9240
caaccatagt cccgccccta actccgccca tcccgcccct aactccgccc agttccgccc 9300
attctccgcc ccatggctga ctaatttttt ttatttatgc agaggccgag gccgcctcgg 9360
cctctgagct attccagaag tagtgaggag gcttttttgg aggcctaggc ttttgcaaaa 9420
agctgtcgac tgcagaggcc tgcatgcaag cttggcgtaa tcatggtcat agctgtttcc 9480
tgtgtgaaat tgttatccgc tcacaattcc acacaacata cgagccggaa gcataaagtg 9540
taaagcctgg ggtgcctaat gagtgagcta actcacatta attgcgttgc gctcactgcc 9600
cgctttccag tcgggaaacc tgtcgtgcca gctgcattaa tgaatcggcc aacgcgcggg 9660
gagaggcggt ttgcgtattg ggcgctcttc cgcttcctcg ctcactgact cgctgcgctc 9720
ggtcgttcgg ctgcggcgag cggtatcagc tcactcaaag gcggtaatac ggttatccac 9780
agaatcaggg gataacgcag gaaagaacat gtgagcaaaa ggccagcaaa aggccaggaa 9840
ccgtaaaaag gccgcgttgc tggcgttttt ccataggctc cgcccccctg acgagcatca 9900
caaaaatcga cgctcaagtc agaggtggcg aaacccgaca ggactataaa gataccaggc 9960
gtttccccct ggaagctccc tcgtgcgctc tcctgttccg accctgccgc ttaccggata 10020
cctgtccgcc tttctccctt cgggaagcgt ggcgctttct catagctcac gctgtaggta 10080
tctcagttcg gtgtaggtcg ttcgctccaa gctgggctgt gtgcacgaac cccccgttca 10140
gcccgaccgc tgcgccttat ccggtaacta tcgtcttgag tccaacccgg taagacacga 10200
cttatcgcca ctggcagcag ccactggtaa caggattagc agagcgaggt atgtaggcgg 10260
tgctacagag ttcttgaagt ggtggcctaa ctacggctac actagaagaa cagtatttgg 10320
tatctgcgct ctgctgaagc cagttacctt cggaaaaaga gttggtagct cttgatccgg 10380
caaacaaacc accgctggta gcggtggttt ttttgtttgc aagcagcaga ttacgcgcag 10440
aaaaaaagga tctcaagaag atcctttgat cttttctacg gggtctgacg ctcagtggaa 10500
cgaaaactca cgttaaggga ttttggtcat gagattatca aaaaggatct tcacctagat 10560
ccttttaaat taaaaatgaa gttttaaatc aatctaaagt atatatgagt aaacttggtc 10620
tgacagttac caatgcttaa tcagtgaggc acctatctca gcgatctgtc tatttcgttc 10680
atccatagtt gcctgactcc ccgtcgtgta gataactacg atacgggagg gcttaccatc 10740
tggccccagt gctgcaatga taccgcgaga cccacgctca ccggctccag atttatcagc 10800
aataaaccag ccagccggaa gggccgagcg cagaagtggt cctgcaactt tatccgcctc 10860
catccagtct attaattgtt gccgggaagc tagagtaagt agttcgccag ttaatagttt 10920
gcgcaacgtt gttgccattg ctacaggcat cgtggtgtca cgctcgtcgt ttggtatggc 10980
ttcattcagc tccggttccc aacgatcaag gcgagttaca tgatccccca tgttgtgcaa 11040
aaaagcggtt agctccttcg gtcctccgat cgttgtcaga agtaagttgg ccgcagtgtt 11100
atcactcatg gttatggcag cactgcataa ttctcttact gtcatgccat ccgtaagatg 11160
cttttctgtg actggtgagt actcaaccaa gtcattctga gaatagtgta tgcggcgacc 11220
gagttgctct tgcccggcgt caatacggga taataccgcg ccacatagca gaactttaaa 11280

```
agtgctcatc attggaaaac gttcttcggg gcgaaaactc tcaaggatct taccgctgtt  11340
gagatccagt tcgatgtaac ccactcgtgc acccaactga tcttcagcat cttttacttt  11400
caccagcgtt tctgggtgag caaaaacagg aaggcaaaat gccgcaaaaa agggaataag  11460
ggcgacacgg aaatgttgaa tactcatact cttccttttt caatattatt gaagcattta  11520
tcagggttat tgtctcatga gcggatacat atttgaatgt atttagaaaa ataaacaaat  11580
aggggttccg cgcacatttc cccgaaaagt gccacctgac gtctaagaaa ccattattat  11640
catgacatta acctataaaa ataggcgtat cacgaggccc tttcgtctcg cgcgtttcgg  11700
tgatgacggt gaaaacctct gacacatgca gctcccggag acggtcacag cttgtctgta  11760
agcggatgcc gggagcagac aagcccgtca gggcgcgtca gcgggtgttg gcgggtgtcg  11820
gggctggctt aactatgcgg catcagagca gattgtactg agagtgcacc atatgcggtg  11880
tgaaataccg cacagatgcg taaggagaaa ataccgcatc aggcgccatt cgccattcag  11940
gctgcgcaac tgttgggaag ggcgatcggt gcgggcctct tcgctattac gccagctggc  12000
gaaaggggga tgtgctgcaa ggcgattaag ttgggtaacg ccagggtttt cccagtcacg  12060
acgttgtaaa acgacggcca gtgaattc                                     12088
```

```
<210> SEQ ID NO 8
<211> LENGTH: 12091
<212> TYPE: DNA
<213> ORGANISM: Artificial Sequence
<220> FEATURE:
<223> OTHER INFORMATION: Synthetic: TL20c-r7SK/sh734-rGbGM

<400> SEQUENCE: 8

ggccgcctcg gccaaacagc ccttgagttt accactccct atcagtgata gagaaaagtg     60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgctttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
```

```
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgca caaaaaagga   2400
tatgcccttg actatgtcgg acaaatagtc aagggcatat cctgaggtac ccaggcggcg   2460
cacaagctat ataaacctga aggaaatctc aactttacac ttaggtcaag ttacttatcg   2520
tactagagct tcagcaggaa atttaactaa aatctaattt aaccagcata gcaaatatca   2580
tttattccca aaatgctaaa gtttgagata aacggacttg atttccggct gttttgacac   2640
tatccagaat gccttgcaga tgggtggggc atgctaaata ctgcacgtcg atacgcgtgg   2700
ggatcctcta gagtcgagct cgcgaggatc atcaccggtg ctagccggag ccagaagcac   2760
cataagggac atgataaggg agccagcaga cctctgatct cttcctgaat gctaatctta   2820
aacatcctga ggaagaatgg gacttccatt tggggtgggc ctatgatagg gtaataagac   2880
agtagtgaat atcaagctac aaaaagcccc ctttcaaatt cttctcagtc ctaacttttc   2940
atactaagcc cagtccttcc aaagcagact gtgaaagagt gatagttccg ggagactagc   3000
accggctagc cgagcttgga acactttccc ttcattaaga accatccttg ctactcagct   3060
gcaatcaatc cagcccccag gtcttcactg aaccttttcc catctcttcc aaaacatctg   3120
tttctgagaa gtcctgtcct atagaggtct ttcttcccac cggatttctc ctacaccatt   3180
tactcccact tgcagaactc ccgtgtacaa gtgtctttac tgcttttatt tgctcaacaa   3240
aatgcacatc tcatataaaa ataaatgagg agcatgcaca caccacaaac acaaacaggc   3300
atgcagaaat acacatacac acttccctca atataaaccc tttgtggctc atatatttaa   3360
aaagatgtaa aaaaaagagc tgaagaaaat catgtgtgat ctctcagcag aatagattta   3420
ttatttgtat tgcttgcaga ataaagccta tccttgaaag ctctgaatca tgggcaagag   3480
gctcagtggt atctggagga cagggcactg gccactgcag tcaccatctt ctgccaggaa   3540
gcctgcacct caggggtgaa ttctttgcca aagtgaatgg ccagcacggt gaccagcacg   3600
```

```
ttgcccagga gctgtgggag gaagataaga ggtatgaaca tgattagcaa aagggcctag   3660
cttggactca gaataatcca gccttatccc aaccataaaa taaaagcaga atggtagctg   3720
gattgtagct gctattagca atatgaaacc tcttacatca gttacaattt atatgcagaa   3780
atatttatat gcagaaatat tgctattgcc ttaacccaga aattatcact gttattcttt   3840
agaatggtgc aaagaggcat gatacattgt atcattattg ccctgaaaga aagagattag   3900
ggaaagtatt agaaataaga taaacaaaaa agtatattaa aagaagaaag catttttttaa   3960
aattacaaat gcaaaattac cctgatttgg tcaatatgtg taccctgtta cttctcccct   4020
tcctatgaca tgaacttaac catagaaaag aaggggaaag aaaacatcaa gggtcccata   4080
gactcacctt gaagttctca ggatccacat gcagcttgtc acagtgcagt tcactcagct   4140
gggcaaaggt gcccttgaga tcatccaggt gctttatggc atctcccaag gaagtcagca   4200
ccttcttgcc atgtgccttg actttggggt tgcccatgat ggcagaggca gaggacaggt   4260
tgccaaagct gtcaaagaac ctctgggtcc atgggtagac aaccaggagc ctgtgagatt   4320
gacaagaaca gtttgacagt cagaaggtgc cacaaatcct gagaagcaac ctggactttt   4380
gccaggcaca gggtccttcc ttccctccct tgtcctggtc accagagcct accttcccag   4440
ggtttctcct ccagcatctt ccacattcac cttgtcccac aggcttgtga tagtagcctt   4500
gtcctcctct gtgaaatgac ccatggtgtc tgtttgaggt tgctagtgaa cacagttgtg   4560
tcagaagcaa atgtaagcaa tagatggctc tgccctgact tttatgccca gccctggctc   4620
ctgccctccc tgctcctggg agtagattgg ccaaccctag ggtgtggctc cacagggtga   4680
ggtctaagtg atgacagccg tacctgtcct tggctcttct ggcactggct taggagttgg   4740
acttcaaacc ctcagccctc cctctaagat atatctcttg gccccatacc atcagtacaa   4800
attgctacta aaaacatcct cctttgcaag tgtatttacg acggtatcga tgtatgtgag   4860
catgtgtcct ctaacagcac aggccttttg ccacctagct gtccaggggt gccttaaaat   4920
ggcaaacaag gtttgttttc ttttcctgtt ttcatgcctt cctcttccat atccttgttt   4980
catattaata catgtgtata gatcctaaaa atctatacac atgtattaat aaagcctgat   5040
tctgccgctt ctaggtatag aggccacctg caagataaat atttgattca caataactaa   5100
tcattctatg gcaattgata acaacaaata tatatatata tatatatata cgtatatgtg   5160
tatatatata tatatattca ggaaataata tattctagaa tatgtcacat tctgtctcag   5220
gcatccattt tctttatgat gccgtttgag gtggagtttt agtcaggtgg tcagcttctc   5280
cttttttttg ccatctgccc tgtaagcatc ctgctgggga cccagatagg agtcatcact   5340
ctaggctgag aacatctggg cacacaccct aagcctcagc atgactcatc atgactcagc   5400
attgctgtgc ttgagccaga aggtttgctt agaaggttac acagaaccag aaggcggggg   5460
tggggcactg accccgacag gggcctggcc agaactgctc atgcttggac tatgggaggt   5520
cactaatgga gacacacaga aatgtaacag gaactaaggg aattccggtg ccctgcttag   5580
gagcttaatc tttaatgaaa gctaagcttt cattaaaaaa agtctaacca gctgcattcg   5640
actttgactg cagcagctgg ttagaaggtt ctactggagg agggtcccag cccattgcta   5700
aattaacatc aggctctgag actggcagta tatctctaac agtggttgat gctatcttct   5760
ggaacttgcc tgctacattg agaccactga cccatacata ggaagcccat agctctgtcc   5820
tgaactgtta ggccactggt ccagagagtg tgcatctcct ttgatcctca taataaccct   5880
atgagataga cacaattatt actcttactt tatagatgat gatcctgaaa acataggagt   5940
caaggcactt gcccctagct gggggtatag gggagcagtc ccatgtagta gtagaatgaa   6000
```

aaatgctgct atgctgtgcc tcccccacct ttcccatgtc tgccctctac tcatggtcta 6060
tctctcctgg ctcctgggag tcatggactc cacccagcac caccaacctg acctaaccac 6120
ctatctgagc ctgccagcct ataacccatc tgggccctga tagctggtgg ccagccctga 6180
ccccacccca ccctccctgg aacctctgat agacacatct ggcacaccag ctcgcaaagt 6240
caccgtgagg gtcttgtgtt tgctgagtca aaattccttg aaatccaagt ccttagagac 6300
tcctgctccc aaatttacag tcatagactt cttcatggct gtctccttta tccacagaat 6360
gattcctttg cttcattgcc ccatccatct gatcctcctc atcagtgcag cacagggccc 6420
atgagcagta gctgcagagt ctcacatagg tctggcactg cctctgacat gtccgacctt 6480
aggcaaatgc ttgactcttc tgagctcgga tcccttgagc tcaggaggtc aaggctgcag 6540
tgagacatga tcttgccact gcactccagc ctggacagca gagtgaaacc ttgcctcacg 6600
aaacagaata caaaaacaaa caaacaaaaa actgctccgc aatgcgcttc cttgatgctc 6660
taccacatag gtctgggtac tttgtacaca ttatctcatt gctgttcata attgttagat 6720
taattttgta atattgatat tattcctaga aagctgaggc ctcaagatga taacttttat 6780
tttctggact tgtaatagct ttctcttgta ttcaccatgt tgtaactttc ttagagtagt 6840
aacaatataa agttattgtg agtttttgca aacacagcaa acacaacgac ccatatagac 6900
attgatgtga aattgtctat tgtcaattta tgggaaaaca agtatgtact ttttctacta 6960
agccattgaa acaggaataa cagaacaaga ttgaaagaat acattttccg aaattacttg 7020
agtattatac aaagacaagc acgtggacct gggaggaggg ttattgtcca tgactggtgt 7080
gtggagacaa atgcaggttt ataatagatg ggatggcatc tagcgcaatg actttgccat 7140
cacttttaga gagctcttgg gggccccagt acacaagagg ggacgcaggg tatatgtaga 7200
catctcattc tttttcttag tgtgagaata agaatagcca tgacctgagt ttatagacaa 7260
tgagcccttt tctctctccc actcagcagc tatgagatgg cttgccctgc ctctctacta 7320
ggctgactca ctccaaggcc cagcaatggg cagggctctg tcagggcttt gatagcacta 7380
tctgcagagc cagggccgag aaggggtgga ctccagagac tctccctccc attcccgagc 7440
agggtttgct tatttatgca tttaaatgat atatttattt taaaagaaat aacaggagac 7500
tgcccagccc tggctgtgac atggaaacta tgtagaatat tttgggttcc attttttttt 7560
ccttctttca gttagaggaa aaggggctca ctgcacatac actagacaga aagtcaggag 7620
ctttgaatcc aagcctgatc atttccatgt catactgaga aagtccccac ccttctctga 7680
gcctcagttt ctctttttat aagtaggagt ctggagtaaa tgatttccaa tggctctcat 7740
ttcaatacaa aatttccgtt tattaaatgc atgagcttcc gttactccaa gactgagaag 7800
gaaattgaac ctgagactca ttgactggca agatgtcccc agaggctctc attcagcaat 7860
aaaattctca ccttcaccca ggcccactag tgtcagattt gcatgcgtta acgcggccgc 7920
atcgatgccg tagtaccttt aagaccaatg acttacaagg cagctgtaga tcttagccac 7980
tttttaaaag aaaagggggg actggaaggg ctaattcact cccaaagaag acaagatccc 8040
tgcaggcatt caaggccagg ctggatgtgg ctctgggcag cctgggctgc tggttgatga 8100
ccctgcacat agcagggggt tggatctgga tgagcactgt gctcctttgc aacccaggcc 8160
gttctatgat tctgtcattc taaatctctc tttcagccta aagctttttc cccgtatccc 8220
cccaggtgtc tgcaggctca aagagcagcg agaagcgttc agaggaaagc gatcccgtgc 8280
caccttcccc gtgcccgggc tgtccccgca cgctgccggc tcggggatgc ggggggagcg 8340

-continued

```
ccggaccgga gcggagcccc gggcggctcg ctgctgcccc ctagcggggg agggacgtaa   8400
ttacatccct gggggctttg gggggggggct gtccccgtga gctccccaga tctgcttttt   8460
gcctgtactg ggtctctctg gttagaccag atctgagcct gggagctctc tggctaacta   8520
gggaacccac tgcttaagcc tcaataaagc ttcagctgct cgagctagca gatctttttc   8580
cctctgccaa aaattatggg gacatcatga agccccttga gcatctgact tctggctaat   8640
aaaggaaatt tattttcatt gcaatagtgt gttggaattt tttgtgtctc tcactcggaa   8700
ggacatatgg gagggcaaat catttaaaac atcagaatga gtatttggtt tagagtttgg   8760
caacatatgc ccatatgctg gctgccatga acaaaggttg gctataaaga ggtcatcagt   8820
atatgaaaca gccccctgct gtccattcct tattccatag aaaagccttg acttgaggtt   8880
agattttttt tatattttgt tttgtgttat ttttttcttt aacatcccta aaattttcct   8940
tacatgtttt actagccaga tttttcctcc tctcctgact actcccagtc atagctgtcc   9000
ctcttctctt atggagatcc ctcgacctgc agcccaagct tggcgtaatc atggtcatag   9060
ctgtttcctg tgtgaaattg ttatccgctc acaattccac acaacatacg agccggaagc   9120
ataaagtgta aagcctgggg tgcctaatga gtgagctaac tcacattaat tgcgttgcgc   9180
tcactgcccg ctttccagtc gggaaacctg tcgtgccagc ggatccgcat ctcaattagt   9240
cagcaaccat agtcccgccc ctaactccgc ccatcccgcc cctaactccg cccagttccg   9300
cccattctcc gccccatggc tgactaattt tttttattta tgcagaggcc gaggccgcct   9360
cggcctctga gctattccag aagtagtgag gaggcttttt tggaggccta ggcttttgca   9420
aaaagctgtc gactgcagag gcctgcatgc aagcttggcg taatcatggt catagctgtt   9480
tcctgtgtga aattgttatc cgctcacaat tccacacaac atacgagccg gaagcataaa   9540
gtgtaaagcc tggggtgcct aatgagtgag ctaactcaca ttaattgcgt tgcgctcact   9600
gcccgctttc cagtcgggaa acctgtcgtg ccagctgcat taatgaatcg gccaacgcgc   9660
ggggagaggc ggtttgcgta ttgggcgctc ttccgcttcc tcgctcactg actcgctgcg   9720
ctcggtcgtt cggctgcggc gagcggtatc agctcactca aaggcggtaa tacggttatc   9780
cacagaatca ggggataacg caggaaagaa catgtgagca aaaggccagc aaaaggccag   9840
gaaccgtaaa aaggccgcgt tgctggcgtt tttccatagg ctccgccccc ctgacgagca   9900
tcacaaaaat cgacgctcaa gtcagaggtg gcgaaacccg acaggactat aaagatacca   9960
ggcgtttccc cctggaagct ccctcgtgcg ctctcctgtt ccgaccctgc cgcttaccgg  10020
atacctgtcc gcctttctcc cttcgggaag cgtggcgctt tctcatagct cacgctgtag  10080
gtatctcagt tcggtgtagg tcgttcgctc caagctgggc tgtgtgcacg aaccccccgt  10140
tcagcccgac cgctgcgcct tatccggtaa ctatcgtctt gagtccaacc cggtaagaca  10200
cgacttatcg ccactggcag cagccactgg taacaggatt agcagagcga ggtatgtagg  10260
cggtgctaca gagttcttga agtggtggcc taactacggc tacactagaa gaacagtatt  10320
tggtatctgc gctctgctga agccagttac cttcggaaaa agagttggta gctcttgatc  10380
cggcaaacaa accaccgctg gtagcggtgg tttttttgtt tgcaagcagc agattacgcg  10440
cagaaaaaaa ggatctcaag aagatccttt gatcttttct acggggtctg acgctcagtg  10500
gaacgaaaac tcacgttaag ggattttggt catgagatta tcaaaaagga tcttcaccta  10560
gatcctttta aattaaaaat gaagttttaa atcaatctaa agtatatatg agtaaacttg  10620
gtctgacagt taccaatgct taatcagtga ggcacctatc tcagcgatct gtctatttcg  10680
ttcatccata gttgcctgac tccccgtcgt gtagataact acgatacggg agggcttacc  10740
```

atctggcccc agtgctgcaa tgataccgcg agacccacgc tcaccggctc cagatttatc 10800
agcaataaac cagccagccg gaagggccga gcgcagaagt ggtcctgcaa ctttatccgc 10860
ctccatccag tctattaatt gttgccggga agctagagta agtagttcgc cagttaatag 10920
tttgcgcaac gttgttgcca ttgctacagg catcgtggtg tcacgctcgt cgtttggtat 10980
ggcttcattc agctccggtt cccaacgatc aaggcgagtt acatgatccc ccatgttgtg 11040
caaaaaagcg gttagctcct tcggtcctcc gatcgttgtc agaagtaagt tggccgcagt 11100
gttatcactc atggttatgg cagcactgca taattctctt actgtcatgc catccgtaag 11160
atgcttttct gtgactggtg agtactcaac caagtcattc tgagaatagt gtatgcggcg 11220
accgagttgc tcttgcccgg cgtcaatacg ggataatacc gcgccacata gcagaacttt 11280
aaaagtgctc atcattggaa aacgttcttc ggggcgaaaa ctctcaagga tcttaccgct 11340
gttgagatcc agttcgatgt aacccactcg tgcacccaac tgatcttcag catcttttac 11400
tttcaccagc gtttctgggt gagcaaaaac aggaaggcaa aatgccgcaa aaaagggaat 11460
aagggcgaca cggaaatgtt gaatactcat actcttcctt tttcaatatt attgaagcat 11520
ttatcagggt tattgtctca tgagcggata catatttgaa tgtatttaga aaaataaaca 11580
aataggggtt ccgcgcacat ttccccgaaa agtgccacct gacgtctaag aaaccattat 11640
tatcatgaca ttaacctata aaaataggcg tatcacgagg ccctttcgtc tcgcgcgttt 11700
cggtgatgac ggtgaaaacc tctgacacat gcagctcccg gagacggtca cagcttgtct 11760
gtaagcggat gccgggagca gacaagcccg tcagggcgcg tcagcgggtg ttggcgggtg 11820
tcggggctgg cttaactatg cggcatcaga gcagattgta ctgagagtgc accatatgcg 11880
gtgtgaaata ccgcacagat gcgtaaggag aaaataccgc atcaggcgcc attcgccatt 11940
caggctgcgc aactgttggg aagggcgatc ggtgcgggcc tcttcgctat tacgccagct 12000
ggcgaaaggg ggatgtgctg caaggcgatt aagttgggta acgccagggt tttcccagtc 12060
acgacgttgt aaaacgacgg ccagtgaatt c 12091

<210> SEQ ID NO 9
<211> LENGTH: 12081
<212> TYPE: DNA
<213> ORGANISM: Artificial Sequence
<220> FEATURE:
<223> OTHER INFORMATION: Synthetic: TL20c-rGbGM-7SKM1/sh734

<400> SEQUENCE: 9
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660

```
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggacccgagct caagcttcga acgcgtgggg atcctctaga   2400
gtcgagctcg cgaggatcat caccggtgct agccggagcc agaagcacca taagggacat   2460
gataagggag ccagcagacc tctgatctct tcctgaatgc taatcttaaa catcctgagg   2520
aagaatggga cttccatttg ggtgggcct atgatagggt aataagacag tagtgaatat   2580
caagctacaa aaagcccccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
```

```
aaaagagctg aagaaaatca tgtgtgatct ctcagcagaa tagatttatt atttgtattg   3120
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca ttttttaaaa ttacaaatgc   3660
aaaattaccc tgatttggtc aatatgtgta ccctgttact tctccccttc ctatgacatg   3720
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
```

-continued

```
gctctgagac tggcagtata tctctaacag tggttgatgc tatcttctgg aacttgcctg   5460
ctacattgag accactgacc catacatagg aagcccatag ctctgtcctg aactgttagg   5520
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
aggaataaca gaacaagatt gaaagaatac attttccgaa attacttgag tattatacaa   6720
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agccctttc    6960
tctctcccac tcagcagcta tgagatggct tgccctgcct ctctactagg ctgactcact   7020
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
gctgtgacat ggaaactatg tagaatattt tgggttccat ttttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gttcgacgtg cagtcgggct   7620
actgccccac ccatagtacc ggcattctgg atagtgtcaa aacagccgga aatcaagtcc   7680
gtttatctca aactttagca ttttgggaat aaatgatatt tgctatgctg gttaaattag   7740
attttagtta aatttcctgc tgaagctcta gtacgataag taacttgacc taagtgtaaa   7800
```

gttgagattt ccttcaggtt tatatagctt gtgcgccgcc tgggtacctc aggatatgcc 7860
cttgactatt tgtccgacat agtcaagggc atatcctttt ttgcggccgc atcgatgccg 7920
tagtaccttt aagaccaatg acttacaagg cagctgtaga tcttagccac tttttaaaag 7980
aaaagggggg actggaaggg ctaattcact cccaaagaag acaagatccc tgcaggcatt 8040
caaggccagg ctggatgtgg ctctgggcag cctgggctgc tggttgatga ccctgcacat 8100
agcagggggt tggatctgga tgagcactgt gctcctttgc aacccaggcc gttctatgat 8160
tctgtcattc taaatctctc tttcagccta aagctttttc cccgtatccc cccaggtgtc 8220
tgcaggctca aagagcagcg agaagcgttc agaggaaagc gatcccgtgc caccttcccc 8280
gtgcccgggc tgtccccgca cgctgccggc tcggggatgc ggggggagcg ccggaccgga 8340
gcggagcccc gggcggctcg ctgctgcccc ctagcggggg agggacgtaa ttacatccct 8400
gggggctttg gggggggggct gtccccgtga gctccccaga tctgcttttt gcctgtactg 8460
ggtctctctg gttagaccag atctgagcct gggagctctc tggctaacta gggaacccac 8520
tgcttaagcc tcaataaagc ttcagctgct cgagctagca gatctttttc cctctgccaa 8580
aaattatggg gacatcatga agccccttga gcatctgact tctggctaat aaaggaaatt 8640
tattttcatt gcaatagtgt gttggaattt tttgtgtctc tcactcggaa ggacatatgg 8700
gagggcaaat catttaaaac atcagaatga gtatttggtt tagagtttgg caacatatgc 8760
ccatatgctg gctgccatga acaaaggttg gctataaaga ggtcatcagt atatgaaaca 8820
gccccctgct gtccattcct tattccatag aaaagccttg acttgaggtt agattttttt 8880
tatattttgt tttgtgttat ttttttcttt aacatcccta aaattttcct tacatgtttt 8940
actagccaga tttttcctcc tctcctgact actcccagtc atagctgtcc ctcttctctt 9000
atggagatcc ctcgacctgc agcccaagct tggcgtaatc atggtcatag ctgtttcctg 9060
tgtgaaattg ttatccgctc acaattccac acaacatacg agccggaagc ataaagtgta 9120
aagcctgggg tgcctaatga gtgagctaac tcacattaat tgcgttgcgc tcactgcccg 9180
ctttccagtc gggaaacctg tcgtgccagc ggatccgcat ctcaattagt cagcaaccat 9240
agtcccgccc ctaactccgc ccatcccgcc cctaactccg cccagttccg cccattctcc 9300
gccccatggc tgactaattt ttttatttta tgcagaggcc gaggccgcct cggcctctga 9360
gctattccag aagtagtgag gaggcttttt tggaggccta ggcttttgca aaaagctgtc 9420
gactgcagag gcctgcatgc aagcttggcg taatcatggt catagctgtt tcctgtgtga 9480
aattgttatc cgctcacaat tccacacaac atacgagccg gaagcataaa gtgtaaagcc 9540
tggggtgcct aatgagtgag ctaactcaca ttaattgcgt tgcgctcact gcccgctttc 9600
cagtcgggaa acctgtcgtg ccagctgcat taatgaatcg gccaacgcgc ggggagaggc 9660
ggtttgcgta ttgggcgctc ttccgcttcc tcgctcactg actcgctgcg ctcggtcgtt 9720
cggctgcggc gagcggtatc agctcactca aaggcggtaa tacggttatc cacagaatca 9780
ggggataacg caggaaagaa catgtgagca aaaggccagc aaaaggccag gaaccgtaaa 9840
aaggccgcgt tgctggcgtt tttccatagg ctccgccccc ctgacgagca tcacaaaaat 9900
cgacgctcaa gtcagaggtg gcgaaacccg acaggactat aaagatacca ggcgtttccc 9960
cctggaagct ccctcgtgcg ctctcctgtt ccgaccctgc cgcttaccgg atacctgtcc 10020
gcctttctcc cttcgggaag cgtggcgctt tctcatagct cacgctgtag gtatctcagt 10080
tcggtgtagg tcgttcgctc caagctgggc tgtgtgcacg aaccccccgt tcagcccgac 10140
cgctgcgcct tatccggtaa ctatcgtctt gagtccaacc cggtaagaca cgacttatcg 10200
ccactggcag cagccactgg taacaggatt agcagagcga ggtatgtagg cggtgctaca 10260
gagttcttga agtggtggcc taactacggc tacactagaa gaacagtatt tggtatctgc 10320
gctctgctga agccagttac cttcggaaaa agagttggta gctcttgatc cggcaaacaa 10380
accaccgctg gtagcggtgg tttttttgtt tgcaagcagc agattacgcg cagaaaaaaa 10440
ggatctcaag aagatccttt gatcttttct acggggtctg acgctcagtg gaacgaaaac 10500
tcacgttaag ggattttggt catgagatta tcaaaaagga tcttcaccta gatcctttta 10560
aattaaaaat gaagttttaa atcaatctaa agtatatatg agtaaacttg gtctgacagt 10620
taccaatgct taatcagtga ggcacctatc tcagcgatct gtctatttcg ttcatccata 10680
gttgcctgac tccccgtcgt gtagataact acgatacggg agggcttacc atctggcccc 10740
agtgctgcaa tgataccgcg agacccacgc tcaccggctc cagatttatc agcaataaac 10800
cagccagccg gaagggccga gcgcagaagt ggtcctgcaa ctttatccgc ctccatccag 10860
tctattaatt gttgccggga agctagagta agtagttcgc cagttaatag tttgcgcaac 10920
gttgttgcca ttgctacagg catcgtggtg tcacgctcgt cgtttggtat ggcttcattc 10980
agctccggtt cccaacgatc aaggcgagtt acatgatccc ccatgttgtg caaaaaagcg 11040
gttagctcct tcggtcctcc gatcgttgtc agaagtaagt tggccgcagt gttatcactc 11100
atggttatgg cagcactgca taattctctt actgtcatgc catccgtaag atgcttttct 11160
gtgactggtg agtactcaac caagtcattc tgagaatagt gtatgcggcg accgagttgc 11220
tcttgcccgg cgtcaatacg ggataatacc gcgccacata gcagaacttt aaaagtgctc 11280
atcattggaa aacgttcttc ggggcgaaaa ctctcaagga tcttaccgct gttgagatcc 11340
agttcgatgt aacccactcg tgcacccaac tgatcttcag catcttttac tttcaccagc 11400
gtttctgggt gagcaaaaac aggaaggcaa aatgccgcaa aaaagggaat aagggcgaca 11460
cggaaatgtt gaatactcat actcttcctt tttcaatatt attgaagcat ttatcagggt 11520
tattgtctca tgagcggata catatttgaa tgtatttaga aaaataaaca aataggggtt 11580
ccgcgcacat ttccccgaaa agtgccacct gacgtctaag aaaccattat tatcatgaca 11640
ttaacctata aaaataggcg tatcacgagg ccctttcgtc tcgcgcgttt cggtgatgac 11700
ggtgaaaacc tctgacacat gcagctcccg gagacggtca cagcttgtct gtaagcggat 11760
gccgggagca gacaagcccg tcagggcgcg tcagcgggtg ttggcgggtg tcggggctgg 11820
cttaactatg cggcatcaga gcagattgta ctgagagtgc accatatgcg gtgtgaaata 11880
ccgcacagat gcgtaaggag aaaataccgc atcaggcgcc attcgccatt caggctgcgc 11940
aactgttggg aagggcgatc ggtgcgggcc tcttcgctat tacgccagct ggcgaaaggg 12000
ggatgtgctg caaggcgatt aagttgggta acgccagggt tttcccagtc acgacgttgt 12060
aaaacgacgg ccagtgaatt c 12081

<210> SEQ ID NO 10
<211> LENGTH: 12084
<212> TYPE: DNA
<213> ORGANISM: Artificial Sequence
<220> FEATURE:
<223> OTHER INFORMATION: Synthetic: TL20c-rGbGM-7SK/sh734

<400> SEQUENCE: 10
ggccgcctcg gccaaacagc ccttgagttt accactccct atcagtgata gagaaaagtg 60
aaagtcgagt ttaccactcc ctatcagtga tagagaaaag tgaaagtcga gtttaccact 120

```
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgctttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgggg atcctctaga   2400
gtcgagctcg cgaggatcat caccggtgct agccggagcc agaagcacca taagggacat   2460
```

-continued

```
gataagggag ccagcagacc tctgatctct tcctgaatgc taatcttaaa catcctgagg   2520
aagaatggga cttccatttg gggtgggcct atgatagggt aataagacag tagtgaatat   2580
caagctacaa aaagcccccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
aaaagagctg aagaaaatca tgtgtgatct ctcagcagaa tagatttatt atttgtattg   3120
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca tttttaaaa ttacaaatgc   3660
aaaattaccc tgatttggtc aatatgtgta ccctgttact tctccccttc ctatgacatg   3720
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
```

```
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
gctctgagac tggcagtata tctctaacag tggttgatgc tatcttctgg aacttgcctg   5460
ctacattgag accactgacc catacatagg aagcccatag ctctgtcctg aactgttagg   5520
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
aggaataaca gaacaagatt gaaagaatac attttccgaa attacttgag tattatacaa   6720
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agccctttc    6960
tctctcccac tcagcagcta tgagatggct tgccctgcct ctctactagg ctgactcact   7020
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
```

-continued

```
gctgtgacat ggaaactatg tagaatattt tgggttccat ttttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gtatcgacgt gcagtattta   7620
gcatgcccca cccatctgca aggcattctg gatagtgtca aaacagccgg aaatcaagtc   7680
cgtttatctc aaactttagc attttgggaa taaatgatat ttgctatgct ggttaaatta   7740
gattttagtt aaatttcctg ctgaagctct agtacgataa gtaacttgac ctaagtgtaa   7800
agttgagatt tccttcaggt ttatatagct tgtgcgccgc ctgggtacct caggatatgc   7860
ccttgactat ttgtccgaca tagtcaaggg catatccttt tttgtgcggc cgcatcgatg   7920
ccgtagtacc tttaagacca atgacttaca aggcagctgt agatcttagc cactttttaa   7980
aagaaaaggg gggactggaa gggctaattc actcccaaag aagacaagat ccctgcaggc   8040
attcaaggcc aggctggatg tggctctggg cagcctgggc tgctggttga tgaccctgca   8100
catagcaggg ggttggatct ggatgagcac tgtgctcctt tgcaacccag gccgttctat   8160
gattctgtca ttctaaatct ctctttcagc ctaaagcttt ttccccgtat ccccccaggt   8220
gtctgcaggc tcaaagagca gcgagaagcg ttcagaggaa agcgatcccg tgccaccttc   8280
cccgtgcccg ggctgtcccc gcacgctgcc ggctcgggga tgcgggggga gcgccggacc   8340
ggagcggagc cccgggcggc tcgctgctgc cccctagcgg gggagggacg taattacatc   8400
cctgggggct ttgggggggg gctgtccccg tgagctcccc agatctgctt tttgcctgta   8460
ctgggtctct ctggttagac cagatctgag cctgggagct ctctggctaa ctagggaacc   8520
cactgcttaa gcctcaataa agcttcagct gctcgagcta gcagatcttt ttccctctgc   8580
caaaaattat ggggacatca tgaagcccct tgagcatctg acttctggct aataaaggaa   8640
atttattttc attgcaatag tgtgttggaa ttttttgtgt ctctcactcg gaaggacata   8700
tgggagggca aatcatttaa aacatcagaa tgagtatttg gtttagagtt tggcaacata   8760
tgcccatatg ctggctgcca tgaacaaagg ttggctataa agaggtcatc agtatatgaa   8820
acagcccccct gctgtccatt ccttattcca tagaaaagcc ttgacttgag gttagatttt   8880
ttttatattt tgttttgtgt tatttttttc tttaacatcc ctaaaatttt ccttacatgt   8940
tttactagcc agatttttcc tcctctcctg actactccca gtcatagctg tccctcttct   9000
cttatggaga tccctcgacc tgcagcccaa gcttggcgta atcatggtca tagctgtttc   9060
ctgtgtgaaa ttgttatccg ctcacaattc cacacaacat acgagccgga agcataaagt   9120
gtaaagcctg gggtgcctaa tgagtgagct aactcacatt aattgcgttg cgctcactgc   9180
ccgctttcca gtcgggaaac ctgtcgtgcc agcggatccg catctcaatt agtcagcaac   9240
catagtcccg cccctaactc cgcccatccc gcccctaact ccgcccagtt ccgcccattc   9300
tccgccccat ggctgactaa ttttttttat ttatgcagag gccgaggccg cctcggcctc   9360
tgagctattc cagaagtagt gaggaggctt ttttggaggc ctaggctttt gcaaaaagct   9420
gtcgactgca gaggcctgca tgcaagcttg gcgtaatcat ggtcatagct gtttcctgtg   9480
tgaaattgtt atccgctcac aattccacac aacatacgag ccggaagcat aaagtgtaaa   9540
gcctggggtg cctaatgagt gagctaactc acattaattg cgttgcgctc actgcccgct   9600
```

```
ttccagtcgg gaaacctgtc gtgccagctg cattaatgaa tcggccaacg cgcggggaga   9660
ggcggtttgc gtattgggcg ctcttccgct tcctcgctca ctgactcgct gcgctcggtc   9720
gttcggctgc ggcgagcggt atcagctcac tcaaaggcgg taatacggtt atccacagaa   9780
tcaggggata acgcaggaaa gaacatgtga gcaaaaggcc agcaaaaggc caggaaccgt   9840
aaaaaggccg cgttgctggc gtttttccat aggctccgcc cccctgacga gcatcacaaa   9900
aatcgacgct caagtcagag gtggcgaaac ccgacaggac tataaagata ccaggcgttt   9960
ccccctggaa gctccctcgt gcgctctcct gttccgaccc tgccgcttac cggatacctg  10020
tccgcctttc tcccttcggg aagcgtggcg ctttctcata gctcacgctg taggtatctc  10080
agttcggtgt aggtcgttcg ctccaagctg ggctgtgtgc acgaaccccc cgttcagccc  10140
gaccgctgcg ccttatccgg taactatcgt cttgagtcca acccggtaag acacgactta  10200
tcgccactgg cagcagccac tggtaacagg attagcagag cgaggtatgt aggcggtgct  10260
acagagttct tgaagtggtg gcctaactac ggctacacta gaagaacagt atttggtatc  10320
tgcgctctgc tgaagccagt taccttcgga aaaagagttg gtagctcttg atccggcaaa  10380
caaaccaccg ctggtagcgg tggttttttt gtttgcaagc agcagattac gcgcagaaaa  10440
aaaggatctc aagaagatcc tttgatcttt tctacggggt ctgacgctca gtggaacgaa  10500
aactcacgtt aagggatttt ggtcatgaga ttatcaaaaa ggatcttcac ctagatcctt  10560
ttaaattaaa aatgaagttt taaatcaatc taaagtatat atgagtaaac ttggtctgac  10620
agttaccaat gcttaatcag tgaggcacct atctcagcga tctgtctatt tcgttcatcc  10680
atagttgcct gactccccgt cgtgtagata actacgatac gggagggctt accatctggc  10740
cccagtgctg caatgatacc gcgagaccca cgctcaccgg ctccagattt atcagcaata  10800
aaccagccag ccggaagggc cgagcgcaga agtggtcctg caactttatc cgcctccatc  10860
cagtctatta attgttgccg ggaagctaga gtaagtagtt cgccagttaa tagtttgcgc  10920
aacgttgttg ccattgctac aggcatcgtg gtgtcacgct cgtcgtttgg tatggcttca  10980
ttcagctccg gttcccaacg atcaaggcga gttacatgat cccccatgtt gtgcaaaaaa  11040
gcggttagct ccttcggtcc tccgatcgtt gtcagaagta agttggccgc agtgttatca  11100
ctcatggtta tggcagcact gcataattct cttactgtca tgccatccgt aagatgcttt  11160
tctgtgactg gtgagtactc aaccaagtca ttctgagaat agtgtatgcg gcgaccgagt  11220
tgctcttgcc cggcgtcaat acgggataat accgcgccac atagcagaac tttaaaagtg  11280
ctcatcattg gaaaacgttc ttcggggcga aaactctcaa ggatcttacc gctgttgaga  11340
tccagttcga tgtaacccac tcgtgcaccc aactgatctt cagcatcttt tactttcacc  11400
agcgtttctg ggtgagcaaa aacaggaagg caaaatgccg caaaaaaggg aataagggcg  11460
acacggaaat gttgaatact catactcttc ctttttcaat attattgaag catttatcag  11520
ggttattgtc tcatgagcgg atacatattt gaatgtattt agaaaaataa acaaataggg  11580
gttccgcgca catttccccg aaaagtgcca cctgacgtct aagaaaccat tattatcatg  11640
acattaacct ataaaaatag gcgtatcacg aggccctttc gtctcgcgcg tttcggtgat  11700
gacggtgaaa acctctgaca catgcagctc ccggagacgg tcacagcttg tctgtaagcg  11760
gatgccggga gcagacaagc ccgtcagggc gcgtcagcgg gtgttggcgg gtgtcggggc  11820
tggcttaact atgcggcatc agagcagatt gtactgagag tgcaccatat gcggtgtgaa  11880
ataccgcaca gatgcgtaag gagaaaatac cgcatcaggc gccattcgcc attcaggctg  11940
```

cgcaactgtt gggaagggcg atcggtgcgg gcctcttcgc tattacgcca gctggcgaaa 12000
gggggatgtg ctgcaaggcg attaagttgg gtaacgccag ggttttccca gtcacgacgt 12060
tgtaaaacga cggccagtga attc 12084

<210> SEQ ID NO 11
<211> LENGTH: 12081
<212> TYPE: DNA
<213> ORGANISM: Artificial Sequence
<220> FEATURE:
<223> OTHER INFORMATION: Synthetic: TL20c-rGbGM-r7SKM1/sh734

<400> SEQUENCE: 11
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840
aacatatagt atgggcaagc agggagctag aacgattcgc agttaatact ggcctgttag 900
aaacatcaga aggctgtaga caaatactgg gacagctaca accatccctt cagacaggat 960
cagaagaact tagatcatta tataatacag tagcaaccct ctattgtgtg catcaaagga 1020
tagagataaa agacaccaag gaagctttag acaagataga ggaagagcaa aacaaaagta 1080
agaaaaaagc acagcaagca gcaggatctt cagacctgga aattccctac aatccccaaa 1140
gtcaaggagt agtagaatct atgaataaag aattaaagaa aattatagga caggtaagag 1200
atcaggctga acatcttaag acagcagtac aaatggcagt attcatccac aattttaaaa 1260
gaaaaggggg gattgggggg tacagtgcag gggaaagaat agtagacata atagcaacag 1320
acatacaaac taaagaatta caaaaacaaa ttacaaaaat tcaaaatttt cgggtttatt 1380
acagggacag cagaaatcca ctttggaaag gaccagcaaa gctcctctgg aaaggtgaag 1440
gggcagtagt aatacaagat aatagtgaca taaaagtagt gccaagaaga aaagcaaaga 1500
tcattaggga ttatggaaaa cagatggcag gtgatgattg tgtggcaagt agacaggatg 1560
aggattagaa catggaaaag tttagtaaaa caccataagg aggagatatg agggacaatt 1620
ggagaagtga attatataaa tataaagtag taaaaattga accattagga gtagcaccca 1680
ccaaggcaaa gagaagagtg gtgcagagag aaaaaagagc agtgggaata ggagctttgt 1740
tccttgggtt cttgggagca gcaggaagca ctatgggcgc agcgtcaatg acgctgacgg 1800
tacaggccag acaattattg tctggtatag tgcagcagca gaacaatttg ctgagggcta 1860
ttgaggcgca acagcatctg ttgcaactca cagtctgggg catcaagcag ctccaggcaa 1920
gaatcctggc tgtggaaaga tacctaaagg atcaacagct cctggggatt tggggttgct 1980
ctggaaaact catttgcacc actgctgtgc cttggaatgc tagttggagt aataaatctc 2040
tggaacagat ttggaatcac acgacctgga tggagtggga cagagaaatt aacaattaca 2100
caagcttaat acactcctta attgaagaat cgcaaaacca gcaagaaaag aatgaacaag 2160
aattattgga attagataaa tgggcaagtt tgtggaattg gtttaacata acaaattggc 2220
tgtggtatat aaaattattc ataatgatag taggaggctt ggtaggttta agaatagttt 2280
ttgctgtact ttctatagtg aatagagtta ggcagggata ttcaccatta tcgtttcaga 2340
cccacctccc aaccccgagg ggaccgagct caagcttcga acgcgtgggg atcctctaga 2400
gtcgagctcg cgaggatcat caccggtgct agccggagcc agaagcacca taagggacat 2460
gataagggag ccagcagacc tctgatctct tcctgaatgc taatcttaaa catcctgagg 2520
aagaatggga cttccatttg ggtgggcct atgatagggt aataagacag tagtgaatat 2580
caagctacaa aaagccccct ttcaaattct tctcagtcct aacttttcat actaagccca 2640
gtccttccaa agcagactgt gaaagagtga tagttccggg agactagcac cggctagccg 2700
agcttggaac actttccctt cattaagaac catccttgct actcagctgc aatcaatcca 2760
gcccccaggt cttcactgaa ccttttccca tctcttccaa aacatctgtt tctgagaagt 2820
cctgtcctat agaggtcttt cttcccaccg gatttctcct acaccattta ctcccacttg 2880
cagaactccc gtgtacaagt gtctttactg cttttatttg ctcaacaaaa tgcacatctc 2940
atataaaaat aaatgaggag catgcacaca ccacaaacac aaacaggcat gcagaaatac 3000
acatacacac ttccctcaat ataaaccctt tgtggctcat atatttaaaa agatgtaaaa 3060
aaaagagctg aagaaaatca tgtgtgatct ctcagcagaa tagatttatt atttgtattg 3120
cttgcagaat aaagcctatc cttgaaagct ctgaatcatg ggcaagaggc tcagtggtat 3180
ctggaggaca gggcactggc cactgcagtc accatcttct gccaggaagc ctgcacctca 3240
ggggtgaatt ctttgccaaa gtgaatggcc agcacggtga ccagcacgtt gcccaggagc 3300
tgtgggagga agataagagg tatgaacatg attagcaaaa gggcctagct tggactcaga 3360
ataatccagc cttatcccaa ccataaaata aaagcagaat ggtagctgga ttgtagctgc 3420
tattagcaat atgaaacctc ttacatcagt tacaatttat atgcagaaat atttatatgc 3480
agaaatattg ctattgcctt aacccagaaa ttatcactgt tattctttag aatggtgcaa 3540
agaggcatga tacattgtat cattattgcc ctgaaagaaa gagattaggg aaagtattag 3600
aaataagata aacaaaaaag tatattaaaa gaagaaagca ttttttaaaa ttacaaatgc 3660
aaaattaccc tgatttggtc aatatgtgta ccctgttact tctccccttc ctatgacatg 3720
aacttaacca tagaaaagaa ggggaaagaa aacatcaagg gtcccataga ctcaccttga 3780
agttctcagg atccacatgc agcttgtcac agtgcagttc actcagctgg gcaaaggtgc 3840
ccttgagatc atccaggtgc tttatggcat ctcccaagga agtcagcacc ttcttgccat 3900
gtgccttgac tttggggttg cccatgatgg cagaggcaga ggacaggttg ccaaagctgt 3960
caaagaacct ctgggtccat gggtagacaa ccaggagcct gtgagattga caagaacagt 4020
ttgacagtca gaaggtgcca caaatcctga gaagcaacct ggacttttgc caggcacagg 4080
gtccttcctt ccctcccttg tcctggtcac cagagcctac cttcccaggg tttctcctcc 4140
agcatcttcc acattcacct tgtcccacag gcttgtgata gtagccttgt cctcctctgt 4200
gaaatgaccc atggtgtctg tttgaggttg ctagtgaaca cagttgtgtc agaagcaaat 4260

-continued

```
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
gctctgagac tggcagtata tctctaacag tggttgatgc tatcttctgg aacttgcctg   5460
ctacattgag accactgacc catacatagg aagcccatag ctctgtcctg aactgttagg   5520
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
```

-continued

```
aggaataaca gaacaagatt gaaagaatac attttccgaa attacttgag tattatacaa   6720
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agccctttttc   6960
tctctcccac tcagcagcta tgagatggct tgccctgcct ctctactagg ctgactcact   7020
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
gctgtgacat ggaaactatg tagaatattt tgggttccat ttttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gtaaaaaagg atatgccctt   7620
gactatgtcg gacaaatagt caagggcata tcctgaggta cccaggcggc gcacaagcta   7680
tataaacctg aaggaaatct caactttaca cttaggtcaa gttacttatc gtactagagc   7740
ttcagcagga aatttaacta aaatctaatt taaccagcat agcaaatatc atttattccc   7800
aaaatgctaa agtttgagat aaacggactt gatttccggc tgttttgaca ctatccagaa   7860
tgccggtact atgggtgggg cagtagcccg actgcacgtc gagcggccgc atcgatgccg   7920
tagtaccttt aagaccaatg acttacaagg cagctgtaga tcttagccac tttttaaaag   7980
aaaagggggg actggaaggg ctaattcact cccaaagaag acaagatccc tgcaggcatt   8040
caaggccagg ctggatgtgg ctctgggcag cctgggctgc tggttgatga ccctgcacat   8100
agcagggggt tggatctgga tgagcactgt gctcctttgc aacccaggcc gttctatgat   8160
tctgtcattc taaatctctc tttcagccta aagcttttttc cccgtatccc cccaggtgtc   8220
tgcaggctca aagagcagcg agaagcgttc agaggaaagc gatcccgtgc caccttcccc   8280
gtgcccgggc tgtccccgca cgctgccggc tcggggatgc ggggggagcg ccggaccgga   8340
gcggagcccc gggcggctcg ctgctgcccc ctagcggggg agggacgtaa ttacatccct   8400
gggggctttg gggggggct gtccccgtga gctccccaga tctgcttttt gcctgtactg   8460
ggtctctctg gttagaccag atctgagcct gggagctctc tggctaacta gggaacccac   8520
tgcttaagcc tcaataaagc ttcagctgct cgagctagca gatctttttc cctctgccaa   8580
aaattatggg gacatcatga agccccttga gcatctgact tctggctaat aaaggaaatt   8640
tattttcatt gcaatagtgt gttggaattt tttgtgtctc tcactcggaa ggacatatgg   8700
gagggcaaat catttaaaac atcagaatga gtatttggtt tagagtttgg caacatatgc   8760
ccatatgctg gctgccatga acaaaggttg gctataaaga ggtcatcagt atatgaaaca   8820
gccccctgct gtccattcct tattccatag aaaagccttg acttgaggtt agattttttt   8880
tatattttgt tttgtgttat ttttttcttt aacatcccta aaattttcct tacatgtttt   8940
actagccaga tttttcctcc tctcctgact actcccagtc atagctgtcc ctcttctctt   9000
```

-continued

```
atggagatcc ctcgacctgc agcccaagct tggcgtaatc atggtcatag ctgtttcctg   9060
tgtgaaattg ttatccgctc acaattccac acaacatacg agccggaagc ataaagtgta   9120
aagcctgggg tgcctaatga gtgagctaac tcacattaat tgcgttgcgc tcactgcccg   9180
ctttccagtc gggaaacctg tcgtgccagc ggatccgcat ctcaattagt cagcaaccat   9240
agtcccgccc ctaactccgc ccatcccgcc cctaactccg cccagttccg cccattctcc   9300
gccccatggc tgactaattt tttttattta tgcagaggcc gaggccgcct cggcctctga   9360
gctattccag aagtagtgag gaggcttttt tggaggccta ggcttttgca aaaagctgtc   9420
gactgcagag gcctgcatgc aagcttggcg taatcatggt catagctgtt tcctgtgtga   9480
aattgttatc cgctcacaat tccacacaac atacgagccg gaagcataaa gtgtaaagcc   9540
tggggtgcct aatgagtgag ctaactcaca ttaattgcgt tgcgctcact gcccgctttc   9600
cagtcgggaa acctgtcgtg ccagctgcat taatgaatcg gccaacgcgc ggggagaggc   9660
ggtttgcgta ttgggcgctc ttccgcttcc tcgctcactg actcgctgcg ctcggtcgtt   9720
cggctgcggc gagcggtatc agctcactca aaggcggtaa tacggttatc cacagaatca   9780
ggggataacg caggaaagaa catgtgagca aaaggccagc aaaaggccag gaaccgtaaa   9840
aaggccgcgt tgctggcgtt tttccatagg ctccgccccc ctgacgagca tcacaaaaat   9900
cgacgctcaa gtcagaggtg gcgaaacccg acaggactat aaagatacca ggcgtttccc   9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg tttttttgtt tgcaagcagc agattacgcg cagaaaaaaa  10440
ggatctcaag aagatccttt gatcttttct acggggtctg acgctcagtg gaacgaaaac  10500
tcacgttaag ggattttggt catgagatta tcaaaaagga tcttcaccta gatcctttta  10560
aattaaaaat gaagttttaa atcaatctaa agtatatatg agtaaacttg gtctgacagt  10620
taccaatgct taatcagtga ggcacctatc tcagcgatct gtctatttcg ttcatccata  10680
gttgcctgac tccccgtcgt gtagataact acgatacggg agggcttacc atctggcccc  10740
agtgctgcaa tgataccgcg agacccacgc tcaccggctc cagatttatc agcaataaac  10800
cagccagccg gaagggccga gcgcagaagt ggtcctgcaa ctttatccgc ctccatccag  10860
tctattaatt gttgccggga agctagagta agtagttcgc cagttaatag tttgcgcaac  10920
gttgttgcca ttgctacagg catcgtggtg tcacgctcgt cgtttggtat ggcttcattc  10980
agctccggtt cccaacgatc aaggcgagtt acatgatccc ccatgttgtg caaaaaagcg  11040
gttagctcct tcggtcctcc gatcgttgtc agaagtaagt tggccgcagt gttatcactc  11100
atggttatgg cagcactgca taattctctt actgtcatgc catccgtaag atgcttttct  11160
gtgactggtg agtactcaac caagtcattc tgagaatagt gtatgcggcg accgagttgc  11220
tcttgcccgg cgtcaatacg ggataatacc gcgccacata gcagaacttt aaaagtgctc  11280
atcattggaa aacgttcttc ggggcgaaaa ctctcaagga tcttaccgct gttgagatcc  11340
agttcgatgt aacccactcg tgcacccaac tgatcttcag catcttttac tttcaccagc  11400
```

gtttctgggt gagcaaaaac aggaaggcaa aatgccgcaa aaaagggaat aagggcgaca 11460
cggaaatgtt gaatactcat actcttcctt tttcaatatt attgaagcat ttatcagggt 11520
tattgtctca tgagcggata catatttgaa tgtatttaga aaaataaaca aataggggtt 11580
ccgcgcacat ttccccgaaa agtgccacct gacgtctaag aaaccattat tatcatgaca 11640
ttaacctata aaaataggcg tatcacgagg ccctttcgtc tcgcgcgttt cggtgatgac 11700
ggtgaaaacc tctgacacat gcagctcccg gagacggtca cagcttgtct gtaagcggat 11760
gccgggagca gacaagcccg tcagggcgcg tcagcgggtg ttggcgggtg tcggggctgg 11820
cttaactatg cggcatcaga gcagattgta ctgagagtgc accatatgcg gtgtgaaata 11880
ccgcacagat gcgtaaggag aaaataccgc atcaggcgcc attcgccatt caggctgcgc 11940
aactgttggg aagggcgatc ggtgcgggcc tcttcgctat tacgccagct ggcgaaaggg 12000
ggatgtgctg caaggcgatt aagttgggta acgccagggt tttcccagtc acgacgttgt 12060
aaaacgacgg ccagtgaatt c 12081

<210> SEQ ID NO 12
<211> LENGTH: 12084
<212> TYPE: DNA
<213> ORGANISM: Artificial Sequence
<220> FEATURE:
<223> OTHER INFORMATION: Synthetic: TL20c-rGbGM-r7SK/sh734

<400> SEQUENCE: 12
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840
aacatatagt atgggcaagc agggagctag aacgattcgc agttaatact ggcctgttag 900
aaacatcaga aggctgtaga caaatactgg gacagctaca accatccctt cagacaggat 960
cagaagaact tagatcatta tataatacag tagcaaccct ctattgtgtg catcaaagga 1020
tagagataaa agacaccaag gaagctttag acaagataga ggaagagcaa aacaaaagta 1080
agaaaaaagc acagcaagca gcaggatctt cagacctgga aattccctac aatccccaaa 1140
gtcaaggagt agtagaatct atgaataaag aattaaagaa aattatagga caggtaagag 1200
atcaggctga acatcttaag acagcagtac aaatggcagt attcatccac aattttaaaa 1260
gaaaaggggg gattgggggg tacagtgcag gggaaagaat agtagacata atagcaacag 1320

-continued

```
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgggg atcctctaga   2400
gtcgagctcg cgaggatcat caccggtgct agccggagcc agaagcacca taagggacat   2460
gataagggag ccagcagacc tctgatctct tcctgaatgc taatcttaaa catcctgagg   2520
aagaatggga cttccatttg gggtgggcct atgatagggt aataagacag tagtgaatat   2580
caagctacaa aaagcccccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
aaaagagctg aagaaaatca tgtgtgatct ctcagcagaa tagatttatt atttgtattg   3120
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca ttttttaaaa ttacaaatgc   3660
aaaattaccc tgatttggtc aatatgtgta ccctgttact tctccccttc ctatgacatg   3720
```

```
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
gctctgagac tggcagtata tctctaacag tggttgatgc tatcttctgg aacttgcctg   5460
ctacattgag accactgacc catacatagg aagcccatag ctctgtcctg aactgttagg   5520
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
```

-continued

```
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
aggaataaca gaacaagatt gaaagaatac attttccgaa attacttgag tattatacaa   6720
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agccctttc    6960
tctctcccac tcagcagcta tgagatggct tgccctgcct ctctactagg ctgactcact   7020
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
gctgtgacat ggaaactatg tagaatattt tgggttccat tttttttcc ttctttcagt    7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gtacaaaaaa ggatatgccc   7620
ttgactatgt cggacaaata gtcaagggca tatcctgagg tacccaggcg gcgcacaagc   7680
tatataaacc tgaaggaaat ctcaacttta cacttaggtc aagttactta tcgtactaga   7740
gcttcagcag gaaatttaac taaaatctaa tttaaccagc atagcaaata tcatttattc   7800
ccaaaatgct aaagtttgag ataaacggac ttgatttccg gctgttttga cactatccag   7860
aatgccttgc agatgggtgg ggcatgctaa atactgcacg tcgatgcggc cgcatcgatg   7920
ccgtagtacc tttaagacca atgacttaca aggcagctgt agatcttagc cactttttaa   7980
aagaaaaggg gggactggaa gggctaattc actcccaaag aagacaagat ccctgcaggc   8040
attcaaggcc aggctggatg tggctctggg cagcctgggc tgctggttga tgaccctgca   8100
catagcaggg ggttggatct ggatgagcac tgtgctcctt tgcaacccag gccgttctat   8160
gattctgtca ttctaaatct ctctttcagc ctaaagcttt ttccccgtat ccccccaggt   8220
gtctgcaggc tcaaagagca gcgagaagcg ttcagaggaa agcgatcccg tgccaccttc   8280
cccgtgcccg ggctgtcccc gcacgctgcc ggctcgggga tgcgggggga gcgccggacc   8340
ggagcggagc cccgggcggc tcgctgctgc cccctagcgg gggagggacg taattacatc   8400
cctgggggct ttgggggggg gctgtccccg tgagctcccc agatctgctt tttgcctgta   8460
```

ctgggtctct ctggttagac cagatctgag cctgggagct ctctggctaa ctagggaacc 8520
cactgcttaa gcctcaataa agcttcagct gctcgagcta gcagatcttt ttccctctgc 8580
caaaaattat ggggacatca tgaagcccct tgagcatctg acttctggct aataaaggaa 8640
atttattttc attgcaatag tgtgttggaa ttttttgtgt ctctcactcg gaaggacata 8700
tgggagggca aatcatttaa aacatcagaa tgagtatttg gtttagagtt tggcaacata 8760
tgcccatatg ctggctgcca tgaacaaagg ttggctataa agaggtcatc agtatatgaa 8820
acagcccccct gctgtccatt ccttattcca tagaaaagcc ttgacttgag gttagatttt 8880
ttttatattt tgttttgtgt tatttttttc tttaacatcc ctaaaatttt ccttacatgt 8940
tttactagcc agatttttcc tcctctcctg actactccca gtcatagctg tccctcttct 9000
cttatggaga tccctcgacc tgcagcccaa gcttggcgta atcatggtca tagctgtttc 9060
ctgtgtgaaa ttgttatccg ctcacaattc cacacaacat acgagccgga agcataaagt 9120
gtaaagcctg gggtgcctaa tgagtgagct aactcacatt aattgcgttg cgctcactgc 9180
ccgctttcca gtcgggaaac ctgtcgtgcc agcggatccg catctcaatt agtcagcaac 9240
catagtcccg cccctaactc cgcccatccc gcccctaact ccgcccagtt ccgcccattc 9300
tccgccccat ggctgactaa ttttttttat ttatgcagag gccgaggccg cctcggcctc 9360
tgagctattc cagaagtagt gaggaggctt ttttggaggc ctaggctttt gcaaaaagct 9420
gtcgactgca gaggcctgca tgcaagcttg gcgtaatcat ggtcatagct gtttcctgtg 9480
tgaaattgtt atccgctcac aattccacac aacatacgag ccggaagcat aaagtgtaaa 9540
gcctggggtg cctaatgagt gagctaactc acattaattg cgttgcgctc actgcccgct 9600
ttccagtcgg gaaacctgtc gtgccagctg cattaatgaa tcggccaacg cgcggggaga 9660
ggcggtttgc gtattgggcg ctcttccgct tcctcgctca ctgactcgct gcgctcggtc 9720
gttcggctgc ggcgagcggt atcagctcac tcaaaggcgg taatacggtt atccacagaa 9780
tcaggggata acgcaggaaa gaacatgtga gcaaaaggcc agcaaaaggc caggaaccgt 9840
aaaaaggccg cgttgctggc gtttttccat aggctccgcc cccctgacga gcatcacaaa 9900
aatcgacgct caagtcagag gtggcgaaac ccgacaggac tataaagata ccaggcgttt 9960
ccccctggaa gctccctcgt gcgctctcct gttccgaccc tgccgcttac cggatacctg 10020
tccgcctttc tcccttcggg aagcgtggcg ctttctcata gctcacgctg taggtatctc 10080
agttcggtgt aggtcgttcg ctccaagctg ggctgtgtgc acgaaccccc cgttcagccc 10140
gaccgctgcg ccttatccgg taactatcgt cttgagtcca acccggtaag acacgactta 10200
tcgccactgg cagcagccac tggtaacagg attagcagag cgaggtatgt aggcggtgct 10260
acagagttct tgaagtggtg gcctaactac ggctacacta gaagaacagt atttggtatc 10320
tgcgctctgc tgaagccagt taccttcgga aaaagagttg gtagctcttg atccggcaaa 10380
caaaccaccg ctggtagcgg tggttttttt gtttgcaagc agcagattac gcgcagaaaa 10440
aaaggatctc aagaagatcc tttgatcttt tctacggggt ctgacgctca gtggaacgaa 10500
aactcacgtt aagggatttt ggtcatgaga ttatcaaaaa ggatcttcac ctagatcctt 10560
ttaaattaaa aatgaagttt taaatcaatc taaagtatat atgagtaaac ttggtctgac 10620
agttaccaat gcttaatcag tgaggcacct atctcagcga tctgtctatt tcgttcatcc 10680
atagttgcct gactccccgt cgtgtagata actacgatac gggagggctt accatctggc 10740
cccagtgctg caatgatacc gcgagaccca cgctcaccgg ctccagattt atcagcaata 10800
aaccagccag ccggaagggc cgagcgcaga agtggtcctg caactttatc cgcctccatc 10860
cagtctatta attgttgccg ggaagctaga gtaagtagtt cgccagttaa tagtttgcgc 10920
aacgttgttg ccattgctac aggcatcgtg gtgtcacgct cgtcgtttgg tatggcttca 10980
ttcagctccg gttcccaacg atcaaggcga gttacatgat cccccatgtt gtgcaaaaaa 11040
gcggttagct ccttcggtcc tccgatcgtt gtcagaagta agttggccgc agtgttatca 11100
ctcatggtta tggcagcact gcataattct cttactgtca tgccatccgt aagatgcttt 11160
tctgtgactg gtgagtactc aaccaagtca ttctgagaat agtgtatgcg gcgaccgagt 11220
tgctcttgcc cggcgtcaat acgggataat accgcgccac atagcagaac tttaaaagtg 11280
ctcatcattg gaaaacgttc ttcggggcga aaactctcaa ggatcttacc gctgttgaga 11340
tccagttcga tgtaacccac tcgtgcaccc aactgatctt cagcatcttt tactttcacc 11400
agcgtttctg ggtgagcaaa aacaggaagg caaaatgccg caaaaaaggg aataagggcg 11460
acacggaaat gttgaatact catactcttc ctttttcaat attattgaag catttatcag 11520
ggttattgtc tcatgagcgg atacatattt gaatgtattt agaaaaataa acaaataggg 11580
gttccgcgca catttccccg aaaagtgcca cctgacgtct aagaaaccat tattatcatg 11640
acattaacct ataaaaatag gcgtatcacg aggccctttc gtctcgcgcg tttcggtgat 11700
gacggtgaaa acctctgaca catgcagctc ccggagacgg tcacagcttg tctgtaagcg 11760
gatgccggga gcagacaagc ccgtcagggc gcgtcagcgg gtgttggcgg gtgtcggggc 11820
tggcttaact atgcggcatc agagcagatt gtactgagag tgcaccatat gcggtgtgaa 11880
ataccgcaca gatgcgtaag gagaaaatac cgcatcaggc gccattcgcc attcaggctg 11940
cgcaactgtt gggaagggcg atcggtgcgg gcctcttcgc tattacgcca gctggcgaaa 12000
gggggatgtg ctgcaaggcg attaagttgg gtaacgccag ggttttccca gtcacgacgt 12060
tgtaaaacga cggccagtga attc 12084

<210> SEQ ID NO 13
<211> LENGTH: 11779
<212> TYPE: DNA
<213> ORGANISM: Artificial Sequence
<220> FEATURE:
<223> OTHER INFORMATION: Synthetic: TL20c-rGbGM

<400> SEQUENCE: 13
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840
aacatatagt atgggcaagc agggagctag aacgattcgc agttaatact ggcctgttag 900
aaacatcaga aggctgtaga caaatactgg gacagctaca accatccctt cagacaggat 960
cagaagaact tagatcatta tataatacag tagcaaccct ctattgtgtg catcaaagga 1020
tagagataaa agacaccaag gaagctttag acaagataga ggaagagcaa aacaaaagta 1080
agaaaaaagc acagcaagca gcaggatctt cagacctgga aattccctac aatccccaaa 1140
gtcaaggagt agtagaatct atgaataaag aattaaagaa aattatagga caggtaagag 1200
atcaggctga acatcttaag acagcagtac aaatggcagt attcatccac aattttaaaa 1260
gaaaaggggg gattgggggg tacagtgcag gggaaagaat agtagacata atagcaacag 1320
acatacaaac taaagaatta caaaaacaaa ttacaaaaat tcaaaatttt cgggtttatt 1380
acagggacag cagaaatcca ctttggaaag gaccagcaaa gctcctctgg aaaggtgaag 1440
gggcagtagt aatacaagat aatagtgaca taaaagtagt gccaagaaga aaagcaaaga 1500
tcattaggga ttatggaaaa cagatggcag gtgatgattg tgtggcaagt agacaggatg 1560
aggattagaa catggaaaag tttagtaaaa caccataagg aggagatatg agggacaatt 1620
ggagaagtga attatataaa tataaagtag taaaaattga accattagga gtagcaccca 1680
ccaaggcaaa gagaagagtg gtgcagagag aaaaaagagc agtgggaata ggagctttgt 1740
tccttgggtt cttgggagca gcaggaagca ctatgggcgc agcgtcaatg acgctgacgg 1800
tacaggccag acaattattg tctggtatag tgcagcagca gaacaatttg ctgagggcta 1860
ttgaggcgca acagcatctg ttgcaactca cagtctgggg catcaagcag ctccaggcaa 1920
gaatcctggc tgtggaaaga tacctaaagg atcaacagct cctggggatt tggggttgct 1980
ctggaaaact catttgcacc actgctgtgc cttggaatgc tagttggagt aataaatctc 2040
tggaacagat ttggaatcac acgacctgga tggagtggga cagagaaatt aacaattaca 2100
caagcttaat acactcctta attgaagaat cgcaaaacca gcaagaaaag aatgaacaag 2160
aattattgga attagataaa tgggcaagtt tgtggaattg gtttaacata acaaattggc 2220
tgtggtatat aaaattattc ataatgatag taggaggctt ggtaggttta agaatagttt 2280
ttgctgtact ttctatagtg aatagagtta ggcagggata ttcaccatta tcgtttcaga 2340
cccacctccc aaccccgagg ggaccgagct caagcttcga acgcgtgggg atcctctaga 2400
gtcgagctcg cgaggatcat caccggtgct agccggagcc agaagcacca taagggacat 2460
gataagggag ccagcagacc tctgatctct tcctgaatgc taatcttaaa catcctgagg 2520
aagaatggga cttccatttg gggtgggcct atgatagggt aataagacag tagtgaatat 2580
caagctacaa aaagccccct ttcaaattct tctcagtcct aacttttcat actaagccca 2640
gtccttccaa agcagactgt gaaagagtga tagttccggg agactagcac cggctagccg 2700
agcttggaac actttccctt cattaagaac catccttgct actcagctgc aatcaatcca 2760
gcccccaggt cttcactgaa ccttttccca tctcttccaa aacatctgtt tctgagaagt 2820
cctgtcctat agaggtcttt cttcccaccg gatttctcct acaccattta ctcccacttg 2880
cagaactccc gtgtacaagt gtctttactg cttttatttg ctcaacaaaa tgcacatctc 2940
atataaaaat aaatgaggag catgcacaca ccacaaacac aaacaggcat gcagaaatac 3000
acatacacac ttccctcaat ataaaccctt tgtggctcat atatttaaaa agatgtaaaa 3060
aaaagagctg aagaaaatca tgtgtgatct ctcagcagaa tagatttatt atttgtattg 3120

```
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca ttttttaaaa ttacaaatgc   3660
aaaattaccc tgatttggtc aatatgtgta ccctgttact tctccccttc ctatgacatg   3720
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
gctctgagac tggcagtata tctctaacag tggttgatgc tatcttctgg aacttgcctg   5460
ctacattgag accactgacc catacatagg aagcccatag ctctgtcctg aactgttagg   5520
```

```
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
aggaataaca gaacaagatt gaaagaatac attttccgaa attacttgag tattatacaa   6720
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agcccttttc   6960
tctctcccac tcagcagcta tgagatggct tgccctgcct ctctactagg ctgactcact   7020
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
gctgtgacat ggaaactatg tagaatattt tgggttccat tttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttaac gcggccgcat cgatgccgta   7620
gtacctttaa gaccaatgac ttacaaggca gctgtagatc ttagccactt tttaaaagaa   7680
aaggggggac tggaagggct aattcactcc caaagaagac aagatccctg caggcattca   7740
aggccaggct ggatgtggct ctgggcagcc tgggctgctg gttgatgacc ctgcacatag   7800
caggggggttg gatctggatg agcactgtgc tcctttgcaa cccaggccgt tctatgattc   7860
```

```
tgtcattcta aatctctctt tcagcctaaa gctttttccc cgtatccccc caggtgtctg   7920
caggctcaaa gagcagcgag aagcgttcag aggaaagcga tcccgtgcca ccttccccgt   7980
gcccgggctg tccccgcacg ctgccggctc ggggatgcgg ggggagcgcc ggaccggagc   8040
ggagccccgg gcggctcgct gctgccccct agcgggggag ggacgtaatt acatccctgg   8100
gggctttggg ggggggctgt ccccgtgagc tccccagatc tgctttttgc ctgtactggg   8160
tctctctggt tagaccagat ctgagcctgg gagctctctg gctaactagg gaacccactg   8220
cttaagcctc aataaagctt cagctgctcg agctagcaga tctttttccc tctgccaaaa   8280
attatgggga catcatgaag ccccttgagc atctgacttc tggctaataa aggaaattta   8340
ttttcattgc aatagtgtgt tggaattttt tgtgtctctc actcggaagg acatatggga   8400
gggcaaatca tttaaaacat cagaatgagt atttggttta gagtttggca acatatgccc   8460
atatgctggc tgccatgaac aaaggttggc tataaagagg tcatcagtat atgaaacagc   8520
cccctgctgt ccattcctta ttccatagaa aagccttgac ttgaggttag atttttttta   8580
tattttgttt tgtgttattt ttttctttaa catccctaaa attttcctta catgttttac   8640
tagccagatt tttcctcctc tcctgactac tcccagtcat agctgtccct cttctcttat   8700
ggagatccct cgacctgcag cccaagcttg gcgtaatcat ggtcatagct gtttcctgtg   8760
tgaaattgtt atccgctcac aattccacac aacatacgag ccggaagcat aaagtgtaaa   8820
gcctggggtg cctaatgagt gagctaactc acattaattg cgttgcgctc actgcccgct   8880
ttccagtcgg gaaacctgtc gtgccagcgg atccgcatct caattagtca gcaaccatag   8940
tcccgcccct aactccgccc atcccgcccc taactccgcc cagttccgcc cattctccgc   9000
cccatggctg actaattttt tttatttatg cagaggccga ggccgcctcg gcctctgagc   9060
tattccagaa gtagtgagga ggcttttttg gaggcctagg cttttgcaaa aagctgtcga   9120
ctgcagaggc ctgcatgcaa gcttggcgta atcatggtca tagctgtttc ctgtgtgaaa   9180
ttgttatccg ctcacaattc cacacaacat acgagccgga agcataaagt gtaaagcctg   9240
gggtgcctaa tgagtgagct aactcacatt aattgcgttg cgctcactgc ccgctttcca   9300
gtcgggaaac ctgtcgtgcc agctgcatta atgaatcggc caacgcgcgg ggagaggcgg   9360
tttgcgtatt gggcgctctt ccgcttcctc gctcactgac tcgctgcgct cggtcgttcg   9420
gctgcggcga gcggtatcag ctcactcaaa ggcggtaata cggttatcca cagaatcagg   9480
ggataacgca ggaaagaaca tgtgagcaaa aggccagcaa aaggccagga accgtaaaaa   9540
ggccgcgttg ctggcgtttt tccataggct ccgcccccct gacgagcatc acaaaaatcg   9600
acgctcaagt cagaggtggc gaaacccgac aggactataa agataccagg cgtttccccc   9660
tggaagctcc ctcgtgcgct ctcctgttcc gaccctgccg cttaccggat acctgtccgc   9720
ctttctccct tcgggaagcg tggcgctttc tcatagctca cgctgtaggt atctcagttc   9780
ggtgtaggtc gttcgctcca agctgggctg tgtgcacgaa ccccccgttc agcccgaccg   9840
ctgcgcctta tccggtaact atcgtcttga gtccaacccg gtaagacacg acttatcgcc   9900
actggcagca gccactggta acaggattag cagagcgagg tatgtaggcg gtgctacaga   9960
gttcttgaag tggtggccta actacggcta cactagaaga acagtatttg gtatctgcgc  10020
tctgctgaag ccagttacct tcggaaaaag agttggtagc tcttgatccg gcaaacaaac  10080
caccgctggt agcggtggtt tttttgtttg caagcagcag attacgcgca gaaaaaaagg  10140
atctcaagaa gatcctttga tcttttctac ggggtctgac gctcagtgga acgaaaactc  10200
acgttaaggg attttggtca tgagattatc aaaaaggatc ttcacctaga tccttttaaa  10260
```

ttaaaaatga agttttaaat caatctaaag tatatatgag taaacttggt ctgacagtta 10320
ccaatgctta atcagtgagg cacctatctc agcgatctgt ctatttcgtt catccatagt 10380
tgcctgactc cccgtcgtgt agataactac gatacgggag ggcttaccat ctggccccag 10440
tgctgcaatg ataccgcgag acccacgctc accggctcca gatttatcag caataaacca 10500
gccagccgga agggccgagc gcagaagtgg tcctgcaact ttatccgcct ccatccagtc 10560
tattaattgt tgccgggaag ctagagtaag tagttcgcca gttaatagtt tgcgcaacgt 10620
tgttgccatt gctacaggca tcgtggtgtc acgctcgtcg tttggtatgg cttcattcag 10680
ctccggttcc caacgatcaa ggcgagttac atgatccccc atgttgtgca aaaaagcggt 10740
tagctccttc ggtcctccga tcgttgtcag aagtaagttg gccgcagtgt tatcactcat 10800
ggttatggca gcactgcata attctcttac tgtcatgcca tccgtaagat gcttttctgt 10860
gactggtgag tactcaacca agtcattctg agaatagtgt atgcggcgac cgagttgctc 10920
ttgcccggcg tcaatacggg ataataccgc gccacatagc agaactttaa aagtgctcat 10980
cattggaaaa cgttcttcgg ggcgaaaact ctcaaggatc ttaccgctgt tgagatccag 11040
ttcgatgtaa cccactcgtg cacccaactg atcttcagca tcttttactt tcaccagcgt 11100
ttctgggtga gcaaaaacag gaaggcaaaa tgccgcaaaa aagggaataa gggcgacacg 11160
gaaatgttga atactcatac tcttcctttt tcaatattat tgaagcattt atcagggtta 11220
ttgtctcatg agcggataca tatttgaatg tatttagaaa aataaacaaa taggggttcc 11280
gcgcacattt ccccgaaaag tgccacctga cgtctaagaa accattatta tcatgacatt 11340
aacctataaa aataggcgta tcacgaggcc ctttcgtctc gcgcgtttcg gtgatgacgg 11400
tgaaaacctc tgacacatgc agctcccgga gacggtcaca gcttgtctgt aagcggatgc 11460
cgggagcaga caagcccgtc agggcgcgtc agcgggtgtt ggcgggtgtc ggggctggct 11520
taactatgcg gcatcagagc agattgtact gagagtgcac catatgcggt gtgaaatacc 11580
gcacagatgc gtaaggagaa aataccgcat caggcgccat tcgccattca ggctgcgcaa 11640
ctgttgggaa gggcgatcgg tgcgggcctc ttcgctatta cgccagctgg cgaaaggggg 11700
atgtgctgca aggcgattaa gttgggtaac gccagggttt tcccagtcac gacgttgtaa 11760
aacgacggcc agtgaattc 11779

<210> SEQ ID NO 14
<211> LENGTH: 11678
<212> TYPE: DNA
<213> ORGANISM: Artificial Sequence
<220> FEATURE:
<223> OTHER INFORMATION: Synthetic: TL20d-7SKM1/sh734-rGbGM

<400> SEQUENCE: 14
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480

```
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgct cgacgtgcag   2400
tcgggctact gccccaccca tagtaccggc attctggata gtgtcaaaac agccggaaat   2460
caagtccgtt tatctcaaac tttagcattt tgggaataaa tgatatttgc tatgctggtt   2520
aaattagatt ttagttaaat ttcctgctga agctctagta cgataagtaa cttgacctaa   2580
gtgtaaagtt gagatttcct tcaggtttat atagcttgtg cgccgcctgg gtacctcagg   2640
atatgccctt gactatttgt ccgacatagt caagggcata tcctttttta cgcgtgggga   2700
tcctctagag tcgagctcgc gaggatcatc accggtgcta gccggagcca gaagcaccat   2760
aagggacatg ataagggagc cagcagacct ctgatctctt cctgaatgct aatcttaaac   2820
atcctgagga agaatgggac ttccatttgg ggtgggccta tgatagggta ataagacagt   2880
```

```
agtgaatatc aagctacaaa aagccccctt tcaaattctt ctcagtccta acttttcata   2940
ctaagcccag tccttccaaa gcagactgtg aaagagtgat agttccggga gactagcacc   3000
ggctagccga gcttggaaca ctttcccttc attaagaacc atccttgcta ctcagctgca   3060
atcaatccag cccccaggtc ttcactgaac cttttcccat ctcttccaaa acatctgttt   3120
ctgagaagtc ctgtcctata gaggtctttc ttcccaccgg atttctccta caccatttac   3180
tcccacttgc agaactcccg tgtacaagtg tctttactgc ttttatttgc tcaacaaaat   3240
gcacatctca tataaaaata aatgaggagc atgcacacac cacaaacaca aacaggcatg   3300
cagaaataca catacacact tccctcaata taaacccttt gtggctcata tatttaaaaa   3360
gatgtaaaaa aaagagctga agaaaatcat gtgtgatctc tcagcagaat agatttatta   3420
tttgtattgc ttgcagaata aagcctatcc ttgaaagctc tgaatcatgg gcaagaggct   3480
cagtggtatc tggaggacag ggcactggcc actgcagtca ccatcttctg ccaggaagcc   3540
tgcacctcag gggtgaattc tttgccaaag tgaatggcca gcacggtgac cagcacgttg   3600
cccaggagct gtgggaggaa gataagaggt atgaacatga ttagcaaaag ggcctagctt   3660
ggactcagaa taatccagcc ttatcccaac cataaaataa aagcagaatg gtagctggat   3720
tgtagctgct attagcaata tgaaacctct tacatcagtt acaatttata tgcagaaata   3780
tttatatgca gaaatattgc tattgcctta acccagaaat tatcactgtt attctttaga   3840
atggtgcaaa gaggcatgat acattgtatc attattgccc tgaaagaaag agattaggga   3900
aagtattaga aataagataa acaaaaaagt atattaaaag aagaaagcat tttttaaaat   3960
tacaaatgca aaattaccct gatttggtca atatgtgtac cctgttactt ctccccttcc   4020
tatgacatga acttaaccat agaaaagaag gggaaagaaa acatcaaggg tcccatagac   4080
tcaccttgaa gttctcagga tccacatgca gcttgtcaca gtgcagttca ctcagctggg   4140
caaaggtgcc cttgagatca tccaggtgct ttatggcatc tcccaaggaa gtcagcacct   4200
tcttgccatg tgccttgact ttggggttgc ccatgatggc agaggcagag gacaggttgc   4260
caaagctgtc aaagaacctc tgggtccatg ggtagacaac caggagcctg tgagattgac   4320
aagaacagtt tgacagtcag aaggtgccac aaatcctgag aagcaacctg gacttttgcc   4380
aggcacaggg tccttccttc cctcccttgt cctggtcacc agagcctacc ttcccagggt   4440
ttctcctcca gcatcttcca cattcacctt gtcccacagg cttgtgatag tagccttgtc   4500
ctcctctgtg aaatgaccca tggtgtctgt ttgaggttgc tagtgaacac agttgtgtca   4560
gaagcaaatg taagcaatag atggctctgc cctgactttt atgcccagcc ctggctcctg   4620
ccctccctgc tcctgggagt agattggcca accctagggt gtggctccac agggtgaggt   4680
ctaagtgatg acagccgtac ctgtccttgg ctcttctggc actggcttag gagttggact   4740
tcaaaccctc agccctccct ctaagatata tctcttggcc ccataccatc agtacaaatt   4800
gctactaaaa acatcctcct ttgcaagtgt atttacgacg gtatcgatgt atgtgagcat   4860
gtgtcctcta acagcacagg ccttttgcca cctagctgtc caggggtgcc ttaaaatggc   4920
aaacaaggtt tgttttcttt tcctgttttc atgccttcct cttccatatc cttgtttcat   4980
attaatacat gtgtatagat cctaaaaatc tatacacatg tattaataaa gcctgattct   5040
gccgcttcta ggtatagagg ccacctgcaa gataaatatt tgattcacaa taactaatca   5100
ttctatggca attgataaca acaaatatat atatatatat atatatacgt atatgtgtat   5160
atatatatat atattcagga aataatatat tctagaatat gtcacattct gtctcaggca   5220
```

-continued

```
tccattttct ttatgatgcc gtttgaggtg gagttttagt caggtggtca gcttctcctt   5280
ttttttgcca tctgccctgt aagcatcctg ctggggaccc agataggagt catcactcta   5340
ggctgagaac atctgggcac acaccctaag cctcagcatg actcatcatg actcagcatt   5400
gctgtgcttg agccagaagg tttgcttaga aggttacaca gaaccagaag gcgggggtgg   5460
ggcactgacc ccgacagggg cctggccaga actgctcatg cttggactat gggaggtcac   5520
taatggagac acacagaaat gtaacaggaa ctaagggaat tccggtgccc tgcttaggag   5580
cttaatcttt aatgaaagct aagctttcat taaaaaaagt ctaaccagct gcattcgact   5640
ttgactgcag cagctggtta gaaggttcta ctggaggagg gtcccagccc attgctaaat   5700
taacatcagg ctctgagact ggcagtatat ctctaacagt ggttgatgct atcttctgga   5760
acttgcctgc tacattgaga ccactgaccc atacatagga agcccatagc tctgtcctga   5820
actgttaggc cactggtcca gagagtgtgc atctcctttg atcctcataa taaccctatg   5880
agatagacac aattattact cttactttat agatgatgat cctgaaaaca taggagtcaa   5940
ggcacttgcc cctagctggg ggtatagggg agcagtccca tgtagtagta gaatgaaaaa   6000
tgctgctatg ctgtgcctcc cccacctttc ccatgtctgc cctctactca tggtctatct   6060
ctcctggctc ctgggagtca tggactccac ccagcaccac caacctgacc taaccaccta   6120
tctgagcctg ccagcctata acccatctgg gccctgatag ctggtggcca gccctgaccc   6180
caccccaccc tccctggaac ctctgataga cacatctggc acaccagctc gcaaagtcac   6240
cgtgagggtc ttgtgtttgc tgagtcaaaa ttccttgaaa tccaagtcct tagagactcc   6300
tgctcccaaa tttacagtca tagacttctt catggctgtc tcctttatcc acagaatgat   6360
tcctttgctt cattgcccca tccatctgat cctcctcatc agtgcagcac agggcccatg   6420
agcagtagct gcagagtctc acataggtct ggcactgcct ctgacatgtc cgaccttagg   6480
caaatgcttg actcttctga gctcggatcc cttgagctca ggaggtcaag gctgcagtga   6540
gacatgatct tgccactgca ctccagcctg gacagcagag tgaaaccttg cctcacgaaa   6600
cagaatacaa aaacaaacaa acaaaaaact gctccgcaat gcgcttcctt gatgctctac   6660
cacataggtc tgggtacttt gtacacatta tctcattgct gttcataatt gttagattaa   6720
ttttgtaata ttgatattat tcctagaaag ctgaggcctc aagatgataa cttttatttt   6780
ctggacttgt aatagctttc tcttgtattc accatgttgt aactttctta gagtagtaac   6840
aatataaagt tattgtgagt ttttgcaaac acagcaaaca caacgaccca tatagacatt   6900
gatgtgaaat tgtctattgt caatttatgg gaaaacaagt atgtactttt tctactaagc   6960
cattgaaaca ggaataacag aacaagattg aaagaataca ttttccgaaa ttacttgagt   7020
attatacaaa gacaagcacg tggacctggg aggagggtta ttgtccatga ctggtgtgtg   7080
gagacaaatg caggtttata atagatggga tggcatctag cgcaatgact ttgccatcac   7140
ttttagagag ctcttggggg ccccagtaca caagagggga cgcagggtat atgtagacat   7200
ctcattcttt ttcttagtgt gagaataaga atagccatga cctgagttta tagacaatga   7260
gcccttttct ctctcccact cagcagctat gagatggctt gccctgcctc tctactaggc   7320
tgactcactc caaggcccag caatgggcag ggctctgtca gggctttgat agcactatct   7380
gcagagccag ggccgagaag gggtggactc cagagactct ccctcccatt cccgagcagg   7440
gtttgcttat ttatgcattt aaatgatata tttattttaa aagaaataac aggagactgc   7500
ccagccctgg ctgtgacatg gaaactatgt agaatatttt gggttccatt tttttttcct   7560
tctttcagtt agaggaaaag gggctcactg cacatacact agacagaaag tcaggagctt   7620
```

tgaatccaag cctgatcatt tccatgtcat actgagaaag tccccaccct tctctgagcc 7680
tcagtttctc tttttataag taggagtctg gagtaaatga tttccaatgg ctctcatttc 7740
aatacaaaat ttccgtttat taaatgcatg agcttccgtt actccaagac tgagaaggaa 7800
attgaacctg agactcattg actggcaaga tgtccccaga ggctctcatt cagcaataaa 7860
attctcacct tcacccaggc ccactagtgt cagatttgca tgcgttaacg cggccgcatc 7920
gatgccgtag tacctttaag accaatgact tacaaggcag ctgtagatct tagccacttt 7980
ttaaaagaaa aggggggact ggaagggcta attcactccc aaagaagaca agatagatct 8040
gctttttgcc tgtactgggt ctctctggtt agaccagatc tgagcctggg agctctctgg 8100
ctaactaggg aacccactgc ttaagcctca ataaagcttc agctgctcga gctagcagat 8160
ctttttccct ctgccaaaaa ttatggggac atcatgaagc cccttgagca tctgacttct 8220
ggctaataaa ggaaatttat tttcattgca atagtgtgtt ggaatttttt gtgtctctca 8280
ctcggaagga catatgggag ggcaaatcat ttaaaacatc agaatgagta tttggtttag 8340
agtttggcaa catatgccca tatgctggct gccatgaaca aaggttggct ataaagaggt 8400
catcagtata tgaaacagcc ccctgctgtc cattccttat tccatagaaa agccttgact 8460
tgaggttaga ttttttttat attttgtttt gtgttatttt tttctttaac atccctaaaa 8520
ttttccttac atgttttact agccagattt ttcctcctct cctgactact cccagtcata 8580
gctgtccctc ttctcttatg gagatccctc gacctgcagc ccaagcttgg cgtaatcatg 8640
gtcatagctg tttcctgtgt gaaattgtta tccgctcaca attccacaca acatacgagc 8700
cggaagcata aagtgtaaag cctggggtgc ctaatgagtg agctaactca cattaattgc 8760
gttgcgctca ctgcccgctt tccagtcggg aaacctgtcg tgccagcgga tccgcatctc 8820
aattagtcag caaccatagt cccgccccta actccgccca tcccgcccct aactccgccc 8880
agttccgccc attctccgcc ccatggctga ctaatttttt ttatttatgc agaggccgag 8940
gccgcctcgg cctctgagct attccagaag tagtgaggag gcttttttgg aggcctaggc 9000
ttttgcaaaa agctgtcgac tgcagaggcc tgcatgcaag cttggcgtaa tcatggtcat 9060
agctgtttcc tgtgtgaaat tgttatccgc tcacaattcc acacaacata cgagccggaa 9120
gcataaagtg taaagcctgg ggtgcctaat gagtgagcta actcacatta attgcgttgc 9180
gctcactgcc cgctttccag tcgggaaacc tgtcgtgcca gctgcattaa tgaatcggcc 9240
aacgcgcggg gagaggcggt ttgcgtattg ggcgctcttc cgcttcctcg ctcactgact 9300
cgctgcgctc ggtcgttcgg ctgcggcgag cggtatcagc tcactcaaag gcggtaatac 9360
ggttatccac agaatcaggg gataacgcag gaaagaacat gtgagcaaaa ggccagcaaa 9420
aggccaggaa ccgtaaaaag gccgcgttgc tggcgttttt ccataggctc cgcccccctg 9480
acgagcatca caaaaatcga cgctcaagtc agaggtggcg aaacccgaca ggactataaa 9540
gataccaggc gtttccccct ggaagctccc tcgtgcgctc tcctgttccg accctgccgc 9600
ttaccggata cctgtccgcc tttctccctt cgggaagcgt ggcgctttct catagctcac 9660
gctgtaggta tctcagttcg gtgtaggtcg ttcgctccaa gctgggctgt gtgcacgaac 9720
cccccgttca gcccgaccgc tgcgccttat ccggtaacta tcgtcttgag tccaacccgg 9780
taagacacga cttatcgcca ctggcagcag ccactggtaa caggattagc agagcgaggt 9840
atgtaggcgg tgctacagag ttcttgaagt ggtggcctaa ctacggctac actagaagaa 9900
cagtatttgg tatctgcgct ctgctgaagc cagttacctt cggaaaaaga gttggtagct 9960

```
cttgatccgg caaacaaacc accgctggta gcggtggttt ttttgtttgc aagcagcaga  10020

ttacgcgcag aaaaaaagga tctcaagaag atcctttgat cttttctacg gggtctgacg  10080

ctcagtggaa cgaaaactca cgttaaggga ttttggtcat gagattatca aaaaggatct  10140

tcacctagat ccttttaaat taaaaatgaa gttttaaatc aatctaaagt atatatgagt  10200

aaacttggtc tgacagttac caatgcttaa tcagtgaggc acctatctca gcgatctgtc  10260

tatttcgttc atccatagtt gcctgactcc ccgtcgtgta gataactacg atacgggagg  10320

gcttaccatc tggccccagt gctgcaatga taccgcgaga cccacgctca ccggctccag  10380

atttatcagc aataaaccag ccagccggaa gggccgagcg cagaagtggt cctgcaactt  10440

tatccgcctc catccagtct attaattgtt gccgggaagc tagagtaagt agttcgccag  10500

ttaatagttt gcgcaacgtt gttgccattg ctacaggcat cgtggtgtca cgctcgtcgt  10560

ttggtatggc ttcattcagc tccggttccc aacgatcaag gcgagttaca tgatccccca  10620

tgttgtgcaa aaaagcggtt agctccttcg gtcctccgat cgttgtcaga agtaagttgg  10680

ccgcagtgtt atcactcatg gttatggcag cactgcataa ttctcttact gtcatgccat  10740

ccgtaagatg cttttctgtg actggtgagt actcaaccaa gtcattctga gaatagtgta  10800

tgcggcgacc gagttgctct tgcccggcgt caatacggga taataccgcg ccacatagca  10860

gaactttaaa agtgctcatc attggaaaac gttcttcggg gcgaaaactc tcaaggatct  10920

taccgctgtt gagatccagt tcgatgtaac ccactcgtgc acccaactga tcttcagcat  10980

cttttacttt caccagcgtt tctgggtgag caaaaacagg aaggcaaaat gccgcaaaaa  11040

agggaataag ggcgacacgg aaatgttgaa tactcatact cttccttttt caatattatt  11100

gaagcattta tcagggttat tgtctcatga gcggatacat atttgaatgt atttagaaaa  11160

ataaacaaat aggggttccg cgcacatttc cccgaaaagt gccacctgac gtctaagaaa  11220

ccattattat catgacatta acctataaaa ataggcgtat cacgaggccc tttcgtctcg  11280

cgcgtttcgg tgatgacggt gaaaacctct gacacatgca gctcccggag acggtcacag  11340

cttgtctgta agcggatgcc gggagcagac aagcccgtca gggcgcgtca gcgggtgttg  11400

gcgggtgtcg gggctggctt aactatgcgg catcagagca gattgtactg agagtgcacc  11460

atatgcggtg tgaaataccg cacagatgcg taaggagaaa ataccgcatc aggcgccatt  11520

cgccattcag gctgcgcaac tgttgggaag ggcgatcggt gcgggcctct tcgctattac  11580

gccagctggc gaaaggggga tgtgctgcaa ggcgattaag ttgggtaacg ccagggtttt  11640

cccagtcacg acgttgtaaa acgacggcca gtgaattc                          11678
```

<210> SEQ ID NO 15
<211> LENGTH: 11681
<212> TYPE: DNA
<213> ORGANISM: Artificial Sequence
<220> FEATURE:
<223> OTHER INFORMATION: Synthetic: TL20d-7SK/sh734-rGbGM

<400> SEQUENCE: 15

```
ggccgcctcg gccaaacagc ccttgagttt accactccct atcagtgata gagaaaagtg     60

aaagtcgagt ttaccactcc ctatcagtga tagagaaaag tgaaagtcga gtttaccact    120

ccctatcagt gatagagaaa agtgaaagtc gagtttacca ctccctatca gtgatagaga    180

aaagtgaaag tcgagtttac cagtccctat cagtgataga gaaaagtgaa agtcgagttt    240

accactccct atcagtgata gagaaaagtg aaagtcgagt ttaccactcc ctatcagtga    300

tagagaaaag tgaaagtcga gctcgccatg ggaggcgtgg cctgggcggg actggggagt    360
```

ggcgagccct cagatcctgc atataagcag ctgcttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840
aacatatagt atgggcaagc agggagctag aacgattcgc agttaatact ggcctgttag 900
aaacatcaga aggctgtaga caaatactgg gacagctaca accatccctt cagacaggat 960
cagaagaact tagatcatta tataatacag tagcaaccct ctattgtgtg catcaaagga 1020
tagagataaa agacaccaag gaagctttag acaagataga ggaagagcaa aacaaaagta 1080
agaaaaaagc acagcaagca gcaggatctt cagacctgga aattccctac aatccccaaa 1140
gtcaaggagt agtagaatct atgaataaag aattaaagaa aattatagga caggtaagag 1200
atcaggctga acatcttaag acagcagtac aaatggcagt attcatccac aattttaaaa 1260
gaaaaggggg gattgggggg tacagtgcag gggaaagaat agtagacata atagcaacag 1320
acatacaaac taaagaatta caaaaacaaa ttacaaaaat tcaaaatttt cgggtttatt 1380
acagggacag cagaaatcca ctttggaaag gaccagcaaa gctcctctgg aaaggtgaag 1440
gggcagtagt aatacaagat aatagtgaca taaaagtagt gccaagaaga aaagcaaaga 1500
tcattaggga ttatggaaaa cagatggcag gtgatgattg tgtggcaagt agacaggatg 1560
aggattagaa catggaaaag tttagtaaaa caccataagg aggagatatg agggacaatt 1620
ggagaagtga attatataaa tataaagtag taaaaattga accattagga gtagcaccca 1680
ccaaggcaaa gagaagagtg gtgcagagag aaaaaagagc agtgggaata ggagctttgt 1740
tccttgggtt cttgggagca gcaggaagca ctatgggcgc agcgtcaatg acgctgacgg 1800
tacaggccag acaattattg tctggtatag tgcagcagca gaacaatttg ctgagggcta 1860
ttgaggcgca acagcatctg ttgcaactca cagtctgggg catcaagcag ctccaggcaa 1920
gaatcctggc tgtggaaaga tacctaaagg atcaacagct cctggggatt tggggttgct 1980
ctggaaaact catttgcacc actgctgtgc cttggaatgc tagttggagt aataaatctc 2040
tggaacagat ttggaatcac acgacctgga tggagtggga cagagaaatt aacaattaca 2100
caagcttaat acactcctta attgaagaat cgcaaaacca gcaagaaaag aatgaacaag 2160
aattattgga attagataaa tgggcaagtt tgtggaattg gtttaacata acaaattggc 2220
tgtggtatat aaaattattc ataatgatag taggaggctt ggtaggttta agaatagttt 2280
ttgctgtact ttctatagtg aatagagtta ggcagggata ttcaccatta tcgtttcaga 2340
cccacctccc aaccccgagg ggaccgagct caagcttcga agcggccgca tcgacgtgca 2400
gtatttagca tgccccaccc atctgcaagg cattctggat agtgtcaaaa cagccggaaa 2460
tcaagtccgt ttatctcaaa ctttagcatt ttgggaataa atgatatttg ctatgctggt 2520
taaattagat tttagttaaa tttcctgctg aagctctagt acgataagta acttgaccta 2580
agtgtaaagt tgagatttcc ttcaggttta tatagcttgt gcgccgcctg ggtacctcag 2640
gatatgccct tgactatttg tccgacatag tcaagggcat atcctttttt gtacgcgtgg 2700

-continued

```
ggatcctcta gagtcgagct cgcgaggatc atcaccggtg ctagccggag ccagaagcac   2760
cataagggac atgataaggg agccagcaga cctctgatct cttcctgaat gctaatctta   2820
aacatcctga ggaagaatgg gacttccatt tggggtgggc ctatgatagg gtaataagac   2880
agtagtgaat atcaagctac aaaaagcccc ctttcaaatt cttctcagtc ctaacttttc   2940
atactaagcc cagtccttcc aaagcagact gtgaaagagt gatagttccg ggagactagc   3000
accggctagc cgagcttgga acactttccc ttcattaaga accatccttg ctactcagct   3060
gcaatcaatc cagcccccag gtcttcactg aaccttttcc catctcttcc aaaacatctg   3120
tttctgagaa gtcctgtcct atagaggtct ttcttcccac cggatttctc ctacaccatt   3180
tactcccact tgcagaactc ccgtgtacaa gtgtctttac tgcttttatt tgctcaacaa   3240
aatgcacatc tcatataaaa ataaatgagg agcatgcaca caccacaaac acaaacaggc   3300
atgcagaaat acacatacac acttccctca atataaaccc tttgtggctc atatatttaa   3360
aaagatgtaa aaaaaagagc tgaagaaaat catgtgtgat ctctcagcag aatagattta   3420
ttatttgtat tgcttgcaga ataaagccta tccttgaaag ctctgaatca tgggcaagag   3480
gctcagtggt atctggagga cagggcactg gccactgcag tcaccatctt ctgccaggaa   3540
gcctgcacct caggggtgaa ttctttgcca aagtgaatgg ccagcacggt gaccagcacg   3600
ttgcccagga gctgtgggag gaagataaga ggtatgaaca tgattagcaa aagggcctag   3660
cttggactca gaataatcca gccttatccc aaccataaaa taaaagcaga atggtagctg   3720
gattgtagct gctattagca atatgaaacc tcttacatca gttacaattt atatgcagaa   3780
atatttatat gcagaaatat tgctattgcc ttaacccaga aattatcact gttattcttt   3840
agaatggtgc aaagaggcat gatacattgt atcattattg ccctgaaaga aagagattag   3900
ggaaagtatt agaaataaga taaacaaaaa agtatattaa aagaagaaag catttttaa    3960
aattacaaat gcaaaattac cctgatttgg tcaatatgtg taccctgtta cttctcccct   4020
tcctatgaca tgaacttaac catagaaaag aaggggaaag aaaacatcaa gggtcccata   4080
gactcacctt gaagttctca ggatccacat gcagcttgtc acagtgcagt tcactcagct   4140
gggcaaaggt gcccttgaga tcatccaggt gctttatggc atctcccaag gaagtcagca   4200
ccttcttgcc atgtgccttg actttggggt tgcccatgat ggcagaggca gaggacaggt   4260
tgccaaagct gtcaaagaac ctctgggtcc atgggtagac aaccaggagc ctgtgagatt   4320
gacaagaaca gtttgacagt cagaaggtgc cacaaatcct gagaagcaac ctggactttt   4380
gccaggcaca gggtccttcc ttccctccct tgtcctggtc accagagcct accttcccag   4440
ggtttctcct ccagcatctt ccacattcac cttgtcccac aggcttgtga tagtagcctt   4500
gtcctcctct gtgaaatgac ccatggtgtc tgtttgaggt tgctagtgaa cacagttgtg   4560
tcagaagcaa atgtaagcaa tagatggctc tgccctgact tttatgccca gccctggctc   4620
ctgccctccc tgctcctggg agtagattgg ccaaccctag ggtgtggctc cacagggtga   4680
ggtctaagtg atgacagccg tacctgtcct tggctcttct ggcactggct taggagttgg   4740
acttcaaacc ctcagccctc cctctaagat atatctcttg gccccatacc atcagtacaa   4800
attgctacta aaaacatcct cctttgcaag tgtatttacg acggtatcga tgtatgtgag   4860
catgtgtcct ctaacagcac aggccttttg ccacctagct gtccaggggt gccttaaaat   4920
ggcaaacaag gtttgttttc ttttcctgtt ttcatgcctt cctcttccat atccttgttt   4980
catattaata catgtgtata gatcctaaaa atctatacac atgtattaat aaagcctgat   5040
tctgccgctt ctaggtatag aggccacctg caagataaat atttgattca caataactaa   5100
```

tcattctatg gcaattgata acaacaaata tatatatata tatatatata cgtatatgtg 5160
tatatatata tatatattca ggaaataata tattctagaa tatgtcacat tctgtctcag 5220
gcatccattt tctttatgat gccgtttgag gtggagtttt agtcaggtgg tcagcttctc 5280
cttttttttg ccatctgccc tgtaagcatc ctgctgggga cccagatagg agtcatcact 5340
ctaggctgag aacatctggg cacacaccct aagcctcagc atgactcatc atgactcagc 5400
attgctgtgc ttgagccaga aggtttgctt agaaggttac acagaaccag aaggcggggg 5460
tggggcactg accccgacag gggcctggcc agaactgctc atgcttggac tatgggaggt 5520
cactaatgga gacacacaga aatgtaacag gaactaaggg aattccggtg ccctgcttag 5580
gagcttaatc tttaatgaaa gctaagcttt cattaaaaaa agtctaacca gctgcattcg 5640
actttgactg cagcagctgg ttagaaggtt ctactggagg agggtcccag cccattgcta 5700
aattaacatc aggctctgag actggcagta tatctctaac agtggttgat gctatcttct 5760
ggaacttgcc tgctacattg agaccactga cccatacata ggaagcccat agctctgtcc 5820
tgaactgtta ggccactggt ccagagagtg tgcatctcct ttgatcctca taataaccct 5880
atgagataga cacaattatt actcttactt tatagatgat gatcctgaaa acataggagt 5940
caaggcactt gcccctagct gggggtatag gggagcagtc ccatgtagta gtagaatgaa 6000
aaatgctgct atgctgtgcc tcccccacct ttcccatgtc tgccctctac tcatggtcta 6060
tctctcctgg ctcctgggag tcatggactc cacccagcac caccaacctg acctaaccac 6120
ctatctgagc ctgccagcct ataacccatc tgggccctga tagctggtgg ccagccctga 6180
ccccacccca ccctccctgg aacctctgat agacacatct ggcacaccag ctcgcaaagt 6240
caccgtgagg gtcttgtgtt tgctgagtca aaattccttg aaatccaagt ccttagagac 6300
tcctgctccc aaatttacag tcatagactt cttcatggct gtctccttta tccacagaat 6360
gattcctttg cttcattgcc ccatccatct gatcctcctc atcagtgcag cacagggccc 6420
atgagcagta gctgcagagt ctcacatagg tctggcactg cctctgacat gtccgacctt 6480
aggcaaatgc ttgactcttc tgagctcgga tcccttgagc tcaggaggtc aaggctgcag 6540
tgagacatga tcttgccact gcactccagc ctggacagca gagtgaaacc ttgcctcacg 6600
aaacagaata caaaaacaaa caaacaaaaa actgctccgc aatgcgcttc cttgatgctc 6660
taccacatag gtctgggtac tttgtacaca ttatctcatt gctgttcata attgttagat 6720
taattttgta atattgatat tattcctaga aagctgaggc ctcaagatga taacttttat 6780
tttctggact tgtaatagct ttctcttgta ttcaccatgt tgtaactttc ttagagtagt 6840
aacaatataa agttattgtg agtttttgca aacacagcaa acacaacgac ccatatagac 6900
attgatgtga aattgtctat tgtcaattta tgggaaaaca agtatgtact ttttctacta 6960
agccattgaa acaggaataa cagaacaaga ttgaaagaat acattttccg aaattacttg 7020
agtattatac aaagacaagc acgtggacct gggaggaggg ttattgtcca tgactggtgt 7080
gtggagacaa atgcaggttt ataatagatg ggatggcatc tagcgcaatg actttgccat 7140
cacttttaga gagctcttgg gggccccagt acacaagagg ggacgcaggg tatatgtaga 7200
catctcattc tttttcttag tgtgagaata agaatagcca tgacctgagt ttatagacaa 7260
tgagcccttt tctctctccc actcagcagc tatgagatgg cttgccctgc ctctctacta 7320
ggctgactca ctccaaggcc cagcaatggg cagggctctg tcagggcttt gatagcacta 7380
tctgcagagc cagggccgag aaggggtgga ctccagagac tctccctccc attcccgagc 7440

-continued

```
agggtttgct tatttatgca tttaaatgat atatttattt taaaagaaat aacaggagac   7500
tgcccagccc tggctgtgac atggaaacta tgtagaatat tttgggttcc attttttttt   7560
ccttctttca gttagaggaa aaggggctca ctgcacatac actagacaga aagtcaggag   7620
ctttgaatcc aagcctgatc atttccatgt catactgaga aagtccccac ccttctctga   7680
gcctcagttt ctctttttat aagtaggagt ctggagtaaa tgatttccaa tggctctcat   7740
ttcaatacaa aatttccgtt tattaaatgc atgagcttcc gttactccaa gactgagaag   7800
gaaattgaac ctgagactca ttgactggca agatgtcccc agaggctctc attcagcaat   7860
aaaattctca ccttcaccca ggcccactag tgtcagattt gcatgcgtta acgcggccgc   7920
atcgatgccg tagtaccttt aagaccaatg acttacaagg cagctgtaga tcttagccac   7980
tttttaaaag aaaagggggg actggaaggg ctaattcact cccaaagaag acaagataga   8040
tctgcttttt gcctgtactg ggtctctctg gttagaccag atctgagcct gggagctctc   8100
tggctaacta gggaacccac tgcttaagcc tcaataaagc ttcagctgct cgagctagca   8160
gatctttttc cctctgccaa aaattatggg gacatcatga agccccttga gcatctgact   8220
tctggctaat aaaggaaatt tattttcatt gcaatagtgt gttggaattt tttgtgtctc   8280
tcactcggaa ggacatatgg gagggcaaat catttaaaac atcagaatga gtatttggtt   8340
tagagtttgg caacatatgc ccatatgctg gctgccatga acaaaggttg gctataaaga   8400
ggtcatcagt atatgaaaca gccccctgct gtccattcct tattccatag aaaagccttg   8460
acttgaggtt agattttttt tatattttgt tttgtgttat ttttttcttt aacatcccta   8520
aaattttcct tacatgtttt actagccaga tttttcctcc tctcctgact actcccagtc   8580
atagctgtcc ctcttctctt atggagatcc ctcgacctgc agcccaagct tggcgtaatc   8640
atggtcatag ctgtttcctg tgtgaaattg ttatccgctc acaattccac acaacatacg   8700
agccggaagc ataaagtgta aagcctgggg tgcctaatga gtgagctaac tcacattaat   8760
tgcgttgcgc tcactgcccg ctttccagtc gggaaacctg tcgtgccagc ggatccgcat   8820
ctcaattagt cagcaaccat agtcccgccc ctaactccgc ccatcccgcc cctaactccg   8880
cccagttccg cccattctcc gccccatggc tgactaattt ttttatttta tgcagaggcc   8940
gaggccgcct cggcctctga gctattccag aagtagtgag gaggcttttt tggaggccta   9000
ggcttttgca aaaagctgtc gactgcagag gcctgcatgc aagcttggcg taatcatggt   9060
catagctgtt tcctgtgtga aattgttatc cgctcacaat tccacacaac atacgagccg   9120
gaagcataaa gtgtaaagcc tggggtgcct aatgagtgag ctaactcaca ttaattgcgt   9180
tgcgctcact gcccgctttc cagtcgggaa acctgtcgtg ccagctgcat taatgaatcg   9240
gccaacgcgc ggggagaggc ggtttgcgta ttgggcgctc ttccgcttcc tcgctcactg   9300
actcgctgcg ctcggtcgtt cggctgcggc gagcggtatc agctcactca aaggcggtaa   9360
tacggttatc cacagaatca ggggataacg caggaaagaa catgtgagca aaaggccagc   9420
aaaaggccag gaaccgtaaa aaggccgcgt tgctggcgtt tttccatagg ctccgccccc   9480
ctgacgagca tcacaaaaat cgacgctcaa gtcagaggtg gcgaaacccg acaggactat   9540
aaagatacca ggcgtttccc cctggaagct ccctcgtgcg ctctcctgtt ccgaccctgc   9600
cgcttaccgg atacctgtcc gcctttctcc cttcgggaag cgtggcgctt tctcatagct   9660
cacgctgtag gtatctcagt tcggtgtagg tcgttcgctc caagctgggc tgtgtgcacg   9720
aaccccccgt tcagcccgac cgctgcgcct tatccggtaa ctatcgtctt gagtccaacc   9780
cggtaagaca cgacttatcg ccactggcag cagccactgg taacaggatt agcagagcga   9840
```

ggtatgtagg cggtgctaca gagttcttga agtggtggcc taactacggc tacactagaa 9900
gaacagtatt tggtatctgc gctctgctga agccagttac cttcggaaaa agagttggta 9960
gctcttgatc cggcaaacaa accaccgctg gtagcggtgg tttttttgtt tgcaagcagc 10020
agattacgcg cagaaaaaaa ggatctcaag aagatccttt gatcttttct acggggtctg 10080
acgctcagtg gaacgaaaac tcacgttaag ggattttggt catgagatta tcaaaaagga 10140
tcttcaccta gatcctttta aattaaaaat gaagttttaa atcaatctaa agtatatatg 10200
agtaaacttg gtctgacagt taccaatgct taatcagtga ggcacctatc tcagcgatct 10260
gtctatttcg ttcatccata gttgcctgac tccccgtcgt gtagataact acgatacggg 10320
agggcttacc atctggcccc agtgctgcaa tgataccgcg agacccacgc tcaccggctc 10380
cagatttatc agcaataaac cagccagccg gaagggccga gcgcagaagt ggtcctgcaa 10440
ctttatccgc ctccatccag tctattaatt gttgccggga agctagagta agtagttcgc 10500
cagttaatag tttgcgcaac gttgttgcca ttgctacagg catcgtggtg tcacgctcgt 10560
cgtttggtat ggcttcattc agctccggtt cccaacgatc aaggcgagtt acatgatccc 10620
ccatgttgtg caaaaaagcg gttagctcct tcggtcctcc gatcgttgtc agaagtaagt 10680
tggccgcagt gttatcactc atggttatgg cagcactgca taattctctt actgtcatgc 10740
catccgtaag atgcttttct gtgactggtg agtactcaac caagtcattc tgagaatagt 10800
gtatgcggcg accgagttgc tcttgcccgg cgtcaatacg ggataatacc gcgccacata 10860
gcagaacttt aaaagtgctc atcattggaa aacgttcttc ggggcgaaaa ctctcaagga 10920
tcttaccgct gttgagatcc agttcgatgt aacccactcg tgcacccaac tgatcttcag 10980
catcttttac tttcaccagc gtttctgggt gagcaaaaac aggaaggcaa aatgccgcaa 11040
aaaagggaat aagggcgaca cggaaatgtt gaatactcat actcttcctt tttcaatatt 11100
attgaagcat ttatcagggt tattgtctca tgagcggata catatttgaa tgtatttaga 11160
aaaataaaca aataggggtt ccgcgcacat ttccccgaaa agtgccacct gacgtctaag 11220
aaaccattat tatcatgaca ttaacctata aaaataggcg tatcacgagg ccctttcgtc 11280
tcgcgcgttt cggtgatgac ggtgaaaacc tctgacacat gcagctcccg gagacggtca 11340
cagcttgtct gtaagcggat gccgggagca gacaagcccg tcagggcgcg tcagcgggtg 11400
ttggcgggtg tcggggctgg cttaactatg cggcatcaga gcagattgta ctgagagtgc 11460
accatatgcg gtgtgaaata ccgcacagat gcgtaaggag aaaataccgc atcaggcgcc 11520
attcgccatt caggctgcgc aactgttggg aagggcgatc ggtgcgggcc tcttcgctat 11580
tacgccagct ggcgaaaggg ggatgtgctg caaggcgatt aagttgggta acgccagggt 11640
tttcccagtc acgacgttgt aaaacgacgg ccagtgaatt c 11681

<210> SEQ ID NO 16
<211> LENGTH: 11678
<212> TYPE: DNA
<213> ORGANISM: Artificial Sequence
<220> FEATURE:
<223> OTHER INFORMATION: Synthetic: TL20d-r7SKM1/sh734-rGbGM

<400> SEQUENCE: 16
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840
aacatatagt atgggcaagc agggagctag aacgattcgc agttaatact ggcctgttag 900
aaacatcaga aggctgtaga caaatactgg gacagctaca accatccctt cagacaggat 960
cagaagaact tagatcatta tataatacag tagcaaccct ctattgtgtg catcaaagga 1020
tagagataaa agacaccaag gaagctttag acaagataga ggaagagcaa aacaaaagta 1080
agaaaaaagc acagcaagca gcaggatctt cagacctgga aattccctac aatccccaaa 1140
gtcaaggagt agtagaatct atgaataaag aattaaagaa aattatagga caggtaagag 1200
atcaggctga acatcttaag acagcagtac aaatggcagt attcatccac aattttaaaa 1260
gaaaaggggg gattgggggg tacagtgcag gggaaagaat agtagacata atagcaacag 1320
acatacaaac taaagaatta caaaaacaaa ttacaaaaat tcaaaatttt cgggtttatt 1380
acagggacag cagaaatcca ctttggaaag gaccagcaaa gctcctctgg aaaggtgaag 1440
gggcagtagt aatacaagat aatagtgaca taaaagtagt gccaagaaga aaagcaaaga 1500
tcattaggga ttatggaaaa cagatggcag gtgatgattg tgtggcaagt agacaggatg 1560
aggattagaa catggaaaag tttagtaaaa caccataagg aggagatatg agggacaatt 1620
ggagaagtga attatataaa tataaagtag taaaaattga accattagga gtagcaccca 1680
ccaaggcaaa gagaagagtg gtgcagagag aaaaaagagc agtgggaata ggagctttgt 1740
tccttgggtt cttgggagca gcaggaagca ctatgggcgc agcgtcaatg acgctgacgg 1800
tacaggccag acaattattg tctggtatag tgcagcagca gaacaatttg ctgagggcta 1860
ttgaggcgca acagcatctg ttgcaactca cagtctgggg catcaagcag ctccaggcaa 1920
gaatcctggc tgtggaaaga tacctaaagg atcaacagct cctggggatt tggggttgct 1980
ctggaaaact catttgcacc actgctgtgc cttggaatgc tagttggagt aataaatctc 2040
tggaacagat ttggaatcac acgacctgga tggagtggga cagagaaatt aacaattaca 2100
caagcttaat acactcctta attgaagaat cgcaaaacca gcaagaaaag aatgaacaag 2160
aattattgga attagataaa tgggcaagtt tgtggaattg gtttaacata acaaattggc 2220
tgtggtatat aaaattattc ataatgatag taggaggctt ggtaggttta agaatagttt 2280
ttgctgtact ttctatagtg aatagagtta ggcagggata ttcaccatta tcgtttcaga 2340
cccacctccc aaccccgagg ggacccgacagg ccaagcttcga agcggccgca aaaaaggata 2400
tgcccttgac tatgtcggac aaatagtcaa gggcatatcc tgaggtaccc aggcggcgca 2460
caagctatat aaacctgaag gaaatctcaa ctttacactt aggtcaagtt acttatcgta 2520
ctagagcttc agcaggaaat ttaactaaaa tctaatttaa ccagcatagc aaatatcatt 2580

```
tattcccaaa atgctaaagt ttgagataaa cggacttgat ttccggctgt tttgacacta   2640
tccagaatgc cggtactatg ggtggggcag tagcccgact gcacgtcgaa cgcgtgggga   2700
tcctctagag tcgagctcgc gaggatcatc accggtgcta gccggagcca gaagcaccat   2760
aagggacatg ataagggagc cagcagacct ctgatctctt cctgaatgct aatcttaaac   2820
atcctgagga agaatgggac ttccatttgg ggtgggccta tgatagggta ataagacagt   2880
agtgaatatc aagctacaaa aagcccccctt tcaaattctt ctcagtccta acttttcata   2940
ctaagcccag tccttccaaa gcagactgtg aaagagtgat agttccggga gactagcacc   3000
ggctagccga gcttggaaca ctttcccttc attaagaacc atccttgcta ctcagctgca   3060
atcaatccag cccccaggtc ttcactgaac cttttcccat ctcttccaaa acatctgttt   3120
ctgagaagtc ctgtcctata gaggtctttc ttcccaccgg atttctccta caccatttac   3180
tcccacttgc agaactcccg tgtacaagtg tctttactgc ttttatttgc tcaacaaaat   3240
gcacatctca tataaaaata aatgaggagc atgcacacac cacaaacaca aacaggcatg   3300
cagaaataca catacacact tccctcaata taaacccttt gtggctcata tatttaaaaa   3360
gatgtaaaaa aaagagctga agaaaatcat gtgtgatctc tcagcagaat agatttatta   3420
tttgtattgc ttgcagaata aagcctatcc ttgaaagctc tgaatcatgg gcaagaggct   3480
cagtggtatc tggaggacag ggcactggcc actgcagtca ccatcttctg ccaggaagcc   3540
tgcacctcag gggtgaattc tttgccaaag tgaatggcca gcacggtgac cagcacgttg   3600
cccaggagct gtgggaggaa gataagaggt atgaacatga ttagcaaaag ggcctagctt   3660
ggactcagaa taatccagcc ttatcccaac cataaaataa aagcagaatg gtagctggat   3720
tgtagctgct attagcaata tgaaacctct tacatcagtt acaatttata tgcagaaata   3780
tttatatgca gaaatattgc tattgcctta acccagaaat tatcactgtt attctttaga   3840
atggtgcaaa gaggcatgat acattgtatc attattgccc tgaaagaaag agattaggga   3900
aagtattaga aataagataa acaaaaaagt atattaaaag aagaaagcat tttttaaaat   3960
tacaaatgca aaattaccct gatttggtca atatgtgtac cctgttactt ctccccttcc   4020
tatgacatga acttaaccat agaaaagaag gggaaagaaa acatcaaggg tcccatagac   4080
tcaccttgaa gttctcagga tccacatgca gcttgtcaca gtgcagttca ctcagctggg   4140
caaaggtgcc cttgagatca tccaggtgct ttatggcatc tcccaaggaa gtcagcacct   4200
tcttgccatg tgccttgact ttggggttgc ccatgatggc agaggcagag gacaggttgc   4260
caaagctgtc aaagaacctc tgggtccatg ggtagacaac caggagcctg tgagattgac   4320
aagaacagtt tgacagtcag aaggtgccac aaatcctgag aagcaacctg gacttttgcc   4380
aggcacaggg tccttccttc cctcccttgt cctggtcacc agagcctacc ttcccagggt   4440
ttctcctcca gcatcttcca cattcacctt gtcccacagg cttgtgatag tagccttgtc   4500
ctcctctgtg aaatgaccca tggtgtctgt ttgaggttgc tagtgaacac agttgtgtca   4560
gaagcaaatg taagcaatag atggctctgc cctgactttt atgcccagcc ctggctcctg   4620
ccctccctgc tcctgggagt agattggcca accctagggt gtggctccac agggtgaggt   4680
ctaagtgatg acagccgtac ctgtccttgg ctcttctggc actggcttag gagttggact   4740
tcaaaccctc agccctccct ctaagatata tctcttggcc ccataccatc agtacaaatt   4800
gctactaaaa acatcctcct ttgcaagtgt atttacgacg gtatcgatgt atgtgagcat   4860
gtgtcctcta acagcacagg ccttttgcca cctagctgtc caggggtgcc ttaaaatggc   4920
```

-continued

```
aaacaaggtt tgttttcttt tcctgttttc atgccttcct cttccatatc cttgtttcat   4980
attaatacat gtgtatagat cctaaaaatc tatacacatg tattaataaa gcctgattct   5040
gccgcttcta ggtatagagg ccacctgcaa gataaatatt tgattcacaa taactaatca   5100
ttctatggca attgataaca acaaatatat atatatatat atatatacgt atatgtgtat   5160
atatatatat atattcagga aataatatat tctagaatat gtcacattct gtctcaggca   5220
tccattttct ttatgatgcc gtttgaggtg gagttttagt caggtggtca gcttctcctt   5280
ttttttgcca tctgccctgt aagcatcctg ctggggaccc agataggagt catcactcta   5340
ggctgagaac atctgggcac acaccctaag cctcagcatg actcatcatg actcagcatt   5400
gctgtgcttg agccagaagg tttgcttaga aggttacaca gaaccagaag gcgggggtgg   5460
ggcactgacc ccgacagggg cctggccaga actgctcatg cttggactat gggaggtcac   5520
taatggagac acacagaaat gtaacaggaa ctaagggaat tccggtgccc tgcttaggag   5580
cttaatcttt aatgaaagct aagctttcat taaaaaaagt ctaaccagct gcattcgact   5640
ttgactgcag cagctggtta gaaggttcta ctggaggagg gtcccagccc attgctaaat   5700
taacatcagg ctctgagact ggcagtatat ctctaacagt ggttgatgct atcttctgga   5760
acttgcctgc tacattgaga ccactgaccc atacatagga agcccatagc tctgtcctga   5820
actgttaggc cactggtcca gagagtgtgc atctcctttg atcctcataa taaccctatg   5880
agatagacac aattattact cttactttat agatgatgat cctgaaaaca taggagtcaa   5940
ggcacttgcc cctagctggg ggtatagggg agcagtccca tgtagtagta gaatgaaaaa   6000
tgctgctatg ctgtgcctcc cccacctttc ccatgtctgc cctctactca tggtctatct   6060
ctcctggctc ctgggagtca tggactccac ccagcaccac caacctgacc taaccaccta   6120
tctgagcctg ccagcctata acccatctgg gccctgatag ctggtggcca gccctgaccc   6180
caccccaccc tccctggaac ctctgataga cacatctggc acaccagctc gcaaagtcac   6240
cgtgagggtc ttgtgtttgc tgagtcaaaa ttccttgaaa tccaagtcct tagagactcc   6300
tgctcccaaa tttacagtca tagacttctt catggctgtc tcctttatcc acagaatgat   6360
tcctttgctt cattgcccca tccatctgat cctcctcatc agtgcagcac agggcccatg   6420
agcagtagct gcagagtctc acataggtct ggcactgcct ctgacatgtc cgaccttagg   6480
caaatgcttg actcttctga gctcggatcc cttgagctca ggaggtcaag gctgcagtga   6540
gacatgatct tgccactgca ctccagcctg gacagcagag tgaaaccttg cctcacgaaa   6600
cagaatacaa aaacaaacaa acaaaaaaact gctccgcaat gcgcttcctt gatgctctac   6660
cacataggtc tgggtacttt gtacacatta tctcattgct gttcataatt gttagattaa   6720
ttttgtaata ttgatattat tcctagaaag ctgaggcctc aagatgataa cttttatttt   6780
ctggacttgt aatagctttc tcttgtattc accatgttgt aactttctta gagtagtaac   6840
aatataaagt tattgtgagt ttttgcaaac acagcaaaca caacgaccca tatagacatt   6900
gatgtgaaat tgtctattgt caatttatgg gaaaacaagt atgtactttt tctactaagc   6960
cattgaaaca ggaataacag aacaagattg aaagaataca ttttccgaaa ttacttgagt   7020
attatacaaa gacaagcacg tggacctggg aggagggtta ttgtccatga ctggtgtgtg   7080
gagacaaatg caggtttata atagatggga tggcatctag cgcaatgact ttgccatcac   7140
ttttagagag ctcttggggg ccccagtaca caagagggga cgcagggtat atgtagacat   7200
ctcattcttt ttcttagtgt gagaataaga atagccatga cctgagttta tagacaatga   7260
gcccttttct ctctcccact cagcagctat gagatggctt gccctgcctc tctactaggc   7320
```

```
tgactcactc caaggcccag caatgggcag ggctctgtca gggctttgat agcactatct   7380
gcagagccag ggccgagaag gggtggactc cagagactct ccctcccatt cccgagcagg   7440
gtttgcttat ttatgcattt aaatgatata tttattttaa aagaaataac aggagactgc   7500
ccagccctgg ctgtgacatg gaaactatgt agaatatttt gggttccatt tttttttcct   7560
tctttcagtt agaggaaaag gggctcactg cacatacact agacagaaag tcaggagctt   7620
tgaatccaag cctgatcatt tccatgtcat actgagaaag tccccaccct tctctgagcc   7680
tcagtttctc tttttataag taggagtctg gagtaaatga tttccaatgg ctctcatttc   7740
aatacaaaat ttccgtttat taaatgcatg agcttccgtt actccaagac tgagaaggaa   7800
attgaacctg agactcattg actggcaaga tgtccccaga ggctctcatt cagcaataaa   7860
attctcacct tcacccaggc ccactagtgt cagatttgca tgcgttaacg cggccgcatc   7920
gatgccgtag tacctttaag accaatgact tacaaggcag ctgtagatct tagccacttt   7980
ttaaaagaaa aggggggact ggaagggcta attcactccc aaagaagaca agatagatct   8040
gctttttgcc tgtactgggt ctctctggtt agaccagatc tgagcctggg agctctctgg   8100
ctaactaggg aacccactgc ttaagcctca ataaagcttc agctgctcga gctagcagat   8160
ctttttccct ctgccaaaaa ttatggggac atcatgaagc cccttgagca tctgacttct   8220
ggctaataaa ggaaatttat tttcattgca atagtgtgtt ggaatttttt gtgtctctca   8280
ctcggaagga catatgggag ggcaaatcat ttaaaacatc agaatgagta tttggtttag   8340
agtttggcaa catatgccca tatgctggct gccatgaaca aaggttggct ataaagaggt   8400
catcagtata tgaaacagcc ccctgctgtc cattccttat tccatagaaa agccttgact   8460
tgaggttaga ttttttttat attttgtttt gtgttatttt tttctttaac atccctaaaa   8520
ttttccttac atgttttact agccagattt ttcctcctct cctgactact cccagtcata   8580
gctgtccctc ttctcttatg gagatccctc gacctgcagc ccaagcttgg cgtaatcatg   8640
gtcatagctg tttcctgtgt gaaattgtta tccgctcaca attccacaca acatacgagc   8700
cggaagcata aagtgtaaag cctggggtgc ctaatgagtg agctaactca cattaattgc   8760
gttgcgctca ctgcccgctt tccagtcggg aaacctgtcg tgccagcgga tccgcatctc   8820
aattagtcag caaccatagt cccgccccta actccgccca tcccgcccct aactccgccc   8880
agttccgccc attctccgcc ccatggctga ctaatttttt ttatttatgc agaggccgag   8940
gccgcctcgg cctctgagct attccagaag tagtgaggag gcttttttgg aggcctaggc   9000
ttttgcaaaa agctgtcgac tgcagaggcc tgcatgcaag cttggcgtaa tcatggtcat   9060
agctgtttcc tgtgtgaaat tgttatccgc tcacaattcc acacaacata cgagccggaa   9120
gcataaagtg taaagcctgg ggtgcctaat gagtgagcta actcacatta attgcgttgc   9180
gctcactgcc cgctttccag tcgggaaacc tgtcgtgcca gctgcattaa tgaatcggcc   9240
aacgcgcggg gagaggcggt ttgcgtattg ggcgctcttc cgcttcctcg ctcactgact   9300
cgctgcgctc ggtcgttcgg ctgcggcgag cggtatcagc tcactcaaag gcggtaatac   9360
ggttatccac agaatcaggg gataacgcag gaaagaacat gtgagcaaaa ggccagcaaa   9420
aggccaggaa ccgtaaaaag gccgcgttgc tggcgttttt ccataggctc cgcccccctg   9480
acgagcatca caaaaatcga cgctcaagtc agaggtggcg aaacccgaca ggactataaa   9540
gataccaggc gtttccccct ggaagctccc tcgtgcgctc tcctgttccg accctgccgc   9600
ttaccggata cctgtccgcc tttctccctt cgggaagcgt ggcgctttct catagctcac   9660
```

```
gctgtaggta tctcagttcg gtgtaggtcg ttcgctccaa gctgggctgt gtgcacgaac   9720
cccccgttca gcccgaccgc tgcgccttat ccggtaacta tcgtcttgag tccaacccgg   9780
taagacacga cttatcgcca ctggcagcag ccactggtaa caggattagc agagcgaggt   9840
atgtaggcgg tgctacagag ttcttgaagt ggtggcctaa ctacggctac actagaagaa   9900
cagtatttgg tatctgcgct ctgctgaagc cagttacctt cggaaaaaga gttggtagct   9960
cttgatccgg caaacaaacc accgctggta gcggtggttt ttttgtttgc aagcagcaga  10020
ttacgcgcag aaaaaaagga tctcaagaag atcctttgat cttttctacg gggtctgacg  10080
ctcagtggaa cgaaaactca cgttaaggga ttttggtcat gagattatca aaaaggatct  10140
tcacctagat ccttttaaat taaaaatgaa gttttaaatc aatctaaagt atatatgagt  10200
aaacttggtc tgacagttac caatgcttaa tcagtgaggc acctatctca gcgatctgtc  10260
tatttcgttc atccatagtt gcctgactcc ccgtcgtgta gataactacg atacgggagg  10320
gcttaccatc tggccccagt gctgcaatga taccgcgaga cccacgctca ccggctccag  10380
atttatcagc aataaaccag ccagccggaa gggccgagcg cagaagtggt cctgcaactt  10440
tatccgcctc catccagtct attaattgtt gccgggaagc tagagtaagt agttcgccag  10500
ttaatagttt gcgcaacgtt gttgccattg ctacaggcat cgtggtgtca cgctcgtcgt  10560
ttggtatggc ttcattcagc tccggttccc aacgatcaag gcgagttaca tgatccccca  10620
tgttgtgcaa aaaagcggtt agctccttcg gtcctccgat cgttgtcaga agtaagttgg  10680
ccgcagtgtt atcactcatg gttatggcag cactgcataa ttctcttact gtcatgccat  10740
ccgtaagatg cttttctgtg actggtgagt actcaaccaa gtcattctga gaatagtgta  10800
tgcggcgacc gagttgctct tgcccggcgt caatacggga taataccgcg ccacatagca  10860
gaactttaaa agtgctcatc attggaaaac gttcttcggg gcgaaaactc tcaaggatct  10920
taccgctgtt gagatccagt tcgatgtaac ccactcgtgc acccaactga tcttcagcat  10980
cttttacttt caccagcgtt tctgggtgag caaaaacagg aaggcaaaat gccgcaaaaa  11040
agggaataag ggcgacacgg aaatgttgaa tactcatact cttccttttt caatattatt  11100
gaagcattta tcagggttat tgtctcatga gcggatacat atttgaatgt atttagaaaa  11160
ataaacaaat aggggttccg cgcacatttc cccgaaaagt gccacctgac gtctaagaaa  11220
ccattattat catgacatta acctataaaa ataggcgtat cacgaggccc tttcgtctcg  11280
cgcgtttcgg tgatgacggt gaaaacctct gacacatgca gctcccggag acggtcacag  11340
cttgtctgta agcggatgcc gggagcagac aagcccgtca gggcgcgtca gcgggtgttg  11400
gcgggtgtcg gggctggctt aactatgcgg catcagagca gattgtactg agagtgcacc  11460
atatgcggtg tgaaataccg cacagatgcg taaggagaaa ataccgcatc aggcgccatt  11520
cgccattcag gctgcgcaac tgttgggaag ggcgatcggt gcgggcctct tcgctattac  11580
gccagctggc gaaaggggga tgtgctgcaa ggcgattaag ttgggtaacg ccagggtttt  11640
cccagtcacg acgttgtaaa acgacggcca gtgaattc                          11678
```

<210> SEQ ID NO 17
<211> LENGTH: 11681
<212> TYPE: DNA
<213> ORGANISM: Artificial Sequence
<220> FEATURE:
<223> OTHER INFORMATION: Synthetic: TL20d-r7SK/sh734-rGbGM

<400> SEQUENCE: 17

```
ggccgcctcg gccaaacagc ccttgagttt accactccct atcagtgata gagaaaagtg     60
```

```
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgctttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgca caaaaaagga   2400
```

-continued

```
tatgcccttg actatgtcgg acaaatagtc aagggcatat cctgaggtac ccaggcggcg   2460
cacaagctat ataaacctga aggaaatctc aactttacac ttaggtcaag ttacttatcg   2520
tactagagct tcagcaggaa atttaactaa aatctaattt aaccagcata gcaaatatca   2580
tttattccca aaatgctaaa gtttgagata aacggacttg atttccggct gttttgacac   2640
tatccagaat gccttgcaga tgggtggggc atgctaaata ctgcacgtcg atacgcgtgg   2700
ggatcctcta gagtcgagct cgcgaggatc atcaccggtg ctagccggag ccagaagcac   2760
cataagggac atgataaggg agccagcaga cctctgatct cttcctgaat gctaatctta   2820
aacatcctga ggaagaatgg gacttccatt tggggtgggc ctatgatagg gtaataagac   2880
agtagtgaat atcaagctac aaaaagcccc ctttcaaatt cttctcagtc ctaacttttc   2940
atactaagcc cagtccttcc aaagcagact gtgaaagagt gatagttccg ggagactagc   3000
accggctagc cgagcttgga acactttccc ttcattaaga accatccttg ctactcagct   3060
gcaatcaatc cagcccccag gtcttcactg aaccttttcc catctcttcc aaaacatctg   3120
tttctgagaa gtcctgtcct atagaggtct ttcttcccac cggatttctc ctacaccatt   3180
tactcccact tgcagaactc ccgtgtacaa gtgtctttac tgcttttatt tgctcaacaa   3240
aatgcacatc tcatataaaa ataaatgagg agcatgcaca caccacaaac acaaacaggc   3300
atgcagaaat acacatacac acttccctca atataaaccc tttgtggctc atatatttaa   3360
aaagatgtaa aaaaaagagc tgaagaaaat catgtgtgat ctctcagcag aatagattta   3420
ttatttgtat tgcttgcaga ataaagccta tccttgaaag ctctgaatca tgggcaagag   3480
gctcagtggt atctggagga cagggcactg gccactgcag tcaccatctt ctgccaggaa   3540
gcctgcacct caggggtgaa ttctttgcca aagtgaatgg ccagcacggt gaccagcacg   3600
ttgcccagga gctgtgggag gaagataaga ggtatgaaca tgattagcaa aagggcctag   3660
cttggactca gaataatcca gccttatccc aaccataaaa taaaagcaga atggtagctg   3720
gattgtagct gctattagca atatgaaacc tcttacatca gttacaattt atatgcagaa   3780
atatttatat gcagaaatat tgctattgcc ttaacccaga aattatcact gttattcttt   3840
agaatggtgc aaagaggcat gatacattgt atcattattg ccctgaaaga aagagattag   3900
ggaaagtatt agaaataaga taaacaaaaa agtatattaa aagaagaaag catttttttaa   3960
aattacaaat gcaaaattac cctgatttgg tcaatatgtg taccctgtta cttctcccct   4020
tcctatgaca tgaacttaac catagaaaag aaggggaaag aaaacatcaa gggtcccata   4080
gactcacctt gaagttctca ggatccacat gcagcttgtc acagtgcagt tcactcagct   4140
gggcaaaggt gcccttgaga tcatccaggt gctttatggc atctcccaag gaagtcagca   4200
ccttcttgcc atgtgccttg actttggggt tgcccatgat ggcagaggca gaggacaggt   4260
tgccaaagct gtcaaagaac ctctgggtcc atgggtagac aaccaggagc ctgtgagatt   4320
gacaagaaca gtttgacagt cagaaggtgc cacaaatcct gagaagcaac ctggactttt   4380
gccaggcaca gggtccttcc ttccctccct tgtcctggtc accagagcct accttcccag   4440
ggtttctcct ccagcatctt ccacattcac cttgtcccac aggcttgtga tagtagcctt   4500
gtcctcctct gtgaaatgac ccatggtgtc tgtttgaggt tgctagtgaa cacagttgtg   4560
tcagaagcaa atgtaagcaa tagatggctc tgccctgact tttatgccca gccctggctc   4620
ctgccctccc tgctcctggg agtagattgg ccaaccctag ggtgtggctc cacagggtga   4680
ggtctaagtg atgacagccg tacctgtcct tggctcttct ggcactggct taggagttgg   4740
acttcaaacc ctcagccctc cctctaagat atatctcttg gccccatacc atcagtacaa   4800
```

-continued

```
attgctacta aaaacatcct cctttgcaag tgtatttacg acggtatcga tgtatgtgag   4860
catgtgtcct ctaacagcac aggccttttg ccacctagct gtccaggggt gccttaaaat   4920
ggcaaacaag gtttgttttc ttttcctgtt ttcatgcctt cctcttccat atccttgttt   4980
catattaata catgtgtata gatcctaaaa atctatacac atgtattaat aaagcctgat   5040
tctgccgctt ctaggtatag aggccacctg caagataaat atttgattca caataactaa   5100
tcattctatg gcaattgata acaacaaata tatatatata tatatatata cgtatatgtg   5160
tatatatata tatatattca ggaaataata tattctagaa tatgtcacat tctgtctcag   5220
gcatccattt tctttatgat gccgtttgag gtggagtttt agtcaggtgg tcagcttctc   5280
cttttttttg ccatctgccc tgtaagcatc ctgctgggga cccagatagg agtcatcact   5340
ctaggctgag aacatctggg cacacaccct aagcctcagc atgactcatc atgactcagc   5400
attgctgtgc ttgagccaga aggtttgctt agaaggttac acagaaccag aaggcggggg   5460
tggggcactg accccgacag gggcctggcc agaactgctc atgcttggac tatgggaggt   5520
cactaatgga gacacacaga aatgtaacag gaactaaggg aattccggtg ccctgcttag   5580
gagcttaatc tttaatgaaa gctaagcttt cattaaaaaa agtctaacca gctgcattcg   5640
actttgactg cagcagctgg ttagaaggtt ctactggagg agggtcccag cccattgcta   5700
aattaacatc aggctctgag actggcagta tatctctaac agtggttgat gctatcttct   5760
ggaacttgcc tgctacattg agaccactga cccatacata ggaagcccat agctctgtcc   5820
tgaactgtta ggccactggt ccagagagtg tgcatctcct ttgatcctca taataaccct   5880
atgagataga cacaattatt actcttactt tatagatgat gatcctgaaa acataggagt   5940
caaggcactt gcccctagct gggggtatag gggagcagtc ccatgtagta gtagaatgaa   6000
aaatgctgct atgctgtgcc tcccccacct ttcccatgtc tgccctctac tcatggtcta   6060
tctctcctgg ctcctgggag tcatggactc cacccagcac caccaacctg acctaaccac   6120
ctatctgagc ctgccagcct ataacccatc tgggccctga tagctggtgg ccagccctga   6180
ccccacccca ccctccctgg aacctctgat agacacatct ggcacaccag ctcgcaaagt   6240
caccgtgagg gtcttgtgtt tgctgagtca aaattccttg aaatccaagt ccttagagac   6300
tcctgctccc aaatttacag tcatagactt cttcatggct gtctccttta tccacagaat   6360
gattcctttg cttcattgcc ccatccatct gatcctcctc atcagtgcag cacagggccc   6420
atgagcagta gctgcagagt ctcacatagg tctggcactg cctctgacat gtccgacctt   6480
aggcaaatgc ttgactcttc tgagctcgga tcccttgagc tcaggaggtc aaggctgcag   6540
tgagacatga tcttgccact gcactccagc ctggacagca gagtgaaacc ttgcctcacg   6600
aaacagaata caaaaacaaa caaacaaaaa actgctccgc aatgcgcttc cttgatgctc   6660
taccacatag gtctgggtac tttgtacaca ttatctcatt gctgttcata attgttagat   6720
taattttgta atattgatat tattcctaga aagctgaggc ctcaagatga taacttttat   6780
tttctggact tgtaatagct ttctcttgta ttcaccatgt tgtaactttc ttagagtagt   6840
aacaatataa agttattgtg agtttttgca aacacagcaa acacaacgac ccatatagac   6900
attgatgtga aattgtctat tgtcaattta tgggaaaaca agtatgtact ttttctacta   6960
agccattgaa acaggaataa cagaacaaga ttgaaagaat acattttccg aaattacttg   7020
agtattatac aaagacaagc acgtggacct gggaggaggg ttattgtcca tgactggtgt   7080
gtggagacaa atgcaggttt ataatagatg ggatggcatc tagcgcaatg actttgccat   7140
```

-continued

```
cacttttaga gagctcttgg gggccccagt acacaagagg ggacgcaggg tatatgtaga   7200
catctcattc tttttcttag tgtgagaata agaatagcca tgacctgagt ttatagacaa   7260
tgagcccttt tctctctccc actcagcagc tatgagatgg cttgccctgc ctctctacta   7320
ggctgactca ctccaaggcc cagcaatggg cagggctctg tcagggcttt gatagcacta   7380
tctgcagagc cagggccgag aaggggtgga ctccagagac tctccctccc attcccgagc   7440
agggtttgct tatttatgca tttaaatgat atatttattt taaaagaaat aacaggagac   7500
tgcccagccc tggctgtgac atggaaacta tgtagaatat tttgggttcc attttttttt   7560
ccttctttca gttagaggaa aaggggctca ctgcacatac actagacaga aagtcaggag   7620
ctttgaatcc aagcctgatc atttccatgt catactgaga aagtccccac ccttctctga   7680
gcctcagttt ctctttttat aagtaggagt ctggagtaaa tgatttccaa tggctctcat   7740
ttcaatacaa aatttccgtt tattaaatgc atgagcttcc gttactccaa gactgagaag   7800
gaaattgaac ctgagactca ttgactggca agatgtcccc agaggctctc attcagcaat   7860
aaaattctca ccttcaccca ggcccactag tgtcagattt gcatgcgtta acgcggccgc   7920
atcgatgccg tagtaccttt aagaccaatg acttacaagg cagctgtaga tcttagccac   7980
tttttaaaag aaaagggggg actggaaggg ctaattcact cccaaagaag acaagataga   8040
tctgcttttt gcctgtactg ggtctctctg gttagaccag atctgagcct gggagctctc   8100
tggctaacta gggaacccac tgcttaagcc tcaataaagc ttcagctgct cgagctagca   8160
gatctttttc cctctgccaa aaattatggg gacatcatga agccccttga gcatctgact   8220
tctggctaat aaaggaaatt tattttcatt gcaatagtgt gttggaattt tttgtgtctc   8280
tcactcggaa ggacatatgg gagggcaaat catttaaaac atcagaatga gtatttggtt   8340
tagagtttgg caacatatgc ccatatgctg gctgccatga acaaaggttg gctataaaga   8400
ggtcatcagt atatgaaaca gccccctgct gtccattcct tattccatag aaaagccttg   8460
acttgaggtt agattttttt tatattttgt tttgtgttat ttttttcttt aacatcccta   8520
aaattttcct tacatgtttt actagccaga tttttcctcc tctcctgact actcccagtc   8580
atagctgtcc ctcttctctt atggagatcc ctcgacctgc agcccaagct tggcgtaatc   8640
atggtcatag ctgtttcctg tgtgaaattg ttatccgctc acaattccac acaacatacg   8700
agccggaagc ataaagtgta aagcctgggg tgcctaatga gtgagctaac tcacattaat   8760
tgcgttgcgc tcactgcccg ctttccagtc gggaaacctg tcgtgccagc ggatccgcat   8820
ctcaattagt cagcaaccat agtcccgccc ctaactccgc ccatcccgcc cctaactccg   8880
cccagttccg cccattctcc gccccatggc tgactaattt tttttattta tgcagaggcc   8940
gaggccgcct cggcctctga gctattccag aagtagtgag gaggcttttt tggaggccta   9000
ggcttttgca aaaagctgtc gactgcagag gcctgcatgc aagcttggcg taatcatggt   9060
catagctgtt tcctgtgtga aattgttatc cgctcacaat tccacacaac atacgagccg   9120
gaagcataaa gtgtaaagcc tggggtgcct aatgagtgag ctaactcaca ttaattgcgt   9180
tgcgctcact gcccgctttc cagtcgggaa acctgtcgtg ccagctgcat taatgaatcg   9240
gccaacgcgc ggggagaggc ggtttgcgta ttgggcgctc ttccgcttcc tcgctcactg   9300
actcgctgcg ctcggtcgtt cggctgcggc gagcggtatc agctcactca aaggcggtaa   9360
tacggttatc cacagaatca ggggataacg caggaaagaa catgtgagca aaaggccagc   9420
aaaaggccag gaaccgtaaa aaggccgcgt tgctggcgtt tttccatagg ctccgccccc   9480
ctgacgagca tcacaaaaat cgacgctcaa gtcagaggtg gcgaaacccg acaggactat   9540
```

```
aaagatacca ggcgtttccc cctggaagct ccctcgtgcg ctctcctgtt ccgaccctgc   9600
cgcttaccgg atacctgtcc gcctttctcc cttcgggaag cgtggcgctt tctcatagct   9660
cacgctgtag gtatctcagt tcggtgtagg tcgttcgctc caagctgggc tgtgtgcacg   9720
aaccccccgt tcagcccgac cgctgcgcct tatccggtaa ctatcgtctt gagtccaacc   9780
cggtaagaca cgacttatcg ccactggcag cagccactgg taacaggatt agcagagcga   9840
ggtatgtagg cggtgctaca gagttcttga agtggtggcc taactacggc tacactagaa   9900
gaacagtatt tggtatctgc gctctgctga agccagttac cttcggaaaa agagttggta   9960
gctcttgatc cggcaaacaa accaccgctg gtagcggtgg tttttttgtt tgcaagcagc  10020
agattacgcg cagaaaaaaa ggatctcaag aagatccttt gatcttttct acggggtctg  10080
acgctcagtg gaacgaaaac tcacgttaag ggattttggt catgagatta tcaaaaagga  10140
tcttcaccta gatcctttta aattaaaaat gaagttttaa atcaatctaa agtatatatg  10200
agtaaacttg gtctgacagt taccaatgct taatcagtga ggcacctatc tcagcgatct  10260
gtctatttcg ttcatccata gttgcctgac tccccgtcgt gtagataact acgatacggg  10320
agggcttacc atctggcccc agtgctgcaa tgataccgcg agacccacgc tcaccggctc  10380
cagatttatc agcaataaac cagccagccg gaagggccga gcgcagaagt ggtcctgcaa  10440
ctttatccgc ctccatccag tctattaatt gttgccggga agctagagta agtagttcgc  10500
cagttaatag tttgcgcaac gttgttgcca ttgctacagg catcgtggtg tcacgctcgt  10560
cgtttggtat ggcttcattc agctccggtt cccaacgatc aaggcgagtt acatgatccc  10620
ccatgttgtg caaaaaagcg gttagctcct tcggtcctcc gatcgttgtc agaagtaagt  10680
tggccgcagt gttatcactc atggttatgg cagcactgca taattctctt actgtcatgc  10740
catccgtaag atgcttttct gtgactggtg agtactcaac caagtcattc tgagaatagt  10800
gtatgcggcg accgagttgc tcttgcccgg cgtcaatacg ggataatacc gcgccacata  10860
gcagaacttt aaaagtgctc atcattggaa aacgttcttc ggggcgaaaa ctctcaagga  10920
tcttaccgct gttgagatcc agttcgatgt aacccactcg tgcacccaac tgatcttcag  10980
catcttttac tttcaccagc gtttctgggt gagcaaaaac aggaaggcaa aatgccgcaa  11040
aaaagggaat aagggcgaca cggaaatgtt gaatactcat actcttcctt tttcaatatt  11100
attgaagcat ttatcagggt tattgtctca tgagcggata catatttgaa tgtatttaga  11160
aaaataaaca aataggggtt ccgcgcacat ttccccgaaa agtgccacct gacgtctaag  11220
aaaccattat tatcatgaca ttaacctata aaaataggcg tatcacgagg ccctttcgtc  11280
tcgcgcgttt cggtgatgac ggtgaaaacc tctgacacat gcagctcccg gagacggtca  11340
cagcttgtct gtaagcggat gccgggagca gacaagcccg tcagggcgcg tcagcgggtg  11400
ttggcgggtg tcggggctgg cttaactatg cggcatcaga gcagattgta ctgagagtgc  11460
accatatgcg gtgtgaaata ccgcacagat gcgtaaggag aaaataccgc atcaggcgcc  11520
attcgccatt caggctgcgc aactgttggg aagggcgatc ggtgcgggcc tcttcgctat  11580
tacgccagct ggcgaaaggg ggatgtgctg caaggcgatt aagttgggta acgccagggt  11640
tttcccagtc acgacgttgt aaaacgacgg ccagtgaatt c                      11681
```

<210> SEQ ID NO 18
<211> LENGTH: 11369
<212> TYPE: DNA
<213> ORGANISM: Artificial Sequence
<220> FEATURE:

<223> OTHER INFORMATION: Synthetic: TL20d-GbGM

<400> SEQUENCE: 18

```
ggccgcctcg gccaaacagc ccttgagttt accactccct atcagtgata gagaaaagtg     60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgctttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
```

```
ttgctgtact ttctatagtg aatagagtta ggcagggata ttcaccatta tcgtttcaga   2340
cccacctccc aaccccgagg ggaccgagct caagcttcga acgcgtgggg atcctctaga   2400
gtcgagctcg cgaggatcat caccggtgct agccggagcc agaagcacca taagggacat   2460
gataagggag ccagcagacc tctgatctct tcctgaatgc taatcttaaa catcctgagg   2520
aagaatggga cttccatttg ggtgggcct atgatagggt aataagacag tagtgaatat   2580
caagctacaa aaagcccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
aaaagagctg aagaaaatca tgtgtgatct ctcagcagaa tagatttatt atttgtattg   3120
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca ttttttaaaa ttacaaatgc   3660
aaaattaccc tgatttggtc aatatgtgta ccctgttact tctccccttc ctatgacatg   3720
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
```

-continued

```
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
gctctgagac tggcagtata tctctaacag tggttgatgc tatcttctgg aacttgcctg   5460
ctacattgag accactgacc catacatagg aagcccatag ctctgtcctg aactgttagg   5520
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
aggaataaca gaacaagatt gaaagaatac attttccgaa attacttgag tattatacaa   6720
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agccctttttc   6960
tctctcccac tcagcagcta tgagatggct tgccctgcct ctctactagg ctgactcact   7020
```

```
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
gctgtgacat ggaaactatg tagaatattt tgggttccat tttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttaac gcggccgcat cgatgccgta   7620
gtacctttaa gaccaatgac ttacaaggca gctgtagatc ttagccactt tttaaaagaa   7680
aaggggggac tggaagggct aattcactcc caaagaagac aagatagatc tgctttttgc   7740
ctgtactggg tctctctggt tagaccagat ctgagcctgg gagctctctg gctaactagg   7800
gaacccactg cttaagcctc aataaagctt cagctgctcg agctagcaga tctttttccc   7860
tctgccaaaa attatgggga catcatgaag ccccttgagc atctgacttc tggctaataa   7920
aggaaattta ttttcattgc aatagtgtgt tggaattttt tgtgtctctc actcggaagg   7980
acatatggga gggcaaatca tttaaaacat cagaatgagt atttggttta gagtttggca   8040
acatatgccc atatgctggc tgccatgaac aaaggttggc tataaagagg tcatcagtat   8100
atgaaacagc cccctgctgt ccattcctta ttccatagaa aagccttgac ttgaggttag   8160
atttttttta tattttgttt tgtgttattt ttttctttaa catccctaaa attttcctta   8220
catgttttac tagccagatt tttcctcctc tcctgactac tcccagtcat agctgtccct   8280
cttctcttat ggagatccct cgacctgcag cccaagcttg gcgtaatcat ggtcatagct   8340
gtttcctgtg tgaaattgtt atccgctcac aattccacac aacatacgag ccggaagcat   8400
aaagtgtaaa gcctggggtg cctaatgagt gagctaactc acattaattg cgttgcgctc   8460
actgcccgct ttccagtcgg gaaacctgtc gtgccagcgg atccgcatct caattagtca   8520
gcaaccatag tcccgcccct aactccgccc atcccgcccc taactccgcc cagttccgcc   8580
cattctccgc cccatggctg actaattttt tttatttatg cagaggccga ggccgcctcg   8640
gcctctgagc tattccagaa gtagtgagga ggcttttttg gaggcctagg cttttgcaaa   8700
aagctgtcga ctgcagaggc ctgcatgcaa gcttggcgta atcatggtca tagctgtttc   8760
ctgtgtgaaa ttgttatccg ctcacaattc cacacaacat acgagccgga agcataaagt   8820
gtaaagcctg gggtgcctaa tgagtgagct aactcacatt aattgcgttg cgctcactgc   8880
ccgctttcca gtcgggaaac ctgtcgtgcc agctgcatta atgaatcggc caacgcgcgg   8940
ggagaggcgg tttgcgtatt gggcgctctt ccgcttcctc gctcactgac tcgctgcgct   9000
cggtcgttcg gctgcggcga gcggtatcag ctcactcaaa ggcggtaata cggttatcca   9060
cagaatcagg ggataacgca ggaaagaaca tgtgagcaaa aggccagcaa aaggccagga   9120
accgtaaaaa ggccgcgttg ctggcgtttt tccataggct ccgcccccct gacgagcatc   9180
acaaaaatcg acgctcaagt cagaggtggc gaaacccgac aggactataa agataccagg   9240
cgtttccccc tggaagctcc ctcgtgcgct ctcctgttcc gaccctgccg cttaccggat   9300
acctgtccgc ctttctccct tcgggaagcg tggcgctttc tcatagctca cgctgtaggt   9360
```

-continued

```
atctcagttc ggtgtaggtc gttcgctcca agctgggctg tgtgcacgaa ccccccgttc   9420
agcccgaccg ctgcgcctta tccggtaact atcgtcttga gtccaacccg gtaagacacg   9480
acttatcgcc actggcagca gccactggta acaggattag cagagcgagg tatgtaggcg   9540
gtgctacaga gttcttgaag tggtggccta actacggcta cactagaaga acagtatttg   9600
gtatctgcgc tctgctgaag ccagttacct tcggaaaaag agttggtagc tcttgatccg   9660
gcaaacaaac caccgctggt agcggtggtt tttttgtttg caagcagcag attacgcgca   9720
gaaaaaaagg atctcaagaa gatcctttga tcttttctac ggggtctgac gctcagtgga   9780
acgaaaactc acgttaaggg attttggtca tgagattatc aaaaaggatc ttcacctaga   9840
tccttttaaa ttaaaaatga agttttaaat caatctaaag tatatatgag taaacttggt   9900
ctgacagtta ccaatgctta atcagtgagg cacctatctc agcgatctgt ctatttcgtt   9960
catccatagt tgcctgactc cccgtcgtgt agataactac gatacgggag ggcttaccat  10020
ctggccccag tgctgcaatg ataccgcgag acccacgctc accggctcca gatttatcag  10080
caataaacca gccagccgga agggccgagc gcagaagtgg tcctgcaact ttatccgcct  10140
ccatccagtc tattaattgt tgccgggaag ctagagtaag tagttcgcca gttaatagtt  10200
tgcgcaacgt tgttgccatt gctacaggca tcgtggtgtc acgctcgtcg tttggtatgg  10260
cttcattcag ctccggttcc caacgatcaa ggcgagttac atgatccccc atgttgtgca  10320
aaaaagcggt tagctccttc ggtcctccga tcgttgtcag aagtaagttg gccgcagtgt  10380
tatcactcat ggttatggca gcactgcata attctcttac tgtcatgcca tccgtaagat  10440
gcttttctgt gactggtgag tactcaacca agtcattctg agaatagtgt atgcggcgac  10500
cgagttgctc ttgcccggcg tcaatacggg ataataccgc gccacatagc agaactttaa  10560
aagtgctcat cattggaaaa cgttcttcgg ggcgaaaact ctcaaggatc ttaccgctgt  10620
tgagatccag ttcgatgtaa cccactcgtg cacccaactg atcttcagca tcttttactt  10680
tcaccagcgt ttctgggtga gcaaaaacag gaaggcaaaa tgccgcaaaa aagggaataa  10740
gggcgacacg gaaatgttga atactcatac tcttcctttt tcaatattat tgaagcattt  10800
atcagggtta ttgtctcatg agcggataca tatttgaatg tatttagaaa aataaacaaa  10860
taggggttcc gcgcacattt ccccgaaaag tgccacctga cgtctaagaa accattatta  10920
tcatgacatt aacctataaa aataggcgta tcacgaggcc ctttcgtctc gcgcgtttcg  10980
gtgatgacgg tgaaaacctc tgacacatgc agctcccgga gacggtcaca gcttgtctgt  11040
aagcggatgc cgggagcaga caagcccgtc agggcgcgtc agcgggtgtt ggcgggtgtc  11100
ggggctggct taactatgcg gcatcagagc agattgtact gagagtgcac catatgcggt  11160
gtgaaatacc gcacagatgc gtaaggagaa aataccgcat caggcgccat tcgccattca  11220
ggctgcgcaa ctgttgggaa gggcgatcgg tgcgggcctc ttcgctatta cgccagctgg  11280
cgaaaggggg atgtgctgca aggcgattaa gttgggtaac gccagggttt tcccagtcac  11340
gacgttgtaa aacgacggcc agtgaattc                                   11369
```

```
<210> SEQ ID NO 19
<211> LENGTH: 11671
<212> TYPE: DNA
<213> ORGANISM: Artificial Sequence
<220> FEATURE:
<223> OTHER INFORMATION: Synthetic: TL20d-rGbGM-7SKM1/sh734

<400> SEQUENCE: 19

ggccgcctcg gccaaacagc ccttgagttt accactccct atcagtgata gagaaaagtg     60
```

```
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgctttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgggg atcctctaga   2400
```

-continued

```
gtcgagctcg cgaggatcat caccggtgct agccggagcc agaagcacca taagggacat   2460
gataagggag ccagcagacc tctgatctct tcctgaatgc taatcttaaa catcctgagg   2520
aagaatggga cttccatttg gggtgggcct atgatagggt aataagacag tagtgaatat   2580
caagctacaa aaagcccccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
aaaagagctg aagaaaatca tgtgtgatct ctcagcagaa tagatttatt atttgtattg   3120
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca ttttttaaaa ttacaaatgc   3660
aaaattaccc tgatttggtc aatatgtgta ccctgttact tctccccttc ctatgacatg   3720
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
```

aattgataac aacaaatata tatatatata tatatatacg tatatgtgta tatatatata 4860
tatattcagg aaataatata ttctagaata tgtcacattc tgtctcaggc atccattttc 4920
tttatgatgc cgtttgaggt ggagttttag tcaggtggtc agcttctcct tttttttgcc 4980
atctgccctg taagcatcct gctggggacc cagataggag tcatcactct aggctgagaa 5040
catctgggca cacaccctaa gcctcagcat gactcatcat gactcagcat tgctgtgctt 5100
gagccagaag gtttgcttag aaggttacac agaaccagaa ggcgggggtg gggcactgac 5160
cccgacaggg gcctggccag aactgctcat gcttggacta tgggaggtca ctaatggaga 5220
cacacagaaa tgtaacagga actaagggaa ttccggtgcc ctgcttagga gcttaatctt 5280
taatgaaagc taagctttca ttaaaaaaag tctaaccagc tgcattcgac tttgactgca 5340
gcagctggtt agaaggttct actggaggag ggtcccagcc cattgctaaa ttaacatcag 5400
gctctgagac tggcagtata tctctaacag tggttgatgc tatcttctgg aacttgcctg 5460
ctacattgag accactgacc catacatagg aagcccatag ctctgtcctg aactgttagg 5520
ccactggtcc agagagtgtg catctccttt gatcctcata ataaccctat gagatagaca 5580
caattattac tcttacttta tagatgatga tcctgaaaac ataggagtca aggcacttgc 5640
ccctagctgg gggtataggg gagcagtccc atgtagtagt agaatgaaaa atgctgctat 5700
gctgtgcctc ccccaccttt cccatgtctg ccctctactc atggtctatc tctcctggct 5760
cctgggagtc atggactcca cccagcacca ccaacctgac ctaaccacct atctgagcct 5820
gccagcctat aacccatctg ggccctgata gctggtggcc agccctgacc ccacccccacc 5880 ctccctggaa cctctgatag acacatctgg cacaccagct cgcaaagtca ccgtgagggt 5940
cttgtgtttg ctgagtcaaa attccttgaa atccaagtcc ttagagactc ctgctcccaa 6000
atttacagtc atagacttct tcatggctgt ctcctttatc cacagaatga ttcctttgct 6060
tcattgcccc atccatctga tcctcctcat cagtgcagca cagggcccat gagcagtagc 6120
tgcagagtct cacataggtc tggcactgcc tctgacatgt ccgaccttag gcaaatgctt 6180
gactcttctg agctcggatc ccttgagctc aggaggtcaa ggctgcagtg agacatgatc 6240
ttgccactgc actccagcct ggacagcaga gtgaaacctt gcctcacgaa acagaataca 6300
aaaacaaaca aacaaaaaac tgctccgcaa tgcgcttcct tgatgctcta ccacataggt 6360
ctgggtactt tgtacacatt atctcattgc tgttcataat tgttagatta attttgtaat 6420
attgatatta ttcctagaaa gctgaggcct caagatgata acttttattt tctggacttg 6480
taatagcttt ctcttgtatt caccatgttg taactttctt agagtagtaa caatataaag 6540
ttattgtgag tttttgcaaa cacagcaaac acaacgaccc atatagacat tgatgtgaaa 6600
ttgtctattg tcaatttatg ggaaaacaag tatgtacttt ttctactaag ccattgaaac 6660
aggaataaca gaacaagatt gaaagaatac attttccgaa attacttgag tattatacaa 6720
agacaagcac gtggacctgg gaggagggtt attgtccatg actggtgtgt ggagacaaat 6780
gcaggtttat aatagatggg atggcatcta gcgcaatgac tttgccatca cttttagaga 6840
gctcttgggg gccccagtac acaagagggg acgcagggta tatgtagaca tctcattctt 6900
tttcttagtg tgagaataag aatagccatg acctgagttt atagacaatg agccctttttc 6960 tctctcccac tcagcagcta tgagatggct tgccctgcct ctctactagg ctgactcact 7020
ccaaggccca gcaatgggca gggctctgtc agggctttga tagcactatc tgcagagcca 7080
gggccgagaa ggggtggact ccagagactc tccctcccat tcccgagcag ggtttgctta 7140

-continued

```
tttatgcatt taaatgatat atttatttta aaagaaataa caggagactg cccagccctg   7200
gctgtgacat ggaaactatg tagaatattt tgggttccat ttttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gttcgacgtg cagtcgggct   7620
actgccccac ccatagtacc ggcattctgg atagtgtcaa aacagccgga aatcaagtcc   7680
gtttatctca aactttagca ttttgggaat aaatgatatt tgctatgctg gttaaattag   7740
attttagtta aatttcctgc tgaagctcta gtacgataag taacttgacc taagtgtaaa   7800
gttgagattt ccttcaggtt tatatagctt gtgcgccgcc tgggtacctc aggatatgcc   7860
cttgactatt tgtccgacat agtcaagggc atatcctttt ttgcggccgc atcgatgccg   7920
tagtaccttt aagaccaatg acttacaagg cagctgtaga tcttagccac tttttaaaag   7980
aaaagggggg actggaaggg ctaattcact cccaaagaag acaagataga tctgcttttt   8040
gcctgtactg ggtctctctg gttagaccag atctgagcct gggagctctc tggctaacta   8100
gggaacccac tgcttaagcc tcaataaagc ttcagctgct cgagctagca gatctttttc   8160
cctctgccaa aaattatggg gacatcatga agccccttga gcatctgact tctggctaat   8220
aaaggaaatt tattttcatt gcaatagtgt gttggaattt tttgtgtctc tcactcggaa   8280
ggacatatgg gagggcaaat catttaaaac atcagaatga gtatttggtt tagagtttgg   8340
caacatatgc ccatatgctg gctgccatga acaaaggttg gctataaaga ggtcatcagt   8400
atatgaaaca gccccctgct gtccattcct tattccatag aaaagccttg acttgaggtt   8460
agattttttt tatattttgt tttgtgttat ttttttcttt aacatcccta aaattttcct   8520
tacatgtttt actagccaga tttttcctcc tctcctgact actcccagtc atagctgtcc   8580
ctcttctctt atggagatcc ctcgacctgc agcccaagct tggcgtaatc atggtcatag   8640
ctgtttcctg tgtgaaattg ttatccgctc acaattccac acaacatacg agccggaagc   8700
ataaagtgta aagcctgggg tgcctaatga gtgagctaac tcacattaat tgcgttgcgc   8760
tcactgcccg ctttccagtc gggaaacctg tcgtgccagc ggatccgcat ctcaattagt   8820
cagcaaccat agtcccgccc ctaactccgc ccatcccgcc cctaactccg cccagttccg   8880
cccattctcc gccccatggc tgactaattt tttttattta tgcagaggcc gaggccgcct   8940
cggcctctga gctattccag aagtagtgag gaggcttttt tggaggccta ggcttttgca   9000
aaaagctgtc gactgcagag gcctgcatgc aagcttggcg taatcatggt catagctgtt   9060
tcctgtgtga aattgttatc cgctcacaat tccacacaac atacgagccg gaagcataaa   9120
gtgtaaagcc tggggtgcct aatgagtgag ctaactcaca ttaattgcgt tgcgctcact   9180
gcccgctttc cagtcgggaa acctgtcgtg ccagctgcat taatgaatcg gccaacgcgc   9240
ggggagaggc ggtttgcgta ttgggcgctc ttccgcttcc tcgctcactg actcgctgcg   9300
ctcggtcgtt cggctgcggc gagcggtatc agctcactca aaggcggtaa tacggttatc   9360
cacagaatca ggggataacg caggaaagaa catgtgagca aaaggccagc aaaaggccag   9420
gaaccgtaaa aaggccgcgt tgctggcgtt tttccatagg ctccgccccc ctgacgagca   9480
tcacaaaaat cgacgctcaa gtcagaggtg gcgaaacccg acaggactat aaagatacca   9540
```

ggcgtttccc cctggaagct ccctcgtgcg ctctcctgtt ccgaccctgc cgcttaccgg 9600
atacctgtcc gcctttctcc cttcgggaag cgtggcgctt tctcatagct cacgctgtag 9660
gtatctcagt tcggtgtagg tcgttcgctc caagctgggc tgtgtgcacg aaccccccgt 9720
tcagcccgac cgctgcgcct tatccggtaa ctatcgtctt gagtccaacc cggtaagaca 9780
cgacttatcg ccactggcag cagccactgg taacaggatt agcagagcga ggtatgtagg 9840
cggtgctaca gagttcttga agtggtggcc taactacggc tacactagaa gaacagtatt 9900
tggtatctgc gctctgctga agccagttac cttcggaaaa agagttggta gctcttgatc 9960
cggcaaacaa accaccgctg gtagcggtgg tttttttgtt tgcaagcagc agattacgcg 10020
cagaaaaaaa ggatctcaag aagatccttt gatcttttct acggggtctg acgctcagtg 10080
gaacgaaaac tcacgttaag ggattttggt catgagatta tcaaaaagga tcttcaccta 10140
gatcctttta aattaaaaat gaagttttaa atcaatctaa agtatatatg agtaaacttg 10200
gtctgacagt taccaatgct taatcagtga ggcacctatc tcagcgatct gtctatttcg 10260
ttcatccata gttgcctgac tccccgtcgt gtagataact acgatacggg agggcttacc 10320
atctggcccc agtgctgcaa tgataccgcg agacccacgc tcaccggctc cagatttatc 10380
agcaataaac cagccagccg gaagggccga gcgcagaagt ggtcctgcaa ctttatccgc 10440
ctccatccag tctattaatt gttgccggga agctagagta agtagttcgc cagttaatag 10500
tttgcgcaac gttgttgcca ttgctacagg catcgtggtg tcacgctcgt cgtttggtat 10560
ggcttcattc agctccggtt cccaacgatc aaggcgagtt acatgatccc ccatgttgtg 10620
caaaaaagcg gttagctcct tcggtcctcc gatcgttgtc agaagtaagt tggccgcagt 10680
gttatcactc atggttatgg cagcactgca taattctctt actgtcatgc catccgtaag 10740
atgcttttct gtgactggtg agtactcaac caagtcattc tgagaatagt gtatgcggcg 10800
accgagttgc tcttgcccgg cgtcaatacg ggataatacc gcgccacata gcagaacttt 10860
aaaagtgctc atcattggaa aacgttcttc ggggcgaaaa ctctcaagga tcttaccgct 10920
gttgagatcc agttcgatgt aacccactcg tgcacccaac tgatcttcag catcttttac 10980
tttcaccagc gtttctgggt gagcaaaaac aggaaggcaa aatgccgcaa aaaagggaat 11040
aagggcgaca cggaaatgtt gaatactcat actcttcctt tttcaatatt attgaagcat 11100
ttatcagggt tattgtctca tgagcggata catatttgaa tgtatttaga aaaataaaca 11160
aataggggtt ccgcgcacat ttccccgaaa agtgccacct gacgtctaag aaaccattat 11220
tatcatgaca ttaacctata aaaataggcg tatcacgagg ccctttcgtc tcgcgcgttt 11280
cggtgatgac ggtgaaaacc tctgacacat gcagctcccg gagacggtca cagcttgtct 11340
gtaagcggat gccgggagca gacaagcccg tcagggcgcg tcagcgggtg ttggcgggtg 11400
tcggggctgg cttaactatg cggcatcaga gcagattgta ctgagagtgc accatatgcg 11460
gtgtgaaata ccgcacagat gcgtaaggag aaaataccgc atcaggcgcc attcgccatt 11520
caggctgcgc aactgttggg aagggcgatc ggtgcgggcc tcttcgctat tacgccagct 11580
ggcgaaaggg ggatgtgctg caaggcgatt aagttgggta acgccagggt tttcccagtc 11640
acgacgttgt aaaacgacgg ccagtgaatt c 11671

<210> SEQ ID NO 20
<211> LENGTH: 11674
<212> TYPE: DNA
<213> ORGANISM: Artificial Sequence
<220> FEATURE:

<223> OTHER INFORMATION: Synthetic: TL20d-rGbGM-7SK/sh734

<400> SEQUENCE: 20

```
ggccgcctcg gccaaacagc ccttgagttt accactccct atcagtgata gagaaaagtg     60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgctttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
```

-continued

```
ttgctgtact ttctatagtg aatagagtta ggcagggata ttcaccatta tcgtttcaga   2340
cccacctccc aaccccgagg ggaccgagct caagcttcga acgcgtgggg atcctctaga   2400
gtcgagctcg cgaggatcat caccggtgct agccggagcc agaagcacca taagggacat   2460
gataagggag ccagcagacc tctgatctct tcctgaatgc taatcttaaa catcctgagg   2520
aagaatggga cttccatttg gggtgggcct atgatagggt aataagacag tagtgaatat   2580
caagctacaa aaagccccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
aaaagagctg aagaaaatca tgtgtgatct ctcagcagaa tagatttatt atttgtattg   3120
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca ttttttaaaa ttacaaatgc   3660
aaaattaccc tgatttggtc aatatgtgta ccctgttact tctccccttc ctatgacatg   3720
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
```

-continued

```
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
gctctgagac tggcagtata tctctaacag tggttgatgc tatcttctgg aacttgcctg   5460
ctacattgag accactgacc catacatagg aagcccatag ctctgtcctg aactgttagg   5520
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
aggaataaca gaacaagatt gaaagaatac attttccgaa attacttgag tattatacaa   6720
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agccctttttc   6960
tctctcccac tcagcagcta tgagatggct tgccctgcct ctctactagg ctgactcact   7020
```

ccaaggccca gcaatgggca gggctctgtc agggctttga tagcactatc tgcagagcca 7080
gggccgagaa ggggtggact ccagagactc tccctcccat tcccgagcag ggtttgctta 7140
tttatgcatt taaatgatat atttatttta aaagaaataa caggagactg cccagccctg 7200
gctgtgacat ggaaactatg tagaatattt tgggttccat tttttttcc ttctttcagt 7260
tagaggaaaa ggggctcact gcacatacac tagacagaaa gtcaggagct ttgaatccaa 7320
gcctgatcat ttccatgtca tactgagaaa gtccccaccc ttctctgagc ctcagtttct 7380
ctttttataa gtaggagtct ggagtaaatg atttccaatg gctctcattt caatacaaaa 7440
tttccgttta ttaaatgcat gagcttccgt tactccaaga ctgagaagga aattgaacct 7500
gagactcatt gactggcaag atgtccccag aggctctcat tcagcaataa aattctcacc 7560
ttcacccagg cccactagtg tcagatttgc atgcgttcgc gtatcgacgt gcagtattta 7620
gcatgcccca cccatctgca aggcattctg gatagtgtca aaacagccgg aaatcaagtc 7680
cgtttatctc aaactttagc attttgggaa taaatgatat ttgctatgct ggttaaatta 7740
gattttagtt aaatttcctg ctgaagctct agtacgataa gtaacttgac ctaagtgtaa 7800
agttgagatt tccttcaggt ttatatagct tgtgcgccgc ctgggtacct caggatatgc 7860
ccttgactat ttgtccgaca tagtcaaggg catatccttt tttgtgcggc cgcatcgatg 7920
ccgtagtacc tttaagacca atgacttaca aggcagctgt agatcttagc cactttttaa 7980
aagaaaaggg gggactggaa gggctaattc actcccaaag aagacaagat agatctgctt 8040
tttgcctgta ctgggtctct ctggttagac cagatctgag cctgggagct ctctggctaa 8100
ctagggaacc cactgcttaa gcctcaataa agcttcagct gctcgagcta gcagatcttt 8160
ttccctctgc caaaaattat ggggacatca tgaagcccct tgagcatctg acttctggct 8220
aataaaggaa atttattttc attgcaatag tgtgttggaa ttttttgtgt ctctcactcg 8280
gaaggacata tgggagggca aatcatttaa aacatcagaa tgagtatttg gtttagagtt 8340
tggcaacata tgcccatatg ctggctgcca tgaacaaagg ttggctataa agaggtcatc 8400
agtatatgaa acagcccccct gctgtccatt ccttattcca tagaaaagcc ttgacttgag 8460
gttagatttt ttttatattt tgttttgtgt tattttttttc tttaacatcc ctaaaatttt 8520
ccttacatgt tttactagcc agatttttcc tcctctcctg actactccca gtcatagctg 8580
tccctcttct cttatggaga tccctcgacc tgcagcccaa gcttggcgta atcatggtca 8640
tagctgtttc ctgtgtgaaa ttgttatccg ctcacaattc cacacaacat acgagccgga 8700
agcataaagt gtaaagcctg gggtgcctaa tgagtgagct aactcacatt aattgcgttg 8760
cgctcactgc ccgctttcca gtcgggaaac ctgtcgtgcc agcggatccg catctcaatt 8820
agtcagcaac catagtcccg cccctaactc cgcccatccc gcccctaact ccgcccagtt 8880
ccgcccattc tccgccccat ggctgactaa ttttttttat ttatgcagag gccgaggccg 8940
cctcggcctc tgagctattc cagaagtagt gaggaggctt ttttggaggc ctaggctttt 9000
gcaaaaagct gtcgactgca gaggcctgca tgcaagcttg gcgtaatcat ggtcatagct 9060
gtttcctgtg tgaaattgtt atccgctcac aattccacac aacatacgag ccggaagcat 9120
aaagtgtaaa gcctggggtg cctaatgagt gagctaactc acattaattg cgttgcgctc 9180
actgcccgct ttccagtcgg gaaacctgtc gtgccagctg cattaatgaa tcggccaacg 9240
cgcggggaga ggcggtttgc gtattgggcg ctcttccgct tcctcgctca ctgactcgct 9300
gcgctcggtc gttcggctgc ggcgagcggt atcagctcac tcaaaggcgg taatacggtt 9360

-continued

```
atccacagaa tcaggggata acgcaggaaa gaacatgtga gcaaaaggcc agcaaaaggc   9420
caggaaccgt aaaaaggccg cgttgctggc gtttttccat aggctccgcc cccctgacga   9480
gcatcacaaa aatcgacgct caagtcagag gtggcgaaac ccgacaggac tataaagata   9540
ccaggcgttt ccccctggaa gctccctcgt gcgctctcct gttccgaccc tgccgcttac   9600
cggatacctg tccgcctttc tcccttcggg aagcgtggcg ctttctcata gctcacgctg   9660
taggtatctc agttcggtgt aggtcgttcg ctccaagctg ggctgtgtgc acgaaccccc   9720
cgttcagccc gaccgctgcg ccttatccgg taactatcgt cttgagtcca acccggtaag   9780
acacgactta tcgccactgg cagcagccac tggtaacagg attagcagag cgaggtatgt   9840
aggcggtgct acagagttct tgaagtggtg gcctaactac ggctacacta gaagaacagt   9900
atttggtatc tgcgctctgc tgaagccagt taccttcgga aaaagagttg gtagctcttg   9960
atccggcaaa caaaccaccg ctggtagcgg tggttttttt gtttgcaagc agcagattac  10020
gcgcagaaaa aaaggatctc aagaagatcc tttgatcttt tctacggggt ctgacgctca  10080
gtggaacgaa aactcacgtt aagggatttt ggtcatgaga ttatcaaaaa ggatcttcac  10140
ctagatcctt ttaaattaaa aatgaagttt taaatcaatc taaagtatat atgagtaaac  10200
ttggtctgac agttaccaat gcttaatcag tgaggcacct atctcagcga tctgtctatt  10260
tcgttcatcc atagttgcct gactccccgt cgtgtagata actacgatac gggagggctt  10320
accatctggc cccagtgctg caatgatacc gcgagaccca cgctcaccgg ctccagattt  10380
atcagcaata aaccagccag ccggaagggc cgagcgcaga agtggtcctg caactttatc  10440
cgcctccatc cagtctatta attgttgccg ggaagctaga gtaagtagtt cgccagttaa  10500
tagtttgcgc aacgttgttg ccattgctac aggcatcgtg gtgtcacgct cgtcgtttgg  10560
tatggcttca ttcagctccg gttcccaacg atcaaggcga gttacatgat cccccatgtt  10620
gtgcaaaaaa gcggttagct ccttcggtcc tccgatcgtt gtcagaagta agttggccgc  10680
agtgttatca ctcatggtta tggcagcact gcataattct cttactgtca tgccatccgt  10740
aagatgcttt tctgtgactg gtgagtactc aaccaagtca ttctgagaat agtgtatgcg  10800
gcgaccgagt tgctcttgcc cggcgtcaat acgggataat accgcgccac atagcagaac  10860
tttaaaagtg ctcatcattg gaaaacgttc ttcggggcga aaactctcaa ggatcttacc  10920
gctgttgaga tccagttcga tgtaacccac tcgtgcaccc aactgatctt cagcatcttt  10980
tactttcacc agcgtttctg ggtgagcaaa aacaggaagg caaaatgccg caaaaaaggg  11040
aataagggcg acacggaaat gttgaatact catactcttc ctttttcaat attattgaag  11100
catttatcag ggttattgtc tcatgagcgg atacatattt gaatgtattt agaaaaataa  11160
acaaataggg gttccgcgca catttccccg aaaagtgcca cctgacgtct aagaaaccat  11220
tattatcatg acattaacct ataaaaatag gcgtatcacg aggccctttc gtctcgcgcg  11280
tttcggtgat gacggtgaaa acctctgaca catgcagctc ccggagacgg tcacagcttg  11340
tctgtaagcg gatgccggga gcagacaagc ccgtcagggc gcgtcagcgg gtgttggcgg  11400
gtgtcggggc tggcttaact atgcggcatc agagcagatt gtactgagag tgcaccatat  11460
gcggtgtgaa ataccgcaca gatgcgtaag gagaaaatac cgcatcaggc gccattcgcc  11520
attcaggctg cgcaactgtt gggaagggcg atcggtgcgg gcctcttcgc tattacgcca  11580
gctggcgaaa gggggatgtg ctgcaaggcg attaagttgg gtaacgccag ggttttccca  11640
gtcacgacgt tgtaaaacga cggccagtga attc                              11674
```

<210> SEQ ID NO 21
<211> LENGTH: 11671
<212> TYPE: DNA
<213> ORGANISM: Artificial Sequence
<220> FEATURE:
<223> OTHER INFORMATION: Synthetic: TL20d-rGbGM-r7SKM1/sh734

<400> SEQUENCE: 21
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840
aacatatagt atgggcaagc agggagctag aacgattcgc agttaatact ggcctgttag 900
aaacatcaga aggctgtaga caaatactgg gacagctaca accatccctt cagacaggat 960
cagaagaact tagatcatta tataatacag tagcaaccct ctattgtgtg catcaaagga 1020
tagagataaa agacaccaag gaagctttag acaagataga ggaagagcaa aacaaaagta 1080
agaaaaaagc acagcaagca gcaggatctt cagacctgga aattccctac aatccccaaa 1140
gtcaaggagt agtagaatct atgaataaag aattaaagaa aattatagga caggtaagag 1200
atcaggctga acatcttaag acagcagtac aaatggcagt attcatccac aattttaaaa 1260
gaaaaggggg gattgggggg tacagtgcag gggaaagaat agtagacata atagcaacag 1320
acatacaaac taaagaatta caaaaacaaa ttacaaaaat tcaaaatttt cgggtttatt 1380
acagggacag cagaaatcca ctttggaaag gaccagcaaa gctcctctgg aaaggtgaag 1440
gggcagtagt aatacaagat aatagtgaca taaaagtagt gccaagaaga aaagcaaaga 1500
tcattaggga ttatggaaaa cagatggcag gtgatgattg tgtggcaagt agacaggatg 1560
aggattagaa catggaaaag tttagtaaaa caccataagg aggagatatg agggacaatt 1620
ggagaagtga attatataaa tataaagtag taaaaattga accattagga gtagcaccca 1680
ccaaggcaaa gagaagagtg gtgcagagag aaaaaagagc agtgggaata ggagctttgt 1740
tccttgggtt cttgggagca gcaggaagca ctatgggcgc agcgtcaatg acgctgacgg 1800
tacaggccag acaattattg tctggtatag tgcagcagca gaacaatttg ctgagggcta 1860
ttgaggcgca acagcatctg ttgcaactca cagtctgggg catcaagcag ctccaggcaa 1920
gaatcctggc tgtggaaaga tacctaaagg atcaacagct cctggggatt tggggttgct 1980
ctggaaaact catttgcacc actgctgtgc cttggaatgc tagttggagt aataaatctc 2040
tggaacagat ttggaatcac acgacctgga tggagtggga cagagaaatt aacaattaca 2100

```
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgggg atcctctaga   2400
gtcgagctcg cgaggatcat caccggtgct agccggagcc agaagcacca taagggacat   2460
gataagggag ccagcagacc tctgatctct tcctgaatgc taatcttaaa catcctgagg   2520
aagaatggga cttccatttg gggtgggcct atgatagggt aataagacag tagtgaatat   2580
caagctacaa aaagcccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
aaaagagctg aagaaaatca tgtgtgatct ctcagcagaa tagatttatt atttgtattg   3120
cttgcagaat aaagcctatc cttgaaagct ctgaatcatg ggcaagaggc tcagtggtat   3180
ctggaggaca gggcactggc cactgcagtc accatcttct gccaggaagc ctgcacctca   3240
ggggtgaatt ctttgccaaa gtgaatggcc agcacggtga ccagcacgtt gcccaggagc   3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca ttttttaaaa ttacaaatgc   3660
aaaattaccc tgatttggtc aatatgtgta ccctgttact tctccccttc ctatgacatg   3720
aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gccctccctg   4320
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat tgctactaaa   4500
```

aacatcctcc tttgcaagtg tatttacgac ggtatcgatg tatgtgagca tgtgtcctct 4560
aacagcacag gccttttgcc acctagctgt ccaggggtgc cttaaaatgg caaacaaggt 4620
ttgttttctt ttcctgtttt catgccttcc tcttccatat ccttgtttca tattaataca 4680
tgtgtataga tcctaaaaat ctatacacat gtattaataa agcctgattc tgccgcttct 4740
aggtatagag gccacctgca agataaatat ttgattcaca ataactaatc attctatggc 4800
aattgataac aacaaatata tatatatata tatatatacg tatatgtgta tatatatata 4860
tatattcagg aaataatata ttctagaata tgtcacattc tgtctcaggc atccattttc 4920
tttatgatgc cgtttgaggt ggagttttag tcaggtggtc agcttctcct ttttttgcc 4980
atctgccctg taagcatcct gctggggacc cagataggag tcatcactct aggctgagaa 5040
catctgggca cacaccctaa gcctcagcat gactcatcat gactcagcat tgctgtgctt 5100
gagccagaag gtttgcttag aaggttacac agaaccagaa ggcgggggtg gggcactgac 5160
cccgacaggg gcctggccag aactgctcat gcttggacta tgggaggtca ctaatggaga 5220
cacacagaaa tgtaacagga actaagggaa ttccggtgcc ctgcttagga gcttaatctt 5280
taatgaaagc taagctttca ttaaaaaaag tctaaccagc tgcattcgac tttgactgca 5340
gcagctggtt agaaggttct actggaggag ggtcccagcc cattgctaaa ttaacatcag 5400
gctctgagac tggcagtata tctctaacag tggttgatgc tatcttctgg aacttgcctg 5460
ctacattgag accactgacc catacatagg aagcccatag ctctgtcctg aactgttagg 5520
ccactggtcc agagagtgtg catctccttt gatcctcata ataaccctat gagatagaca 5580
caattattac tcttacttta tagatgatga tcctgaaaac ataggagtca aggcacttgc 5640
ccctagctgg gggtataggg gagcagtccc atgtagtagt agaatgaaaa atgctgctat 5700
gctgtgcctc ccccaccttt cccatgtctg ccctctactc atggtctatc tctcctggct 5760
cctgggagtc atggactcca cccagcacca ccaacctgac ctaaccacct atctgagcct 5820
gccagcctat aacccatctg ggccctgata gctggtggcc agccctgacc ccaccccacc 5880
ctccctggaa cctctgatag acacatctgg cacaccagct cgcaaagtca ccgtgagggt 5940
cttgtgtttg ctgagtcaaa attccttgaa atccaagtcc ttagagactc ctgctcccaa 6000
atttacagtc atagacttct tcatggctgt ctcctttatc cacagaatga ttcctttgct 6060
tcattgcccc atccatctga tcctcctcat cagtgcagca cagggcccat gagcagtagc 6120
tgcagagtct cacataggtc tggcactgcc tctgacatgt ccgaccttag gcaaatgctt 6180
gactcttctg agctcggatc ccttgagctc aggaggtcaa ggctgcagtg agacatgatc 6240
ttgccactgc actccagcct ggacagcaga gtgaaacctt gcctcacgaa acagaataca 6300
aaaacaaaca aacaaaaaac tgctccgcaa tgcgcttcct tgatgctcta ccacataggt 6360
ctgggtactt tgtacacatt atctcattgc tgttcataat tgttagatta attttgtaat 6420
attgatatta ttcctagaaa gctgaggcct caagatgata acttttattt tctggacttg 6480
taatagcttt ctcttgtatt caccatgttg taactttctt agagtagtaa caatataaag 6540
ttattgtgag tttttgcaaa cacagcaaac acaacgaccc atatagacat tgatgtgaaa 6600
ttgtctattg tcaatttatg ggaaaacaag tatgtacttt ttctactaag ccattgaaac 6660
aggaataaca gaacaagatt gaaagaatac attttccgaa attacttgag tattatacaa 6720
agacaagcac gtggacctgg gaggagggtt attgtccatg actggtgtgt ggagacaaat 6780
gcaggtttat aatagatggg atggcatcta gcgcaatgac tttgccatca cttttagaga 6840

```
gctcttgggg gccccagtac acaagagggg acgcagggta tatgtagaca tctcattctt   6900
tttcttagtg tgagaataag aatagccatg acctgagttt atagacaatg agcccttttc   6960
tctctcccac tcagcagcta tgagatggct tgccctgcct ctctactagg ctgactcact   7020
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
gctgtgacat ggaaactatg tagaatattt tgggttccat tttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gtaaaaaagg atatgccctt   7620
gactatgtcg gacaaatagt caagggcata tcctgaggta cccaggcggc gcacaagcta   7680
tataaacctg aaggaaatct caactttaca cttaggtcaa gttacttatc gtactagagc   7740
ttcagcagga aatttaacta aaatctaatt taaccagcat agcaaatatc atttattccc   7800
aaaatgctaa agtttgagat aaacggactt gatttccggc tgttttgaca ctatccagaa   7860
tgccggtact atgggtgggg cagtagcccg actgcacgtc gagcggccgc atcgatgccg   7920
tagtaccttt aagaccaatg acttacaagg cagctgtaga tcttagccac tttttaaaag   7980
aaaagggggg actggaaggg ctaattcact cccaaagaag acaagataga tctgcttttt   8040
gcctgtactg ggtctctctg gttagaccag atctgagcct gggagctctc tggctaacta   8100
gggaacccac tgcttaagcc tcaataaagc ttcagctgct cgagctagca gatctttttc   8160
cctctgccaa aaattatggg gacatcatga agccccttga gcatctgact tctggctaat   8220
aaaggaaatt tattttcatt gcaatagtgt gttggaattt tttgtgtctc tcactcggaa   8280
ggacatatgg gagggcaaat catttaaaac atcagaatga gtatttggtt tagagtttgg   8340
caacatatgc ccatatgctg gctgccatga acaaaggttg gctataaaga ggtcatcagt   8400
atatgaaaca gccccctgct gtccattcct tattccatag aaaagccttg acttgaggtt   8460
agattttttt tatattttgt tttgtgttat ttttttcttt aacatcccta aaattttcct   8520
tacatgtttt actagccaga tttttcctcc tctcctgact actcccagtc atagctgtcc   8580
ctcttctctt atggagatcc ctcgacctgc agcccaagct tggcgtaatc atggtcatag   8640
ctgtttcctg tgtgaaattg ttatccgctc acaattccac acaacatacg agccggaagc   8700
ataaagtgta aagcctgggg tgcctaatga gtgagctaac tcacattaat tgcgttgcgc   8760
tcactgcccg ctttccagtc gggaaacctg tcgtgccagc ggatccgcat ctcaattagt   8820
cagcaaccat agtcccgccc ctaactccgc ccatcccgcc cctaactccg cccagttccg   8880
cccattctcc gccccatggc tgactaattt tttttattta tgcagaggcc gaggccgcct   8940
cggcctctga gctattccag aagtagtgag gaggcttttt tggaggccta ggcttttgca   9000
aaaagctgtc gactgcagag gcctgcatgc aagcttggcg taatcatggt catagctgtt   9060
tcctgtgtga aattgttatc cgctcacaat tccacacaac atacgagccg gaagcataaa   9120
gtgtaaagcc tggggtgcct aatgagtgag ctaactcaca ttaattgcgt tgcgctcact   9180
gcccgctttc cagtcgggaa acctgtcgtg ccagctgcat taatgaatcg gccaacgcgc   9240
```

```
ggggagaggc ggtttgcgta ttgggcgctc ttccgcttcc tcgctcactg actcgctgcg   9300
ctcggtcgtt cggctgcggc gagcggtatc agctcactca aaggcggtaa tacggttatc   9360
cacagaatca ggggataacg caggaaagaa catgtgagca aaaggccagc aaaaggccag   9420
gaaccgtaaa aaggccgcgt tgctggcgtt tttccatagg ctccgccccc ctgacgagca   9480
tcacaaaaat cgacgctcaa gtcagaggtg gcgaaacccg acaggactat aaagatacca   9540
ggcgtttccc cctggaagct ccctcgtgcg ctctcctgtt ccgaccctgc cgcttaccgg   9600
atacctgtcc gcctttctcc cttcgggaag cgtggcgctt tctcatagct cacgctgtag   9660
gtatctcagt tcggtgtagg tcgttcgctc caagctgggc tgtgtgcacg aaccccccgt   9720
tcagcccgac cgctgcgcct tatccggtaa ctatcgtctt gagtccaacc cggtaagaca   9780
cgacttatcg ccactggcag cagccactgg taacaggatt agcagagcga ggtatgtagg   9840
cggtgctaca gagttcttga agtggtggcc taactacggc tacactagaa gaacagtatt   9900
tggtatctgc gctctgctga agccagttac cttcggaaaa agagttggta gctcttgatc   9960
cggcaaacaa accaccgctg gtagcggtgg tttttttgtt tgcaagcagc agattacgcg  10020
cagaaaaaaa ggatctcaag aagatccttt gatcttttct acggggtctg acgctcagtg  10080
gaacgaaaac tcacgttaag ggattttggt catgagatta tcaaaaagga tcttcaccta  10140
gatcctttta aattaaaaat gaagttttaa atcaatctaa agtatatatg agtaaacttg  10200
gtctgacagt taccaatgct taatcagtga ggcacctatc tcagcgatct gtctatttcg  10260
ttcatccata gttgcctgac tccccgtcgt gtagataact acgatacggg agggcttacc  10320
atctggcccc agtgctgcaa tgataccgcg agacccacgc tcaccggctc cagatttatc  10380
agcaataaac cagccagccg gaagggccga gcgcagaagt ggtcctgcaa ctttatccgc  10440
ctccatccag tctattaatt gttgccggga agctagagta agtagttcgc cagttaatag  10500
tttgcgcaac gttgttgcca ttgctacagg catcgtggtg tcacgctcgt cgtttggtat  10560
ggcttcattc agctccggtt cccaacgatc aaggcgagtt acatgatccc ccatgttgtg  10620
caaaaaagcg gttagctcct tcggtcctcc gatcgttgtc agaagtaagt tggccgcagt  10680
gttatcactc atggttatgg cagcactgca taattctctt actgtcatgc catccgtaag  10740
atgcttttct gtgactggtg agtactcaac caagtcattc tgagaatagt gtatgcggcg  10800
accgagttgc tcttgcccgg cgtcaatacg ggataatacc gcgccacata gcagaacttt  10860
aaaagtgctc atcattggaa aacgttcttc ggggcgaaaa ctctcaagga tcttaccgct  10920
gttgagatcc agttcgatgt aacccactcg tgcacccaac tgatcttcag catcttttac  10980
tttcaccagc gtttctgggt gagcaaaaac aggaaggcaa aatgccgcaa aaaagggaat  11040
aagggcgaca cggaaatgtt gaatactcat actcttcctt tttcaatatt attgaagcat  11100
ttatcagggt tattgtctca tgagcggata catatttgaa tgtatttaga aaaataaaca  11160
aataggggtt ccgcgcacat ttccccgaaa agtgccacct gacgtctaag aaaccattat  11220
tatcatgaca ttaacctata aaaataggcg tatcacgagg ccctttcgtc tcgcgcgttt  11280
cggtgatgac ggtgaaaacc tctgacacat gcagctcccg gagacggtca cagcttgtct  11340
gtaagcggat gccgggagca gacaagcccg tcagggcgcg tcagcgggtg ttggcgggtg  11400
tcggggctgg cttaactatg cggcatcaga gcagattgta ctgagagtgc accatatgcg  11460
gtgtgaaata ccgcacagat gcgtaaggag aaaataccgc atcaggcgcc attcgccatt  11520
caggctgcgc aactgttggg aagggcgatc ggtgcgggcc tcttcgctat tacgccagct  11580
```

ggcgaaaggg ggatgtgctg caaggcgatt aagttgggta acgccagggt tttcccagtc 11640
acgacgttgt aaaacgacgg ccagtgaatt c 11671

<210> SEQ ID NO 22
<211> LENGTH: 11674
<212> TYPE: DNA
<213> ORGANISM: Artificial Sequence
<220> FEATURE:
<223> OTHER INFORMATION: Synthetic: TL20d-rGbGM-r7SK/sh734

<400> SEQUENCE: 22
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840
aacatatagt atgggcaagc agggagctag aacgattcgc agttaatact ggcctgttag 900
aaacatcaga aggctgtaga caaatactgg gacagctaca accatccctt cagacaggat 960
cagaagaact tagatcatta tataatacag tagcaaccct ctattgtgtg catcaaagga 1020
tagagataaa agacaccaag gaagctttag acaagataga ggaagagcaa aacaaaagta 1080
agaaaaaagc acagcaagca gcaggatctt cagacctgga aattccctac aatccccaaa 1140
gtcaaggagt agtagaatct atgaataaag aattaaagaa aattatagga caggtaagag 1200
atcaggctga acatcttaag acagcagtac aaatggcagt attcatccac aattttaaaa 1260
gaaaaggggg gattgggggg tacagtgcag gggaaagaat agtagacata atagcaacag 1320
acatacaaac taaagaatta caaaaacaaa ttacaaaaat tcaaaatttt cgggtttatt 1380
acagggacag cagaaatcca ctttggaaag gaccagcaaa gctcctctgg aaaggtgaag 1440
gggcagtagt aatacaagat aatagtgaca taaaagtagt gccaagaaga aaagcaaaga 1500
tcattaggga ttatggaaaa cagatggcag gtgatgattg tgtggcaagt agacaggatg 1560
aggattagaa catggaaaag tttagtaaaa caccataagg aggagatatg agggacaatt 1620
ggagaagtga attatataaa tataaagtag taaaaattga accattagga gtagcaccca 1680
ccaaggcaaa gagaagagtg gtgcagagag aaaaaagagc agtgggaata ggagctttgt 1740
tccttgggtt cttgggagca gcaggaagca ctatgggcgc agcgtcaatg acgctgacgg 1800
tacaggccag acaattattg tctggtatag tgcagcagca gaacaatttg ctgagggcta 1860
ttgaggcgca acagcatctg ttgcaactca cagtctgggg catcaagcag ctccaggcaa 1920
gaatcctggc tgtggaaaga tacctaaagg atcaacagct cctggggatt tggggttgct 1980
ctggaaaact catttgcacc actgctgtgc cttggaatgc tagttggagt aataaatctc 2040
tggaacagat ttggaatcac acgacctgga tggagtggga cagagaaatt aacaattaca 2100
caagcttaat acactcctta attgaagaat cgcaaaacca gcaagaaaag aatgaacaag 2160
aattattgga attagataaa tgggcaagtt tgtggaattg gtttaacata acaaattggc 2220
tgtggtatat aaaattattc ataatgatag taggaggctt ggtaggttta agaatagttt 2280
ttgctgtact ttctatagtg aatagagtta ggcagggata ttcaccatta tcgtttcaga 2340
cccacctccc aaccccgagg ggaccgagct caagcttcga acgcgtgggg atcctctaga 2400
gtcgagctcg cgaggatcat caccggtgct agccggagcc agaagcacca taagggacat 2460
gataagggag ccagcagacc tctgatctct tcctgaatgc taatcttaaa catcctgagg 2520
aagaatggga cttccatttg gggtgggcct atgatagggt aataagacag tagtgaatat 2580
caagctacaa aaagcccct ttcaaattct tctcagtcct aacttttcat actaagccca 2640
gtccttccaa agcagactgt gaaagagtga tagttccggg agactagcac cggctagccg 2700
agcttggaac actttccctt cattaagaac catccttgct actcagctgc aatcaatcca 2760
gcccccaggt cttcactgaa ccttttccca tctcttccaa aacatctgtt tctgagaagt 2820
cctgtcctat agaggtcttt cttcccaccg gatttctcct acaccattta ctcccacttg 2880
cagaactccc gtgtacaagt gtctttactg cttttatttg ctcaacaaaa tgcacatctc 2940
atataaaaat aaatgaggag catgcacaca ccacaaacac aaacaggcat gcagaaatac 3000
acatacacac ttccctcaat ataaaccctt tgtggctcat atatttaaaa agatgtaaaa 3060
aaaagagctg aagaaaatca tgtgtgatct ctcagcagaa tagatttatt atttgtattg 3120
cttgcagaat aaagcctatc cttgaaagct ctgaatcatg ggcaagaggc tcagtggtat 3180
ctggaggaca gggcactggc cactgcagtc accatcttct gccaggaagc ctgcacctca 3240
ggggtgaatt ctttgccaaa gtgaatggcc agcacggtga ccagcacgtt gcccaggagc 3300
tgtgggagga agataagagg tatgaacatg attagcaaaa gggcctagct tggactcaga 3360
ataatccagc cttatcccaa ccataaaata aaagcagaat ggtagctgga ttgtagctgc 3420
tattagcaat atgaaacctc ttacatcagt tacaatttat atgcagaaat atttatatgc 3480
agaaatattg ctattgcctt aacccagaaa ttatcactgt tattctttag aatggtgcaa 3540
agaggcatga tacattgtat cattattgcc ctgaaagaaa gagattaggg aaagtattag 3600
aaataagata aacaaaaaag tatattaaaa gaagaaagca ttttttaaaa ttacaaatgc 3660
aaaattaccc tgatttggtc aatatgtgta ccctgttact tctccccttc ctatgacatg 3720
aacttaacca tagaaaagaa ggggaaagaa aacatcaagg gtcccataga ctcaccttga 3780
agttctcagg atccacatgc agcttgtcac agtgcagttc actcagctgg gcaaaggtgc 3840
ccttgagatc atccaggtgc tttatggcat ctcccaagga agtcagcacc ttcttgccat 3900
gtgccttgac tttggggttg cccatgatgg cagaggcaga ggacaggttg ccaaagctgt 3960
caaagaacct ctgggtccat gggtagacaa ccaggagcct gtgagattga caagaacagt 4020
ttgacagtca gaaggtgcca caaatcctga gaagcaacct ggacttttgc caggcacagg 4080
gtccttcctt ccctcccttg tcctggtcac cagagcctac cttcccaggg tttctcctcc 4140
agcatcttcc acattcacct tgtcccacag gcttgtgata gtagccttgt cctcctctgt 4200
gaaatgaccc atggtgtctg tttgaggttg ctagtgaaca cagttgtgtc agaagcaaat 4260
gtaagcaata gatggctctg ccctgacttt tatgcccagc cctggctcct gccctccctg 4320

-continued

```
ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc ccataccat cagtacaaat tgctactaaa    4500
aacatcctcc tttgcaagtg tatttacgac ggtatcgatg tatgtgagca tgtgtcctct   4560
aacagcacag gccttttgcc acctagctgt ccaggggtgc cttaaaatgg caaacaaggt   4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
aattgataac aacaaatata tatatatata tatatatacg tatatgtgta tatatatata   4860
tatattcagg aaataatata ttctagaata tgtcacattc tgtctcaggc atccattttc   4920
tttatgatgc cgtttgaggt ggagttttag tcaggtggtc agcttctcct tttttttgcc   4980
atctgccctg taagcatcct gctggggacc cagataggag tcatcactct aggctgagaa   5040
catctgggca cacaccctaa gcctcagcat gactcatcat gactcagcat tgctgtgctt   5100
gagccagaag gtttgcttag aaggttacac agaaccagaa ggcgggggtg gggcactgac   5160
cccgacaggg gcctggccag aactgctcat gcttggacta tgggaggtca ctaatggaga   5220
cacacagaaa tgtaacagga actaagggaa ttccggtgcc ctgcttagga gcttaatctt   5280
taatgaaagc taagctttca ttaaaaaaag tctaaccagc tgcattcgac tttgactgca   5340
gcagctggtt agaaggttct actggaggag ggtcccagcc cattgctaaa ttaacatcag   5400
gctctgagac tggcagtata tctctaacag tggttgatgc tatcttctgg aacttgcctg   5460
ctacattgag accactgacc catacatagg aagcccatag ctctgtcctg aactgttagg   5520
ccactggtcc agagagtgtg catctccttt gatcctcata ataaccctat gagatagaca   5580
caattattac tcttacttta tagatgatga tcctgaaaac ataggagtca aggcacttgc   5640
ccctagctgg gggtataggg gagcagtccc atgtagtagt agaatgaaaa atgctgctat   5700
gctgtgcctc ccccaccttt cccatgtctg ccctctactc atggtctatc tctcctggct   5760
cctgggagtc atggactcca cccagcacca ccaacctgac ctaaccacct atctgagcct   5820
gccagcctat aacccatctg ggccctgata gctggtggcc agccctgacc ccaccccacc   5880
ctccctggaa cctctgatag acacatctgg cacaccagct cgcaaagtca ccgtgagggt   5940
cttgtgtttg ctgagtcaaa attccttgaa atccaagtcc ttagagactc ctgctcccaa   6000
atttacagtc atagacttct tcatggctgt ctcctttatc cacagaatga ttcctttgct   6060
tcattgcccc atccatctga tcctcctcat cagtgcagca cagggcccat gagcagtagc   6120
tgcagagtct cacataggtc tggcactgcc tctgacatgt ccgaccttag gcaaatgctt   6180
gactcttctg agctcggatc ccttgagctc aggaggtcaa ggctgcagtg agacatgatc   6240
ttgccactgc actccagcct ggacagcaga gtgaaacctt gcctcacgaa acagaataca   6300
aaaacaaaca aacaaaaaac tgctccgcaa tgcgcttcct tgatgctcta ccacataggt   6360
ctgggtactt tgtacacatt atctcattgc tgttcataat tgttagatta attttgtaat   6420
attgatatta ttcctagaaa gctgaggcct caagatgata acttttattt tctggacttg   6480
taatagcttt ctcttgtatt caccatgttg taactttctt agagtagtaa caatataaag   6540
ttattgtgag tttttgcaaa cacagcaaac acaacgaccc atatagacat tgatgtgaaa   6600
ttgtctattg tcaatttatg ggaaaacaag tatgtacttt ttctactaag ccattgaaac   6660
aggaataaca gaacaagatt gaaagaatac attttccgaa attacttgag tattatacaa   6720
```

-continued

```
agacaagcac gtggacctgg gaggagggtt attgtccatg actggtgtgt ggagacaaat   6780
gcaggtttat aatagatggg atggcatcta gcgcaatgac tttgccatca cttttagaga   6840
gctcttgggg gccccagtac acaagagggg acgcagggta tatgtagaca tctcattctt   6900
tttcttagtg tgagaataag aatagccatg acctgagttt atagacaatg agcccttttc   6960
tctctcccac tcagcagcta tgagatggct tgccctgcct ctctactagg ctgactcact   7020
ccaaggccca gcaatgggca gggctctgtc agggctttga tagcactatc tgcagagcca   7080
gggccgagaa ggggtggact ccagagactc tccctcccat tcccgagcag ggtttgctta   7140
tttatgcatt taaatgatat atttatttta aaagaaataa caggagactg cccagccctg   7200
gctgtgacat ggaaactatg tagaatattt tgggttccat ttttttttcc ttctttcagt   7260
tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380
ctttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gtacaaaaaa ggatatgccc   7620
ttgactatgt cggacaaata gtcaagggca tatcctgagg tacccaggcg gcgcacaagc   7680
tatataaacc tgaaggaaat ctcaacttta cacttaggtc aagttactta tcgtactaga   7740
gcttcagcag gaaatttaac taaaatctaa tttaaccagc atagcaaata tcatttattc   7800
ccaaaatgct aaagtttgag ataaacggac ttgatttccg gctgttttga cactatccag   7860
aatgccttgc agatgggtgg ggcatgctaa atactgcacg tcgatgcggc cgcatcgatg   7920
ccgtagtacc tttaagacca atgacttaca aggcagctgt agatcttagc cactttttaa   7980
aagaaaaggg gggactggaa gggctaattc actcccaaag aagacaagat agatctgctt   8040
tttgcctgta ctgggtctct ctggttagac cagatctgag cctgggagct ctctggctaa   8100
ctagggaacc cactgcttaa gcctcaataa agcttcagct gctcgagcta gcagatcttt   8160
ttccctctgc caaaaattat ggggacatca tgaagcccct tgagcatctg acttctggct   8220
aataaaggaa atttattttc attgcaatag tgtgttggaa tttttttgtgt ctctcactcg   8280
gaaggacata tgggagggca aatcatttaa aacatcagaa tgagtatttg gtttagagtt   8340
tggcaacata tgcccatatg ctggctgcca tgaacaaagg ttggctataa agaggtcatc   8400
agtatatgaa acagcccccct gctgtccatt ccttattcca tagaaaagcc ttgacttgag   8460
gttagatttt ttttatattt tgttttgtgt tattttttttc tttaacatcc ctaaaatttt   8520
ccttacatgt tttactagcc agatttttcc tcctctcctg actactccca gtcatagctg   8580
tccctcttct cttatggaga tccctcgacc tgcagcccaa gcttggcgta atcatggtca   8640
tagctgtttc ctgtgtgaaa ttgttatccg ctcacaattc cacacaacat acgagccgga   8700
agcataaagt gtaaagcctg gggtgcctaa tgagtgagct aactcacatt aattgcgttg   8760
cgctcactgc ccgctttcca gtcgggaaac ctgtcgtgcc agcggatccg catctcaatt   8820
agtcagcaac catagtcccg cccctaactc cgcccatccc gcccctaact ccgcccagtt   8880
ccgcccattc tccgccccat ggctgactaa ttttttttat ttatgcagag gccgaggccg   8940
cctcggcctc tgagctattc cagaagtagt gaggaggctt ttttggaggc ctaggctttt   9000
gcaaaaagct gtcgactgca gaggcctgca tgcaagcttg gcgtaatcat ggtcatagct   9060
```

-continued

```
gtttcctgtg tgaaattgtt atccgctcac aattccacac aacatacgag ccggaagcat   9120
aaagtgtaaa gcctggggtg cctaatgagt gagctaactc acattaattg cgttgcgctc   9180
actgcccgct ttccagtcgg gaaacctgtc gtgccagctg cattaatgaa tcggccaacg   9240
cgcggggaga ggcggtttgc gtattgggcg ctcttccgct tcctcgctca ctgactcgct   9300
gcgctcggtc gttcggctgc ggcgagcggt atcagctcac tcaaaggcgg taatacggtt   9360
atccacagaa tcaggggata acgcaggaaa gaacatgtga gcaaaaggcc agcaaaaggc   9420
caggaaccgt aaaaaggccg cgttgctggc gtttttccat aggctccgcc cccctgacga   9480
gcatcacaaa aatcgacgct caagtcagag gtggcgaaac ccgacaggac tataaagata   9540
ccaggcgttt ccccctggaa gctccctcgt gcgctctcct gttccgaccc tgccgcttac   9600
cggatacctg tccgcctttc tcccttcggg aagcgtggcg ctttctcata gctcacgctg   9660
taggtatctc agttcggtgt aggtcgttcg ctccaagctg ggctgtgtgc acgaaccccc   9720
cgttcagccc gaccgctgcg ccttatccgg taactatcgt cttgagtcca acccggtaag   9780
acacgactta tcgccactgg cagcagccac tggtaacagg attagcagag cgaggtatgt   9840
aggcggtgct acagagttct tgaagtggtg gcctaactac ggctacacta gaagaacagt   9900
atttggtatc tgcgctctgc tgaagccagt taccttcgga aaaagagttg gtagctcttg   9960
atccggcaaa caaaccaccg ctggtagcgg tggttttttt gtttgcaagc agcagattac  10020
gcgcagaaaa aaaggatctc aagaagatcc tttgatcttt tctacggggt ctgacgctca  10080
gtggaacgaa aactcacgtt aagggatttt ggtcatgaga ttatcaaaaa ggatcttcac  10140
ctagatcctt ttaaattaaa aatgaagttt taaatcaatc taaagtatat atgagtaaac  10200
ttggtctgac agttaccaat gcttaatcag tgaggcacct atctcagcga tctgtctatt  10260
tcgttcatcc atagttgcct gactccccgt cgtgtagata actacgatac gggagggctt  10320
accatctggc cccagtgctg caatgatacc gcgagaccca cgctcaccgg ctccagattt  10380
atcagcaata aaccagccag ccggaagggc cgagcgcaga agtggtcctg caactttatc  10440
cgcctccatc cagtctatta attgttgccg ggaagctaga gtaagtagtt cgccagttaa  10500
tagtttgcgc aacgttgttg ccattgctac aggcatcgtg gtgtcacgct cgtcgtttgg  10560
tatggcttca ttcagctccg gttcccaacg atcaaggcga gttacatgat cccccatgtt  10620
gtgcaaaaaa gcggttagct ccttcggtcc tccgatcgtt gtcagaagta agttggccgc  10680
agtgttatca ctcatggtta tggcagcact gcataattct cttactgtca tgccatccgt  10740
aagatgcttt tctgtgactg gtgagtactc aaccaagtca ttctgagaat agtgtatgcg  10800
gcgaccgagt tgctcttgcc cggcgtcaat acgggataat accgcgccac atagcagaac  10860
tttaaaagtg ctcatcattg gaaaacgttc ttcggggcga aaactctcaa ggatcttacc  10920
gctgttgaga tccagttcga tgtaacccac tcgtgcaccc aactgatctt cagcatcttt  10980
tactttcacc agcgtttctg ggtgagcaaa aacaggaagg caaaatgccg caaaaaaggg  11040
aataagggcg acacggaaat gttgaatact catactcttc ctttttcaat attattgaag  11100
catttatcag ggttattgtc tcatgagcgg atacatattt gaatgtattt agaaaaataa  11160
acaaataggg gttccgcgca catttccccg aaaagtgcca cctgacgtct aagaaaccat  11220
tattatcatg acattaacct ataaaaatag gcgtatcacg aggccctttc gtctcgcgcg  11280
tttcggtgat gacggtgaaa acctctgaca catgcagctc ccggagacgg tcacagcttg  11340
tctgtaagcg gatgccggga gcagacaagc ccgtcagggc gcgtcagcgg gtgttggcgg  11400
gtgtcggggc tggcttaact atgcggcatc agagcagatt gtactgagag tgcaccatat  11460
```

gcggtgtgaa ataccgcaca gatgcgtaag gagaaaatac cgcatcaggc gccattcgcc 11520
attcaggctg cgcaactgtt gggaagggcg atcggtgcgg gcctcttcgc tattacgcca 11580
gctggcgaaa gggggatgtg ctgcaaggcg attaagttgg gtaacgccag ggttttccca 11640
gtcacgacgt tgtaaaacga cggccagtga attc 11674

<210> SEQ ID NO 23
<211> LENGTH: 111
<212> TYPE: RNA
<213> ORGANISM: Artificial Sequence
<220> FEATURE:
<223> OTHER INFORMATION: Synthetic: miRNA734 de novo (RNA form)

<400> SEQUENCE: 23
acccguacau auuuuugugu agcucuaguu uauagucaag ggcauauccu uguguuuuuu 60
uugaaggaua ugcccuugac uauaaacuag cgcuacacuu uuucgucuug u 111

<210> SEQ ID NO 24
<211> LENGTH: 111
<212> TYPE: RNA
<213> ORGANISM: Artificial Sequence
<220> FEATURE:
<223> OTHER INFORMATION: Synthetic: miRNA211 de novo (RNA form)

<400> SEQUENCE: 24
acccguacau auuuuugugu agcucuaguu auaaaucaag gucauaaccu uguguuuuuu 60
uugaagguua ugaccuugau uuauaacuag cgcuacacuu uuucgucuug u 111

<210> SEQ ID NO 25
<211> LENGTH: 166
<212> TYPE: DNA
<213> ORGANISM: Artificial Sequence
<220> FEATURE:
<223> OTHER INFORMATION: Synthetic: miRNA211-3G

<400> SEQUENCE: 25
ccggatcaac gccctaggtt tatgtttgga tgaactgaca tacgcgtatc cgtcttttaa 60
atcaaggtca taaccgtagt gaaatatata ttaaacaggt tatgaccttg atttaaaata 120
cggtaacgcg gaattcgcaa ctattttatc aattttttgc gtcgac 166

<210> SEQ ID NO 26
<211> LENGTH: 166
<212> TYPE: DNA
<213> ORGANISM: Artificial Sequence
<220> FEATURE:
<223> OTHER INFORMATION: Synthetic: miRNA734-3G

<400> SEQUENCE: 26
ccggatcaac gccctaggtt tatgtttgga tgaactgaca tacgcgtatc cgtcttatag 60
tcaagggcat atcctgtagt gaaatatata ttaaacaagg atatgccctt gactataata 120
cggtaacgcg gaattcgcaa ctattttatc aattttttgc gtcgac 166

<210> SEQ ID NO 27
<211> LENGTH: 56
<212> TYPE: DNA
<213> ORGANISM: Artificial Sequence
<220> FEATURE:
<223> OTHER INFORMATION: Synthetic: shHPRT 616

<400> SEQUENCE: 27

-continued gcaggcagta taatccaaat acctgaccca tatttggatt atactgcctg cttttt 56

<210> SEQ ID NO 28
<211> LENGTH: 55
<212> TYPE: DNA
<213> ORGANISM: Artificial Sequence
<220> FEATURE:
<223> OTHER INFORMATION: Synthetic: shHPRT 211

<400> SEQUENCE: 28
ggttatgacc ttgatttata cctgacccat attaaatcaa ggtcataacc ttttt 55

<210> SEQ ID NO 29
<211> LENGTH: 56
<212> TYPE: DNA
<213> ORGANISM: Artificial Sequence
<220> FEATURE:
<223> OTHER INFORMATION: Synthetic: shHPRT 734.1

<400> SEQUENCE: 29
gggatatgcc cttgactaat acctgaccca tattagtcaa gggcatatcc cttttt 56

<210> SEQ ID NO 30
<211> LENGTH: 52
<212> TYPE: DNA
<213> ORGANISM: Artificial Sequence
<220> FEATURE:
<223> OTHER INFORMATION: Synthetic: shHPRT 734

<400> SEQUENCE: 30
aggatatgcc cttgactatt tgtccgacat agtcaagggc atatcctttt tt 52

<210> SEQ ID NO 31
<211> LENGTH: 51
<212> TYPE: RNA
<213> ORGANISM: Artificial Sequence
<220> FEATURE:
<223> OTHER INFORMATION: Synthetic: Modified sh734

<400> SEQUENCE: 31
aggauaugcc cuugacuaug cccugaccca gcauagucaa gggcauaucc u 51

<210> SEQ ID NO 32
<211> LENGTH: 248
<212> TYPE: DNA
<213> ORGANISM: Homo sapiens
<220> FEATURE:
<221> NAME/KEY: misc_feature
<223> OTHER INFORMATION: Homo sapiens cell-line HEK-293 7SK RNA promoter region

<400> SEQUENCE: 32
tcgacgtgca gtatttagca tgccccaccc atctgcaagg cattctggat agtgtcaaaa 60
cagccggaaa tcaagtccgt ttatctcaaa ctttagcatt ttgggaataa atgatatttg 120
ctatgctggt taaattagat tttagttaaa tttcctgctg aagctctagt acgataagta 180
acttgaccta agtgtaaagt tgagatttcc ttcaggttta tatagcttgt gcgccgcctg 240
ggtacctc 248

<210> SEQ ID NO 33
<211> LENGTH: 248
<212> TYPE: DNA
<213> ORGANISM: Homo sapiens
<220> FEATURE:
<221> NAME/KEY: misc_feature
<223> OTHER INFORMATION: Homo sapiens cell-line HEK-293 7SK RNA promoter region with mutation 1

<400> SEQUENCE: 33
tcgacgtgca gtcgggctac tgccccaccc atagtaccgg cattctggat agtgtcaaaa 60
cagccggaaa tcaagtccgt ttatctcaaa ctttagcatt ttgggaataa atgatatttg 120
ctatgctggt taaattagat tttagttaaa tttcctgctg aagctctagt acgataagta 180
acttgaccta agtgtaaagt tgagatttcc ttcaggttta tatagcttgt gcgccgcctg 240
ggtacctc 248

<210> SEQ ID NO 34
<211> LENGTH: 9
<212> TYPE: RNA
<213> ORGANISM: Artificial Sequence
<220> FEATURE:
<223> OTHER INFORMATION: Synthetic: hsa-miR-22 loop sequence

<400> SEQUENCE: 34 ccugaccca 9

<210> SEQ ID NO 35
<211> LENGTH: 9
<212> TYPE: DNA
<213> ORGANISM: Artificial Sequence
<220> FEATURE:
<223> OTHER INFORMATION: Synthetic: Hairpin loop sequence of sh734 (5 to 3)

<400> SEQUENCE: 35 ttgtccgac 9

<210> SEQ ID NO 36
<211> LENGTH: 483
<212> TYPE: DNA
<213> ORGANISM: Artificial Sequence
<220> FEATURE:
<223> OTHER INFORMATION: Synthetic: EF1a-miRNA734-Denovo-SV40 polyA

<400> SEQUENCE: 36
ggatatcggc tccggtgccc gtcagtgggc agagcgcaca tcgcccacag tccccgagaa 60
gttgggggga ggggtcggca attgaaccgg tgcctagaga aggtggcgcg gggtaaactg 120
ggaaagtgat gtcgtgtact ggctccgcct ttttcccgag ggtgggggag aaccgtatat 180
aagtgcagta gtcgccgtga acgttctttt cgcaacgggt ttgccgccag aacacaggat 240
gacccgtaca tatttttgtg tagctctagt tataaatcaa ggtcataacc ttgtgttttt 300
tttgaaggtt atgaccttga tttataacta gcgctacact tttcgtctt gttagaactt 360 gtttattgca gcttataatg gttacaaata aagcaatagc atcacaaatt tcacaaataa 420
agcatttttt tcactgcatt ctagttgtgg tttgtccaaa ctcatcaatg tatcttatca 480
tct 483

<210> SEQ ID NO 37
<211> LENGTH: 483
<212> TYPE: DNA
<213> ORGANISM: Artificial Sequence
<220> FEATURE:
<223> OTHER INFORMATION: Synthetic: EF1a-miRNA211-Denovo-SV40 polyA

<400> SEQUENCE: 37
ggatatcggc tccggtgccc gtcagtgggc agagcgcaca tcgcccacag tccccgagaa 60
gttgggggga ggggtcggca attgaaccgg tgcctagaga aggtggcgcg gggtaaactg 120
ggaaagtgat gtcgtgtact ggctccgcct ttttcccgag ggtgggggag aaccgtatat 180
aagtgcagta gtcgccgtga acgttctttt cgcaacgggt ttgccgccag aacacaggat 240
gacccgtaca tatttttgtg tagctctagt ttatagtcaa gggcatatcc ttgtgttttt 300
tttgaaggat atgcccttga ctataaacta gcgctacact tttcgtcttt gttagaactt 360
gtttattgca gcttataatg gttacaaata aagcaatagc atcacaaatt tcacaaataa 420
agcatttttt tcactgcatt ctagttgtgg tttgtccaaa ctcatcaatg tatcttatca 480
tct 483

<210> SEQ ID NO 38
<211> LENGTH: 537
<212> TYPE: DNA
<213> ORGANISM: Artificial Sequence
<220> FEATURE:
<223> OTHER INFORMATION: Synthetic: EF1a-miRNA734-3G-SV40 polyA

<400> SEQUENCE: 38
ggatatcggc tccggtgccc gtcagtgggc agagcgcaca tcgcccacag tccccgagaa 60
gttgggggga ggggtcggca attgaaccgg tgcctagaga aggtggcgcg gggtaaactg 120
ggaaagtgat gtcgtgtact ggctccgcct ttttcccgag ggtgggggag aaccgtatat 180
aagtgcagta gtcgccgtga acgttctttt cgcaacgggt ttgccgccag aacacaggat 240
gccggatcaa cgccctaggt ttatgtttgg atgaactgac atacgcgtat ccgtcttata 300
gtcaagggca tatccagtag tgaaatatat attaaactgg atatgccctt gactataata 360
cggtaacgcg gaattcgcaa ctattttatc aatttttttgc gtcgactaga acttgtttat 420
tgcagcttat aatggttaca aataaagcaa tagcatcaca aatttcacaa ataaagcatt 480
tttttcactg cattctagtt gtggtttgtc caaactcatc aatgtatctt atcatct 537

<210> SEQ ID NO 39
<211> LENGTH: 696
<212> TYPE: DNA
<213> ORGANISM: Artificial Sequence
<220> FEATURE:
<223> OTHER INFORMATION: Synthetic: EF1a-miRNA211-3G-SV40 polyA

<400> SEQUENCE: 39
ggatatcggc tccggtgccc gtcagtgggc agagcgcaca tcgcccacag tccccgagaa 60
gttgggggga ggggtcggca attgaaccgg tgcctagaga aggtggcgcg gggtaaactg 120
ggaaagtgat gtcgtgtact ggctccgcct ttttcccgag ggtgggggag aaccgtatat 180
aagtgcagta gtcgccgtga acgttctttt cgcaacgggt ttgccgccag aacacaggcc 240
ggatcaacgc cctaggttta tgtttggatg aactgacata cgcgtatccg tctataaatc 300
aaggtcataa cctgtagtga aatatatatt aaacaaggtt atgaccttga tttattacgg 360
taacgcggaa ttcgcaacta ttttatcaat tttttgcgtc gacccggatc aacgccctag 420
gtttatgttt ggatgaactg acatacgcgt atccgtctat aaatcaaggt cataacctgt 480
agtgaaatat atattaaaca aggttatgac cttgatttat tacggtaacg cggaattcgc 540
aactatttta tcaatttttt gcgtcgacaa cttgtttatt gcagcttata atggttacaa 600
ataaagcaat agcatcacaa atttcacaaa taaagcattt ttttcactgc attctagttg 660
tggtttgtcc aaactcatca atgtatctta tcatct 696

<210> SEQ ID NO 40
<211> LENGTH: 809
<212> TYPE: DNA
<213> ORGANISM: Artificial Sequence
<220> FEATURE:
<223> OTHER INFORMATION: Synthetic: Left Arm 150-EF1a-miRNA734-Denovo-
SV40 polyA-Right Arm 150

<400> SEQUENCE: 40
gcttcttctc tggaatcttc ttcatcatcc tcctgacaat cgataggtac ctggctgtcg 60
tccatgctgt gtttgcttta aaagccagga cggtcacctt tggggtggtg acaagtgtga 120
tcacttgggt ggtggctgtg tttgcgtctc aagcttttcg aagcggccgc ggatatcggc 180
tccggtgccc gtcagtgggc agagcgcaca tcgcccacag tccccgagaa gttgggggga 240
ggggtcggca attgaaccgg tgcctagaga aggtggcgcg gggtaaactg ggaaagtgat 300
gtcgtgtact ggctccgcct ttttcccgag ggtgggggag aaccgtatat aagtgcagta 360
gtcgccgtga acgttctttt cgcaacgggt ttgccgccag aacacaggat gacccgtaca 420
tatttttgtg tagctctagt tataaatcaa ggtcataacc ttgtgttttt tttgaaggtt 480
atgaccttga tttataacta gcgctacact ttttcgtctt gttagaactt gtttattgca 540
gcttataatg gttacaaata aagcaatagc atcacaaatt tcacaaataa agcatttttt 600
tcactgcatt ctagttgtgg tttgtccaaa ctcatcaatg tatcttatca tctacgcgtc 660
caggaatcat ctttaccaga tctcaaaaag aaggtcttca ttacacctgc agctctcatt 720
ttccatacag tcagtatcaa ttctggaaga atttccagac attaaagata gtcatcttgg 780
ggctggtcct gccgctgctt gtcatggtc 809

<210> SEQ ID NO 41
<211> LENGTH: 809
<212> TYPE: DNA
<213> ORGANISM: Artificial Sequence
<220> FEATURE:
<223> OTHER INFORMATION: Synthetic: miRNA211-Denovo

<400> SEQUENCE: 41
gcttcttctc tggaatcttc ttcatcatcc tcctgacaat cgataggtac ctggctgtcg 60
tccatgctgt gtttgcttta aaagccagga cggtcacctt tggggtggtg acaagtgtga 120
tcacttgggt ggtggctgtg tttgcgtctc aagcttttcg aagcggccgc ggatatcggc 180
tccggtgccc gtcagtgggc agagcgcaca tcgcccacag tccccgagaa gttgggggga 240
ggggtcggca attgaaccgg tgcctagaga aggtggcgcg gggtaaactg ggaaagtgat 300
gtcgtgtact ggctccgcct ttttcccgag ggtgggggag aaccgtatat aagtgcagta 360
gtcgccgtga acgttctttt cgcaacgggt ttgccgccag aacacaggat gacccgtaca 420
tatttttgtg tagctctagt ttatagtcaa gggcatatcc ttgtgttttt tttgaaggat 480
atgcccttga ctataaacta gcgctacact ttttcgtctt gttagaactt gtttattgca 540
gcttataatg gttacaaata aagcaatagc atcacaaatt tcacaaataa agcatttttt 600
tcactgcatt ctagttgtgg tttgtccaaa ctcatcaatg tatcttatca tctacgcgtc 660
caggaatcat ctttaccaga tctcaaaaag aaggtcttca ttacacctgc agctctcatt 720
ttccatacag tcagtatcaa ttctggaaga atttccagac attaaagata gtcatcttgg 780
ggctggtcct gccgctgctt gtcatggtc 809

<210> SEQ ID NO 42

<211> LENGTH: 863
<212> TYPE: DNA
<213> ORGANISM: Artificial Sequence
<220> FEATURE:
<223> OTHER INFORMATION: Synthetic: miRNA734-3G

<400> SEQUENCE: 42

```
gcttcttctc tggaatcttc ttcatcatcc tcctgacaat cgataggtac ctggctgtcg      60

tccatgctgt gtttgcttta aaagccagga cggtcacctt tggggtggtg acaagtgtga     120

tcacttgggt ggtggctgtg tttgcgtctc aagcttttcg aagcggccgc ggatatcggc     180

tccggtgccc gtcagtgggc agagcgcaca tcgcccacag tccccgagaa gttgggggga     240

ggggtcggca attgaaccgg tgcctagaga aggtggcgcg gggtaaactg ggaaagtgat     300

gtcgtgtact ggctccgcct ttttcccgag ggtgggggag aaccgtatat aagtgcagta     360

gtcgccgtga acgttctttt cgcaacgggt ttgccgccag aacacaggat gccggatcaa     420

cgccctaggt ttatgtttgg atgaactgac atacgcgtat ccgtcttata gtcaagggca     480

tatccagtag tgaaatatat attaaactgg atatgccctt gactataata cggtaacgcg     540

gaattcgcaa ctattttatc aattttttgc gtcgactaga acttgtttat tgcagcttat     600

aatggttaca aataaagcaa tagcatcaca aatttcacaa ataaagcatt tttttcactg     660

cattctagtt gtggtttgtc caaactcatc aatgtatctt atcatctacg cgtccaggaa     720

tcatctttac cagatctcaa aaagaaggtc ttcattacac ctgcagctct cattttccat     780

acagtcagta tcaattctgg aagaatttcc agacattaaa gatagtcatc ttggggctgg     840

tcctgccgct gcttgtcatg gtc                                             863
```

<210> SEQ ID NO 43
<211> LENGTH: 1022
<212> TYPE: DNA
<213> ORGANISM: Artificial Sequence
<220> FEATURE:
<223> OTHER INFORMATION: Synthetic: miRNA211-3G

<400> SEQUENCE: 43

```
gcttcttctc tggaatcttc ttcatcatcc tcctgacaat cgataggtac ctggctgtcg      60

tccatgctgt gtttgcttta aaagccagga cggtcacctt tggggtggtg acaagtgtga     120

tcacttgggt ggtggctgtg tttgcgtctc aagcttttcg aagcggccgc ggatatcggc     180

tccggtgccc gtcagtgggc agagcgcaca tcgcccacag tccccgagaa gttgggggga     240

ggggtcggca attgaaccgg tgcctagaga aggtggcgcg gggtaaactg ggaaagtgat     300

gtcgtgtact ggctccgcct ttttcccgag ggtgggggag aaccgtatat aagtgcagta     360

gtcgccgtga acgttctttt cgcaacgggt ttgccgccag aacacaggcc ggatcaacgc     420

cctaggttta tgtttggatg aactgacata cgcgtatccg tctataaatc aaggtcataa     480

cctgtagtga aatatatatt aaacaaggtt atgaccttga tttattacgg taacgcggaa     540

ttcgcaacta ttttatcaat tttttgcgtc gacccggatc aacgccctag gtttatgttt     600

ggatgaactg acatacgcgt atccgtctat aaatcaaggt cataacctgt agtgaaatat     660

atattaaaca aggttatgac cttgatttat tacggtaacg cggaattcgc aactatttta     720

tcaatttttt gcgtcgacaa cttgtttatt gcagcttata atggttacaa ataaagcaat     780

agcatcacaa atttcacaaa taaagcattt ttttcactgc attctagttg tggtttgtcc     840

aaactcatca atgtatctta tcatctacgc gtccaggaat catctttacc agatctcaaa     900

aagaaggtct tcattacacc tgcagctctc attttccata cagtcagtat caattctgga     960
```

agaatttcca gacattaaag atagtcatct tggggctggt cctgccgctg cttgtcatgg 1020
tc 1022

<210> SEQ ID NO 44
<211> LENGTH: 20
<212> TYPE: DNA
<213> ORGANISM: Artificial Sequence
<220> FEATURE:
<223> OTHER INFORMATION: Synthetic: GbGM F 5-3

<400> SEQUENCE: 44
tgacttcctt gggagatgcc 20

<210> SEQ ID NO 45
<211> LENGTH: 20
<212> TYPE: DNA
<213> ORGANISM: Artificial Sequence
<220> FEATURE:
<223> OTHER INFORMATION: Synthetic: GbGM R 5-3

<400> SEQUENCE: 45
caaagtgaat ggccagcacg 20

<210> SEQ ID NO 46
<211> LENGTH: 20
<212> TYPE: DNA
<213> ORGANISM: Artificial Sequence
<220> FEATURE:
<223> OTHER INFORMATION: Synthetic: Probe 5- 3

<400> SEQUENCE: 46
agctcctggg caacgtgctg 20

<210> SEQ ID NO 47
<211> LENGTH: 6565
<212> TYPE: DNA
<213> ORGANISM: Artificial Sequence
<220> FEATURE:
<223> OTHER INFORMATION: Synthetic: PTL20c

<400> SEQUENCE: 47
ggccgcctcg gccaaacagc ccttgagttt accactccct atcagtgata gagaaaagtg 60
aaagtcgagt ttaccactcc ctatcagtga tagagaaaag tgaaagtcga gtttaccact 120
ccctatcagt gatagagaaa agtgaaagtc gagtttacca ctccctatca gtgatagaga 180
aaagtgaaag tcgagtttac cagtccctat cagtgataga gaaaagtgaa agtcgagttt 240
accactccct atcagtgata gagaaaagtg aaagtcgagt ttaccactcc ctatcagtga 300
tagagaaaag tgaaagtcga gctcgccatg ggaggcgtgg cctgggcggg actggggagt 360
ggcgagccct cagatcctgc atataagcag ctgctttttg cctgtactgg gtctctctgg 420
ttagaccaga tctgagcctg ggagctctct ggctaactag ggaacccact gcttaagcct 480
caataaagct tgccttgagt gcttcaagta gtgtgtgccc gtctgttgtg tgactctggt 540
aactagagat ccctcagacc cttttagtca gtgtggaaaa tctctagcag tggcgcccga 600
acagggactt gaaagcgaaa gggaaaccag aggagctctc tcgacgcagg actcggcttg 660
ctgaagcgcg cacggcaaga ggcgaggggc ggcgactggt gagtacgcca aaaattttga 720
ctagcggagg ctagaaggag agagatgggt gcgagagcgt cagtattaag cgggggagaa 780
ttagatcgcg atgggaaaaa attcggttaa ggccaggggg aaagaaaaaa tataaattaa 840

-continued

```
aacatatagt atgggcaagc agggagctag aacgattcgc agttaatact ggcctgttag     900
aaacatcaga aggctgtaga caaatactgg gacagctaca accatccctt cagacaggat     960
cagaagaact tagatcatta tataatacag tagcaaccct ctattgtgtg catcaaagga    1020
tagagataaa agacaccaag gaagctttag acaagataga ggaagagcaa aacaaaagta    1080
agaaaaaagc acagcaagca gcaggatctt cagacctgga aattccctac aatccccaaa    1140
gtcaaggagt agtagaatct atgaataaag aattaaagaa aattatagga caggtaagag    1200
atcaggctga acatcttaag acagcagtac aaatggcagt attcatccac aattttaaaa    1260
gaaaaggggg gattgggggg tacagtgcag gggaaagaat agtagacata atagcaacag    1320
acatacaaac taaagaatta caaaaacaaa ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca cagtctgggg catcaagcag ctccaggcaa    1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga acgcgtgcgg ccgcatcgat    2400
gccgtagtac ctttaagacc aatgacttac aaggcagctg tagatcttag ccacttttta    2460
aaagaaaagg ggggactgga agggctaatt cactcccaaa gaagacaaga tccctgcagg    2520
cattcaaggc caggctggat gtggctctgg gcagcctggg ctgctggttg atgaccctgc    2580
acatagcagg gggttggatc tggatgagca ctgtgctcct ttgcaaccca ggccgttcta    2640
tgattctgtc attctaaatc tctctttcag cctaaagctt tttccccgta tccccccagg    2700
tgtctgcagg ctcaaagagc agcgagaagc gttcagagga aagcgatccc gtgccacctt    2760
ccccgtgccc gggctgtccc cgcacgctgc cggctcgggg atgcgggggg agcgccggac    2820
cggagcggag ccccgggcgg ctcgctgctg ccccctagcg ggggagggac gtaattacat    2880
ccctgggggc tttggggggg ggctgtcccc gtgagctccc cagatctgct ttttgcctgt    2940
actgggtctc tctggttaga ccagatctga gcctgggagc tctctggcta actagggaac    3000
ccactgctta agcctcaata aagcttcagc tgctcgagct agcagatctt tttccctctg    3060
ccaaaaatta tggggacatc atgaagcccc ttgagcatct gacttctggc taataaagga    3120
aatttatttt cattgcaata gtgtgttgga attttttgtg tctctcactc ggaaggacat    3180
atgggagggc aaatcattta aaacatcaga atgagtattt ggtttagagt ttggcaacat    3240
```

```
atgcccatat gctggctgcc atgaacaaag gttggctata aagaggtcat cagtatatga   3300
aacagccccc tgctgtccat tccttattcc atagaaaagc cttgacttga ggttagattt   3360
tttttatatt ttgttttgtg ttattttttt ctttaacatc cctaaaattt tccttacatg   3420
ttttactagc cagatttttc ctcctctcct gactactccc agtcatagct gtccctcttc   3480
tcttatggag atccctcgac ctgcagccca agcttggcgt aatcatggtc atagctgttt   3540
cctgtgtgaa attgttatcc gctcacaatt ccacacaaca tacgagccgg aagcataaag   3600
tgtaaagcct ggggtgccta atgagtgagc taactcacat taattgcgtt gcgctcactg   3660
cccgctttcc agtcgggaaa cctgtcgtgc cagcggatcc gcatctcaat tagtcagcaa   3720
ccatagtccc gcccctaact ccgcccatcc cgcccctaac tccgcccagt tccgcccatt   3780
ctccgcccca tggctgacta attttttta tttatgcaga ggccgaggcc gcctcggcct   3840
ctgagctatt ccagaagtag tgaggaggct tttttggagg cctaggcttt tgcaaaaagc   3900
tgtcgactgc agaggcctgc atgcaagctt ggcgtaatca tggtcatagc tgtttcctgt   3960
gtgaaattgt tatccgctca caattccaca caacatacga gccggaagca taaagtgtaa   4020
agcctggggt gcctaatgag tgagctaact cacattaatt gcgttgcgct cactgcccgc   4080
tttccagtcg ggaaacctgt cgtgccagct gcattaatga atcggccaac gcgcggggag   4140
aggcggtttg cgtattgggc gctcttccgc ttcctcgctc actgactcgc tgcgctcggt   4200
cgttcggctg cggcgagcgg tatcagctca ctcaaaggcg gtaatacggt tatccacaga   4260
atcaggggat aacgcaggaa agaacatgtg agcaaaaggc cagcaaaagg ccaggaaccg   4320
taaaaaggcc gcgttgctgg cgtttttcca taggctccgc ccccctgacg agcatcacaa   4380
aaatcgacgc tcaagtcaga ggtggcgaaa cccgacagga ctataaagat accaggcgtt   4440
tccccctgga agctccctcg tgcgctctcc tgttccgacc ctgccgctta ccggatacct   4500
gtccgccttt ctcccttcgg gaagcgtggc gctttctcat agctcacgct gtaggtatct   4560
cagttcggtg taggtcgttc gctccaagct gggctgtgtg cacgaacccc ccgttcagcc   4620
cgaccgctgc gccttatccg gtaactatcg tcttgagtcc aacccggtaa gacacgactt   4680
atcgccactg gcagcagcca ctggtaacag gattagcaga gcgaggtatg taggcggtgc   4740
tacagagttc ttgaagtggt ggcctaacta cggctacact agaagaacag tatttggtat   4800
ctgcgctctg ctgaagccag ttaccttcgg aaaaagagtt ggtagctctt gatccggcaa   4860
acaaaccacc gctggtagcg gtggtttttt tgtttgcaag cagcagatta cgcgcagaaa   4920
aaaaggatct caagaagatc ctttgatctt ttctacgggg tctgacgctc agtggaacga   4980
aaactcacgt taagggattt tggtcatgag attatcaaaa aggatcttca cctagatcct   5040
tttaaattaa aaatgaagtt ttaaatcaat ctaaagtata tatgagtaaa cttggtctga   5100
cagttaccaa tgcttaatca gtgaggcacc tatctcagcg atctgtctat ttcgttcatc   5160
catagttgcc tgactccccg tcgtgtagat aactacgata cgggagggct taccatctgg   5220
ccccagtgct gcaatgatac cgcgagaccc acgctcaccg gctccagatt tatcagcaat   5280
aaaccagcca gccggaaggg ccgagcgcag aagtggtcct gcaactttat ccgcctccat   5340
ccagtctatt aattgttgcc gggaagctag agtaagtagt tcgccagtta atagtttgcg   5400
caacgttgtt gccattgcta caggcatcgt ggtgtcacgc tcgtcgtttg gtatggcttc   5460
attcagctcc ggttcccaac gatcaaggcg agttacatga tcccccatgt tgtgcaaaaa   5520
agcggttagc tccttcggtc ctccgatcgt tgtcagaagt aagttggccg cagtgttatc   5580
```

-continued

```
actcatggtt atggcagcac tgcataattc tcttactgtc atgccatccg taagatgctt   5640

ttctgtgact ggtgagtact caaccaagtc attctgagaa tagtgtatgc ggcgaccgag   5700

ttgctcttgc ccggcgtcaa tacgggataa taccgcgcca catagcagaa ctttaaaagt   5760

gctcatcatt ggaaaacgtt cttcggggcg aaaactctca aggatcttac cgctgttgag   5820

atccagttcg atgtaaccca ctcgtgcacc caactgatct tcagcatctt ttactttcac   5880

cagcgtttct gggtgagcaa aaacaggaag gcaaaatgcc gcaaaaaagg gaataagggc   5940

gacacggaaa tgttgaatac tcatactctt cctttttcaa tattattgaa gcatttatca   6000

gggttattgt ctcatgagcg gatacatatt tgaatgtatt tagaaaaata aacaaatagg   6060

ggttccgcgc acatttcccc gaaaagtgcc acctgacgtc taagaaacca ttattatcat   6120

gacattaacc tataaaaata ggcgtatcac gaggcccttt cgtctcgcgc gtttcggtga   6180

tgacggtgaa aacctctgac acatgcagct cccggagacg gtcacagctt gtctgtaagc   6240

ggatgccggg agcagacaag cccgtcaggg cgcgtcagcg ggtgttggcg ggtgtcgggg   6300

ctggcttaac tatgcggcat cagagcagat tgtactgaga gtgcaccata tgcggtgtga   6360

aataccgcac agatgcgtaa ggagaaaata ccgcatcagg cgccattcgc cattcaggct   6420

gcgcaactgt tgggaagggc gatcggtgcg ggcctcttcg ctattacgcc agctggcgaa   6480

agggggatgt gctgcaaggc gattaagttg ggtaacgcca gggttttccc agtcacgacg   6540

ttgtaaaacg acggccagtg aattc                                         6565
```

<210> SEQ ID NO 48
<211> LENGTH: 3901
<212> TYPE: DNA
<213> ORGANISM: Artificial Sequence
<220> FEATURE:
<223> OTHER INFORMATION: Synthetic: PTL20c backbone including a 400bp cHS4 insulator

<400> SEQUENCE: 48

```
ggccgcctcg gccaaacagc ccttgagttt accactccct atcagtgata gagaaaagtg     60

aaagtcgagt ttaccactcc ctatcagtga tagagaaaag tgaaagtcga gtttaccact    120

ccctatcagt gatagagaaa agtgaaagtc gagtttacca ctccctatca gtgatagaga    180

aaagtgaaag tcgagtttac cagtccctat cagtgataga gaaaagtgaa agtcgagttt    240

accactccct atcagtgata gagaaaagtg aaagtcgagt ttaccactcc ctatcagtga    300

tagagaaaag tgaaagtcga gctcgccatg ggaggcgtgg cctgggcggg actggggagt    360

ggcgagccct cagatcctgc atataagcag ctgctttttg cctgtactgg gtctctctgg    420

ttagaccaga tctgagcctg ggagctctct ggctaactag ggaacccact gcttaagcct    480

caataaagct tgccttgagt gcttcaagta gtgtgtgccc gtctgttgtg tgactctggt    540

aactagagat ccctcagacc cttttagtca gtgtggaaaa tctctagcag tggcgcccga    600

acagggactt gaaagcgaaa gggaaaccag aggagctctc tcgacgcagg actcggcttg    660

ctgaagcgcg cacggcaaga ggcgaggggc ggcgactggt gagtacgcca aaaattttga    720

ctagcggagg ctagaaggag agagatgggt gcgagagcgt cagtattaag cgggggagaa    780

ttagatcgcg atgggaaaaa attcggttaa ggccaggggg aaagaaaaaa tataaattaa    840

aacatatagt atgggcaagc agggagctag aacgattcgc agttaatact ggcctgttag    900

aaacatcaga aggctgtaga caaatactgg gacagctaca accatccctt cagacaggat    960

cagaagaact tagatcatta tataatacag tagcaaccct ctattgtgtg catcaaagga   1020
```

```
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tggcaagttt gtggaattgg tttaacata acaaattggc    2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgcgg ccgcatcgat   2400
gccgtagtac ctttaagacc aatgacttac aaggcagctg tagatcttag ccacttttta   2460
aaagaaaagg ggggactgga agggctaatt cactcccaaa gaagacaaga tccctgcagg   2520
cattcaaggc caggctggat gtggctctgg gcagcctggg ctgctggttg atgaccctgc   2580
acatagcagg gggttggatc tggatgagca ctgtgctcct ttgcaaccca ggccgttcta   2640
tgattctgtc attctaaatc tctctttcag cctaaagctt tttccccgta tccccccagg   2700
tgtctgcagg ctcaaagagc agcgagaagc gttcagagga aagcgatccc gtgccacctt   2760
ccccgtgccc gggctgtccc cgcacgctgc cggctcgggg atgcgggggg agcgccggac   2820
cggagcggag ccccgggcgg ctcgctgctg ccccctagcg gggggaggac gtaattacat   2880
ccctgggggc tttggggggg ggctgtcccc gtgagctccc cagatctgct ttttgcctgt   2940
actgggtctc tctggttaga ccagatctga gcctgggagc tctctggcta actagggaac   3000
ccactgctta agcctcaata aagcttcagc tgctcgagct agcagatctt tttccctctg   3060
ccaaaaatta tggggacatc atgaagcccc ttgagcatct gacttctggc taataaagga   3120
aatttatttt cattgcaata gtgtgttgga atttttttgtg tctctcactc ggaaggacat  3180
atgggagggc aaatcattta aaacatcaga atgagtattt ggtttagagt ttggcaacat   3240
atgcccatat gctggctgcc atgaacaaag gttggctata aagaggtcat cagtatatga   3300
aacagccccc tgctgtccat tccttattcc atagaaaagc cttgacttga ggttagattt   3360
tttttatatt ttgttttgtg ttattttttt ctttaacatc cctaaaattt tccttacatg   3420
```

ttttactagc cagatttttc ctcctctcct gactactccc agtcatagct gtccctcttc 3480
tcttatggag atccctcgac ctgcagccca agcttggcgt aatcatggtc atagctgttt 3540
cctgtgtgaa attgttatcc gctcacaatt ccacacaaca tacgagccgg aagcataaag 3600
tgtaaagcct ggggtgccta atgagtgagc taactcacat taattgcgtt gcgctcactg 3660
cccgctttcc agtcgggaaa cctgtcgtgc cagcggatcc gcatctcaat tagtcagcaa 3720
ccatagtccc gcccctaact ccgcccatcc cgcccctaac tccgcccagt tccgcccatt 3780
ctccgcccca tggctgacta attttttta tttatgcaga ggccgaggcc gcctcggcct 3840
ctgagctatt ccagaagtag tgaggaggct tttttggagg cctaggcttt tgcaaaaagc 3900
t 3901

<210> SEQ ID NO 49
<211> LENGTH: 412
<212> TYPE: DNA
<213> ORGANISM: Artificial Sequence
<220> FEATURE:
<223> OTHER INFORMATION: Synthetic: cHS4 insulator

<400> SEQUENCE: 49
atccctgcag gcattcaagg ccaggctgga tgtggctctg ggcagcctgg gctgctggtt 60
gatgaccctg cacatagcag gggttggat ctggatgagc actgtgctcc tttgcaaccc 120
aggccgttct atgattctgt cattctaaat ctctctttca gcctaaagct tttccccgt 180 atcccccag gtgtctgcag gctcaaagag cagcgagaag cgttcagagg aaagcgatcc 240
cgtgccacct tccccgtgcc cggctgtcc ccgcacgctg ccggctcggg gatgcggggg 300
gagcgccgga ccggagcgga gccccgggcg gctcgctgct gccccctagc gggggaggga 360
cgtaattaca tccctgggg ctttgggggg gggctgtccc cgtgagctcc cc 412

<210> SEQ ID NO 50
<211> LENGTH: 5221
<212> TYPE: DNA
<213> ORGANISM: Artificial Sequence
<220> FEATURE:
<223> OTHER INFORMATION: Synthetic: sGbGM vector cassette

<400> SEQUENCE: 50
ggagccagaa gcaccataag ggacatgggg atcctctaga gtcgagctcg cgaggatcat 60
caccggtgct agccgataag ggagccagca gacctctgat ctcttcctga atgctaatct 120
taaacatcct gaggaagaat gggacttcca tttggggtgg gcctatgata gggtaataag 180
acagtagtga atatcaagct acaaaaagcc ccctttcaaa ttcttctcag tcctaacttt 240
tcatactaag cccagtcctt ccaaagcaga ctgtgaaaga gtgatagttc cgggagacta 300
gcaccggcta gccgagcttg gaacactttc ccttcattaa gaaccatcct tgctactcag 360
ctgcaatcaa tccagccccc aggtcttcac tgaacctttt cccatctctt ccaaaacatc 420
tgtttctgag aagtcctgtc ctatagaggt ctttcttccc accggatttc tcctacacca 480
tttactccca cttgcagaac tcccgtgtac aagtgtcttt actgctttta tttgctcaac 540
aaaatgcaca tctcatataa aaataaatga ggagcatgca cacaccacaa acacaaacag 600
gcatgcagaa atacacatac acacttccct caatataaac cctttgtggc tcatatattt 660
aaaaagatgt aaaaaaaaga gctgaagaaa atcatgtgtg atctctcagc agaatagatt 720
tattatttgt attgcttgca gaataaagcc tatccttgaa agctctgaat catgggcaag 780

-continued

```
aggctcagtg gtatctggag gacagggcac tggccactgc agtcaccatc ttctgccagg    840
aagcctgcac ctcaggggtg aattctttgc caaagtgaat ggccagcacg gtgaccagca    900
cgttgcccag gagctgtggg aggaagataa gaggtatgaa catgattagc aaaagggcct    960
agcttggact cagaataatc cagccttatc ccaaccataa aataaaagca gaatggtagc   1020
tggattgtag ctgctattag caatatgaaa cctcttacat cagttacaat ttatatgcag   1080
aaatatttat atgcagaaat attgctattg ccttaaccca gaaattatca ctgttattct   1140
ttagaatggt gcaaagaggc atgatacatt gtatcattat tgccctgaaa gaaagagatt   1200
agggaaagta ttagaaataa gataaacaaa aaagtatatt aaaagaagaa agcatttttt   1260
aaaattacaa atgcaaaatt accctgattt ggtcaatatg tgtaccctgt tacttctccc   1320
cttcctatga catgaactta accatagaaa agaaggggaa agaaaacatc aagggtccca   1380
tagactcacc ttgaagttct caggatccac atgcagcttg tcacagtgca gttcactcag   1440
ctgggcaaag gtgcccttga gatcatccag gtgctttatg gcatctccca aggaagtcag   1500
caccttcttg ccatgtgcct tgactttggg gttgcccatg atggcagagg cagaggacag   1560
gttgccaaag ctgtcaaaga acctctgggt ccatgggtag acaaccagga gcctgtgaga   1620
ttgacaagaa cagtttgaca gtcagaaggt gccacaaatc ctgagaagca acctggactt   1680
ttgccaggca cagggtcctt ccttccctcc cttgtcctgg tcaccagagc ctaccttccc   1740
agggtttctc ctccagcatc ttccacattc accttgtccc acaggcttgt gatagtagcc   1800
ttgtcctcct ctgtgaaatg acccatggtg tctgtttgag gttgctagtg aacacagttg   1860
tgtcagaagc aaatgtaagc aatagatggc tctgccctga cttttatgcc cagccctggc   1920
tcctgccctc cctgctcctg ggagtagatt ggccaaccct agggtgtggc tccacagggt   1980
gaggtctaag tgatgacagc cgtacctgtc cttggctctt ctggcactgg cttaggagtt   2040
ggacttcaaa ccctcagccc tccctctaag atatatctct tggccccata ccatcagtac   2100
aaattgctac taaaaacatc ctcctttgca agtgtattta cgacggtatc gatgtatgtg   2160
agcatgtgtc ctctaacagc acaggccttt tgccacctag ctgtccaggg gtgccttaaa   2220
atggcaaaca aggtttgttt tcttttcctg ttttcatgcc ttcctcttcc atatccttgt   2280
ttcatattaa tacatgtgta tagatcctaa aaatctatac acatgtatta ataaagcctg   2340
attctgccgc ttctaggtat agaggccacc tgcaagataa atatttgatt cacaataact   2400
aatcattcta tggcaattga taacaacaaa tatatatata tatatatata tacgtatatg   2460
tgtatatata tatatatata tatatattca ggaaataata tattctagaa tatgtcacat   2520
tctgtctcag gcatccattt tctttatgat gccgtttgag gtggagtttt agtcaggtgg   2580
tcagcttctc cttttttttg ccatctgccc tgtaagcatc ctgctgggga cccagatagg   2640
agtcatcact ctaggctgag aacatctggg cacacaccct aagcctcagc atgactcatc   2700
atgactcagc attgctgtgc ttgagccaga aggtttgctt agaaggttac acagaaccag   2760
aaggcggggg tggggcactg accccgacag gggcctggcc agaactgctc atgcttggac   2820
tatgggaggt cactaatgga gacacacaga aatgtaacag gaactaaggg aattccggtg   2880
ccctgcttag gagcttaatc tttaatgaaa gctaagcttt cattaaaaaa agtctaacca   2940
gctgcattcg actttgactg cagcagctgg ttagaaggtt ctactggagg agggtcccag   3000
cccattgcta aattaacatc aggctctgag actggcagta tatctctaac agtggttgat   3060
gctatcttct ggaacttgcc tgctacattg agaccactga cccatacata ggaagcccat   3120
agctctgtcc tgaactgtta ggccactggt ccagagagtg tgcatctcct ttgatcctca   3180
```

taataaccct atgagataga cacaattatt actcttactt tatagatgat gatcctgaaa 3240
acataggagt caaggcactt gcccctagct gggggtatag gggagcagtc ccatgtagta 3300
gtagaatgaa aaatgctgct atgctgtgcc tcccccacct ttcccatgtc tgccctctac 3360
tcatggtcta tctctcctgg ctcctgggag tcatggactc cacccagcac caccaacctg 3420
acctaaccac ctatctgagc ctgccagcct ataacccatc tgggccctga tagctggtgg 3480
ccagccctga ccccacccca ccctccctgg aacctctgat agacacatct ggcacaccag 3540
ctcgcaaagt caccgtgagg gtcttgtgtt tgctgagtca aaattccttg aaatccaagt 3600
ccttagagac tcctgctccc aaatttacag tcatagactt cttcatggct gtctccttta 3660
tccacagaat gattcctttg cttcattgcc ccatccatct gatcctcctc atcagtgcag 3720
cacagggccc atgagcagta gctgcagagt ctcacatagg tctggcactg cctctgacat 3780
gtccgacctt aggcaaatgc ttgactcttc tgagctcgga tcccttgagc tcaggaggtc 3840
aaggctgcag tgagacatga tcttgccact gcactccagc ctggacagca gagtgaaacc 3900
ttgcctcacg aaacagaata caaaaacaaa caaacaaaaa actgctccgc aatgcgcttc 3960
cttgatgctc taccacatag gtctgggtac tttgtacaca ttatctcatt gctgttcata 4020
attgttagat taattttgta atattgatat tattcctaga aagctgaggc ctcaagatga 4080
taacttttat tttctggact tgtaatagct ttctcttgta ttcaccatgt tgtaactttc 4140
ttagagtagt aacaatataa agttattgtg agtttttgca aacacagcaa acacaacgac 4200
ccatatagac attgatgtga aattgtctat tgtcaattta tgggaaaaca agtatgtact 4260
ttttctacta agccattgaa acaggaataa cagaacaaga ttgaaagaat acattttccg 4320
aaattacttg agtattatac aaagacaagc acgtggacct gggaggaggg ttattgtcca 4380
tgactggtgt gtggagacaa atgcaggttt ataatagatg ggatggcatc tagcgcaatg 4440
actttgccat cacttttaga gagctcttgg gggccccagt acacaagagg ggacgcaggg 4500
tatatgtaga catctcattc tttttcttag tgtgagaata agaatagcca tgacctgagt 4560
ttatagacaa tgagcccttt tctctctccc actcagcagc tatgagatgg cttgccctgc 4620
ctctctacta ggctgactca ctccaaggcc cagcaatggg cagggctctg tcagggcttt 4680
gatagcacta tctgcagagc cagggccgag aaggggtgga ctccagagac tctccctccc 4740
attcccgagc agggtttgct tatttatgca tttaaatgat atatttattt taaaagaaat 4800
aacaggagac tgcccagccc tggctgtgac atggaaacta tgtagaatat tttgggttcc 4860
attttttttt ccttctttca gttagaggaa aaggggctca ctgcacatac actagacaga 4920
aagtcaggag ctttgaatcc aagcctgatc atttccatgt catactgaga aagtccccac 4980
ccttctctga gcctcagttt ctctttttat aagtaggagt ctggagtaaa tgatttccaa 5040
tggctctcat ttcaatacaa aatttccgtt tattaaatgc atgagcttct gttactccaa 5100
gactgagaag gaaattgaac ctgagactca ttgactggca agatgtcccc agaggctctc 5160
attcagcaat aaaattctca ccttcaccca ggcccactga gtgtcagatt tgcatgcgga 5220
t 5221

<210> SEQ ID NO 51
<211> LENGTH: 100
<212> TYPE: DNA
<213> ORGANISM: Artificial Sequence
<220> FEATURE:
<223> OTHER INFORMATION: Synthetic: Exon 1 (HBG17101-7152; sGbGm reverse strand 1735-1834)

<400> SEQUENCE: 51
cttcccaggg tttctcctcc agcatcttcc acattcacct tgtcccacag gcttgtgata 60
gtagccttgt cctcctctgt gaaatgaccc atggtgtctg 100

<210> SEQ ID NO 52
<211> LENGTH: 223
<212> TYPE: DNA
<213> ORGANISM: Artificial Sequence
<220> FEATURE:
<223> OTHER INFORMATION: Synthetic: Exon 2 (HBG17323-7545; sGbGm reverse strand 1612-1320)

<400> SEQUENCE: 52
cttgaagttc tcaggatcca catgcagctt gtcacagtgc agttcactca gctgggcaaa 60
ggtgcccttg agatcatcca ggtgctttat ggcatctccc aaggaagtca gcaccttctt 120
gccatgtgcc ttgactttgg ggttgcccat gatggcagag gcagaggaca ggttgccaaa 180
gctgtcaaag aacctctggg tccatgggta gacaaccagg agc 223

<210> SEQ ID NO 53
<211> LENGTH: 216
<212> TYPE: DNA
<213> ORGANISM: Artificial Sequence
<220> FEATURE:
<223> OTHER INFORMATION: Synthetic: Exon 3 (HBG1 8412-8627; sGbGm reverse strand 698-913)

<400> SEQUENCE: 53
gtgatctctc agcagaatag atttattatt tgtattgctt gcagaataaa gcctatcctt 60
gaaagctctg aatcatgggc aagaggctca gtggtatctg gaggacaggg cactggccac 120
tgcagtcacc atcttctgcc aggaagcctg cacctcaggg gtgaattctt tgccaaagtg 180
aatggccagc acggtgacca gcacgttgcc caggag 216

<210> SEQ ID NO 54
<211> LENGTH: 303
<212> TYPE: DNA
<213> ORGANISM: Artificial Sequence
<220> FEATURE:
<223> OTHER INFORMATION: Synthetic: 7SK-sh734 Sequence cassette

<400> SEQUENCE: 54
atcgacgtgc agtatttagc atgccccacc catctgcaag gcattctgga tagtgtcaaa 60
acagccggaa atcaagtccg tttatctcaa actttagcat tttgggaata aatgatattt 120
gctatgctgg ttaaattaga ttttagttaa atttcctgct gaagctctag tacgataagt 180
aacttgacct aagtgtaaag ttgagatttc cttcaggttt atatagcttg tgcgccgcct 240
gggtacctca ggatatgccc ttgactattt gtccgacata gtcaagggca tatccttttt 300
tgt 303

<210> SEQ ID NO 55
<211> LENGTH: 539
<212> TYPE: DNA
<213> ORGANISM: Artificial Sequence
<220> FEATURE:
<223> OTHER INFORMATION: Synthetic: sGbGm A gamma-globin sequence 5-3 complementary strand

<400> SEQUENCE: 55
cagacaccat gggtcatttc acagaggagg acaaggctac tatcacaagc ctgtgggaca 60
aggtgaatgt ggaagatgct ggaggagaaa ccctgggaag gctcctggtt gtctacccat 120
ggacccagag gttctttgac agctttggca acctgtcctc tgcctctgcc atcatgggca 180
accccaaagt caaggcacat ggcaagaagg tgctgacttc cttgggagat gccataaagc 240
acctggatga tctcaagggc acctttgccc agctgagtga actgcactgt gacaagctgc 300
atgtggatcc tgagaacttc aagctcctgg gcaacgtgct ggtcaccgtg ctggccattc 360
actttggcaa agaattcacc cctgaggtgc aggcttcctg gcagaagatg gtgactgcag 420
tggccagtgc cctgtcctcc agataccact gagcctcttg cccatgattc agagctttca 480
aggataggct ttattctgca agcaatacaa ataataaatc tattctgctg agagatcac 539

<210> SEQ ID NO 56
<211> LENGTH: 769
<212> TYPE: DNA
<213> ORGANISM: Artificial Sequence
<220> FEATURE:
<223> OTHER INFORMATION: Synthetic: REV response element (RRE)

<400> SEQUENCE: 56
aggaggagat atgagggaca attggagaag tgaattatat aaatataaag tagtaaaaat 60
tgaaccatta ggagtagcac ccaccaaggc aaagagaaga gtggtgcaga gagaaaaaag 120
agcagtggga ataggagctt tgttccttgg gttcttggga gcagcaggaa gcactatggg 180
cgcagcgtca atgacgctga cggtacaggc cagacaatta ttgtctggta tagtgcagca 240
gcagaacaat ttgctgaggg ctattgaggc gcaacagcat ctgttgcaac tcacagtctg 300
gggcatcaag cagctccagg caagaatcct ggctgtggaa agatacctaa aggatcaaca 360
gctcctgggg atttggggtt gctctggaaa actcatttgc accactgctg tgccttggaa 420
tgctagttgg agtaataaat ctctggaaca gatttggaat cacacgacct ggatggagtg 480
ggacagagaa attaacaatt acacaagctt aatacactcc ttaattgaag aatcgcaaaa 540
ccagcaagaa aagaatgaac aagaattatt ggaattagat aaatgggcaa gtttgtggaa 600
ttggtttaac ataacaaatt ggctgtggta tataaaatta ttcataatga tagtaggagg 660
cttggtaggt ttaagaatag tttttgctgt actttctata gtgaatagag ttaggcaggg 720
atattcacca ttatcgtttc agacccacct cccaaccccg aggggaccg 769

<210> SEQ ID NO 57
<211> LENGTH: 3055
<212> TYPE: DNA
<213> ORGANISM: Artificial Sequence
<220> FEATURE:
<223> OTHER INFORMATION: Synthetic: Locus Control Region

<400> SEQUENCE: 57
gtatgtgagc atgtgtcctc taacagcaca ggccttttgc cacctagctg tccaggggtg 60
ccttaaaatg gcaaacaagg tttgttttct ttcctgtttt tcatgccttc ctcttccata 120
tccttgtttc atattaatac atgtgtatag atcctaaaaa tctatacaca tgtattaata 180
aagcctgatt ctgccgcttc taggtataga ggccacctgc aagataaata tttgattcac 240
aataactaat cattctatgg caattgataa caacaaatat atatatatat atatatatac 300
gtatatgtgt atatatatat atatattcag gaaataatat attctagaat atgtcacatt 360
ctgtctcagg catccatttt ctttatgatg ccgtttgagg tggagtttta gtcaggtggt 420
cagcttctcc tttttttgc catctgccct gtaagcatcc tgctggggac ccagatagga 480
gtcatcactc taggctgaga acatctgggc acacacccta agcctcagca tgactcatca 540
tgactcagca ttgctgtgct tgagccagaa ggtttgctta gaaggttaca cagaaccaga 600
aggcgggggt ggggcactga ccccgacagg ggcctggcca gaactgctca tgcttggact 660
atgggaggtc actaatggag acacacagaa atgtaacagg aactaaggga attccggtgc 720
cctgcttagg agcttaatct ttaatgaaag ctaagctttc attaaaaaaa gtctaaccag 780
ctgcattcga ctttgactgc agcagctggt tagaaggttc tactggagga gggtcccagc 840
ccattgctaa attaacatca ggctctgaga ctggcagtat atctctaaca gtggttgatg 900
ctatcttctg gaacttgcct gctacattga gaccactgac ccatacatag gaagcccata 960
gctctgtcct gaactgttag gccactggtc cagagagtgt gcatctcctt tgatcctcat 1020
aataacccta tgagatagac acaattatta ctcttacttt atagatgatg atcctgaaaa 1080
cataggagtc aaggcacttg cccctagctg gggtatagg ggagcagtcc catgtagtag 1140
tagaatgaaa aatgctgcta tgctgtgcct cccccacctt tcccatgtct gccctctact 1200
catggtctat ctctcctggc tcctgggagt catggactcc acccagcacc accaacctga 1260
cctaaccacc tatctgagcc tgccagccta taacccatct gggccctgat agctggtggc 1320
cagccctgac cccaccccac cctccctgga acctctgata gacacatctg gcacaccagc 1380
tcgcaaagtc accgtgaggg tcttgtgttt gctgagtcaa aattccttga aatccaagtc 1440
cttagagact cctgctccca aatttacagt catagacttc ttcatggctg tctcctttat 1500
ccacagaatg attcctttgc ttcattgccc catccatctg atcctcctca tcagtgcagc 1560
acagggccca tgagcagtag ctgcagagtc tcacataggt ctggcactgc ctctgacatg 1620
tccgacctta ggcaaatgct tgactcttct gagctcggat cccttgagct caggaggtca 1680
aggctgcagt gagacatgat cttgccactg cactccagcc tggacagcag agtgaaacct 1740
tgcctcacga aacagaatac aaaaacaaac aaacaaaaaa ctgctccgca atgcgcttcc 1800
ttgatgctct accacatagg tctgggtact ttgtacacat tatctcattg ctgttcataa 1860
ttgttagatt aattttgtaa tattgatatt attcctagaa agctgaggcc tcaagatgat 1920
aacttttatt ttctggactt gtaatagctt tctcttgtat tcaccatgtt gtaactttct 1980
tagagtagta acaatataaa gttattgtga gtttttgcaa acacagcaaa cacaacgacc 2040
catatagaca ttgatgtgaa attgtctatt gtcaatttat gggaaaacaa gtatgtactt 2100
tttctactaa gccattgaaa caggaataac agaacaagat tgaaagaata cattttccga 2160
aattacttga gtattataca aagacaagca cgtggacctg ggaggagggt tattgtccat 2220
gactggtgtg tggagacaaa tgcaggttta taatagatgg gatggcatct agcgcaatga 2280
ctttgccatc acttttagag agctcttggg ggccccagta cacaagaggg gacgcagggt 2340
atatgtagac atctcattct ttttcttagt gtgagaataa gaatagccat gacctgagtt 2400
tatagacaat gagccctttt ctctctccca ctcagcagct atgagatggc ttgccctgcc 2460
tctctactag gctgactcac tccaaggccc agcaatgggc agggctctgt cagggctttg 2520
atagcactat ctgcagagcc agggccgaga aggggtggac tccagagact ctccctccca 2580
ttcccgagca gggtttgctt atttatgcat ttaaatgata tatttatttt aaaagaaata 2640
acaggagact gcccagccct ggctgtgaca tggaaactat gtagaatatt ttgggttcca 2700
tttttttttc cttctttcag ttagaggaaa aggggctcac tgcacataca ctagacagaa 2760
agtcaggagc tttgaatcca agcctgatca tttccatgtc atactgagaa agtccccacc 2820
cttctctgag cctcagtttc tctttttata agtaggagtc tggagtaaat gatttccaat 2880
ggctctcatt tcaatacaaa atttccgttt attaaatgca tgagcttccg ttactccaag 2940
actgagaagg aaattgaacc tgagactcat tgactggcaa gatgtcccca gaggctctca 3000
ttcagcaata aaattctcac cttcacccag gcccactagt gtcagatttg catgc 3055

<210> SEQ ID NO 58
<211> LENGTH: 43
<212> TYPE: DNA
<213> ORGANISM: Artificial Sequence
<220> FEATURE:
<223> OTHER INFORMATION: Synthetic: Agosh 734 5-3

<400> SEQUENCE: 58
atagtcaagg gcatatcctc aagaaggata tgcccttgac tac 43

<210> SEQ ID NO 59
<211> LENGTH: 1435
<212> TYPE: DNA
<213> ORGANISM: Homo sapiens
<220> FEATURE:
<221> NAME/KEY: misc_feature
<223> OTHER INFORMATION: Homo sapiens hypoxanthine phosphoribosyltransferase 1 (HPRT1), mRNA

<400> SEQUENCE: 59
ggcggggcct gcttctcctc agcttcaggc ggctgcgacg agccctcagg cgaacctctc 60
ggctttcccg cgcggcgccg cctcttgctg cgcctccgcc tcctcctctg ctccgccacc 120
ggcttcctcc tcctgagcag tcagcccgcg cgccggccgg ctccgttatg gcgacccgca 180
gccctggcgt cgtgattagt gatgatgaac caggttatga ccttgattta ttttgcatac 240
ctaatcatta tgctgaggat ttggaaaggg tgtttattcc tcatggacta attatggaca 300
ggactgaacg tcttgctcga gatgtgatga aggagatggg aggccatcac attgtagccc 360
tctgtgtgct caaggggggc tataaattct ttgctgacct gctggattac atcaaagcac 420
tgaatagaaa tagtgataga tccattccta tgactgtaga ttttatcaga ctgaagagct 480
attgtaatga ccagtcaaca ggggacataa aagtaattgg tggagatgat ctctcaactt 540
taactggaaa gaatgtcttg attgtggaag atataattga cactggcaaa acaatgcaga 600
ctttgctttc cttggtcagg cagtataatc caaagatggt caaggtcgca agcttgctgg 660
tgaaaaggac cccacgaagt gttggatata agccagactt tgttggattt gaaattccag 720
acaagtttgt tgtaggatat gcccttgact ataatgaata cttcagggat ttgaatcatg 780
tttgtgtcat tagtgaaact ggaaaagcaa aatacaaagc ctaagatgag agttcaagtt 840
gagtttggaa acatctggag tcctattgac atcgccagta aaattatcaa tgttctagtt 900
ctgtggccat ctgcttagta gagctttttg catgtatctt ctaagaattt tatctgtttt 960
gtactttaga aatgtcagtt gctgcattcc taaactgttt atttgcacta tgagcctata 1020
gactatcagt tccctttggg cggattgttg tttaacttgt aaatgaaaaa attctcttaa 1080
accacagcac tattgagtga aacattgaac tcatatctgt aagaaataaa gagaagatat 1140
attagttttt taattggtat tttaattttt atatatgcag gaaagaatag aagtgattga 1200
atattgttaa ttataccacc gtgtgttaga aaagtaagaa gcagtcaatt ttcacatcaa 1260
agacagcatc taagaagttt tgttctgtcc tggaattatt ttagtagtgt ttcagtaatg 1320
ttgactgtat tttccaactt gttcaaatta ttaccagtga atctttgtca gcagttccct 1380
tttaaatgca aatcaataaa ttcccaaaaa tttaaaaaaa aaaaaaaaaa aaaaa 1435

<210> SEQ ID NO 60
<211> LENGTH: 42
<212> TYPE: DNA
<213> ORGANISM: Artificial Sequence
<220> FEATURE:
<223> OTHER INFORMATION: Synthetic: miRNA 451 hairpin sequence

<400> SEQUENCE: 60
aaaccgttac cattactgag tttagtaatg gtaatggttc tc 42

<210> SEQ ID NO 61
<211> LENGTH: 23
<212> TYPE: DNA
<213> ORGANISM: Artificial Sequence
<220> FEATURE:
<223> OTHER INFORMATION: Synthetic: sgRNA candidate for knock down of human HPRT

<400> SEQUENCE: 61
gttatggcga cccgcagccc tgg 23

<210> SEQ ID NO 62
<211> LENGTH: 212
<212> TYPE: DNA
<213> ORGANISM: Artificial Sequence
<220> FEATURE:
<223> OTHER INFORMATION: Synthetic: left homology arm from target CCR5 gene region

<400> SEQUENCE: 62
gcttcttctc tggaatcttc ttcatcatcc tcctgacaat cgataggtac ctggctgtcg 60
tccatgctgt gtttgcttta aaagccagga cggtcacctt tggggtggtg acaagtgtga 120
tcacttgggt ggtggctgtg tttgcgtctc aagcttttcg aagcggccgc ggatatcggc 180
tccggtgccc gtcagtgggc agagcgcaca tc 212

<210> SEQ ID NO 63
<211> LENGTH: 221
<212> TYPE: DNA
<213> ORGANISM: Artificial Sequence
<220> FEATURE:
<223> OTHER INFORMATION: Synthetic: left homology arm from target CCR5 gene region

<400> SEQUENCE: 63
aaagcatttt tttcactgca ttctagttgt ggtttgtcca aactcatcaa tgtatcttat 60
catctacgcg tccaggaatc atctttacca gatctcaaaa agaaggtctt cattacacct 120
gcagctctca ttttccatac agtcagtatc aattctggaa gaatttccag acattaaaga 180
tagtcatctt ggggctggtc ctgccgctgc ttgtcatggt c 221

<210> SEQ ID NO 64
<211> LENGTH: 238
<212> TYPE: DNA
<213> ORGANISM: Artificial Sequence
<220> FEATURE:
<223> OTHER INFORMATION: Synthetic: EF1a promoter

<400> SEQUENCE: 64
ggatatcggc tccggtgccc gtcagtgggc agagcgcaca tcgcccacag tccccgagaa 60
gttgggggga ggggtcggca attgaaccgg tgcctagaga aggtggcgcg gggtaaactg 120
ggaaagtgat gtcgtgtact ggctccgcct ttttcccgag ggtgggggag aaccgtatat 180
aagtgcagta gtcgccgtga acgttctttt cgcaacgggt ttgccgccag aacacagg 238

<210> SEQ ID NO 65
<211> LENGTH: 128
<212> TYPE: DNA
<213> ORGANISM: Artificial Sequence
<220> FEATURE:
<223> OTHER INFORMATION: Synthetic: SV40 promoter

<400> SEQUENCE: 65
aacttgttta ttgcagctta taatggttac aaataaagca atagcatcac aaatttcaca 60
aataaagcat ttttttcact gcattctagt tgtggtttgt ccaaactcat caatgtatct 120
tatcatct 128

<210> SEQ ID NO 66
<211> LENGTH: 87
<212> TYPE: DNA
<213> ORGANISM: Artificial Sequence
<220> FEATURE:
<223> OTHER INFORMATION: Synthetic: Beta globin promoter

<400> SEQUENCE: 66
ggtgtctgtt tgaggttgct agtgaacaca gttgtgtcag aagcaaatgt aagcaataga 60
tggctctgcc ctgactttta tgcccag 87

<210> SEQ ID NO 67
<211> LENGTH: 111
<212> TYPE: DNA
<213> ORGANISM: Artificial Sequence
<220> FEATURE:
<223> OTHER INFORMATION: Synthetic: miRNA734 de novo (DNA form)

<400> SEQUENCE: 67
acccgtacat atttttgtgt agctctagtt tatagtcaag ggcatatcct tgtgtttttt 60
ttgaaggata tgcccttgac tataaactag cgctacactt tttcgtcttg t 111

<210> SEQ ID NO 68
<211> LENGTH: 111
<212> TYPE: DNA
<213> ORGANISM: Artificial Sequence
<220> FEATURE:
<223> OTHER INFORMATION: Synthetic: miRNA211 de novo (DNA form)

<400> SEQUENCE: 68
acccgtacat atttttgtgt agctctagtt ataaatcaag gtcataacct tgtgtttttt 60
ttgaaggtta tgaccttgat ttataactag cgctacactt tttcgtcttg t 111

<210> SEQ ID NO 69
<211> LENGTH: 23
<212> TYPE: DNA
<213> ORGANISM: Artificial Sequence
<220> FEATURE:
<223> OTHER INFORMATION: Synthetic: sgRNA candidate for knock down of human HPRT

<400> SEQUENCE: 69
gcgggtcgcc ataacggagc cgg 23

COMPOSITIONS AND METHODS FOR TREATING BETA-HEMOGLOBINOPATHIES

CROSS REFERENCE TO RELATED APPLICATIONS

The present application is a continuation of U.S. patent application Ser. No. 16/037,726 filed on Jul. 17, 2018, which application claims the benefit of the filing date of U.S. Provisional Patent Application No. 62/653,913, filed on Apr. 6, 2018; the benefit of the filing date of U.S. Provisional Patent Application No. 62/541,931, filed on Aug. 7, 2017; and also, the benefit of the filing date of U.S. Provisional Patent Application No. 62/533,719 filed on Jul. 18, 2017, the disclosures of which are each hereby incorporated by reference herein in their entireties.

FIELD OF DISCLOSURE

This disclosure generally relates to the fields of molecular biology and, in particular, vectors and host cells transduced by vectors.

BACKGROUND OF THE DISCLOSURE

β-Hemoglobinopathies, including beta-thalassemia and sickle-cell disease (SCD), are a heterogeneous group of commonly inherited disorders affecting the function or levels of hemoglobin. SCD and β-thalassemia are the most common monogenic disorders in the world with approximately 400,000 affected births each year. Clinical manifestations typically appear several months after birth during the switch from fetal hemoglobin (HbF) to adult β-globin (HbA) and can be severe with substantial morbidity and mortality. Allogenic bone marrow transplantation is curative but limited to those patients with an appropriately matched donor. Autologous gene therapy, which utilizes a patient's own cells, is an attractive therapeutic option.

β-thalassemia is an inherited blood disorder characterized by reduced levels of functional hemoglobin. β-thalassemias are caused by mutations in hemoglobin subunit beta (hereinafter the "HBB gene"), which is believed to be inherited in an autosomal recessive fashion. β-thalassemia major, defined clinically as transfusion-dependent, is caused by reduced or absent synthesis of the beta chain of hemoglobin. The severity of the disease depends on the nature of the mutation with variable outcomes ranging from severe anemia to clinically asymptomatic individuals.

Hundreds of different mutations have been described affecting beta-globin levels via effects on a wide range of processes, including transcription, mRNA splicing/processing, RNA stability, translation, and globin peptide stability. It is believed that the low beta-globin content allows the excess alpha-globin chains to precipitate in erythroid precursors. It is further believed that the alpha-globin aggregates cause cell membrane damage and lead to early erythroid precursor death. The resultant ineffective erythropoiesis found in patients, if severe, may necessitate frequent blood transfusions.

Sickle cell anemia ("SCA") results from a single point mutation in Exon 1 of the beta-globin gene leading to the replacement of Glutamic acid with Valine at position 6 in the mutated sickled form of hemoglobin, hemoglobin S (HbS). There are other genotypes, in addition to homozygous hemoglobin S ("HbSS"), that can result in SCD. While classical SCA is often defined as homozygous HbSS, homozygous hemoglobin C ("HbSC") and thalassemia ("HbS/$\beta^0$") are common genotypes that have essentially the same disease manifestations. HbS polymerizes upon deoxygenation resulting in sickle-shaped red blood cells ("RBCs") that occlude microvasculature. SCD is characterized clinically by varying degree of anemia, and episodic vasoocculsive crisis leading to multi-organ damage and premature death. Besides sickling, excessive hemolysis and a state of chronic inflammation exist.

SCD patients account for approximately 75,000 USA hospitalizations per year, resulting in an estimated annual expenditure of $475 million dollars. Worldwide, SCD is second only to thalassemia in incidence of monogenic disorders, with more than 200,000 children born annually in Africa with this disease. Medical management options currently available for SCD include supportive management of vasoocclusive crisis, long-term transfusions to avoid or prevent recurrence of severe complications of SCD such as stroke or acute chest syndrome, and fetal hemoglobin (HbF) induction with hydroxyurea. A matched allogeneic hematopoietic stem cell (HSC) transplantation is believed to be curative but restricted by the availability of matched related donors and has potential serious complications. In fetal life, the gamma-globin gene (resulting in HbF; $alpha_2gamma_2$) is the predominant gene expressed by the beta-globin locus and the beta-globin gene expression is repressed. However, after birth, the expression of fetal gamma-globin gene decreases to negligible levels, with a concomitant increase in beta-globin expression. In adult life, fetal gamma-globin transcripts are highly silenced, i.e. gene expression is regulated to prevent or reduce expression of gamma-globin. This change of expression results in decreased HbF with a corresponding increase in HbA ($alpha_2beta_2$). Gamma-globin is known to have anti-sickling properties and, thus the addition of this gene is considered for gene therapy.

Hemoglobinopathies, especially SCD, are prime targets for gene therapy for a variety of reasons. Their high prevalence, significant morbidity and mortality, and the resulting high cost of lifelong palliative medical care portends that a curative therapy can greatly improve patient outcomes and significantly reduce associated medical costs. Gene therapy for β-hemoglobinopathies by ex vivo lentiviral transfer of a therapeutic β-globin gene into autologous $CD34^+$ hematopoietic stem/progenitor cells (HSPC) has been evaluated in human clinical trials for over the past 9 years. Autologous HSC transplantation based on myeloablative therapy has resulted in transfusion independence or a reduction in transfusion volumes in β-thalassemia patients greater than 12 months after gene therapy. Recently, curative response has been reported in an adolescent with SSD (see Thompson et. al., "Gene therapy in patients with transfusion-dependent Beta-Thalassemia," N Engl J Med. 2018 Apr. 19; 378(16): 1479-1493, the disclosure of which is hereby incorporated by reference herein in its entirety). Despite promising results, the majority of subjects in these trials failed to achieve levels of engraftment of gene-corrected autologous HSPC or reach a threshold level of expression of the therapeutic protein associated with clinical benefit.

BRIEF SUMMARY OF THE DISCLOSURE

Gene therapy strategies to modify human stem cells hold great promise for curing many human diseases, included hemoglobinopathies. It is believed that the engraftment of gene modified stem cells may be enhanced by engineering stem cells in which hypoxanthine guanine phosphoribosyitransferase ("HPRT") expression is knocked down, thereby enabling the selection of genetically modified cells by conferring resistance to a guanine analog antimetabolite.

In one aspect of the present disclosure is a composition including components which introduce a therapeutic gene into a hematopoietic stem cell ("HSC") which also contemporaneously decrease expression of HPRT in the HSC. In some embodiments, the composition includes a first component designed to effectuate a decrease in HPRT expression (e.g. an agent designed to knockdown HPRT or an agent designed to knockout HPRT). In some embodiments, the composition includes a second component, namely a nucleic acid encoding a therapeutic gene. In some embodiments, the composition includes a lentiviral expression vector including a first nucleic acid encoding an agent designed to knockdown the HPRT gene or otherwise effectuate a decrease in HPRT expression; and a second nucleic acid sequence encoding the therapeutic gene. In some embodiments, the lentiviral expression vector may be incorporated within a nanocapsule, such as one adapted to target HSCs. In some embodiments, the therapeutic gene is gamma globin.

In some embodiments, the first component is designed to knockdown HPRT. In some embodiments, the first component is an RNAi, such as an siRNA, a shRNA or a miRNA. In some embodiments, the first component is an antisense oligonucleotide that targets unspliced HPRT mRNA.

In some embodiments, the first component is designed to knockout HPRT. In some embodiments, the first component is a fusion protein comprising a zinc finger protein that binds to an endogenous hypoxanthine-guanine HPRT gene and a cleavage domain, wherein the fusion protein modifies the endogenous HPRT gene. In some embodiments, a single guide RNA (sgRNA) loaded with Cas9 may be used to target the CCR5 region (target sequence, 5'-GAGCAAGCTCAGTTTACACC-3') in the CCR5 gene locus (human chromosome 3) to "knock in" a Pol-II-driven shHPRT so as effectuate "knockdown expression" of HPRT (see, for example, SEQ ID NOS: 61 and 69). In some embodiments, the first component designed to knockout HPRT is included within a non-viral delivery vehicle. In some embodiments, the first component designed to knockout HPRT is included within a nanocapsule, such as a nanocapsule adapted to target HSCs. In some embodiments, the composition includes (i) a nanocapsule configured to deliver and/or release the first component designed to knockout HPRT; and (ii) a lentiviral expression vector including the second component, i.e. the nucleic acid encoding the therapeutic gene.

In another aspect of the present disclosure is an expression vector including (i) a first nucleic acid sequence encoding an RNAi, an antisense oligonucleotide, or an exon skipping agent targeting an HPRT gene; and (ii) a second nucleic acid sequence encoding a therapeutic gene. In some embodiments, the first nucleic acid encoding the RNAi encodes a small hairpin ribonucleic acid molecule ("shRNA") targeting HPRT. In some embodiments, the first nucleic acid encoding the shRNA targeting the HPRT gene has a sequence having at least 80% identity to that of SEQ ID NO: 30. In some embodiments, the first nucleic acid sequence encoding the shRNA targeting the HPRT gene has a sequence having at least 90% identity to that of SEQ ID NO: 30. In some embodiments, the first nucleic acid sequence encoding the shRNA targeting the HPRT gene has a sequence having at least 95% identity to that of SEQ ID NO: 30. In some embodiments, the first nucleic acid sequence encoding the shRNA targeting the HPRT gene has a sequence having at least 97% identity to that of SEQ ID NO: 30. In some embodiments, the first nucleic acid sequence encoding the shRNA targeting the HPRT gene has a sequence of SEQ ID NO: 30.

In some embodiments, the first nucleic acid sequence encoding the shRNA targeting the HPRT gene has a sequence having at least 80% identity to any one of SEQ ID NOS: 27-29. In some embodiments, the first nucleic acid sequence encoding the shRNA targeting the HPRT gene has a sequence having at least 90% identity to any one of SEQ ID NOS: 27-29. In some embodiments, the first nucleic acid sequence encoding the shRNA targeting the HPRT gene has a sequence having at least 95% identity to any one of SEQ ID NOS: 27-29. In some embodiments, the first nucleic acid sequence encoding the shRNA targeting the HPRT gene has a sequence having at least 97% identity to any one of SEQ ID NOS: 27-29. In some embodiments, the first nucleic acid sequence encoding the shRNA targeting the HPRT gene has a sequence of SEQ ID NO: 27. In some embodiments, the first nucleic acid sequence encoding the shRNA targeting the HPRT gene has a sequence of SEQ ID NO: 28. In some embodiments, the first nucleic acid sequence encoding the shRNA targeting the HPRT gene has a sequence of SEQ ID NO: 29.

In some embodiments, the first nucleic acid sequence encoding the shRNA targeting the HPRT gene has a sequence having at least 80% identity to that of SEQ ID NO: 31. In some embodiments, the first nucleic acid sequence encoding the shRNA targeting the HPRT gene has a sequence having at least 90% identity to that of SEQ ID NO: 31. In some embodiments, the first nucleic acid sequence encoding the shRNA targeting the HPRT gene has a sequence having at least 95% identity to that of SEQ ID NO: 31. In some embodiments, the first nucleic acid sequence encoding the shRNA targeting the HPRT gene has a sequence having at least 97% identity to that of SEQ ID NO: 31 In some embodiments, the first nucleic acid sequence encoding the shRNA targeting the HPRT gene has a sequence of SEQ ID NO: 31.

In some embodiments, the second nucleic acid encoding the therapeutic gene is one which may genetically correct sickle cell disease or β-thalassemia; or reduce symptoms thereof (including the symptoms of severe SCD). In other embodiments, the nucleic acid encoding the therapeutic gene is one which may genetically correct immune deficiencies, hereditary diseases, blood diseases (e.g. hemophilia, hemoglobin disorders), neurological diseases, and/or lysosomal storage diseases; or reduce symptoms thereof. In some embodiments, the vector is a lentiviral vector. In some embodiments, the therapeutic gene is gamma globin. In some embodiments, the second nucleic acid sequence encoding the therapeutic gene has a sequence having at least 80% identity to that of SEQ ID NO: 55. In some embodiments, the second nucleic acid sequence encoding the therapeutic gene has a sequence having at least 90% identity to that of SEQ ID NO: 55. In some embodiments, the second nucleic acid sequence encoding the therapeutic gene has a sequence having at least 95% identity to that of SEQ ID NO: 55. In some embodiments, the second nucleic acid sequence encoding the therapeutic gene has a sequence having at least 97% identity to that of SEQ ID NO: 55. In some embodiments, the second nucleic acid sequence encoding the therapeutic gene has a sequence of SEQ ID NO: 55.

In another aspect of the present disclosure is a lentiviral expression vector including a first nucleic acid sequence encoding an anti-HPRT shRNA or an anti-HPRT shRNA embedded within a microRNA; and a second nucleic acid sequence encoding a therapeutic gene. In some embodiments, the lentiviral expression vectors are suitable for transducing HSCs ex vivo. In some embodiments, the lentiviral expression vectors are suitable for producing selectable genetically modified cells, such as HSCs. In some embodiments, the HSCs transduced ex vivo may be administered to a patient in need of treatment, e.g. for the treatment of hemoglobinopathies, including beta-thalassemia and sickle-cell disease.

In some embodiments, the therapeutic gene is gamma globin gene. In some embodiments, the second nucleic acid sequence encoding the gamma globin gene is a hybrid gamma globin gene including a point mutation that confers a competitive advantage for the α-globin chain, skewing the formation of tetrameric HbF versus HbS. In some embodiments, the second nucleic acid sequence encoding the gamma-globin gene is operably linked to a beta globin promoter. In some embodiments, the second nucleic acid sequence encoding the gamma-globin gene has at least 95% sequence identity to that of SEQ ID NO: 55.

In some embodiments, the first nucleic acid sequence is operably linked to a Pol III promoter. In some embodiments, the Pol III promoter is a *Homo sapiens* cell-line HEK-293 7sk RNA promoter (see, for example, SEQ ID NO: 32). In some embodiments, the Pol III promoter is a 7sk promoter which includes a single mutation in its nucleic acid sequence as compared with SEQ ID NO: 32. In some embodiments, the Pol III promoter is a 7sk promoter which includes multiple mutations in its nucleic acid sequence as compared with SEQ ID NO: 32. In some embodiments, the Pol III promoter is a 7sk promoter which includes a deletion in its nucleic acid sequence as compared with SEQ ID NO: 32. In some embodiments, the Pol III promoter is a 7sk promoter which includes both a mutation and a deletion in its nucleic acid sequence as compared with SEQ ID NO: 32. In some embodiments, the first nucleic acid sequence is operably linked to promoter having at least 95% identity to that of SEQ ID NO: 32. In some embodiments, the first nucleic acid sequence is operably linked to promoter having at least 95% identity to that of SEQ ID NO: 33. In some embodiments, the first nucleic acid sequence is operably linked to promoter having at least 97% identity to that of SEQ ID NO: 33. In some embodiments, the first nucleic acid sequence is operably linked to promoter having at least 98% identity to that of SEQ ID NO: 33. In some embodiments, the first nucleic acid sequence is operably linked to promoter having at least 99% identity to that of SEQ ID NO: 33. In some embodiments, the first nucleic acid sequence is operably linked to a promoter having SEQ ID NO: 33. In some embodiments, the lentiviral expression vector further comprises an expression control sequence having a 5' long terminal repeat upstream of the second nucleic acid sequence, and a 3' long terminal repeat downstream of the nucleic acid encoding the gamma-globin gene.

In another aspect of the present disclosure is a vector comprising (i) a nucleic acid sequence encoding a micro-RNA based shRNA targeting a HPRT gene; and (ii) a nucleic acid sequence encoding a therapeutic gene. In some embodiments, the therapeutic gene is used to genetically correct sickle cell anemia or β-thalassemia; or reduce symptoms thereof. In some embodiments, the nucleic acid sequence encoding the micro-RNA based shRNA targeting the HPRT gene has a sequence having at least 80% identity to that of SEQ ID NO: 67. In some embodiments, the nucleic acid sequence encoding the micro-RNA based shRNA targeting the HPRT gene has a sequence having at least 90% identity to that of SEQ ID NO: 67. In some embodiments, the nucleic acid sequence encoding the micro-RNA based shRNA targeting the HPRT gene has a sequence having at least 95% identity to that of SEQ ID NO: 67. In some embodiments, the nucleic acid sequence encoding the micro-RNA based shRNA targeting the HPRT gene has a sequence of SEQ ID NO: 67.

In some embodiments, the nucleic acid sequence encoding the micro-RNA based shRNA targeting the HPRT gene has a sequence having at least 80% identity to that of SEQ ID NO: 68. In some embodiments, the nucleic acid sequence encoding the micro-RNA based shRNA targeting the HPRT gene has a sequence having at least 90% identity to that of SEQ ID NO: 68. In some embodiments, the nucleic acid sequence encoding the micro-RNA based shRNA targeting the HPRT gene has a sequence having at least 95% identity to that of SEQ ID NO: 68. In some embodiments, the nucleic acid sequence encoding the micro-RNA based shRNA targeting the HPRT gene has a sequence of SEQ ID NO: 68.

In some embodiments, the nucleic acid sequence encoding the micro-RNA based shRNA targeting the HPRT gene has a sequence having at least 80% identity to that of SEQ ID NO: 25. In some embodiments, the nucleic acid sequence encoding the micro-RNA based shRNA targeting the HPRT gene has a sequence having at least 90% identity to that of SEQ ID NO: 25. In some embodiments, the nucleic acid sequence encoding the micro-RNA based shRNA targeting the HPRT gene has a sequence having at least 95% identity to that of SEQ ID NO: 25. In some embodiments, the nucleic acid sequence encoding the micro-RNA based shRNA targeting the HPRT gene has a sequence of SEQ ID NO: 25.

In some embodiments, the nucleic acid sequence encoding the micro-RNA based shRNA targeting the HPRT gene has a sequence having at least 80% identity to that of SEQ ID NO: 26. In some embodiments, the nucleic acid sequence encoding the micro-RNA based shRNA targeting the HPRT gene has a sequence having at least 90% identity to that of SEQ ID NO: 26. In some embodiments, the nucleic acid sequence encoding the micro-RNA based shRNA targeting the HPRT gene has a sequence having at least 95% identity to that of SEQ ID NO: 26. In some embodiments, the nucleic acid sequence encoding the micro-RNA based shRNA targeting the HPRT gene has a sequence of SEQ ID NO: 26.

In another aspect of the present disclosure is a lentiviral expression vector suitable for transducing human cells (e.g. HSCs) comprising a first nucleic acid sequence operably linked to a first promoter (e.g. a Pol III promoter) and a second nucleic acid sequence operably linked to a second promoter (e.g. a Pol II promoter), wherein the first nucleic acid sequence encodes an agent that knocks down HPRT or otherwise decreases the expression of HPRT, and wherein the second nucleic acid sequence encodes a therapeutic gene. In some embodiments, the first nucleic acid sequence has at least 95% sequence identity to that of SEQ ID NO: 30. In some embodiments, the first nucleic acid sequence has at least 95% sequence identity to that of SEQ ID NO: 31. In some embodiments, the first nucleic acid sequence has the sequence of SEQ ID NO: 31. In some embodiments, the second nucleic acid encodes for gamma globin (e.g. any of SEQ ID NOS: 3 or 55). In some embodiments, the second nucleic acid sequence has at least 95% sequence identity to that of SEQ ID NO: 55. In some embodiments, the first promoter is a 7sk promoter. In some embodiments, the 7sk promoter has at least 95% sequence identity to that of SEQ ID NO: 32. In some embodiments, the second promoter is a beta globin promoter. In some embodiments, the beta globin promoter has at least 95% sequence identity to that of SEQ ID NO: 66. In some embodiments, the lentiviral expression vector has a sequence having at least 85% sequence identity to any of SEQ ID NOS: 5-22. In some embodiments, the lentiviral expression vector has a sequence having at least 90% sequence identity to any of SEQ ID NOS: 5-22. In some embodiments, the lentiviral expression vector has a sequence having at least 95% sequence identity to any of SEQ ID NOS: 5-22. In some embodiments, the lentiviral expression vector has a sequence having at least 96% sequence identity to any of SEQ ID NOS: 5-22. In some embodiments, the lentiviral expression vector has a sequence having at least 97% sequence identity to any of SEQ ID NOS: 5-22. In some embodiments, the lentiviral expression vector has a sequence having at least 98% sequence identity to any of SEQ ID NOS: 5-22. In some embodiments, the lentiviral expression vector has a sequence having at least 99% sequence identity to any of SEQ ID NOS: 5-22.

In another aspect of the present disclosure is a polynucleotide sequence including (a) a sequence encoding an shRNA targeting HPRT; (b) a sequence encoding a gamma globin gene; (c) a sequence encoding a first promoter to drive expression of the sequence encoding the shRNA targeting HPRT; (d) a sequence encoding a second promoter to drive expression of the sequence encoding the gamma globin gene; (e) a sequence encoding a central polypurine tract element; and (f) a sequence encoding a Rev response element (SEQ ID NO: 56). In some embodiments, the polynucleotide further includes a locus control region (SEQ ID NO: 57). In some embodiments, the polynucleotide sequence has at least 85% identity to any of SEQ ID NOS: 5-22. In some embodiments, the polynucleotide sequence has at least 90% identity to any of SEQ ID NOS: 5-22. In some embodiments, the polynucleotide sequence has at least 91% identity to any of SEQ ID NOS: 5-22. In some embodiments, the polynucleotide sequence has at least 92% identity to any of SEQ ID NOS: 5-22. In some embodiments, the polynucleotide sequence has at least 93% identity to any of SEQ ID NOS: 5-22. In some embodiments, the polynucleotide sequence has at least 94% identity to any of SEQ ID NOS: 5-22. In some embodiments, the polynucleotide sequence has at least 95% identity to any of SEQ ID NOS: 5-22. In some embodiments, the polynucleotide sequence has at least 96% identity to any of SEQ ID NOS: 5-22. In some embodiments, the polynucleotide sequence has at least 97% identity to any of SEQ ID NOS: 5-22. In some embodiments, the polynucleotide sequence has at least 98% identity to any of SEQ ID NOS: 5-22. In some embodiments, the polynucleotide sequence has at least 99% identity to any of SEQ ID NOS: 5-22. In some embodiments, the first promoter is a pol III promoter. In some embodiments, the first promoter is a 7sk promoter. In some embodiments, the 7sk promoter has at least 90% sequence identity to that of SEQ ID NO: 32. In some embodiments, the second promoter is a pol II promoter. In some embodiments, the second promoter is a beta-globin promoter. In some embodiments, the polynucleotide sequence includes between 11,000 and 12,750 nucleotides. In some embodiments, the polynucleotide sequence includes between 11,500 and 12,000 nucleotides.

In another aspect of the present disclosure is a pharmaceutical composition comprising a (a) a vector, such as an expression vector, including (i) a nucleic acid sequence encoding a shRNA targeting an HPRT gene; and (ii) a nucleic acid sequence encoding a therapeutic gene (e.g. a gamma-globin gene); and (b) a pharmaceutically acceptable carrier. In some embodiments, the pharmaceutical composition is formulated as an emulsion. In some embodiments, the pharmaceutical composition is formulated within micelles. In some embodiments, the pharmaceutical composition is encapsulated within a polymer. In some embodiments, the pharmaceutical composition is encapsulated within a liposome. In some embodiments, the pharmaceutical composition is encapsulated within minicells or nanocapsules.

In another aspect of the present disclosure is a method of producing genetically modified cells, comprising: contacting the cells with a first agent which "knocks down" the HPRT gene, and a second agent that introduces a therapeutic gene for expression. In some embodiments, the cells are genetically modified by contacting the cells with a lentiviral expression vector including nucleic acid sequences encoding both the first and second agents. In some embodiments, the cells are HSCs.

In another aspect of the present disclosure is a method of producing genetically modified cells, comprising: contacting the cells with a first agent which "knocks out" the HPRT gene, and a second agent that introduces a therapeutic gene for expression. In some embodiments, a non-viral delivery vehicle is utilized to introduce the first agent to the cells; and a lentiviral expression vector is utilized to introduce the second agent to the cells. In some embodiments, the non-viral delivery vehicle is a nanocapsule. In some embodiments, the cells are HSCs.

In another aspect of the present disclosure are HSCs (e.g. $CD34^+$ HSCs) which have been transduced with an expression vector including a therapeutic gene and an agent designed to reduce HPRT expression (e.g. by knockdown or by knockout of HPRT). In some embodiments, the transduced HSCs constitute a cell therapy product which may be administered to a subject in need of treatment thereof. In some embodiments, the therapeutic gene is a gamma globin gene. In some embodiments, the gamma globin gene encodes a peptide having at least 90% sequence identity to that of SEQ ID NO: 4.

In another aspect of the present disclosure are HSCs which have been transduced with an expression vector including a nucleic acid sequence encoding a hybrid gamma globin gene (e.g. SEQ ID NOS: 3 or 55) and a nucleic acid encoding an anti-HPRT shRNA (e.g. SEQ ID NOS: 1, 2, 30 or 31). In some embodiments, the anti-HPRT shRNA is driven by a 7sk promoter (e.g. SEQ ID NOS: 32 or 33). In some embodiments, 7sk/sh734 is oriented either upstream or downstream in the sense or anti-sense direction relative to a hybrid gamma-globin cassette. In some embodiments, the transduced HSCs constitute a cell therapy product which may be administered (such as in a pharmaceutical composition including a pharmaceutically acceptable vehicle) to a subject in need of treatment thereof (e.g. a mammal; a human patient) (e.g. for the treatment of sickle cell disease).

In another aspect of the present disclosure is a method of treating a hemoglobinopathy in a patient (e.g. a human patient) in need of treatment thereof comprising (a) transducing HSCs with a lentiviral expression vector, wherein the lentiviral expression vector includes a first nucleic acid sequence encoding an anti-HPRT shRNA or an anti-HPRT shRNA embedded within a microRNA; and a second nucleic acid sequence encoding a gamma globin gene; and (b) transplanting the transduced HSCs within the patient. In some embodiments, the HSCs are autologous or allogeneic. In some embodiments, the anti-HPRT shRNA has a sequence of any of SEQ ID NOS: 30 or 31. In some embodiments, the nucleic acid encoding the gamma globin gene has a sequence of SEQ ID NO: 55. In some embodiments, the patient is pre-treated with myeloablative conditioning prior to the transplanting of the transduced HSCs administration (e.g. such as with a purine analog, including 6-thioguanine ("6TG"); with a chemotherapy agent; with radiation; with an antibody-drug conjugate, such as those described in US Patent Publication Nos. 2017/0360954 and 2018/0147294, and PCT Publication Nos. WO/2017/219025 and WO/2017/219029, the disclosures of which are each incorporated by reference herein in their entireties). In some embodiments, the transduced HSCs are selected for in vivo following the transplantation (e.g. such as with 6TG). In some embodiments, methotrexate ("MTX") or mycophenolic acid ("MPA") are administered to ameliorate any side effects of transplantation of the transduced HSCs (e.g. graft versus host disease).

It is believed that with a strategy of combined conditioning and chemoselection (such as with a purine analog), efficient and high engraftment of HPRT-deficient, gamma globin gene-containing hematopoietic stem cells can be achieved, and it is believed that such high engraftment may be accomplished with low overall toxicity. It is believed that the enhanced engraftment and chemoselection of the gene-modified HSCs, combined with lineage-specific expression of the gamma globin gene, may result in a sufficient frequency of red blood cells expressing the therapeutic gamma globin transgene, allowing for increased levels of fetal hemoglobin formation to correct for SCD and/or beta thalassemia. As a safety measure, HPRT-deficient cells can be negatively selected, such as by introducing MTX or MPA, to inhibit the enzyme dihydrofolate reductase (DHFR) in the purine de novo synthetic pathway, thus killing HPRT deficient cells.

It is further believed that HPRT-deficient HSCs can be selected in vivo using a regimen of a purine analog (e.g. 6TG) to enhance engraftment. It is also believed that the expanded gene-modified HSCs can differentiate into erythrocytes expressing the therapeutic gamma globin transgene. The gene therapy compositions described herein have the potential to not only correct SCD and beta thalassemia, but also to greatly improve on the current "gold standards" for autologous hematopoietic stem cell transplantation. Improvements may allow for (i) out-patient procedures using the gene-modified HSCs; (ii) low adverse events (AEs), including avoiding infertility associated with other clinical therapies; (iii) low dose oral administration for conditioning (as compared with high-dose IV conditioning); (iv) in vivo selection of gene-modified cells; and/or (v) low procedure mortality rate related to transplantation and conditioning.

BRIEF DESCRIPTION OF THE FIGURES

FIG. 25A illustrates GFP expression of K562 cells transfected with EF1a-GFP nanocapsules measured on day 3. FIG. 25B illustrates the live cell number measured using TC10 on days 5 and 7.

FIG. 27A shows that about 99.6% of the cells fail to express HPRT. In a control, 100% of the untransduced cells (FIG. 27B) stain positive for HPRT expression.

FIG. 37 provides the full-length Homo sapiens hypoxanthine phosphoribosyltransferase 1 (HPRT1), mRNA_NM_000194.2 (SEQ ID NO: 59) The location of target sequences for siRNA/shRNA described are highlighted in in bold text within the coding sequence of HPRT (underlined text).

FIG. 38 illustrates a CRISPR/Cas9 gene editing strategy and sgRNA candidates for knock down of human HPRT gene expression (see SEQ ID NOS: 61 and 69).

FIG. 39 sets forth the hybrid gamma-globin sequence sGbG$^M$ and illustrates the differences shown in bold and underlined text between an aligned human endogenous gamma-globin (see SEQ ID NO: 55).

FIG. 49K sets forth a table providing additional data corresponding to the graphs set forth in FIG. 49J.

SEQUENCE LISTING

Figure 1A:
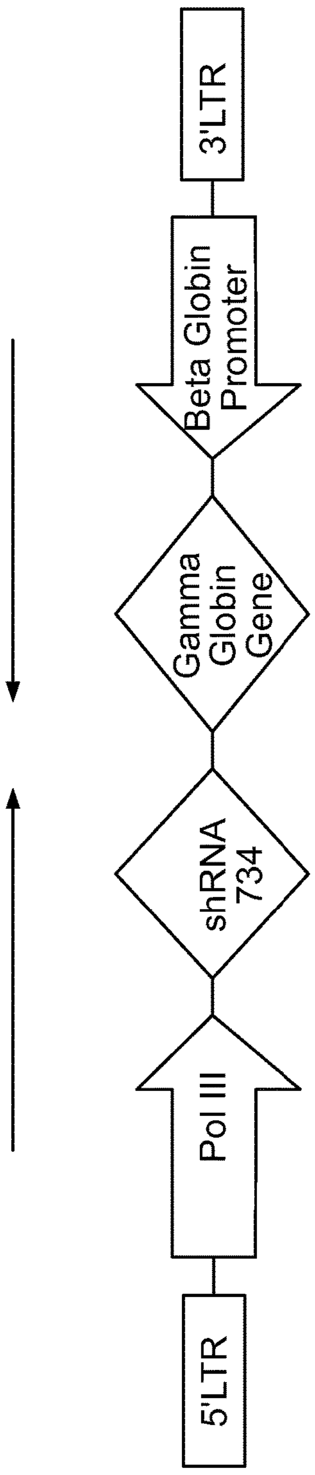
FIGS. 1A and 1B provide schematics of an expression vector according to certain embodiments of the present disclosure.

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "2018-07-16_Calimmune-051WO_ST25.txt" created on Jul. 16, 2018, 323 KB, which is incorporated by reference herein.

DETAILED DESCRIPTION

Definitions

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless the context clearly indicates otherwise. Similarly, the word "or" is intended to include "and" unless the context clearly indicates otherwise.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein, the terms "administer" or "administering" mean providing a composition, formulation, or specific agent to a subject (e.g. a human patient) in need of treatment, including those described herein.

As used herein, the terms "hematopoietic cell transplant" or "hematopoietic cell transplantation" refer to bone marrow transplantation, peripheral blood stem cell transplantation, umbilical vein blood transplantation, or any other source of pluripotent hematopoietic stem cells. Likewise, the terms "stem cell transplant," or "transplant," refer to a composition comprising stem cells that are in contact with (e.g. suspended in) a pharmaceutically acceptable carrier. Such compositions are capable of being administered to a subject through a catheter.

As used herein, the term "functional nucleic acid" refers to molecules having the capacity to reduce expression of a protein by directly interacting with a transcript that encodes the protein. siRNA molecules, ribozymes, and antisense nucleic acids constitute exemplary functional nucleic acids.

As used herein, the term "gene" refers broadly to any segment of DNA associated with a biological function. A gene encompasses sequences including but not limited to a coding sequence, a promoter region, a cis-regulatory sequence, a non-expressed DNA segment is a specific recognition sequence for regulatory proteins, a non-expressed DNA segment that contributes to gene expression, a DNA segment designed to have desired parameters, or combinations thereof.

As used herein, the term "gene silencing" is meant to describe the downregulation, knock-down, degradation, inhibition, suppression, repression, prevention, or decreased expression of a gene, transcript and/or polypeptide product. Gene silencing and interference also describe the prevention of translation of mRNA transcripts into a polypeptide. In some embodiments, translation is prevented, inhibited, or decreased by degrading mRNA transcripts or blocking mRNA translation.

As used herein, the term "gene expression" refers to the cellular processes by which a biologically active polypeptide is produced from a DNA sequence.

As used herein, "HPRT" is an enzyme involved in purine metabolism encoded by the HPRT1 gene. HPRT1 is located on the X chromosome, and thus is present in single copy in males. HPRT1 encodes the transferase that catalyzes the conversion of hypoxanthine to inosine monophosphate and guanine to guanosine monophosphate by transferring the 5-phosphorobosyl group from 5-phosphoribosyl 1-pyrophosphate to the purine. The enzyme functions primarily to salvage purines from degraded DNA for use in renewed purine synthesis (see also FIG. 37).

As used herein, the term "lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which causes immune deficiency and encephalopathy in sub-human primates.

As used herein, the term "lentiviral vector" is used to denote any form of a nucleic acid derived from a lentivirus and used to transfer genetic material into a cell via transduction. The term encompasses lentiviral vector nucleic acids, such as DNA and RNA, encapsulated forms of these nucleic acids, and viral particles in which the viral vector nucleic acids have been packaged.

As used herein, the terms "knock down" or "knockdown" when used in reference to an effect of RNAi on gene expression, means that the level of gene expression is inhibited, or is reduced to a level below that generally observed when examined under substantially the same conditions, but in the absence of RNAi.

As used herein, the term "knock-in" refers to the replacement of endogenous genetic material (e.g., a gene or a portion of a gene) with exogenous genetic material (i.e., a recombinant nucleic acid). The term "knock-in" as used herein also includes alterations of genetic material by introduction of one or more additional copies of the recombinant nucleic acid, with or without replacing the endogenous gene.

As used herein, the term "knock-out" refers to partial or complete suppression of the expression of an endogenous gene. This is generally accomplished by deleting a portion of the gene or by replacing a portion with a second sequence, but may also be caused by other modifications to the gene such as the introduction of stop codons, the mutation of critical amino acids, the removal of an intron junction, etc. Accordingly, a "knock-out" construct is a nucleic acid sequence, such as a DNA construct, which, when introduced into a cell, results in suppression (partial or complete) of expression of a polypeptide or protein encoded by endogenous DNA in the cell. In some embodiments, a "knockout" includes mutations such as, a point mutation, an insertion, a deletion, a frameshift, or a missense mutation As used herein, the term "minicell" refers to anucleate forms of bacterial cells, engendered by a disturbance in the coordination, during binary fission, of cell division with DNA segregation. Minicells are distinct from other small vesicles that are generated and released spontaneously in certain situations and, in contrast to minicells, are not due to specific genetic rearrangements or episomal gene expression. Minicells of the present disclosure are anucleate forms of *E. coli* or other bacterial cells, engendered by a disturbance in the coordination, during binary fission, of cell division with DNA segregation. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an anucleate minicell. See de Boer et al., 1992; Raskin & de Boer, 1999; Hu & Lutkenhaus, 1999; Harry, 2001. Minicells are distinct from other small vesicles that are generated and released spontaneously in certain situations and, in contrast to minicells, are not due to specific genetic rearrangements or episomal gene expression. For practicing the present disclosure, it is desirable for minicells to have intact cell walls ("intact minicells"). In addition to min operon mutations, anucleate minicells also are generated following a range of other genetic rearrangements or mutations that affect septum formation, for example in the divIVB1 in *B. subtilis*. See Reeve and Cornett, 1975; Levin et al., 1992. Minicells also can be formed following a perturbation in the levels of gene expression of proteins involved in cell division/chromosome segregation. For example, overexpression of minE leads to polar division and production of minicells. Similarly, chromosome-less minicells may result from defects in chromosome segregation for example the smc mutation in *Bacillus subtilis* (Britton et al., 1998), spoOJ deletion in *B. subtilis* (Ireton et al., 1994), mukB mutation in *E. coli* (Hiraga et al., 1989), and parC mutation in *E. coli* (Stewart and D'Ari, 1992). Gene products may be supplied in trans. When over-expressed from a high-copy number plasmid, for example, CafA may enhance the rate of cell division and/or inhibit chromosome partitioning after replication (Okada et al., 1994), resulting in formation of chained cells and anucleate minicells (Wachi et al., 1989; Okada et al., 1993). Minicells can be prepared from any bacterial cell of Gram-positive or Gram-negative origin.

As used herein, the term "mutated" refers to a change in a sequence, such as a nucleotide or amino acid sequence, from a native, wild-type, standard, or reference version of the respective sequence, i.e. the non-mutated sequence. A mutated gene can result in a mutated gene product. A mutated gene product will differ from the non-mutated gene product by one or more amino acid residues. In some embodiments, a mutated gene which results in a mutated gene product can have a sequence identity of 70%, 75%, 80%, 85%, 90%, 95%, or greater to the corresponding non-mutated nucleotide sequence.

As used herein, the term "operably linked" refers to functional linkage between a nucleic acid expression control sequence (such as a promoter, signal sequence, enhancer or array of transcription factor binding sites) and a second nucleic acid sequence, wherein the expression control sequence affects transcription and/or translation of the nucleic acid corresponding to the second sequence when the appropriate molecules (e.g., transcriptional activator proteins) are bound to the expression control sequence.

As used herein, the term "retroviruses" refers to viruses having an RNA genome that is reverse transcribed by retroviral reverse transcriptase to a cDNA copy that is integrated into the host cell genome. Retroviral vectors and methods of making retroviral vectors are known in the art. Briefly, to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., Cell, Vol. 33:153-159, 1983). When a recombinant plasmid containing a cDNA, together with the retroviral LTR and packaging sequences, is introduced into this cell line, the packaging sequence allows the RNA transcript of the recombinant plasmid to be packaged into viral particles, which are then secreted into the culture media. The media containing the recombinant retroviruses is then collected, optionally concentrated, and used for gene transfer.

As used herein, the terms "small hairpin RNA" or "shRNA" refer to RNA molecules comprising an antisense region, a loop portion and a sense region, wherein the sense region has complementary nucleotides that base pair with the antisense region to form a duplex stem. Following post-transcriptional As used herein, the term "subject" refers to a mammal such as a human, mouse or primate. Typically, the mammal is a human (*Homo sapiens*).

As used herein, the term "therapeutic gene" refers to a gene that can be administered to a subject for the purpose of treating or preventing a disease.

As used herein, the terms "transduce" or "transduction" refers to the delivery of a gene(s) using a viral or retroviral vector by means of infection rather than by transfection. For example, an anti-HPRT gene carried by a retroviral vector (a modified retrovirus used as a vector for introduction of nucleic acid into cells) can be transduced into a cell through infection and provirus integration. Thus, a "transduced gene" is a gene that has been introduced into the cell via lentiviral or vector infection and provirus integration. Viral vectors (e.g., "transducing vectors") transduce genes into "target cells" or host cells.

As used herein, the terms "treatment," "treating," or "treat," with respect to a specific condition, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present disclosure to mitigate a disease or a disorder in a host, preferably in a mammalian subject, more preferably in humans. Thus, the term "treatment" can include includes: preventing a disorder from occurring in a host, particularly when the host is predisposed to acquiring the disease but has not yet been diagnosed with the disease; inhibiting the disorder; and/or alleviating or reversing the disorder. Insofar as the methods of the present disclosure are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present disclosure can occur prior to onset of a disease. The term does not mean that the disease state must be completely avoided.

As used herein, the term "vector" refers to a nucleic acid molecule capable of mediating entry of, e.g., transferring, transporting, etc., another nucleic acid molecule into a cell. The transferred nucleic acid is generally linked to, e.g., inserted into, the vector nucleic acid molecule. A vector may include sequences that direct autonomous replication or may include sequences sufficient to allow integration into host cell DNA. As will be evident to one of ordinary skill in the art, viral vectors may include various viral components in addition to nucleic acid(s) that mediate entry of the transferred nucleic acid. Numerous vectors are known in the art including, but not limited to, linear polynucleotides, polynucleotides associated with ionic or amphiphilic compounds, plasmids, and viral vectors. Examples of viral vectors include, but are not limited to, adenoviral vectors, adeno-associated virus vectors, retroviral vectors (including lentiviral vectors), and the like.

Expression Vectors

The present disclosure provides, in some embodiments, expression vectors (e.g. lentiviral expression vectors) including at least two nucleic acid sequences for expression. In some embodiments, the nucleic acid sequences encode a nucleic acid molecule (e.g. RNA, mRNA) (e.g. a molecule which may be found in the cytoplasm of a cell, e.g. a host cell). In some embodiments, the expression vectors include a first nucleic acid sequence encoding an agent designed to knockdown the HPRT gene or otherwise effectuate a decrease in HPRT expression. In some embodiments, the expression vectors include a second nucleic acid encoding a therapeutic gene (e.g. a nucleic acid sequence encoding a gamma globin gene or a mutated gamma globin gene).

In some embodiments, the expression vector is a self-inactivating lentiviral vector. In other embodiments, the expression vector is a retroviral vector. A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)); O Narayan and Clements (1989) J. Gen. Virology, Vol. 70:1617-1639; Fields et al. (1990) Fundamental Virology Raven Press.; Miyoshi H, Blamer U, Takahashi M, Gage F H, Verma I M. (1998) J Virol., Vol. 72(10):8150 7, and U.S. Pat. No. 6,013,516. Examples of lentiviral vectors that have been used to infect HSCs are described in the publications which follows, each of which are hereby incorporated herein by reference in their entireties: Evans et al., Hum Gene Ther., Vol. 10:1479-1489, 1999; Case et al., Proc Natl Acad Sci USA, Vol. 96:2988-2993, 1999; Uchida et al., Proc Natl Acad Sci USA, Vol. 95:11939-11944, 1998; Miyoshi et al., Science, Vol. 283:682-686, 1999; and Sutton et al., J. Virol., Vol. 72:5781-5788, 1998.

In some embodiments, the expression vector is a modified lentivirus, and thus is able to infect both dividing and non-dividing cells. In some embodiments, the modified lentiviral genome lacks genes for lentiviral proteins required for viral replication, thus preventing undesired replication, such as replication in the target cells. In some embodiments, the required proteins for replication of the modified genome are provided in trans in the packaging cell line during production of the recombinant retrovirus or lentivirus.

In some embodiments, the expression vector comprises sequences from the 5' and 3' long terminal repeats (LTRs) of a lentivirus. In some embodiments, the vector comprises the R and U5 sequences from the 5' LTR of a lentivirus and an inactivated or self-inactivating 3' LTR from a lentivirus. In some embodiments, the LTR sequences are HIV LTR sequences.

Additional components of a lentiviral expression vector (and methods of synthesizing and/or producing such vectors) are disclosed in United States Patent Application Publication No. 2018/0112220, the disclosure of which is hereby incorporated by reference herein in its entirety.

Agents to Knockdown the HPRT Gene or Decrease its Expression

In some embodiments, the nucleic acid sequence encoding the agent designed to knockdown the HPRT gene or otherwise effectuate a decrease in its expression is an RNAi agent. In some embodiments, the RNAi agent is an shRNA, a microRNA, or a hybrid thereof. In other embodiments, the nucleic acid sequence encoding the agent designed to knockdown the HPRT gene or otherwise effectuate a decrease in its expression is an agent other than an RNAi, such as an antisense RNA, or an antisense oligonucleotide. Both RNAi agents and non-RNAi agents are described further herein.

RNAi

In some embodiments, the expression vector comprises a first nucleic acid sequence encoding a RNA interference (RNAi) agent. RNA interference is an approach for post-transcriptional silencing of gene expression by triggering degradation of homologous transcripts through a complex multistep enzymatic process, e.g. a process involving sequence-specific double-stranded small interfering RNA (siRNA). A simplified model for the RNAi pathway is based on two steps, each involving a ribonuclease enzyme. In the first step, the trigger RNA (either dsRNA or miRNA primary transcript) is processed into a short, interfering RNA (siRNA) by the RNase II enzymes Dicer and Drosha. In the second step, siRNAs are loaded into the effector complex RNA-induced silencing complex (RISC). The siRNA is unwound during RISC assembly and the single-stranded RNA hybridizes with mRNA target. It is believed that gene silencing is a result of nucleolytic degradation of the targeted mRNA by the RNase H enzyme Argonaute (Slicer). If the siRNA/mRNA duplex contains mismatches the mRNA is not cleaved. Rather, gene silencing is a result of translational inhibition.

In some embodiments, the RNAi agent is an inhibitory or silencing nucleic acid. As used herein, a “silencing nucleic acid” refers to any polynucleotide which is capable of interacting with a specific sequence to inhibit gene expression. Examples of silencing nucleic acids include RNA duplexes (e.g. siRNA, shRNA), locked nucleic acids (“LNAs”), antisense RNA, DNA polynucleotides which encode sense and/or antisense sequences of the siRNA or shRNA, DNAzymses, or ribozymes. The skilled artisan will appreciate that the inhibition of gene expression need not necessarily be gene expression from a specific enumerated sequence, and may be, for example, gene expression from a sequence controlled by that specific sequence.

While the RNAi agent may be delivered and expressed via an expression vector, it is also possible that the RNAi agent may be directly delivered through the use of a suitable nanocapsule or other non-viral delivery vehicle as described further herein. For example, an siRNA or miRNA may be “packaged” within a nanocapsule and directly delivered as noted herein.

Methods for constructing interfering RNAs are known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA may be assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering RNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. When expressed, such an RNA molecule desirably forms a “hairpin” structure and is referred to herein as an “shRNA.” In some embodiments, the loop region is generally between about 2 and about 10 nucleotides in length (by way of example only, see SEQ ID NO: 35). In other embodiments, the loop region is from about 6 to about 9 nucleotides in length. In some embodiments, the sense region and the antisense region are between about 15 and about 30 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. Further details are described by see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); *Sui*, Proc. Natl. Acad. Sd. USA, 99(6), 5515-5520, (2002); and Yu et al. Proc NatlAcadSci USA 99:6047-6052, (2002), the disclosures of which are hereby incorporated by reference herein in their entireties.

shRNA

Figure 30A:
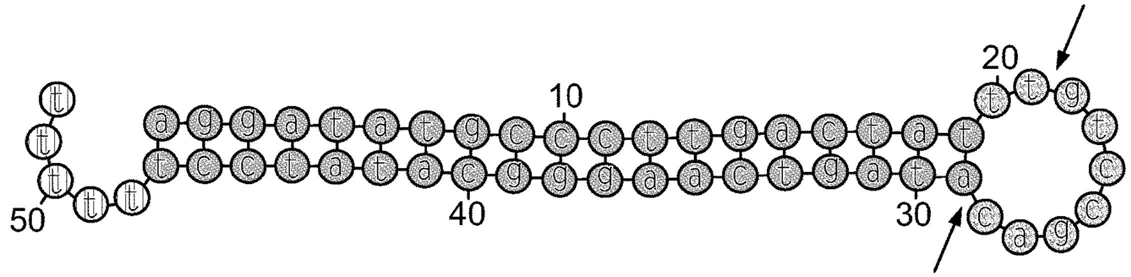
FIG. 30A illustrates the secondary structure and theoretical primary DICER cleavage sites (arrows) of sh734 (see also SEQ ID NO: 30). The secondary structure has a MFE value of about −30.9 kcal/mol.

In some embodiments, the first nucleic acid sequence encodes a shRNA targeting an HPRT gene. In some embodiments, the first nucleic acid sequence encoding a shRNA targeting an HPRT gene has a sequence having at least 80% identify to that of SEQ ID NO: 30 (referred to herein as "sh734"). In other embodiments, the first nucleic acid sequence encoding a shRNA targeting an HPRT gene has a sequence having at least 90% identify to that of SEQ ID NO:1. In yet other embodiments the first nucleic acid sequence encoding a shRNA targeting an HPRT gene has a sequence having at least 95% identity to that of SEQ ID NO: 30. In further embodiments, the first nucleic acid sequence encoding a shRNA targeting an HPRT gene has a sequence having at least 97% identity to that of SEQ ID NO: 30. In even further embodiments, the first nucleic acid sequence encoding a shRNA targeting an HPRT gene has a sequence having at least 98% identity to that of SEQ ID NO: 30. In yet further embodiments, the first nucleic acid sequence encoding a shRNA targeting an HPRT gene has a sequence having at least 99% identity to that of SEQ ID NO: 30. In other embodiments, the first nucleic acid sequence encoding a shRNA targeting an HPRT gene has the sequence of SEQ ID NO: 30 (see also FIG. 30A).

In some embodiments, the nucleic acid sequence of SEQ ID NO: 30 may be modified. In some embodiments, modifications include: (i) the incorporation of a hsa-miR-22 loop sequence (e.g. CCUGACCCA) (SEQ ID NO: 34); (ii) the addition of a 5'-3' nucleotide spacer, such as one having two or three nucleotides (e.g. TA); (iii) a 5' start modification, such as the addition of one or more nucleotides (e.g. G); and/or (iv) the addition of two nucleotides 5' and 3' to the stem and loop (e.g. 5' A and 3' T). In general, first generation shRNAs are processed into a heterogenous mix of small RNAs, and the accumulation of precursor transcripts has been shown to induce both sequence-dependent and independent nonspecific off-target effects in vivo. Therefore, based on the current understanding of DICER processing and specificity, design rules were applied design that would optimize the structure of the sh734 and DICER processivity and efficiency. (see also Gu, S., Y. Zhang, L. Jin, Y. Huang, F. Zhang, M. C. Bassik, M. Kampmann, and M. A. Kay. 2014. Weak base pairing in both seed and 3' regions reduces RNAi off-targets and enhances si/shRNA designs. Nucleic Acids Research 42:12169-12176).

In some embodiments, the nucleic acid sequence of SEQ ID NO: 30 is modified by adding two nucleotides 5' and 3' (e.g., G and C, respectively) to the hairpin loop (SEQ ID NO: 35), thereby lengthening the guide strand from about 19 nucleotides to about 21 nucleotides in length and replacing the loop with the hsa-miR-22 loop CCUGACCCA (SEQ ID NO: 34), to provide the nucleotide sequence of SEQ ID NO: 31. In some embodiments, the nucleic acid sequence encoding a shRNA targeting an HPRT gene has a sequence having at least 90% identity to that of SEQ ID NO: 31. In other embodiments, the first nucleic acid sequence encoding a shRNA targeting an HPRT gene has a sequence having at least 95% identity to that of SEQ ID NO: 31. In other embodiments, the first nucleic acid sequence encoding a shRNA targeting an HPRT gene has a sequence having at least 97% identity to that of SEQ ID NO: 31. In other embodiments, the first nucleic acid sequence encoding a shRNA targeting an HPRT gene has a sequence having at least 98% identity to that of SEQ ID NO: 31. In other embodiments, the first nucleic acid sequence encoding a shRNA targeting an HPRT gene has a sequence having at least 99% identity to that of SEQ ID NO: 31. In yet other embodiments, the nucleic acid sequence encoding a shRNA targeting an HPRT gene has the sequence of SEQ ID NO: 31. It is believed that the shRNA encoded by SEQ ID NO: 31 achieves similar knockdown of HPRT as compared with either SEQ ID NO: 30. Likewise, it is believed that a cell rendered HPRT deficient through the knockdown of HPRT via expression of the shRNA encoded by SEQ ID NO: 31 allows for selection using a thioguanine analog (e.g. 6TG).

In some embodiments, the RNAi present within the vector encodes for a nucleic acid molecule, such as one having SEQ ID NO: 1 or SEQ ID NO: 2. In some embodiments, the nucleic acid molecules are found in the cytoplasm of a host cell. In some embodiments, the present disclosure provides for a host cell including at least one nucleic acid molecule selected from SED ID NO: 1 or SEQ ID NO: 2.

Figure 31A:
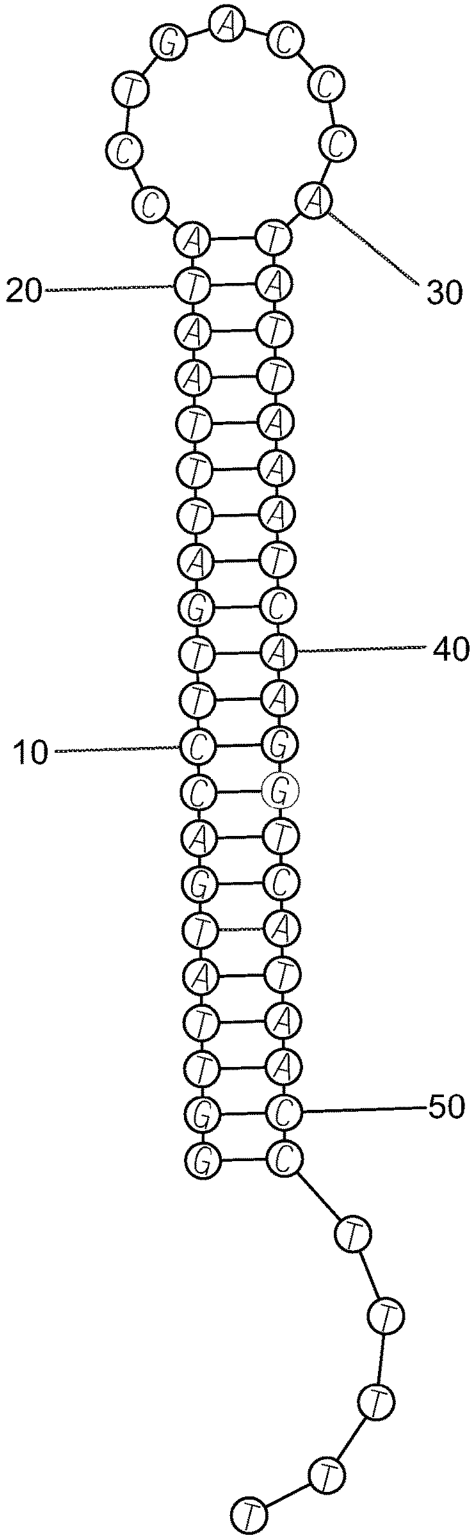
FIG. 31A illustrates the secondary RNA structure and minimum free energy (6G) for sh211 (see also SEQ ID NO: 28).
Figure 31B:
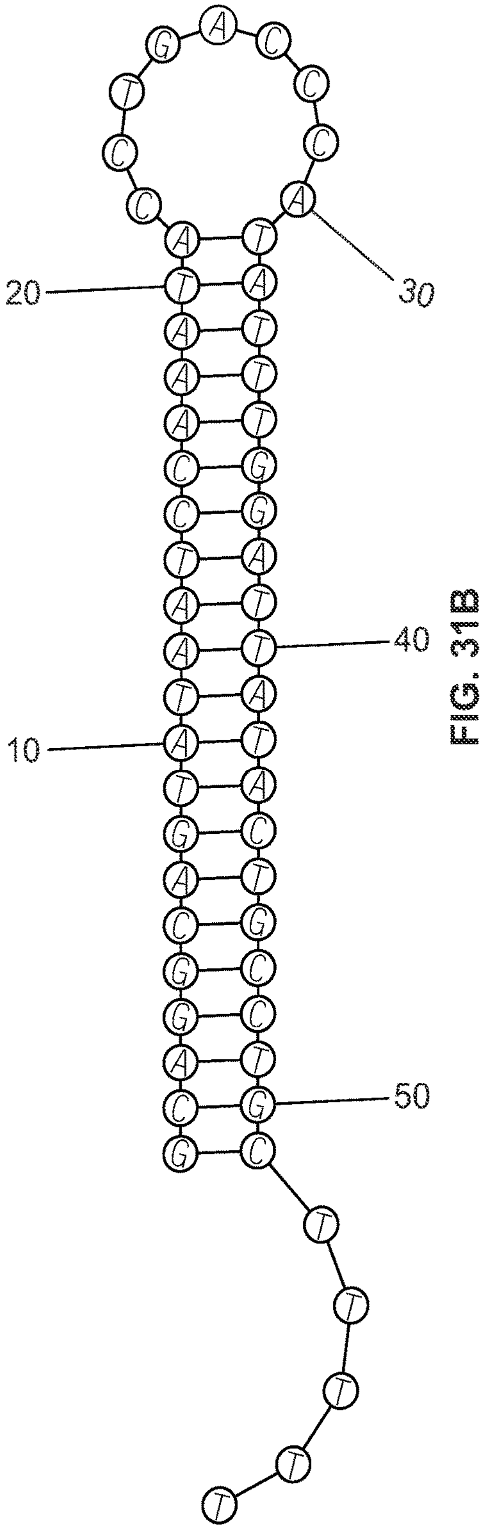
FIG. 31B illustrates the secondary RNA structure and minimum free energy (6G) for sh616 (see also SEQ ID NO: 27).

In some embodiments, the first nucleic acid sequence encoding a shRNA targeting an HPRT gene has a sequence having at least 80% identify to that of SEQ ID NO: 27 (referred to herein as "shHPRT 616"). In other embodiments, the nucleic acid sequence encoding a shRNA targeting an HPRT gene has a sequence having at least 90% identify to that of SEQ ID NO:27. In yet other embodiments, the nucleic acid sequence encoding a shRNA targeting an HPRT gene shRNA has a sequence having at least 95% identity to that of SEQ ID NO: 27. In further embodiments, the nucleic acid sequence encoding a shRNA targeting an HPRT gene has a sequence having at least 97% identity to that of SEQ ID NO: 27. In even further embodiments, the nucleic acid sequence encoding a shRNA targeting an HPRT gene has a sequence having at least 98% identity to that of SEQ ID NO: 27. In yet further embodiments, the nucleic acid sequence encoding a shRNA targeting an HPRT gene has a sequence having at least 99% identity to that of SEQ ID NO: 27. In other embodiments, the nucleic acid sequence encoding a shRNA targeting an HPRT gene has the sequence of SEQ ID NO: 27 (see also FIG. 31B).

In some embodiments, the first nucleic acid sequence encoding a shRNA targeting an HPRT gene has a sequence having at least 80% identify to that of SEQ ID NO: 28 (referred to herein as "shHPRT 211"). In other embodiments, the nucleic acid sequence encoding a shRNA targeting an HPRT gene has a sequence having at least 90% identify to that of SEQ ID NO:28. In yet other embodiments, the nucleic acid sequence encoding a shRNA targeting an HPRT gene shRNA has a sequence having at least 95% identity to that of SEQ ID NO: 28. In further embodiments, the nucleic acid sequence encoding a shRNA targeting an HPRT gene has a sequence having at least 97% identity to that of SEQ ID NO: 28. In even further embodiments, the nucleic acid sequence encoding a shRNA targeting an HPRT gene has a sequence having at least 98% identity to that of SEQ ID NO: 28. In yet further embodiments, the nucleic acid sequence encoding a shRNA targeting an HPRT gene has a sequence having at least 99% identity to that of SEQ ID NO: 28. In other embodiments, the nucleic acid sequence encoding a shRNA targeting an HPRT gene has the sequence of SEQ ID NO: 28 (see also FIG. 31A).

Figure 30B:
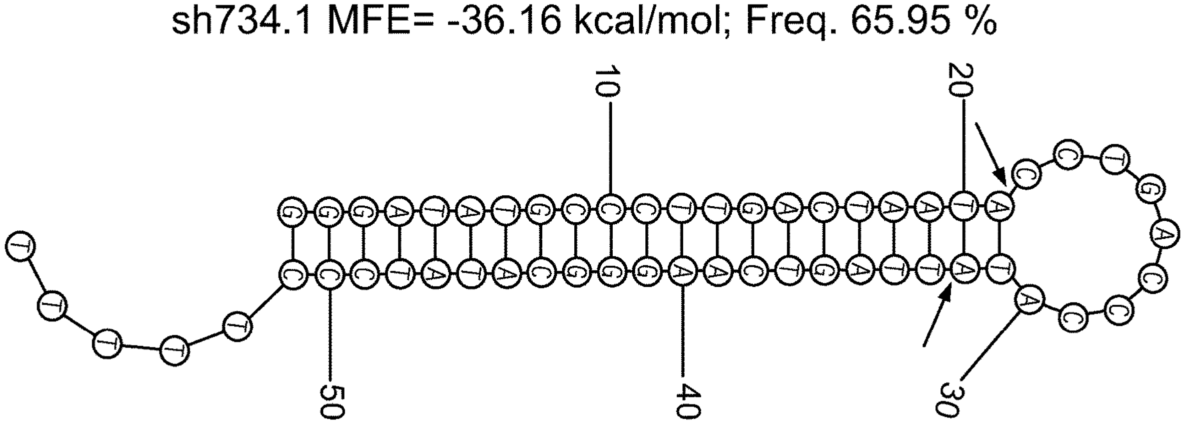
FIG. 30B illustrates a modified version of sh734 (sh734.1) (see also SEQ ID NO: 31). The secondary structure has a MFE value of −36.16 kcal/mol.

In some embodiments, the nucleic acid sequence encoding a shRNA targeting an HPRT gene has a sequence having at least 80% identify to that of SEQ ID NO: 29 (referred to herein as "shHPRT 734.1") (see also FIG. 30B). In other embodiments, the nucleic acid sequence encoding a shRNA targeting an HPRT gene has a sequence having at least 90% identify to that of SEQ ID NO:29. In yet other embodiments, the nucleic acid sequence encoding a shRNA targeting an HPRT gene shRNA has a sequence having at least 95% identity to that of SEQ ID NO: 28. In further embodiments, the nucleic acid sequence encoding a shRNA targeting an HPRT gene has a sequence having at least 97% identity to that of SEQ ID NO: 29. In even further embodiments, the nucleic acid sequence encoding a shRNA targeting an HPRT gene has a sequence having at least 98% identity to that of SEQ ID NO: 29. In yet further embodiments, the nucleic acid sequence encoding a shRNA targeting an HPRT gene has a sequence having at least 99% identity to that of SEQ ID NO: 29. In other embodiments, the nucleic acid sequence encoding a shRNA targeting an HPRT gene has the sequence of SEQ ID NO: 29 (see also FIG. 30B).

MiroRNA

MicroRNAs (miRs) are a group of non-coding RNAs which post-transcriptionally regulate the expression of their target genes. It is believed that these single stranded molecules form a miRNA-mediated silencing complex (miRISC) complex with other proteins which bind to the 3' untranslated region (UTR) of their target mRNAs so as to prevent their translation in the cytoplasm.

In some embodiments, shRNA sequences are embedded into micro-RNA secondary structures ("micro-RNA based shRNA"). In some embodiments, shRNA nucleic acid sequences targeting HPRT are embedded within micro-RNA secondary structures. In some embodiments, the micro-RNA based shRNAs target coding sequences within HPRT to achieve knockdown of HPRT expression, which is believed to be equivalent to the utilization of shRNA targeting HPRT without attendant pathway saturation and cellular toxicity or off-target effects. In some embodiments, the micro-RNA based shRNA is a de novo artificial microRNA shRNA. The production of such de novo micro-RNA based shRNAs are described by Fang, W. & Bartel, David P. The Menu of Features that Define Primary MicroRNAs and Enable De Novo Design of MicroRNA Genes. Molecular Cell 60, 131-145, the disclosure of which is hereby incorporated by reference herein in its entirety.

Figure 32A:
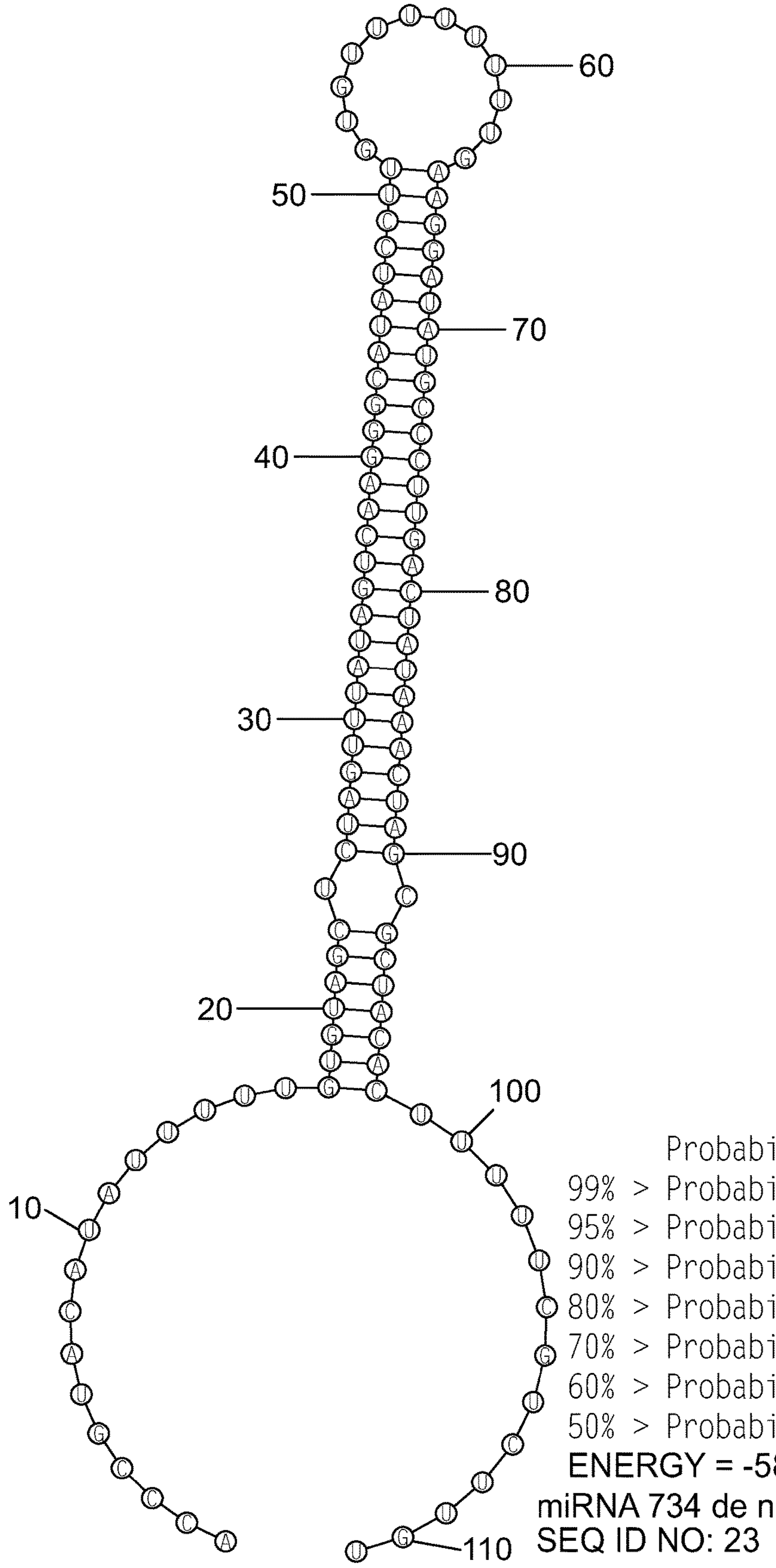
FIG. 32A illustrates the de novo design of an artificial miRNA734 (111nt). 5' and 3' DROSHA target sites and 5' and 3' Dicer cut sites are indicated by arrows in the miRNA 211 secondary structure (see also SEQ ID NO: 23).

In some embodiments, the micro-RNA based shRNA has a sequence having at least 80% identify to that of SEQ ID NO: 67. In some embodiments, the micro-RNA based shRNA has a sequence having at least 90% identify to that of SEQ ID NO: 67. In some embodiments, the micro-RNA based shRNA has a sequence having at least 95% identify to that of SEQ ID NO: 67. In some embodiments, the micro-RNA based shRNA has the sequence of SEQ ID NO: 67 ("miRNA734-Denovo") (see also FIG. 32A). The RNA form of SEQ ID NO: 67 is found at SEQ ID NO: 23.

Figure 32B:
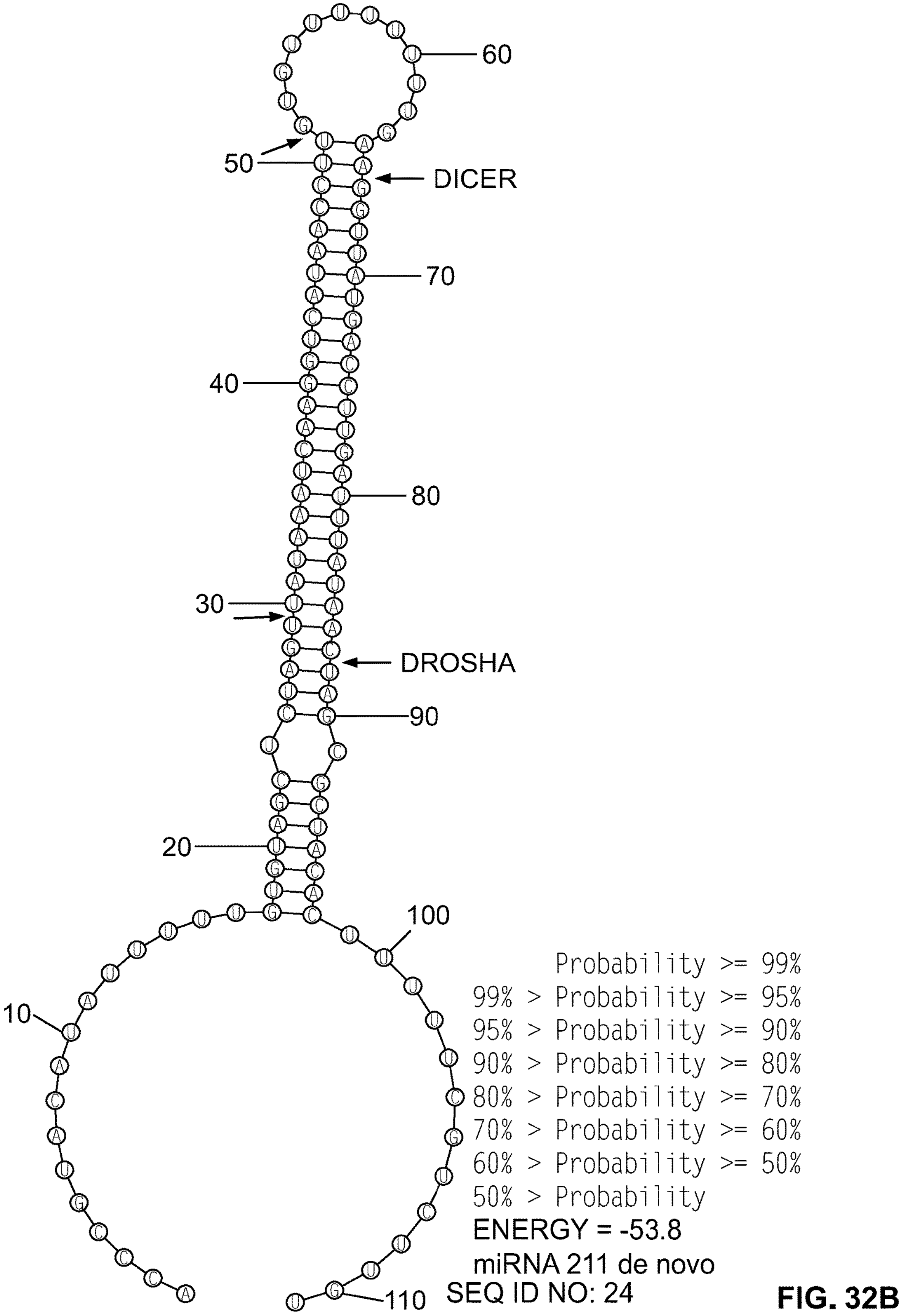
FIG. 32B illustrates the de novo design of an artificial miRNA211 (111nt) (see also SEQ ID NO: 24).

In some embodiments, the micro-RNA based shRNA has a sequence having at least 80% identify to that of SEQ ID NO: 68. In some embodiments, the micro-RNA based shRNA has a sequence having at least 90% identify to that of SEQ ID NO: 68. In some embodiments, the micro-RNA based shRNA has a sequence having at least 95% identify to that of SEQ ID NO: 68. In some embodiments, the micro-RNA based shRNA has the sequence of SEQ ID NO: 68 ("miRNA211-Denovo") (see also FIG. 32B). The RNA form of SEQ ID NO: 68 is found at SEQ ID NO: 24.

Figure 28:
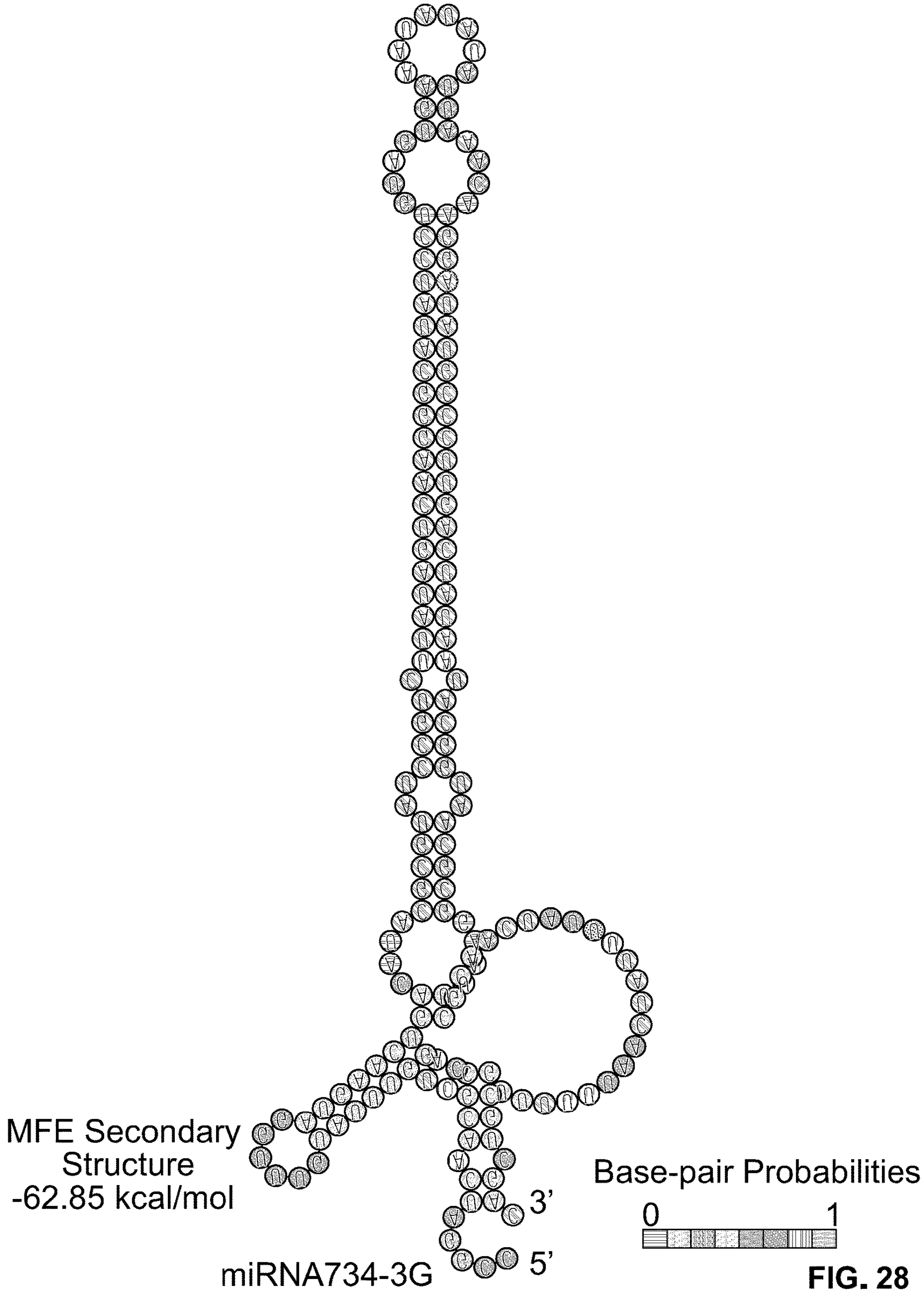
FIG. 28 illustrates a sh734 embedded in the miRNA-3G backbone, a third generation miRNA scaffold derived from the native miRNA 16-2 structure (see also SEQ ID NO: 26).
Figure 29:
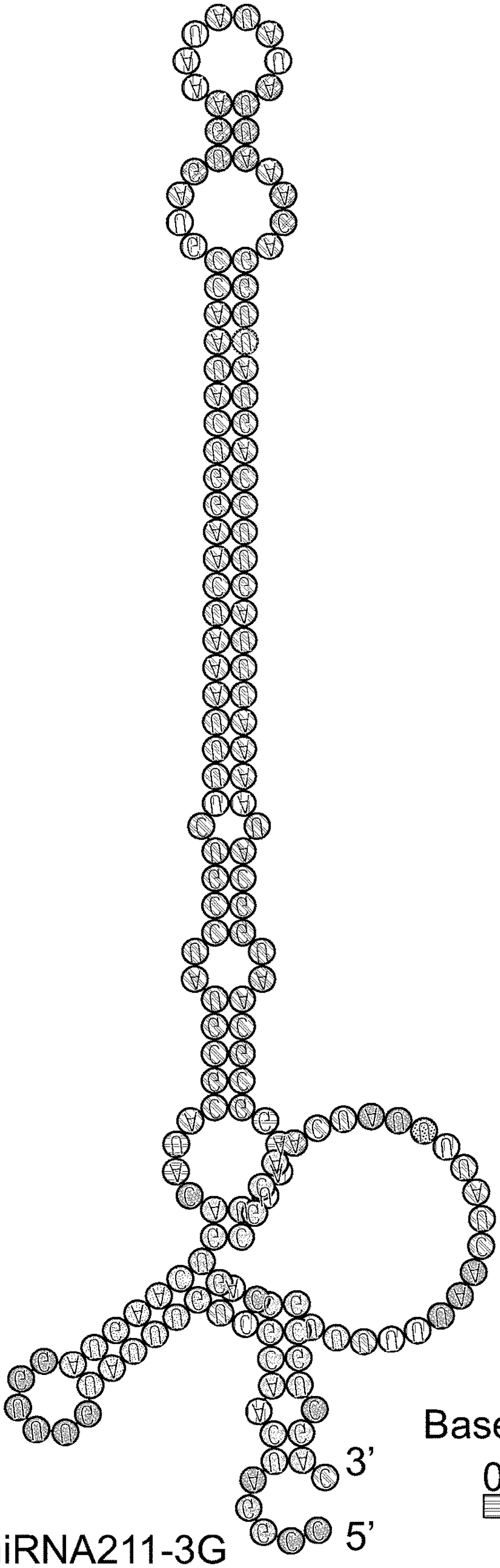
FIG. 29 illustrates the sh211 embedded in the miRNA-3G backbone, a 3rd generation miRNA scaffold derived from the native miRNA 16-2 structure (see also SEQ ID NO: 25).

In other embodiments, the micro-RNA based shRNA is a third generation miRNA scaffold modified miRNA 16-2 (hereinafter "miRNA-3G") (see, e.g. FIGS. 28 and 29). The synthesis of such miRNA-3G molecules is described by Watanabe, C., Cuellar, T. L. & Haley, B. "Quantitative evaluation of first, second, and third generation hairpin systems reveals the limit of mammalian vector-based RNAi," RNA Biology 13, 25-33 (2016), the disclosure of which is hereby incorporated by reference herein in its entirety.

In some embodiments, the miRNA-3G has a sequence having at least 80% identify to that of SEQ ID NO: 25. In some embodiments, the miRNA-3G has a sequence having at least 90% identify to that of SEQ ID NO: 25. In some embodiments, the miRNA-3G has a sequence having at least 95% identify to that of SEQ ID NO: 25. In some embodiments, the miRNA-3G has the sequence of SEQ ID NO: 25 ("miRNA211-3G") (see also FIG. 29).

In some embodiments, the miRNA-3G has a sequence having at least 80% identify to that of SEQ ID NO: 26. In some embodiments, the miRNA-3G has a sequence having at least 90% identify to that of SEQ ID NO: 26. In some embodiments, the miRNA-3G has a sequence having at least 95% identify to that of SEQ ID NO: 25. In other embodiments, the miRNA-3G has the sequence of SEQ ID NO: 26 ("miRNA734-3G") (see also FIG. 28).

Figure 33:
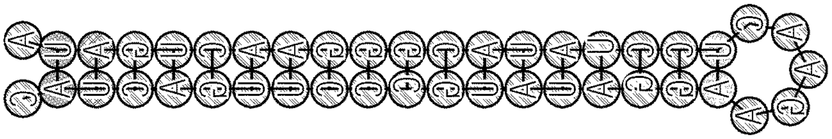
FIG. 33 illustrates the Ago-sh734 secondary structure (mimicking the human miRNA451 structure) (see also SEQ ID NO: 58).
Figure 34:
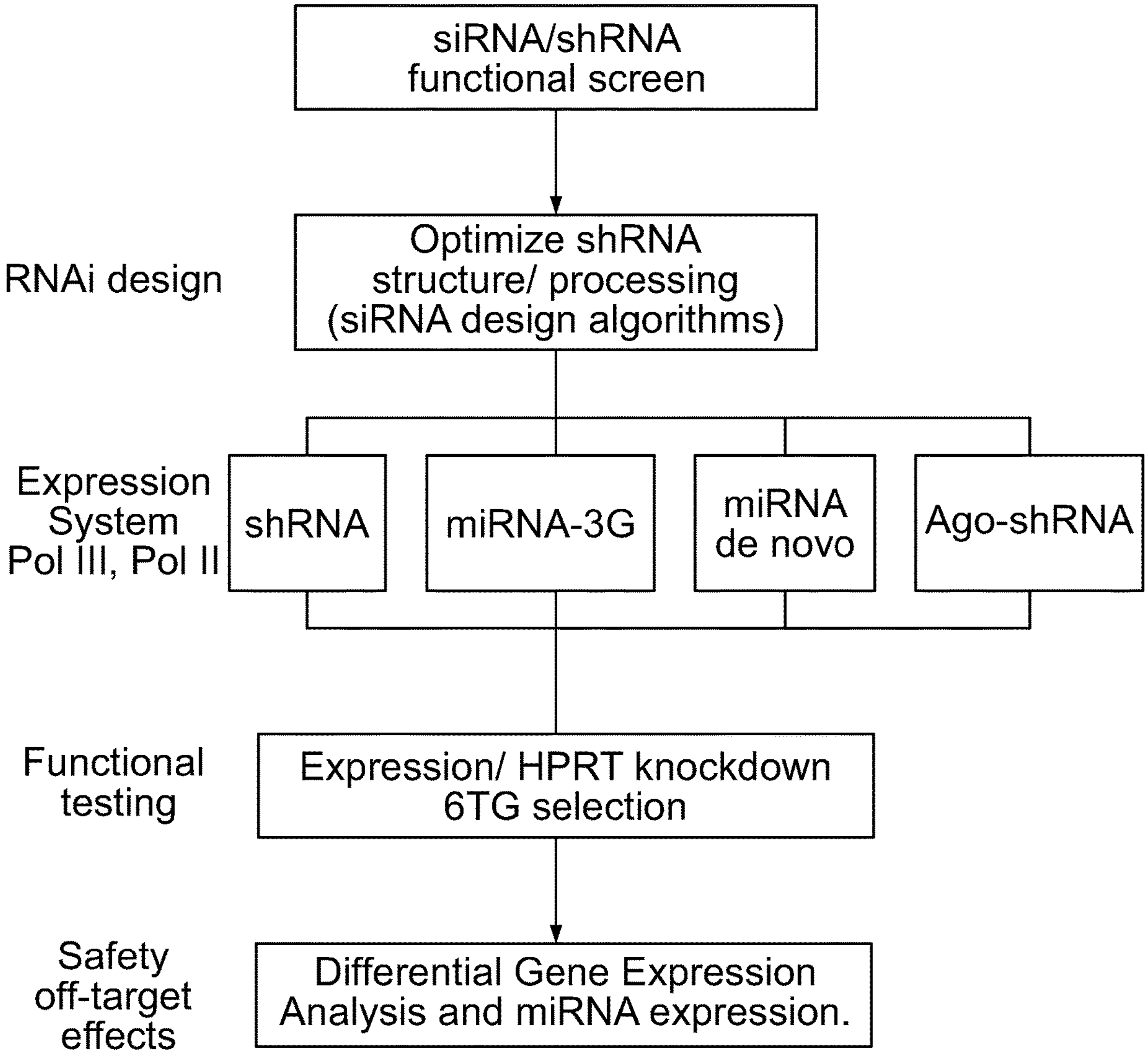
FIG. 34 sets forth a flowchart illustrating a process of four steps for RNAi design, choice of promoter and structure, functional testing and safety evaluation. In some embodiments, siRNA design algorithms are used to obtain candidates of shRNA target. Subsequently, different shRNA expression system with different promoters (Pol III or Pol II) and different shRNA designs (shRNA, 3rd-generation miRNA, miRNA de novo and dicer-independent Ago-shRNA) are designed and synthesized for functional tests and safety study. Functional tests are performed by measuring knockdown of HPRT and selection with 6-TG in transduced cell lines. Cell viability and miRNA expression are analyzed for safety evaluation. Preclinical testing and safety studies are performed in in vitro primary cells including hematopoietic stem cell and progenitor cells, and established cell lines and in in vivo murine and non-human primate models.

In some embodiments, the sh734 shRNA is adapted to mimic a miRNA-451 (see SEQ ID NO: 60) structure with a 17 nucleotide base pair stem and a 4-nucleotide loop (miR-451 regulates the drug-transporter protein P-glycoprotein). Notably, this structure does not require processing by DICER. It is believed that the pre-451 mRNA structure is cleaved by Ago2 and subsequently by poly(A)-specific ribonuclease (PARN) to generate the mature miRNA-451 structural mimic. The secondary structure for a miRNA-451-like Agosh734 sequence is shown in FIG. 33 herein (SEQ ID NO: 58). It is believed that Ago-shRNA mimics of the structure of the endogenous miR-451 and may have the advantage of being DICER independent. This is believed to restrict off target effects of passenger loading, with variable 3'-5' exonucleolytic activity (23-26nt mature) (see Herrera-Carrillo, E., and B. Berkhout. 2017. Dicer-independent processing of small RNA duplexes: mechanistic insights and applications. Nucleic Acids Res. 45:10369-10379). It is also believed that there exist advantages of utilizing alternate dicer independent processing of shRNAs, including efficient reduced off-target effects of single RNAi-active guide, no saturation of cellular RNAi Dicer machinery, and shorter RNA duplexes are less likely to trigger innate RIG-I response.

Alternatives to RNAi

As an alternative to the incorporation of a RNAi, in some embodiments, the expression vectors may include a nucleic acid sequence which encodes antisense oligonucleotides that bind sites in messenger RNA (mRNA). Antisense oligonucleotides of the present disclosure specifically hybridize with a nucleic acid encoding a protein and interfere with transcription or translation of the protein. In some embodiments, an antisense oligonucleotide targets DNA and interferes with its replication and/or transcription. In other embodiments, an antisense oligonucleotide specifically hybridizes with RNA, including pre-mRNA (i.e. precursor mRNA which is an immature single strand of mRNA), and mRNA. Such antisense oligonucleotides may affect, for example, translocation of the RNA to the site of protein translation, translation of protein from the RNA, splicing of the RNA to yield one or more mRNA species, and catalytic activity that may be engaged in or facilitated by the RNA. The overall effect of such interference is to modulate, decrease, or inhibit target protein expression.

In some embodiments, the expression vectors incorporate a nucleic acid sequence encoding for an exon skipping agent or exon skipping transgene. As used herein, the phrase "exon skipping transgene" or "exon skipping agent" refers to any nucleic acid that encodes an antisense oligonucleotide that can generate exon skipping. "Exon skipping" refers to an exon that is skipped and removed at the pre-mRNA level during protein production. It is believed that antisense oligonucleotides may interfere with splice sites or regulatory elements within an exon. This can lead to truncated, partially functional, protein despite the presence of a genetic mutation. Generally, the antisense oligonucleotides may be mutation-specific and bind to a mutation site in the pre-messenger RNA to induce exon skipping.

Exon skipping transgenes encode agents that can result in exon skipping, and such agents are antisense oligonucleotides. The antisense oligonucleotides may interfere with splice sites or regulatory elements within an exon to lead to truncated, partially functional, protein despite the presence of a genetic mutation. Additionally, the antisense oligonucleotides may be mutation-specific and bind to a mutation site in the pre-messenger RNA to induce exon skipping. Antisense oligonucleotides for exon skipping are known in the art and are generally referred to as AONs. Such AONs include small nuclear RNAs ("snRNAs"), which are a class of small RNA molecules that are confined to the nucleus and which are involved in splicing or other RNA processing reactions. Examples of antisense oligonucleotides, methods of designing them, and related production methods are disclosed, for example, in U.S. Publication Nos. 20150225718, 20150152415, 20150140639, 20150057330, 20150045415, 20140350076, 20140350067, and 20140329762, the disclosures of which are hereby incorporated by reference herein in their entireties.

In some embodiments, the expression vectors of the present disclosure include a nucleic acid which encodes an exon skipping agent which results in exon skipping during the expression of HPRT or which causes an HPRT duplication mutation (e.g. a duplication mutation in Exon 4) (see Baba S, et al. Novel mutation in HPRT1 causing a splicing error with multiple variations. Nucleosides Nucleotides Nucleic Acids. 2017 Jan. 2; 36(1):1-6, the disclosure of which is hereby incorporated by reference herein in its entirety). In some embodiments, phosphorothioate-modified antisense oligonucleotides to target sequences within the coding region of HPRT (see FIG. 38) can bind mRNA transcripts and inhibit translation of functional protein. In addition to their incorporation within expression vectors, oligonucleotides may be delivered via nanocapsules, minicells, liposomes or another suitable transfection vehicle. For example, in accordance with the present disclosure, minicells may include a functional nucleic acid, e.g. a siRNA or shRNA, or an expression vector that encodes a functional nucleic acid that can be effectively packaged for in vivo delivery.

In some embodiments, HPRT may be replaced with a modified mutated sequence by spliceosome trans-splicing, thus facilitating knockdown of HPRT. In some embodiments, this (1) requires a mutated coding region to replace the coding sequence in a target RNA, (2) a 5' or 3' splice site, and/or (3) a binding domain, i.e., antisense oligonucleotide sequence, which is complementary to the target HPRT RNA. In some embodiments, all three components are required.

Therapeutic Gene

As noted herein, the expression vectors (e.g. the lentiviral expression vectors) of the present disclosure may also include a second nucleic acid sequence encoding a therapeutic gene (e.g. gamma globin), whereby the therapeutic gene may correct a defect in a target cell (e.g. HSCs). As will be understood by those in the art, the term "therapeutic gene" includes genomic sequences, cDNA sequences, and smaller engineered gene segments that express, or may be adapted to express, proteins, polypeptides, domains, fusion proteins, and mutants that maintain some or all of the therapeutic function of the full-length polypeptide encoded by the therapeutic gene. Encompassed within the definition of "therapeutic gene" is a "biologically functional equivalent" therapeutic gene. Accordingly, sequences that have about 70% sequence homology to about 99% sequence homology and any range or amount of sequence homology derivable therein, such as, for example, about 70% to about 80%, and more preferably about 85% and about 90%; or even more preferably, between about 95% and about 99%; of amino acids that are identical or functionally equivalent to the amino acids of the therapeutic gene will be sequences that are biologically functional equivalents provided the biological activity of the polypeptide is maintained.

In some embodiments, the therapeutic gene corrects a single-gene disorder. In some embodiments, the therapeutic gene is used to treat immune deficiencies, hereditary diseases, blood diseases (e.g. hemophilia, hemoglobin disorders), lysosomal storage diseases, neurological diseases, angiogenic disorders, or cancer.

In some embodiments, the therapeutic gene is a gene encoding an enzyme adenosine deaminase, a gene encoding alpha-1-antitrypsin, a gene encoding a cystic fibrosis transmembrane conductance regulator, a gene encoding the enzyme Galactose-1-phosphate uridylyltransferase, a gene encoding a clotting factor (e.g. human Factor IX), a gene encoding a lipoprotein lipase gene, one or more genes encoding the enzymes required for dopamine synthesis, a gene encoding for glial cell line-derived neurotrophic factor (GDNF), a gene encoding interleukin-2 receptor subunit gamma (IL-2RG), a gene encoding Gp91phox, a gene encoding the Wiskott-Aldrich syndrome protein, a gene encoding a globin protein, a gene encoding a mutated globin protein (e.g. one having antisickling properties, a gene encoding a mutated beta-globin, a gene encoding gamma-globin, a gene encoding an anti-CD19 antibody, etc. In other embodiments, the therapeutic gene is selected from the group consisting of a globin gene, sphingomyelinase gene, alpha-L-iduronudase gene, huntingtin gene, neurofibromin 1 gene, MLH1 gene, MSH2 gene, MSH6 gene, PMS2 gene, cystic fibrosis transmembrane conductance regulator gene, hexosaminidase A gene dystrophin gene, FMR1 gene, phenylalanine hydroxylase gene and low-density lipoprotein gene.

Examples of classes of therapeutic genes include, but are not limited to, tumor suppressor genes, genes that induce or prevent apoptosis, genes encoding enzymes, genes encoding antibodies, genes encoding hormones, genes encoding receptors, and genes encoding cytokines, chemokines, or angiogenic factors. Specific examples of therapeutic genes include, but are not limited to, Rb, CFTR, p16, p21, p27, p57, p73, C-CAM, APC, CTS-I, zacl, scFV, ras, DCC, NF-I, NF-2, WT-I, MEN-I, MEN-II, BRCA1, VHL, MMAC1, FCC, MCC, BRCA2, IL-I, IL-2, IL-3, IL-4, IL-5, IL-6, IL-7, IL-8, IL-9, IL-IO, IL-11 IL-12, IL-15Ra, IL-15, IL-21, GM-CSF, G-CSF, thymidine kinase, mda7, FUS1, interferon alpha, interferon beta, interferon gamma, ADP, p53, ABLI, BLCl, BLC6, CBFAl, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCLI, MYCN, NRAS, PIMI, PML, RET, SRC, TALI, TCL3, YES, MADH4, RB1, TP53, WT1, TNF, BDNF, CNTF, NGF, IGF, GMF, aFGF, bFGF, NT3, NT5, ApoAI, ApoATV, ApoE, RaplA, cytosine deaminase, Fab, ScFv, BRCA2, zacl, ATM, HIC-I, DPC-4, FHIT, PTEN, INGI, NOEYl, NOEY2, OVCA1, MADR2, 53BP2, IRF-I, zacl, DBCCR-I, rks-3, COX-I, TFPI, PGS, Dp, E2F, ras, myc, neu, raf, erb, fins, trk, ret, gsp, hst, abl, ElA, p300, VEGF, FGF, thrombospondin, BAI-I, GDAIF, MCC, 41BBL, CD80, CD86, or OX40.

Other examples of therapeutic genes are the tumor suppressor genes including, but not limited to, FUS1, Gene 26 (CACNA2D2), PL6, LUCA-1 (HYAL1), LUCA-2 (HYAL2), 123F2 (RASSF1), 101F6, Gene 21 (NPRL2), SEM A3, NF1, NF2, and p53.

Yet other examples of therapeutic genes are genes encoding enzymes including, but not limited to, ACP desaturase, ACP hydroxylase, ADP-glucose pyrophorylase, PDE8A (camp Phosphodiesterase), ATPase, alcohol dehydrogenase, amylase, amyloglucosidase, catalase, cellulase, cyclooxygenase, decarboxylase, dextrinase, esterase, DNA polymerase, RNA polymerase, hyaluron synthase, galactosidase, glucanase, glucose oxidase, GTPase, helicase, hemicellulase, hyaluronidase, integrase, invertase, isomerase, kinase, lactase, lipase, lipoxygenase, lyase, lysozyme, pectinesterase, a peroxidase, a phosphatase, a phospholipase, a phosphorylase, polygalacturonase, proteinase, peptidase, pullanase, recombinase, reverse transcriptase, topoisomerase or xylanase. Further examples of therapeutic genes include the genes encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta. -synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, alpha-L-idurom, dase, glucose-6-phosphate dehydrogenase, HSV thymidine kinase, or human thymidine kinase.

Further examples of therapeutic genes include genes encoding hormones including, but not limited to, growth hormone, prolactin, placental lactogen, luteinizing hormone, follicle-stimulating hormone, chorionic gonadotropin, uiyroid-stimulating hormone, leptin, adrenocorticotropin, angiotensin I, angiotensin II, alpha-endorphin, beta-melanocyte stimulating hormone, cholecystokinin, endothelin I, galanin, gastric inhibitory peptide, glucagon, insulin, lipotropins, neurophysins, somatostatin, calcitonin, calcitonin gene related peptide, beta-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

Gamma-Globin Gene

In some embodiments, the expression vector comprises a nucleic acid sequence encoding a gamma-globin gene (see, e.g. FIG. 39). In some embodiments, the nucleic acid sequence encoding the gamma-globin gene has a sequence having at least 80% identity to that of SEQ ID NO: 55. In other embodiments, the nucleic acid sequence encoding the gamma-globin gene has a sequence having at least 85% identity to that of SEQ ID NO: 55. In yet other embodiments, the nucleic acid sequence encoding the gamma-globin gene has a sequence having at least 90% identity to that of SEQ ID NO: 55. In further embodiments, the nucleic acid sequence encoding the gamma-globin gene has a sequence having at least 95% identity to that of SEQ ID NO: 55. In yet further embodiments, the nucleic acid sequence encoding the gamma-globin gene has a sequence having at least 97% identity to that of SEQ ID NO: 55. In even further embodiments, the nucleic acid sequence encoding the gamma-globin gene has a sequence having at least 98% identity to that of SEQ ID NO: 55. In even further embodiments, the nucleic acid sequence encoding the gamma-globin gene has a sequence having at least 99% identity to that of SEQ ID NO: 55. It is believed that the point mutation in the gamma globin gene of SEQ ID NO: 55 encoding a G16D amino acid change in the polypeptide has an increased affinity to bind alpha globin without altering its function, thereby greatly improving the efficiency of HbF formation in RBCs and resulting in a far more efficient anti-sickling effect that will, it is believed, correct the SCD phenotype. Exons 1, 2, and 3 of the gamma globin gene are set forth as SEQ ID NOS: 51, 52, and 53, respectively.

In some embodiments, the nucleic acid sequence encoding the gamma-globin gene has a sequence having at least 90% identity to that of SEQ ID NO: 3. In other embodiments, the nucleic acid sequence encoding the gamma-globin gene has a sequence having at least 95% identity to that of SEQ ID NO: 3. In yet other embodiments, the nucleic acid sequence encoding the gamma-globin gene has a sequence having at least 97% identity to that of SEQ ID NO: 3. In yet other embodiments, the nucleic acid sequence encoding the gamma-globin gene has a sequence having at least 98% identity to that of SEQ ID NO: 3. In yet other embodiments, the nucleic acid sequence encoding the gamma-globin gene has a sequence having at least 99% identity to that of SEQ ID NO: 3.

In some embodiments, the expression vector comprises a nucleic acid which encodes for an amino acid sequence having an identity of at least about 80% to that of SEQ ID NO: 4. In other embodiments, the nucleic acid sequence encodes an amino acid having an identity of at least about 85% to that of SEQ ID NO: 4. In yet other embodiments, the nucleic acid sequence encodes an amino acid having an identity of at least about 90% to that of SEQ ID NO: 4. In further embodiments, the nucleic acid sequence encodes an amino acid having an identity of at least about 95% to that of SEQ ID NO: 4. In yet further embodiments, the nucleic acid sequence encodes an amino acid having an identity of at least about 97% to that of SEQ ID NO: 4. In even further embodiments, the nucleic acid sequence encodes an amino acid having an identity of at least about 98% to that of SEQ ID NO: 4. In even further embodiments, the nucleic acid sequence encodes an amino acid having an identity of at least about 99% to that of SEQ ID NO: 4.

Gamma globin genes, methods of their synthesis, and incorporation into vectors are described in United States Patent Publication No. 2017/0145077, the disclosure of which is hereby incorporated by reference herein in its entirety.

Therapeutic Genes for Treating Other Diseases

Yet other therapeutic genes may be incorporated into an expression, including those genes described below.

Adenosine Deaminase-Severe Combined Immunodeficiency (ADA-SCID) deficiency results in the accumulation of toxic metabolites that destroy the immune system, causing severe combined immunodeficiency (ADA-SCID), often referred to as the "bubble boy" disease. In some embodiments, the second nucleic acid of the expression vectors described herein encodes for the human ADA cDNA sequence.

Severe Combined Immunodeficiency (SCID-X1) Disease is the most common form of SCID, accounting for 40-50% of SCID cases reported worldwide. Mutations in the IL2RG gene are leads to defective expression of the common gamma chain (γc), a subunit shared by a host of cytokine receptors, including interleukin (IL)-2, 4, 7, 9, 15, and 21 receptor complexes, which play a vital role in lymphocyte development and function. In some embodiments, the second nucleic acid of the expression vectors described herein encodes the human γc cDNA sequence.

Chronic granulomatous disease (CGD) is caused by defects in the subunits (gp91phox, p22phox, p47phox, p40phox or p67phox) of the phagocyte-derived NADPH oxidase. Mutations in the CYBB gene—encoding the gp91phox subunit—are responsible for the X-linked form of CGD, which accounts for approximately 70% of patients. X-linked CGD is characterized by severe, life-threatening bacterial and fungal infections due to an impaired production of superoxide anions and other reactive oxygen intermediates by neutrophils, eosinophils, monocytes and macrophages. Another aspect of the disease is the sterile, chronic, granulomatous inflammation affecting organs such as the gut or lung, mainly caused by increased production of pro-inflammatory cytokines, delayed apoptosis of inflammatory cells and deficient secretion of anti-inflammatory mediators by activated neutrophils. The poor outcome is associated with a history of invasive fungal infection, liver abscesses and chronic granulomatous inflammation. Available therapeutic strategies include antibiotic long-life prophylaxis, IFN-γ administration, and HCT. In some embodiments, the second nucleic acid of the expression vectors described herein encodes the human subunit cDNA sequence.

Metachromatic leukodystrophy (MLD) MLD is a rare autosomal-recessive lysosomal storage disease caused by mutations in the arylsulfatase A (ARSA) gene that result in enzyme deficiency and accumulation of the undegraded substrate cerebroside 3-sulphate (sulphatide) in neural and glial cells in the central nervous system and peripheral nervous system. This accumulation of sulphatide leads to progressive demyelination and neurodegeneration. In some embodiments, the second nucleic acid of the expression vectors described herein encodes the human ARSA cDNA sequence.

Mucopolysaccharidosis I (MPS-I) or Hurler syndrome is a lysosomal storage disorder caused by a deficiency of the alpha-L-iduronidase enzyme (IDUA). The disease is characterized by inappropriate storage of glycosamminoglycans (GAGs) with accompanying organ enlargement and damage, excretion of abnormal quantities of GAGs in urine, and disrupted GAG turnover that especially affects connective tissues. Clinical manifestations include skeletal abnormalities, hepatosplenomegaly, mental retardation, and cardiovascular and respiratory dysfunction. IDUA deficiency can result in a wide range of phenotypic presentations, and MPS I Hurler (MPS IH) represents the most severe disease variant within this spectrum, characterized by a chronic, progressive, and disabling disease course involving multiple organs and the central nervous system. The disease is fatal in childhood if untreated, with death usually occurring within the first decade of life because of cardiorespiratory failure. In some embodiments, the second nucleic acid of the expression vectors described herein encodes the human cDNA of alpha-iduronidase (IDUA).

Gaucher's disease is the most common of the lysosomal storage diseases. It is an autosomal recessive lysosomal storage disease, caused by deficiency of the enzyme glucocerebrosidase (GBA), required for the degradation of glycosphingolipids. Clinical manifestations include hepatosplenomegaly, thrombocytopenia, bone disease and a bleeding diathesis, frequently resulting in presentation to haematologists. Gene therapy represents a therapeutic alternative for patients to enzyme replacement therapy and those lacking a suitable bone marrow donor. In some embodiments, the second nucleic acid of the expression vectors described herein encodes the human cDNA of the GBA gene.

Lysosomal storage diseases (LSDs) are rare inherited metabolic disorders characterized by a dysfunction in lysosomes. LSDs encompass approximately 70 genetically distinct diseases, with a collective incidence of 1:5000 live births. Examples include Fabry disease (alpha-galactosidase A deficiency), Pompe disease (α-glucosidase [GAA] deficiency), Hunter syndrome (iduronate-2-sulfatase [I2S] deficiency), Sanfilippo syndrome (deficiency in one of the enzymes needed to break down the glycosaminoglycan heparan sulfate) and Krabbe disease (gal-actocerebrosidase deficiency). Likewise, inherited metabolic disorders are one cause of metabolic disorders, and occur when a defective gene causes an enzyme deficiency. It is believed that an expression vectors of the present disclosure may be adapted to incorporate a second nucleic acid sequence which encodes a gene suitable for use in treating any of the above-identified conditions.

Pyruvate kinase deficiency (PKD) is a monogenic metabolic disease caused by mutations in the PKLR gene that leads to hemolytic anemia of variable symptomatology and that can be fatal during the neonatal period. PKD recessive inheritance trait and its curative treatment by allogeneic bone marrow transplantation provide an ideal scenario for developing gene therapy approaches. In some embodiments, the second nucleic acid of the expression vectors described herein encodes the human PKLR cDNA.

Adrenoleukodystrophy (ALD) is a rare X-linked metabolic disorder caused by mutations in the ABCD1 gene which result in a deficiency in adrenoleukodystrophy protein (ALDP) and subsequent accumulation of very long chain fatty acids (VLCFA). VLCFA accumulation occurs in plasma and all tissue types but primarily affects the adrenal cortex and white matter of the brain and spinal cord, leading to a range of clinical outcomes. The most severe form of ALD, the inflammatory cerebral phenotype known as cerebral ALD (CALD), involves a progressive destruction of myelin, the protective sheath of the nerve cells in the brain that are responsible for thinking and muscle control. Symptoms of CALD usually occur in early childhood and progress rapidly if untreated, leading to severe loss of neurological function and eventual death in most patients. In some embodiments, the second nucleic acid of the expression vectors described herein encodes the human adrenoleukodystrophy protein (ALDP).

Fanconi anemia (FA) is an inherited bone marrow failure syndrome. A defect in 1 of at least 16 DNA repair genes leads to aplasia and enhanced risk for malignancies, especially AML and MDS. Additionally, the risk for adenoma, adenocarcinomas and squamous cell carcinomas is increased. Most patients also have a short stature, various morphological abnormalities and developmental disorders. Supportive treatment includes regular transfusions of blood products and growth hormone substitution due to concomitant endocrinopathies in FA patients. HSCT in the donor-matched setting has been the only curative option and is thus an attractive option for gene therapy. Despite the heterogeneity in genes affected, more than 60% of the patients have mutations in the FANCA gene. In some embodiments, the second nucleic acid of the expression vectors described herein encodes the human FANCA cDNA.

Promoters

In some embodiments, different promoters are used to drive expression of each of the nucleic acid sequences incorporated within the disclosed expression vectors. For example, a first nucleic acid sequence encoding an RNAi (e.g. an anti-HPRT shRNA) may be expressed from a first promoter, and a second nucleic acid sequence encoding a therapeutic gene (e.g. a gamma-globin gene) may be expressed from a second promoter, wherein the first and second promoters are different. Likewise, and by way of another example, a first nucleic acid sequence encoding a micro-RNA based shRNA to downregulate HPRT may be expressed from a first promoter and a second nucleic acid sequence encoding a therapeutic gene (e.g. the gamma-globin gene) may be expressed from a second promoter, wherein the first and second promoters are different.

In some embodiments, the promoters may be constitutive promoters or inducible promoters as known to those of ordinary skill in the art. In some embodiments, the promoter includes at least a portion of an HIV LTR (e.g. TAR).

Examples of suitable promoters include, but are not limited to, RNA polymerase I (pol I), polymerase II (pol II), or polymerase III (pol III) promoters. By “RNA polymerase III promoter” or “RNA pol III promoter” or “polymerase III promoter” or “pol III promoter” it is meant any invertebrate, vertebrate, or mammalian promoter, e.g., human, murine, porcine, bovine, primate, simian, etc. that, in its native context in a cell, associates or interacts with RNA polymerase III to transcribe its operably linked gene, or any variant thereof, natural or engineered, that will interact in a selected host cell with an RNA polymerase III to transcribe an operably linked nucleic acid sequence. RNA pol III promoters suitable for use in the expression vectors of the disclosure include, but are not limited, to human U6, mouse U6, and human H1 others.

Examples of pol II promoters include, but are not limited to, Ef1 alpha, CMV, and ubiquitin. Other specific pol II promoters include, but are not limited to, ankyrin promoter (Sabatino D E, et al., Proc Natl Acad Sd USA. (24):13294-9 (2000)), spectrin promoter (Gallagher P G, et al., J Biol Chem. 274(10):6062-73, (2000)), transferrin receptor promoter (Marziali G, et al., Oncogene. 21(52):7933-44, (2002)), band 3/anion transporter promoter (Frazar T F, et al., MoI Cell Biol (14):4753-63, (2003)), band 4.1 promoter (Harrison P R, et al., Exp Cell Res. 155(2):321-44, (1984)), BcI-Xl promoter (Tian C, et al., Blood 15; 101(6):2235-42 (2003)), EKLF promoter (Xue L, et al., Blood. 103(11): 4078-83 (2004)). Epub 2004 Feb. 5), ADD2 promoter (Yenerel M N, et al., Exp Hematol. 33(7):758-66 (2005)), DYRK3 promoter (Zhang D, et al., Genomics 85(1): 117-30 (2005)), SOCS promoter (Sarna M K, et al., Oncogene 22(21):3221-30 (2003)), LAF promoter (To M D, et al., bit J Cancer 1; 115(4):568-74, (2005)), PSMA promoter (Zeng H, et al., JAndrol (2):215-21, (2005)), PSA promoter (Li H W, et al., Biochem Biophys Res Commun 334(4): 1287-91, (2005)), Probasin promoter (Zhang J, et al., 145(1):134-48, (2004)). Epub 2003 Sep. 18), ELAM-Ipromoter/E-Selectin (Walton T, et al., Anticancer Res. 18(3A):1357-60, (1998)), Synapsin promoter (Thiel G, et al., ProcNatl Acad Sd USA., 88(8):3431-5(1988)), Willebrand factor promoter (Jahroudi N, Lynch D C. MoI Cell –5zo/.14(2):999-1008, (1994)), FLTl (Nicklin S A, et al., Hypertension 38(1):65-70, (2001)), Tau promoter (Sadot E, et al., JMoI Biol. 256(5):805-12, (1996)), Tyrosinase promoter (Lillehammer T, et al., Cancer Gene Ther. (2005)), pander promoter (Burkhardt B R, et al., Biochim Biophys Acta. (2005)), neuron-specific enolase promoter (Levy Y S, et al., JMolNeurosci.21(2):121-32, (2003)), hTERT promoter (Ito H, et al., Hum Gene Ther 16(6):685-98, (2005)), HRE responsive element (Chadderton N, et al., IntJRadiat Oncol Biol Phys.62(1):2U-22, (2005)), lck promoter (Zhang D J, et al., J Immunol. 174(11):6725-31, (2005)), MHCII promoter (De Geest B R, et al., Blood. 101(7):2551-6, (2003), Epub 2002 Nov. 21), and CDl Ic promoter (Lopez-Rodriguez C, et al., J Biol Chem. 272(46):29120-6 (1997)).

In some embodiments, the promoter driving expression of the agent designed to knockdown HPRT or otherwise decrease its expression is a RNA pol III promoter. In some embodiments, the promoter driving expression of the agent designed to knockdown HPRT or otherwise decrease its expression is a 7sk promoter (e.g. a 7SK human 7S K RNA promoter). In some embodiments, the 7sk promoter has the sequence provided by ACCESSION AY578685 (*Homo sapiens* cell-line HEK-293 7SK RNA promoter region, complete sequence, ACCESSION AY578685).

Figure 35:
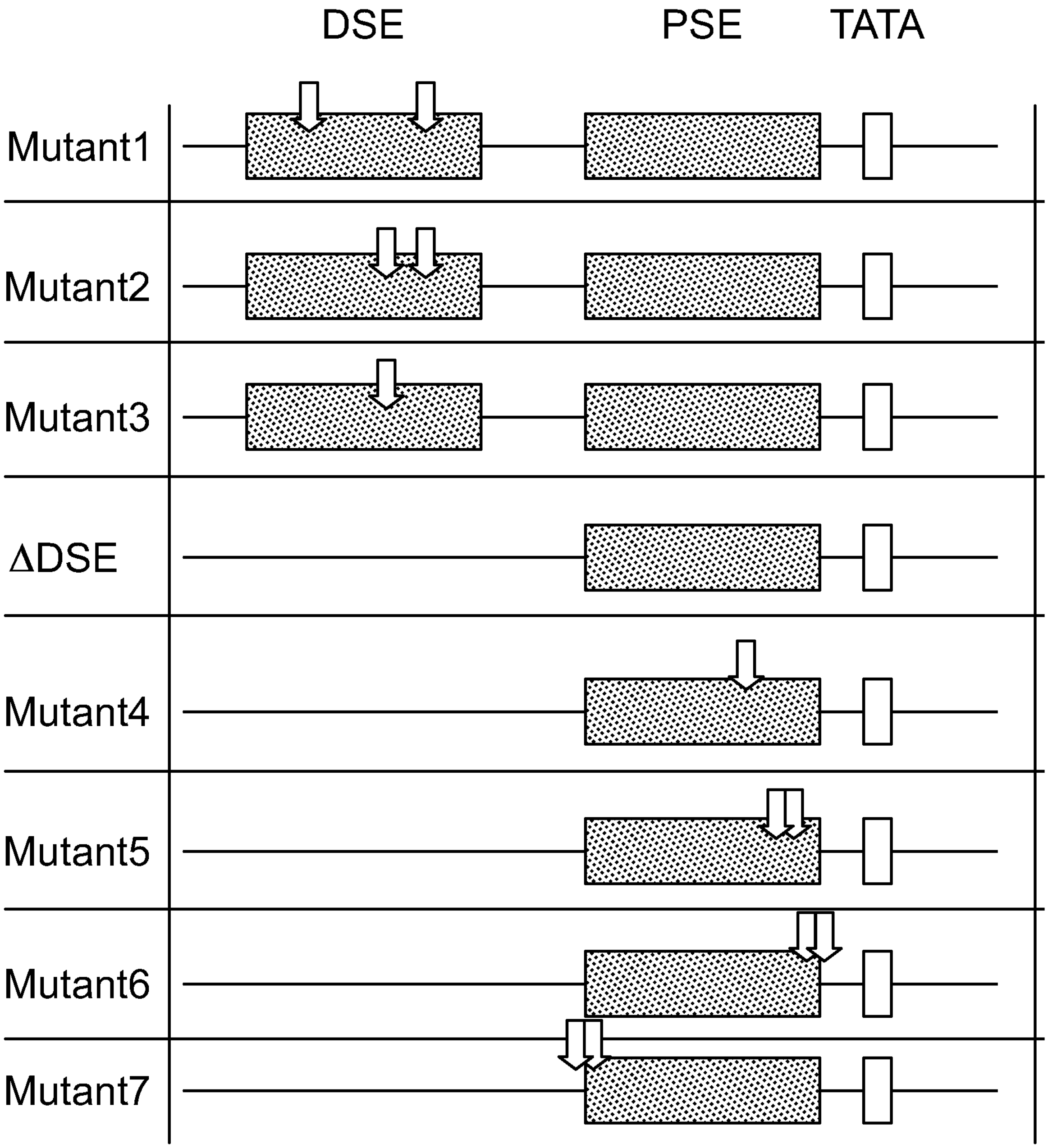
FIG. 35 illustrate human 7sk promoter mutations. Mutations (arrows) and deletions introduced into the cis-distal sequence enhancer (DSE) and proximal sequence enhancer (PSE) elements (long, wide boxes) in the 7sk promoter relative to the TATA box (tall, thin boxes) are illustrated.
Figure 36:
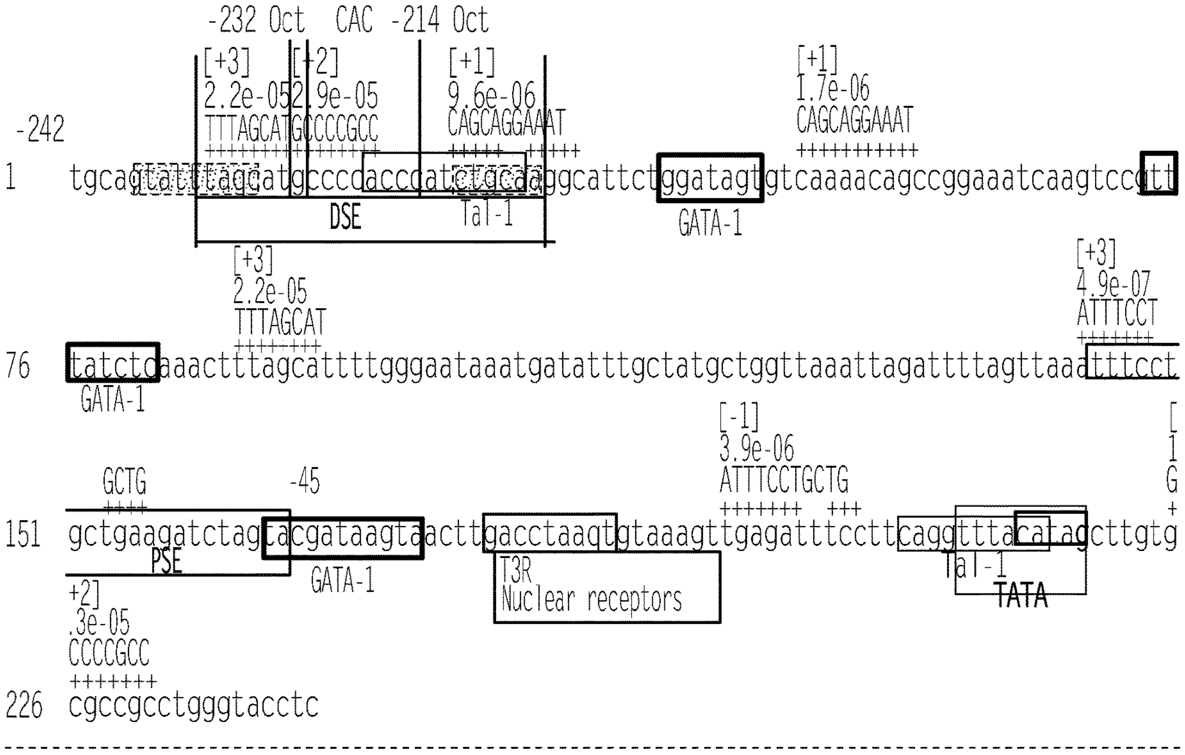
FIG. 36 illustrates the location and probability of transcription binding sites within the 7sk promoter and highlights the two mutated OCT transcription factor binding sites in the distal sequence enhancer (DSE). Also shown are the predicted binding sites within the promoter for the erythroid lineage transcription factors TAL-1 and GATA-1.

In some embodiments, the 7sk promoter utilized comprises at least one mutation and/or deletion in its nucleic acid sequence in comparison to the 7sk promoter (see FIGS. 35 and 36). In other embodiments, the 7sk promoter comprises multiple mutations and/or deletions in its nucleic acid sequence in comparison to the 7sk promoter (ACCESSION AY578685). In yet other embodiments, the 7sk promoter has 95% identity to the sequence of SEQ ID NO: 32. In yet further embodiments, the 7sk promoter has the sequence of SEQ ID NO: 32. It is believed that the 7sk promoter expressed the shRNA to HPRT at a moderate level and was more effective than other Pol III promoters, e.g. U6 and H1. It is believed that the introduction of allowed for the modulation of the expression of shRNA to HPRT at therapeutic levels.

In some embodiments, the 7sk promoter has a sequence having at least 95% identity to that of SEQ ID NOS: 32. In some embodiments, the 7sk promoter has a sequence having at least 96% identity to that of SEQ ID NOS: 32. In some embodiments, the 7sk promoter has a sequence having at least 97% identity to that of SEQ ID NOS: 32. In some embodiments, the 7sk promoter has a sequence having at least 98% identity to that of SEQ ID NOS: 32. In some embodiments, the 7sk promoter has a sequence having at least 99% identity to that of SEQ ID NOS: 32. In some embodiments, the 7sk promoter has the sequence set forth in SEQ ID NOS: 32.

In some embodiments, functional mutations or deletions in the 7sk promoter are made in cis-regulatory elements to regulate expression levels of the promoter-driven transgene, including sh734 (see SEQ ID NO: 33). (see Boyd, D. C., Turner, P. C., Watkins, N.J., Gerster, T. & Murphy, S. Functional Redundancy of Promoter Elements Ensures Efficient Transcription of the Human 7SK Gene in vivo. *Journal of Molecular Biology* 253, 677-690 (1995). The mutations described are used to establish the correlation between sh734 expression levels driven by the Pol III promoter and to introduce functionality to undergo stable selection in the presence of 6TG therapy and long-term stability and safety.

The location of 7sk promoter mutations are depicted in FIG. 35. The 7skM1 Oct binding site mutations in the distal sequence enhancer (DSE) and predicted TAL-1 and GATA-1 binding sites are shown in FIG. 36.

In some embodiments, the 7sk promoter has a sequence having at least 95% identity to that of SEQ ID NOS: 33. In some embodiments, the 7sk promoter has a sequence having at least 96% identity to that of SEQ ID NOS: 33. In some embodiments, the 7sk promoter has a sequence having at least 97% identity to that of SEQ ID NOS: 33. In some embodiments, the 7sk promoter has a sequence having at least 98% identity to that of SEQ ID NOS: 33. In some embodiments, the 7sk promoter has a sequence having at least 99% identity to that of SEQ ID NOS: 32. In some embodiments, the 7sk promoter has the sequence set forth in SEQ ID NOS: 33.

Figure 1B:
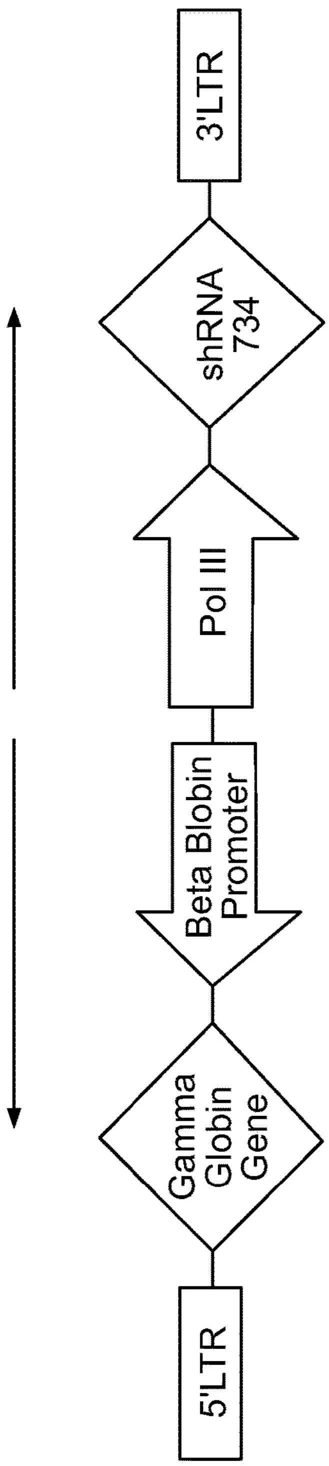

In some embodiments, the promoter that drives expression of a nucleic acid sequence encoding a therapeutic gene is a H1 promoter, a U6 promoter, or a mutant 7SK promoter. In some embodiments, the promoter that drives expression of a nucleic acid sequence encoding gamma-globin is a beta-globin promoter, such as illustrated in FIGS. 1A and 1B. In some embodiments, the beta-globin promoter is the wild-type human beta-globin promoter. In other embodiments, the beta globin promoter has a nucleic acid sequence having at least 90% sequence identity to that of SEQ ID NO: 66. In other embodiments, the beta globin promoter has a nucleic acid sequence having at least 95% sequence identity to that of SEQ ID NO: 66. In other embodiments, the beta globin promoter has a nucleic acid sequence having at least 99% sequence identity to that of SEQ ID NO: 66. In yet other embodiments, the beta globin promoter has the nucleic acid sequence of SEQ ID NO: 66. It is believed that the beta globin promoter is advantageous since it is subject to the normal regulation of the human beta-globin promoter expressed in red blood cells.

In other embodiments, the promoter is a tissue specific promoter. Several non-limiting examples of tissue specific promoters that may be used include lck (see, for example, Garvin et al., MoI. Cell Biol. 8:3058-3064, (1988)) and Takadera et al., MoI. Cell Biol. 9:2173-2180, (1989)), myogenin (Yee et al., Genes and Development 7:1277-1289 (1993), and thyl (Gundersen et al., Gene 113:207-214, (1992)).

It is also contemplated that a combination of promoters (e.g. UbC and H1 promoters) may be used to obtain the desired expression of the therapeutic gene and/or interfering RNA. In some embodiments, the expression vector includes a Pol II promoter and a Pol III promoter, e.g. Pol II beta-globin promoter for gamma-globin expression and Pol III 7SK promoter for knockdown of HPRT. Promoters having tissue specificity are advantageous, in that they can specifically direct expression of the gene of interest and interfering RNA, thereby controlling the biological effect as desired.

Examples of Vectors Having a Nucleic Acid Encoding a shRNA Targeting an HPRT Gene and a Nucleic Acid Encoding a Gamma-Globin Gene Examples of lentiviral expression vectors designed to knockdown HPRT and cause the expression of a gamma globin are described below. Any of the recited expression vectors are suitable for transducing HSCs, such as ex vivo.

In some embodiments, the lentiviral expression vector includes (a) a sequence encoding an RNAi targeting HPRT; (b) a sequence encoding a gamma globin gene; (c) a sequence encoding a first promoter to drive expression of the sequence encoding the RNAi targeting HPRT; (d) a sequence encoding a second promoter to drive expression of the sequence encoding the gamma globin gene; and (e) a sequence encoding a central polypurine tract (cPPT); and (f) a sequence encoding a Rev response element (RRE). In some embodiments, the cPPT comprises about 85 base pairs of the Vif sequence of wild-type HIV. In some embodiments, the RRE comprises about 26 base pairs of the Rev sequence, about 25 base pairs of the tat sequence, and about 769 base pairs of the Env sequence of wild-type HIV. In some embodiments, the lentiviral vector further includes a locus control region. In some embodiments, the lentiviral vector further includes a self-inactivating long terminal repeat. Creation of a SIN LTR is achieved by inactivating the U3 region of the 3' LTR (preferably by deletion of a portion thereof, e.g. removal of a TATA sequence). The alteration is transferred to the 5' LTR after reverse transcription, thus eliminating the transcriptional unit of the LTRs in the provirus, which is believed to prevent mobilization by replication competent virus. An additional safety enhancement is provided by replacing the U3 region of the 5' LTR with a heterologous promoter to drive transcription of the viral genome during production of viral particles. In some embodiments, the lentiviral expression vector has at least 80%, at least 85%, at least 90%, at least 95%, at least 97%, at least 98%, or at least 99% sequence identity to one of SEQ ID NOS: 5-22. In some embodiments, the RNAi is an shRNA.

Figure 6:
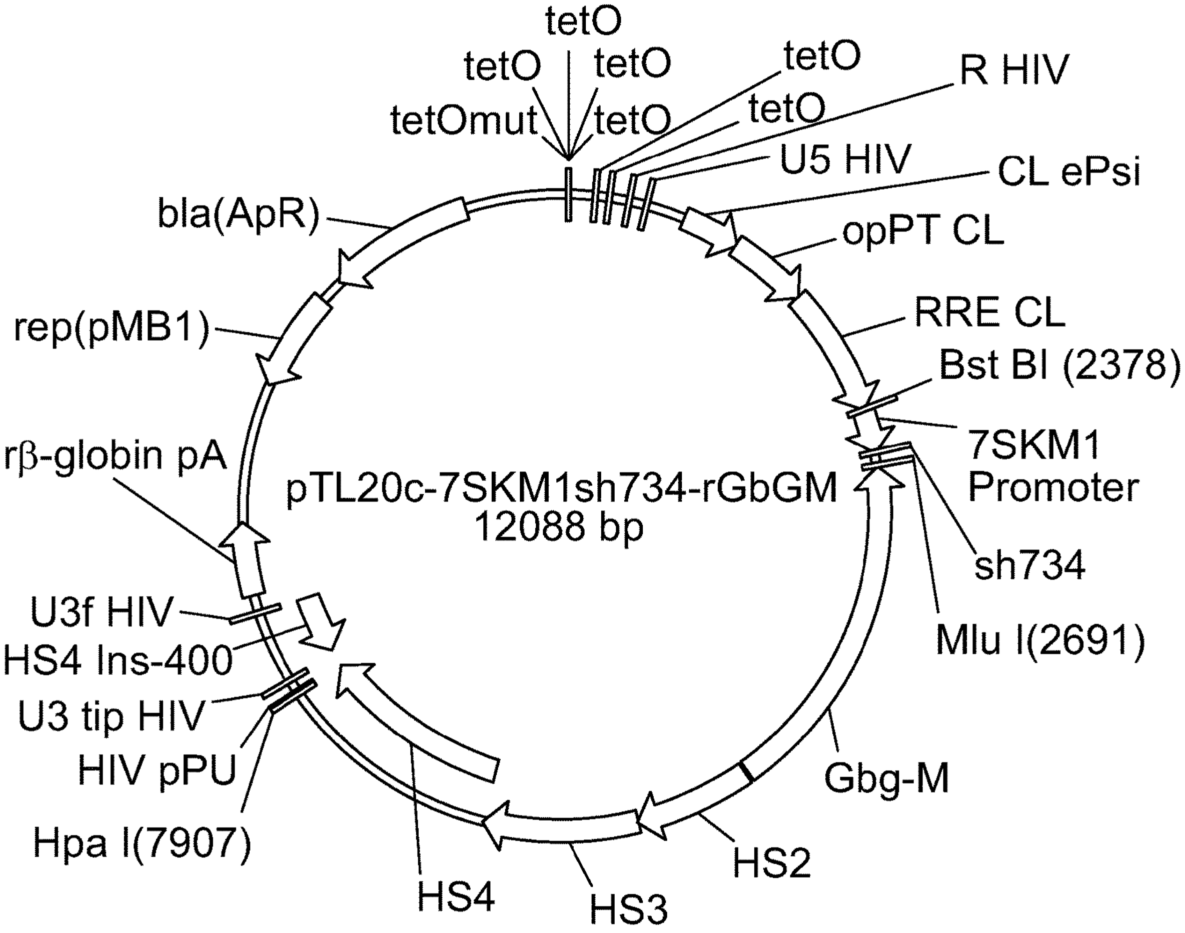
FIG. 6 provides a vector map of TL20c-7SK$^{M1}$/sh734-rGbG$^{M}$.

In some embodiments, the vector has a nucleic acid sequence having at least 90% sequence identity to that of SEQ ID NO: 5 (TL20c-7skM1/sh734-rGbGM). In other embodiments, the vector has a nucleic acid sequence having at least 95% sequence identity to that of SEQ ID NO: 5. In yet other embodiments, the vector has a nucleic acid sequence having at least 98% sequence identity to that of SEQ ID NO: 5. In further other embodiments, the vector has the nucleic acid sequence of SEQ ID NO: 5 (see also FIG. 6).

Figure 7:
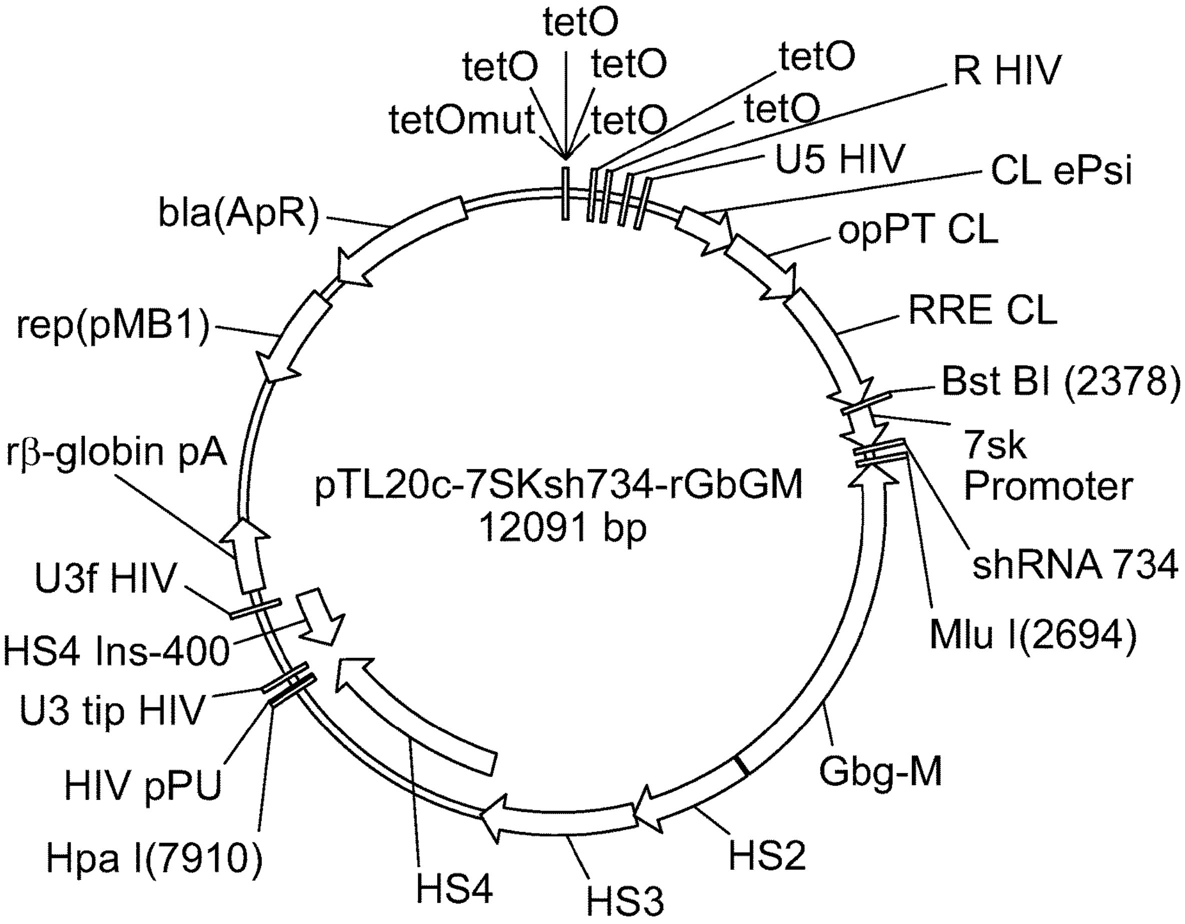
FIG. 7 provides a vector map of TL20c-7SK/sh734-rGbG$^{M}$.

In some embodiments, the vector has a nucleic acid sequence having at least 90% sequence identity to that of SEQ ID NO: 6 (TL20c-7sk/sh734-rGbGM). In other embodiments, the vector has a nucleic acid sequence having at least 95% sequence identity to that of SEQ ID NO: 6. In yet other embodiments, the vector has a nucleic acid sequence having at least 98% sequence identity to that of SEQ ID NO: 6. In further other embodiments, the vector has the nucleic acid sequence of SEQ ID NO: 6 (see also FIG. 7).

Figure 8:
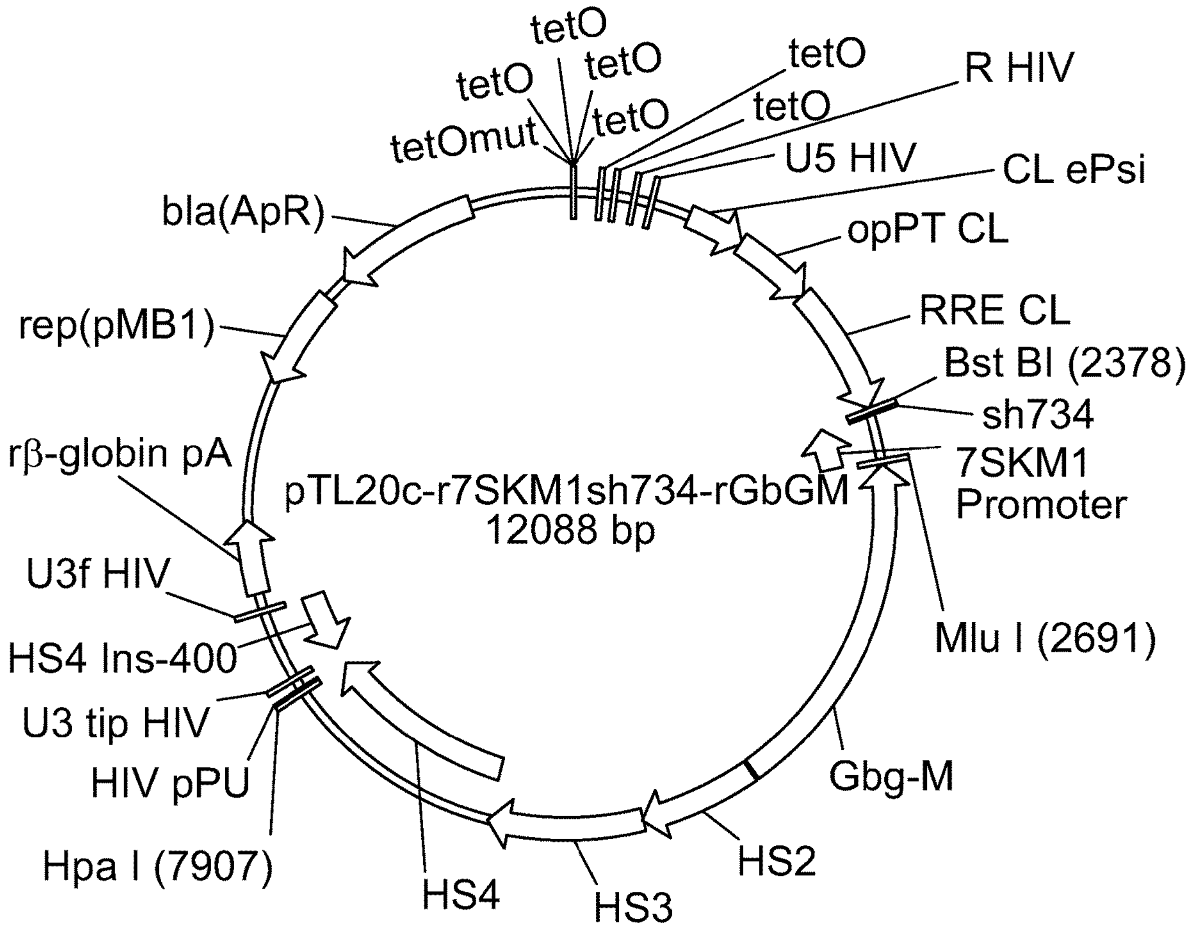
FIG. 8 provides a vector map of TL20c-r7SK$^{M1}$/sh734-rGbG$^{M}$.

In some embodiments, the vector has a nucleic acid sequence having at least 90% sequence identity to that of SEQ ID NO: 7 (TL20c-r7skM1/sh734-rGbGM). In other embodiments, the vector has a nucleic acid sequence having at least 95% sequence identity to that of SEQ ID NO: 7. In yet other embodiments, the vector has a nucleic acid sequence having at least 98% sequence identity to that of SEQ ID NO: 7. In further other embodiments, the vector has the nucleic acid sequence of SEQ ID NO: 7 (see also FIG. 8).

In some embodiments, the vector has a nucleic acid sequence having at least 90% sequence identity to that of SEQ ID NO: 8 (TL20c-r7sk/sh734-rGbGM). In other embodiments, the vector has a nucleic acid sequence having at least 95% sequence identity to that of SEQ ID NO: 8. In yet other embodiments, the vector has a nucleic acid sequence having at least 98% sequence identity to that of SEQ ID NO: 8. In further other embodiments, the vector has the nucleic acid sequence of SEQ ID NO: 8 (see also FIG. 9).

Figure 10:
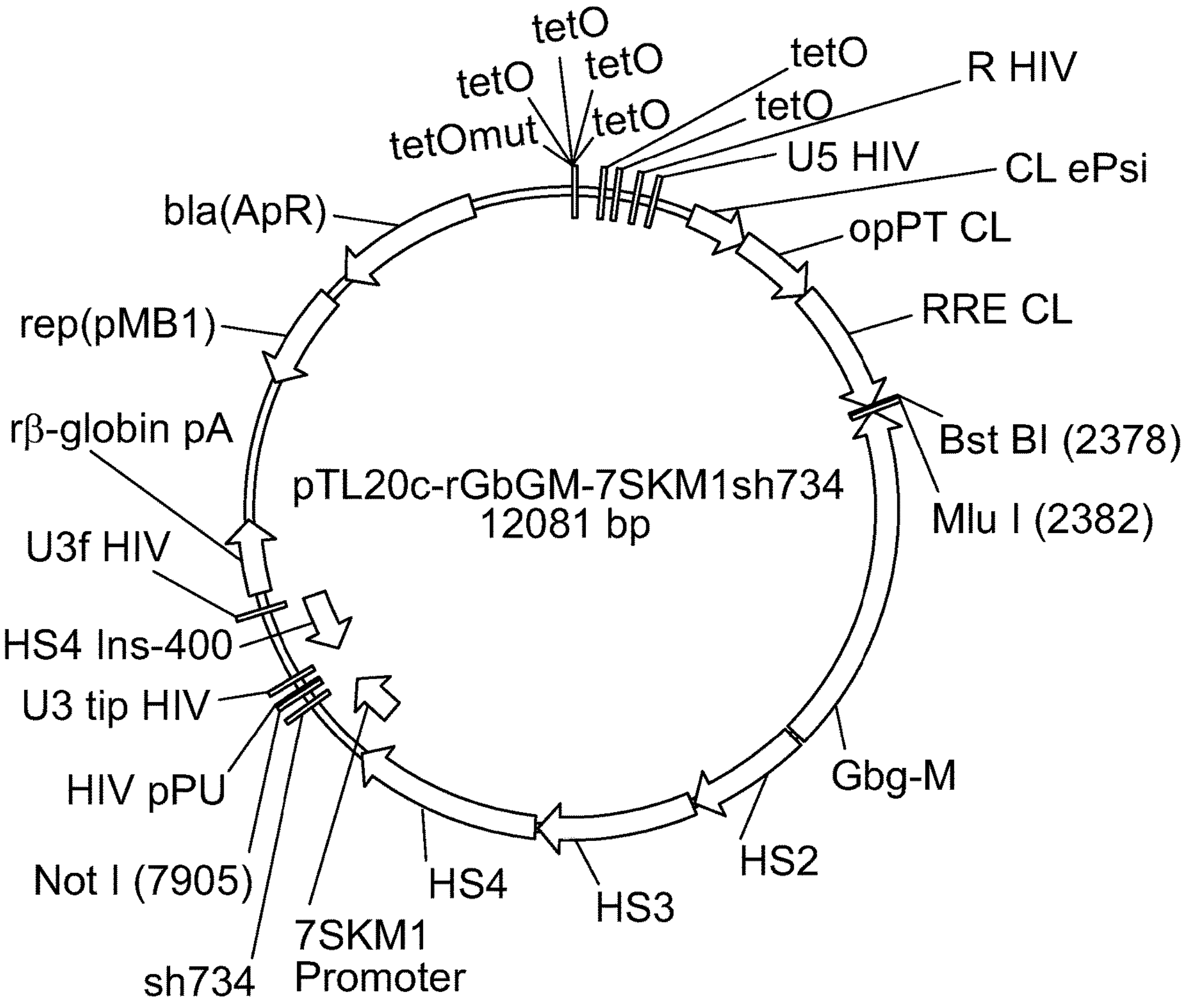
FIG. 10 provides a vector map of TL20c-rGbG$^{M}$-7SK$^{M1}$/sh734.

In some embodiments, the vector has a nucleic acid sequence having at least 90% sequence identity to that of SEQ ID NO: 9 (TL20c-rGbGM-7skM1/sh734). In other embodiments, the vector has a nucleic acid sequence having at least 95% sequence identity to that of SEQ ID NO: 9. In yet other embodiments, the vector has a nucleic acid sequence having at least 98% sequence identity to that of SEQ ID NO: 9. In further other embodiments, the vector has the nucleic acid sequence of SEQ ID NO: 9 (see also FIG. 10).

Figure 11:
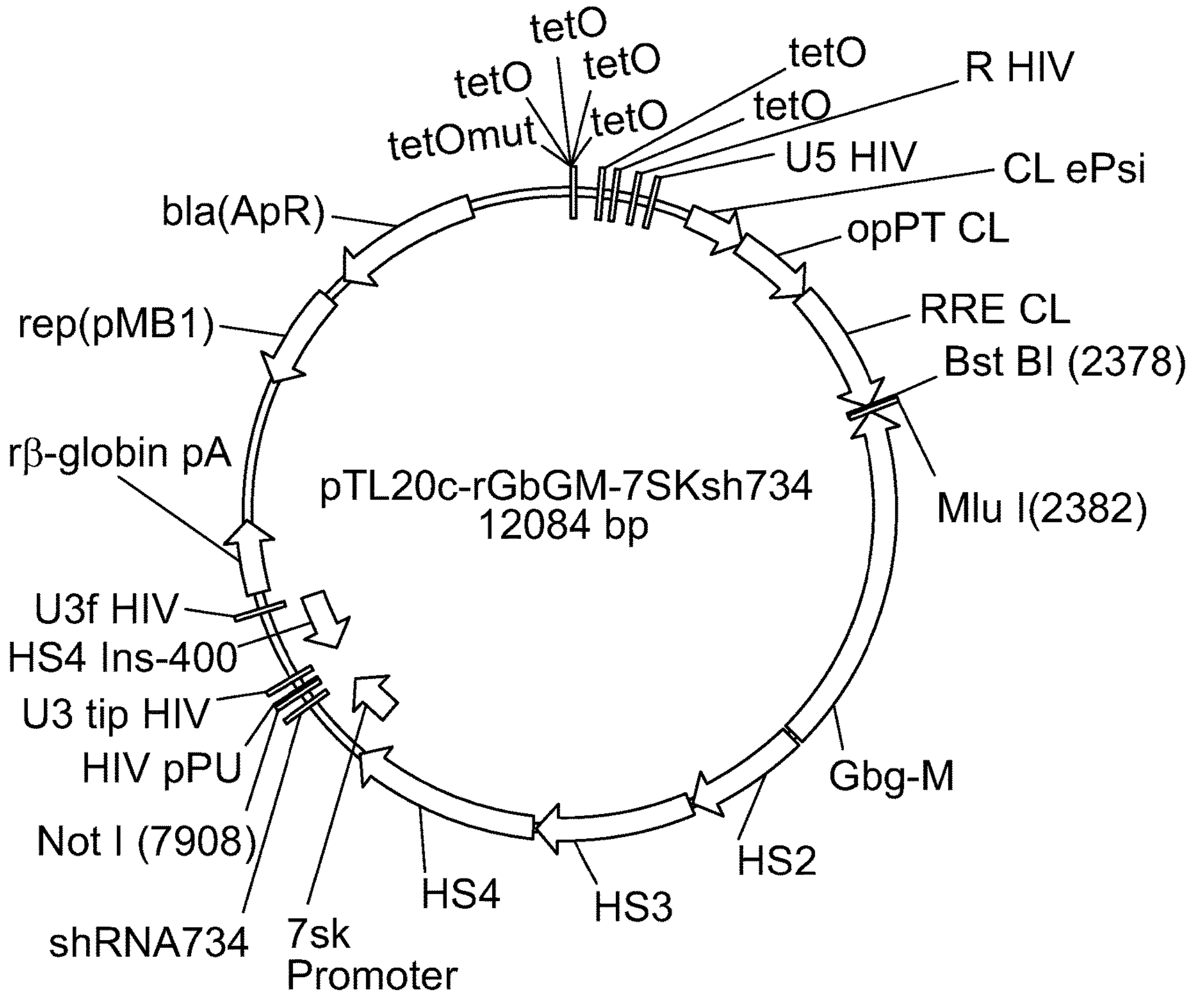
FIG. 11 provides a vector map of TL20c-rGbG$^{M}$-7SK/sh734.

In some embodiments, the vector has a nucleic acid sequence having at least 90% sequence identity to that of SEQ ID NO: 10 (TL20c-rGbGM-7sk/sh734). In other embodiments, the vector has a nucleic acid sequence having at least 95% sequence identity to that of SEQ ID NO: 10. In yet other embodiments, the vector has a nucleic acid sequence having at least 98% sequence identity to that of SEQ ID NO: 10. In further other embodiments, the vector has the nucleic acid sequence of SEQ ID NO: 10 (see also FIG. 11).

Figure 12:
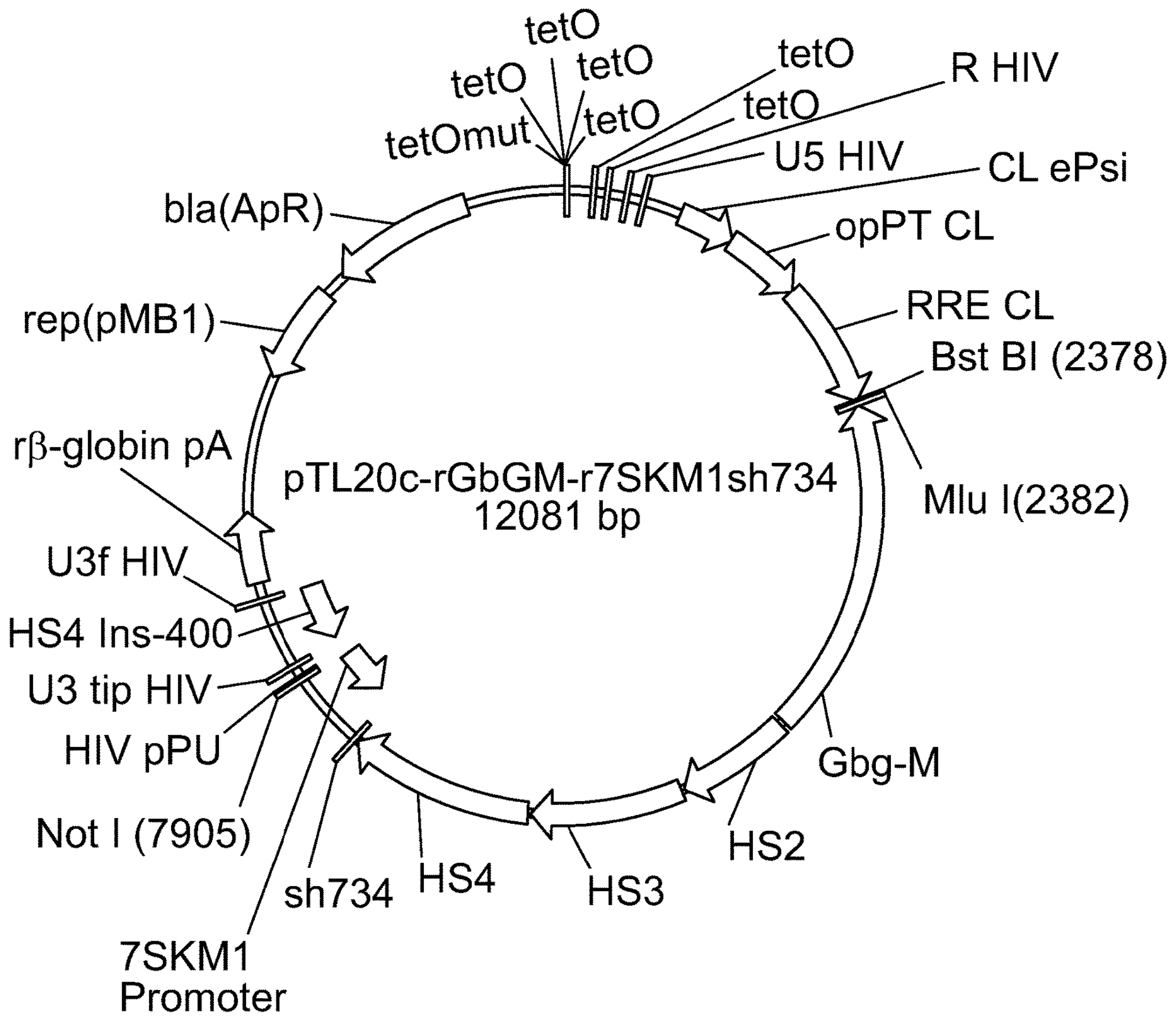
FIG. 12 provides a vector map of TL20c-rGbG$^{M}$_r7SK$^{M1}$/sh734.

In some embodiments, the vector has a nucleic acid sequence having at least 90% sequence identity to that of SEQ ID NO: 11 (TL20c-rGbGM-r7skM1/sh734). In other embodiments, the vector has a nucleic acid sequence having at least 95% sequence identity to that of SEQ ID NO: 11. In yet other embodiments, the vector has a nucleic acid sequence having at least 98% sequence identity to that of SEQ ID NO: 11. In further other embodiments, the vector has the nucleic acid sequence of SEQ ID NO: 11 (see also FIG. 12).

Figure 13:
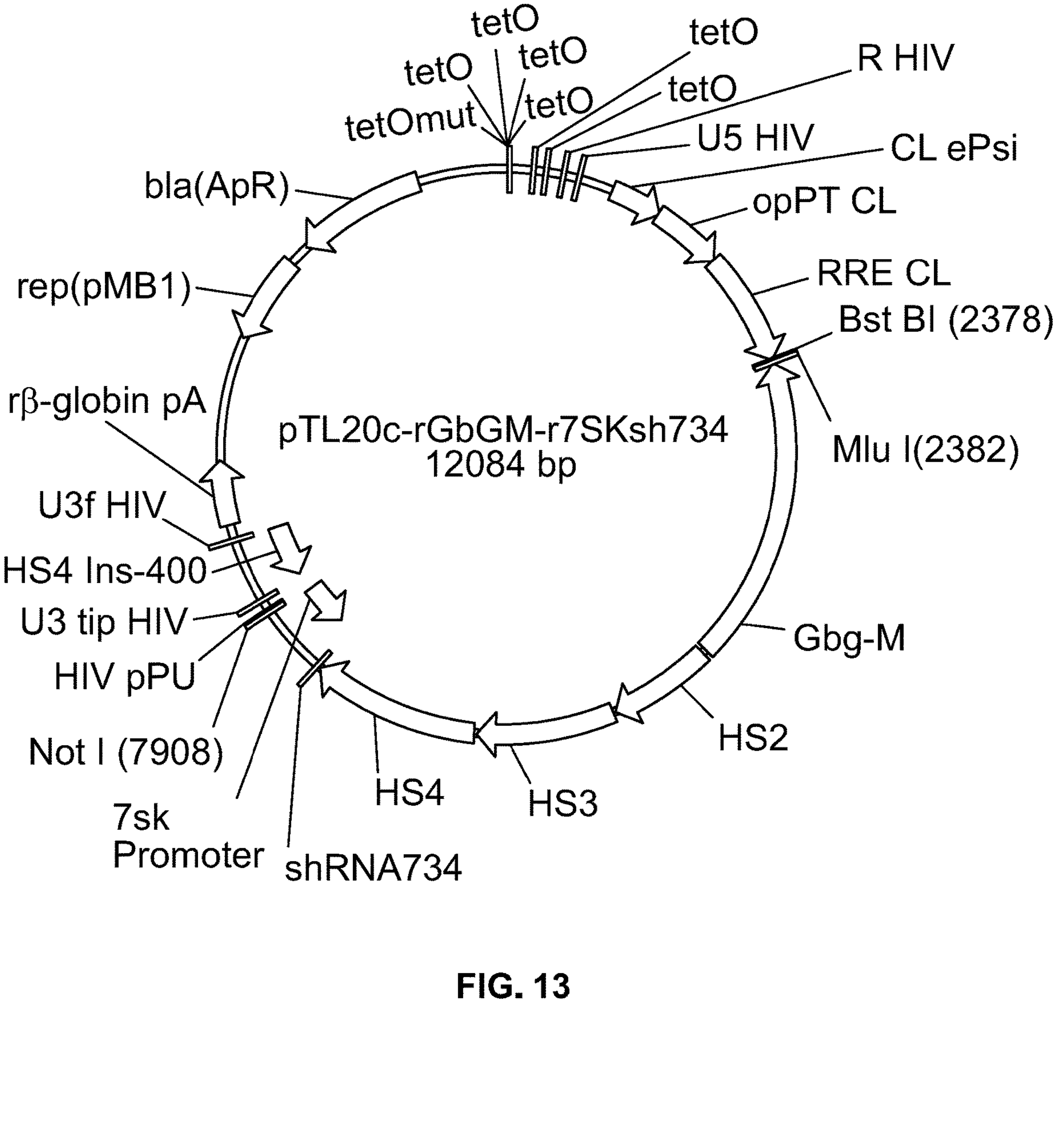
FIG. 13 provides a vector map of TL20c-rGbG$^{M}$_r7SK/sh734.

In some embodiments, the vector has a nucleic acid sequence having at least 90% sequence identity to that of SEQ ID NO: 12 (TL20c-rGbGM-r7sk/sh734). In other embodiments, the vector has a nucleic acid sequence having at least 95% sequence identity to that of SEQ ID NO: 12. In yet other embodiments, the vector has a nucleic acid sequence having at least 98% sequence identity to that of SEQ ID NO: 12. In further other embodiments, the vector has the nucleic acid sequence of SEQ ID NO: 12 (see also FIG. 13).

Figure 14:
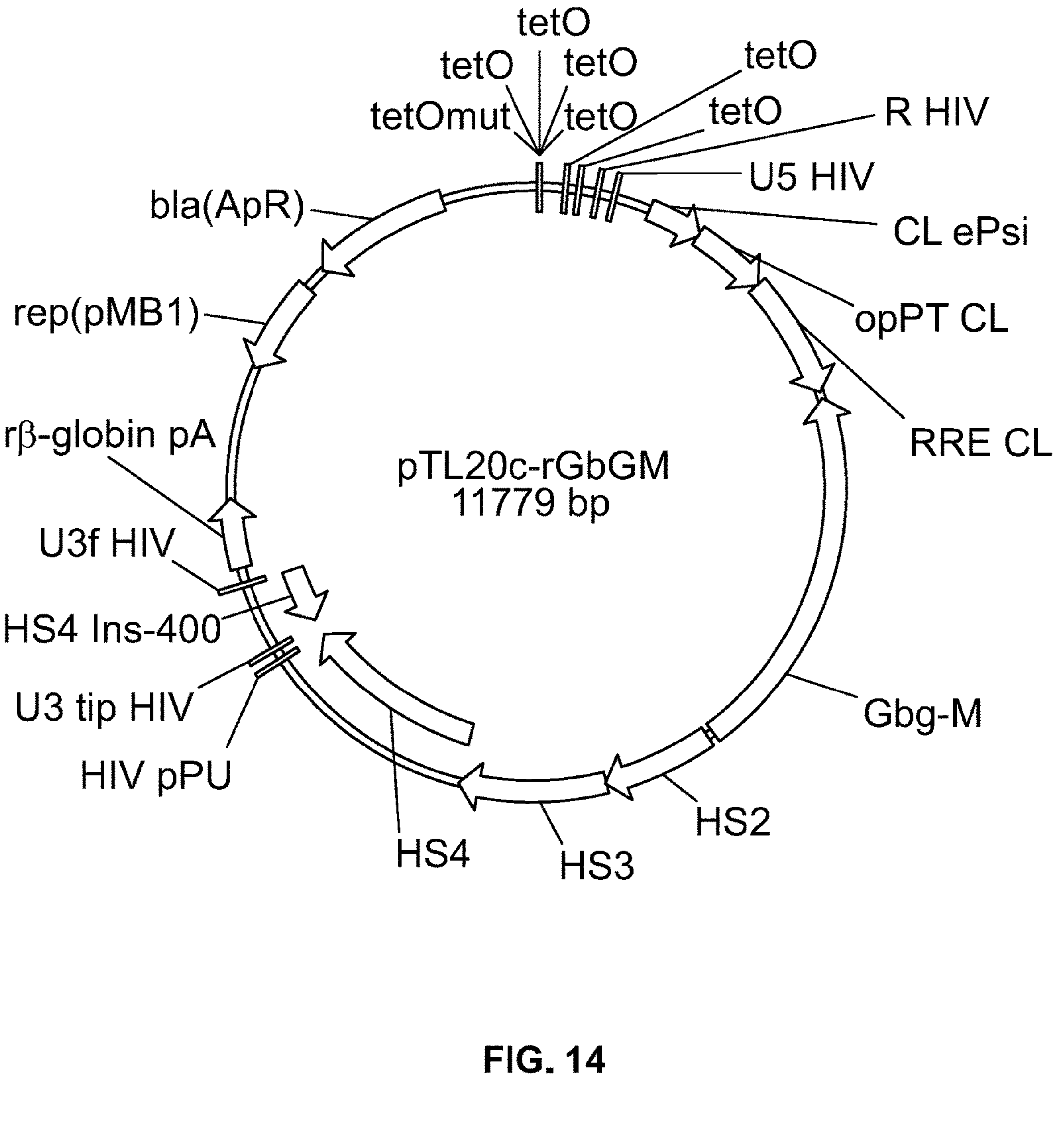
FIG. 14 provides a vector map of TL20c-rGbG$^{M}$.

In some embodiments, the vector has a nucleic acid sequence having at least 90% sequence identity to that of SEQ ID NO: 13 (TL20c-rGbGM). In other embodiments, the vector has a nucleic acid sequence having at least 95% sequence identity to that of SEQ ID NO: 13. In yet other embodiments, the vector has a nucleic acid sequence having at least 98% sequence identity to that of SEQ ID NO: 13. In further other embodiments, the vector has the nucleic acid sequence of SEQ ID NO: 13 (see also FIG. 14).

Figure 15:
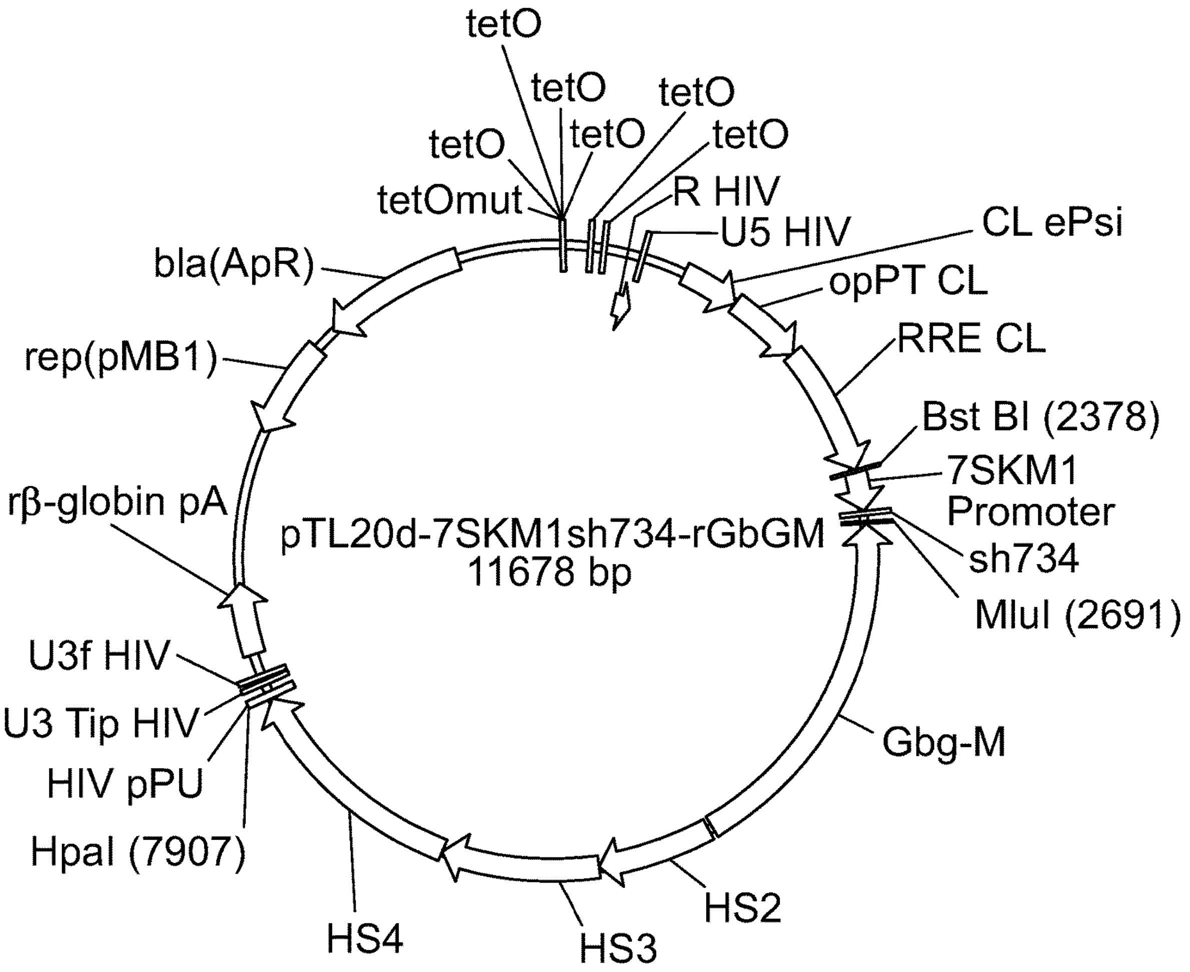
FIG. 15 provides a vector map of TL20d-7SK$^{M1}$/sh734-rGbG$^{M}$.

In some embodiments, the vector has a nucleic acid sequence having at least 90% sequence identity to that of SEQ ID NO: 14 (TL20d-7skM1/sh734-rGbGM). In other embodiments, the vector has a nucleic acid sequence having at least 95% sequence identity to that of SEQ ID NO: 14. In yet other embodiments, the vector has a nucleic acid sequence having at least 98% sequence identity to that of SEQ ID NO: 14. In further other embodiments, the vector has the nucleic acid sequence of SEQ ID NO: 14 (see also FIG. 15).

Figure 16:
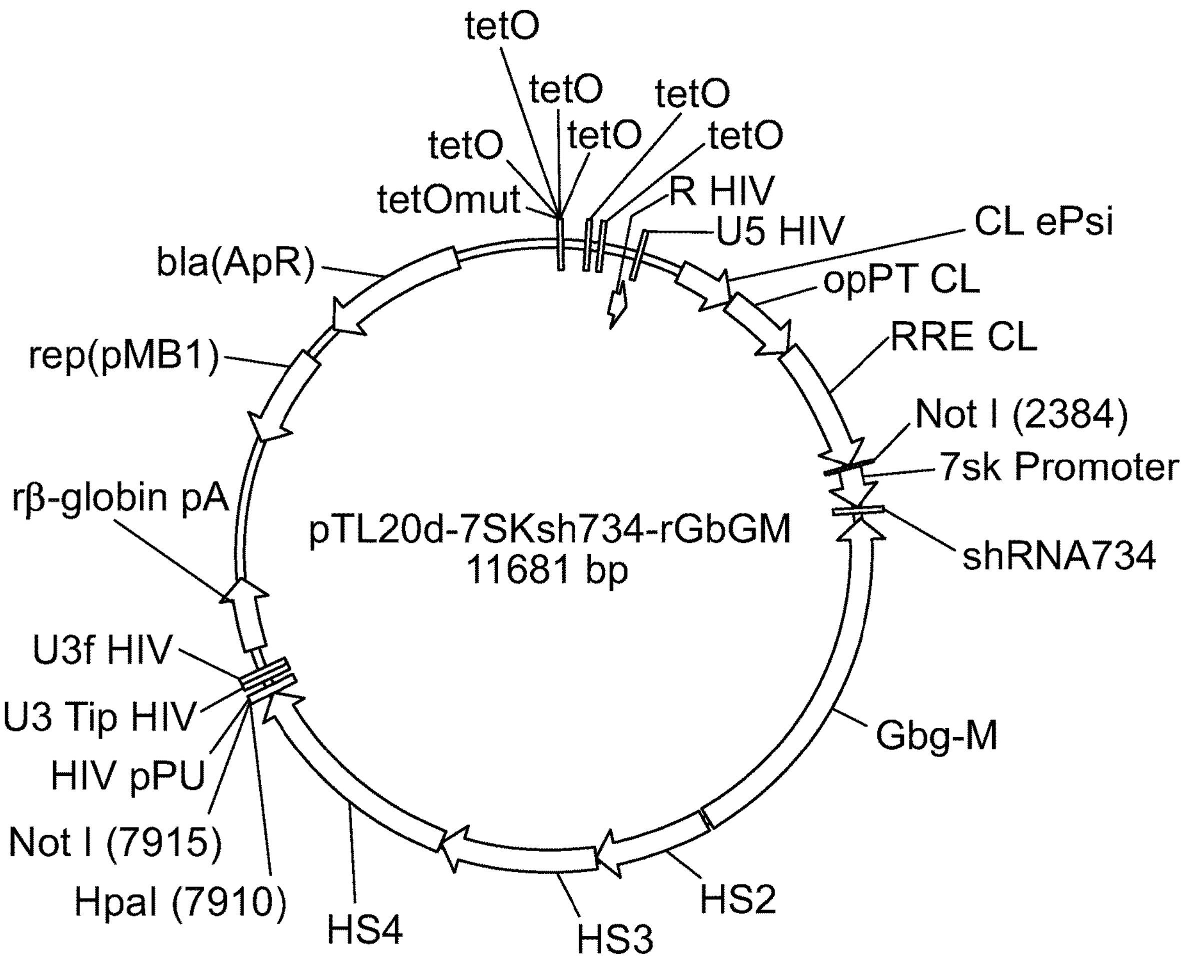
FIG. 16 provides a vector map of TL20d-7SK/sh734-rGbG$^{M}$.

In some embodiments, the vector has a nucleic acid sequence having at least 90% sequence identity to that of SEQ ID NO: 15 (TL20d-7sk/sh734-rGbGM). In other embodiments, the vector has a nucleic acid sequence having at least 95% sequence identity to that of SEQ ID NO: 15. In yet other embodiments, the vector has a nucleic acid sequence having at least 98% sequence identity to that of SEQ ID NO: 15. In further other embodiments, the vector has the nucleic acid sequence of SEQ ID NO: 15 (see also FIG. 16

Figure 17:
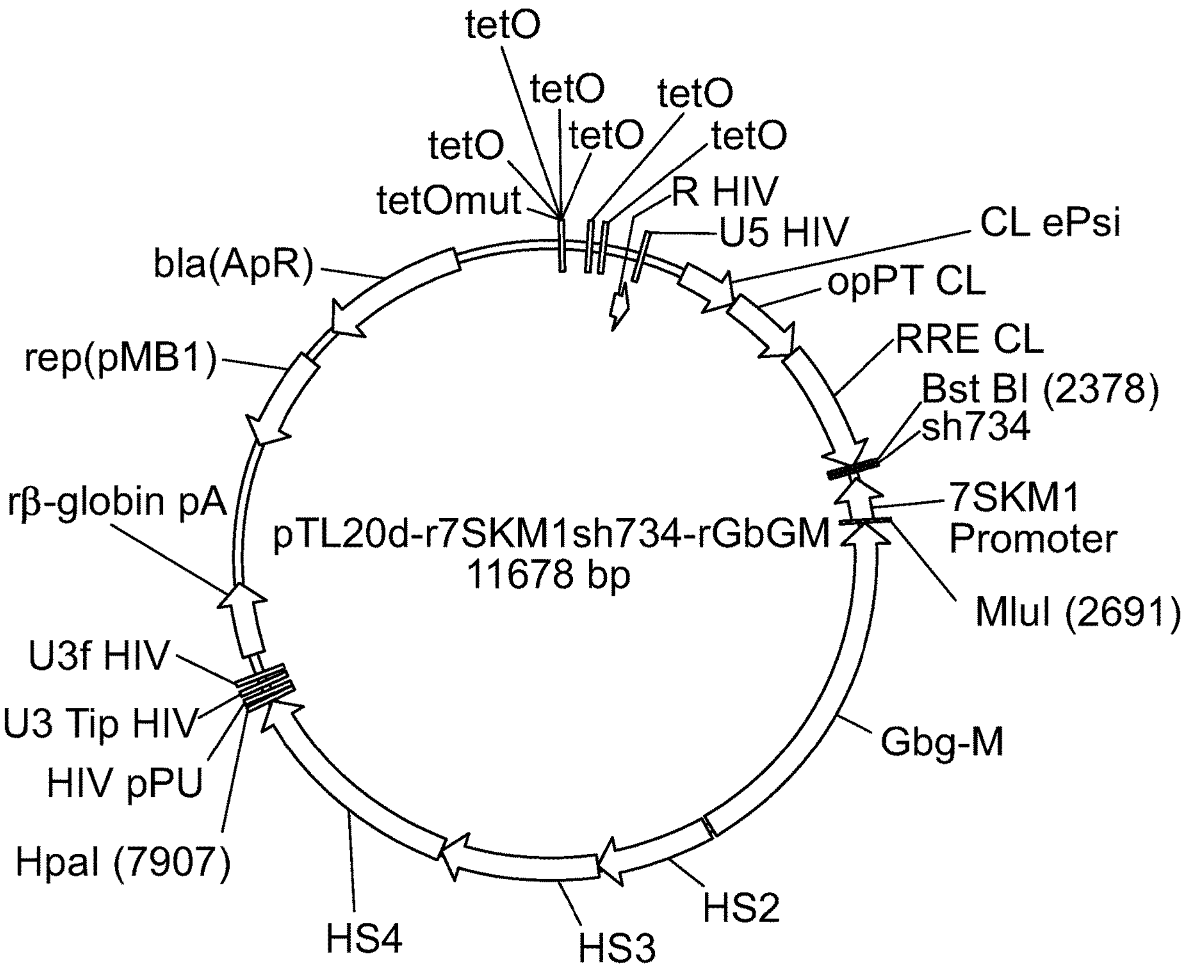
FIG. 17 provides a vector map of TL20d-r7SK$^{M1}$/sh734-rGbG$^{M}$.

In some embodiments, the vector has a nucleic acid sequence having at least 90% sequence identity to that of SEQ ID NO: 16 (TL20d-r7skM1/sh734-rGbGM). In other embodiments, the vector has a nucleic acid sequence having at least 95% sequence identity to that of SEQ ID NO: 16. In yet other embodiments, the vector has a nucleic acid sequence having at least 98% sequence identity to that of SEQ ID NO: 16. In further other embodiments, the vector has the nucleic acid sequence of SEQ ID NO: 16 (see also FIG. 17).

Figure 18:
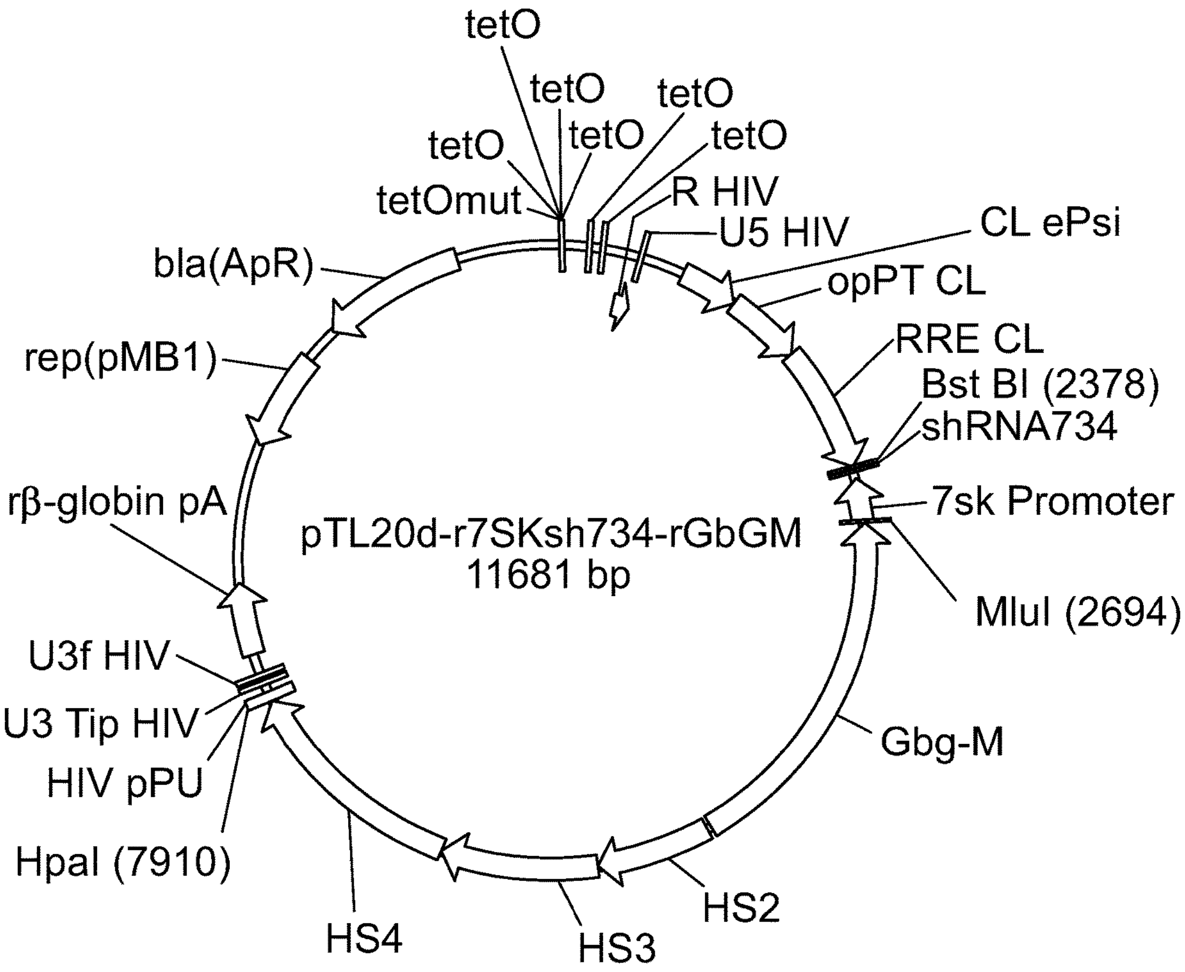
FIG. 18 provides a vector map of TL20d-r7SK/sh734-rGbG$^{M}$.

In some embodiments, the vector has a nucleic acid sequence having at least 90% sequence identity to that of SEQ ID NO: 17 (TL20d-r7sk/sh734-rGbGM). In other embodiments, the vector has a nucleic acid sequence having at least 95% sequence identity to that of SEQ ID NO: 17. In yet other embodiments, the vector has a nucleic acid sequence having at least 98% sequence identity to that of SEQ ID NO: 17. In further other embodiments, the vector has the nucleic acid sequence of SEQ ID NO: 17 (see also FIG. 18).

Figure 19:
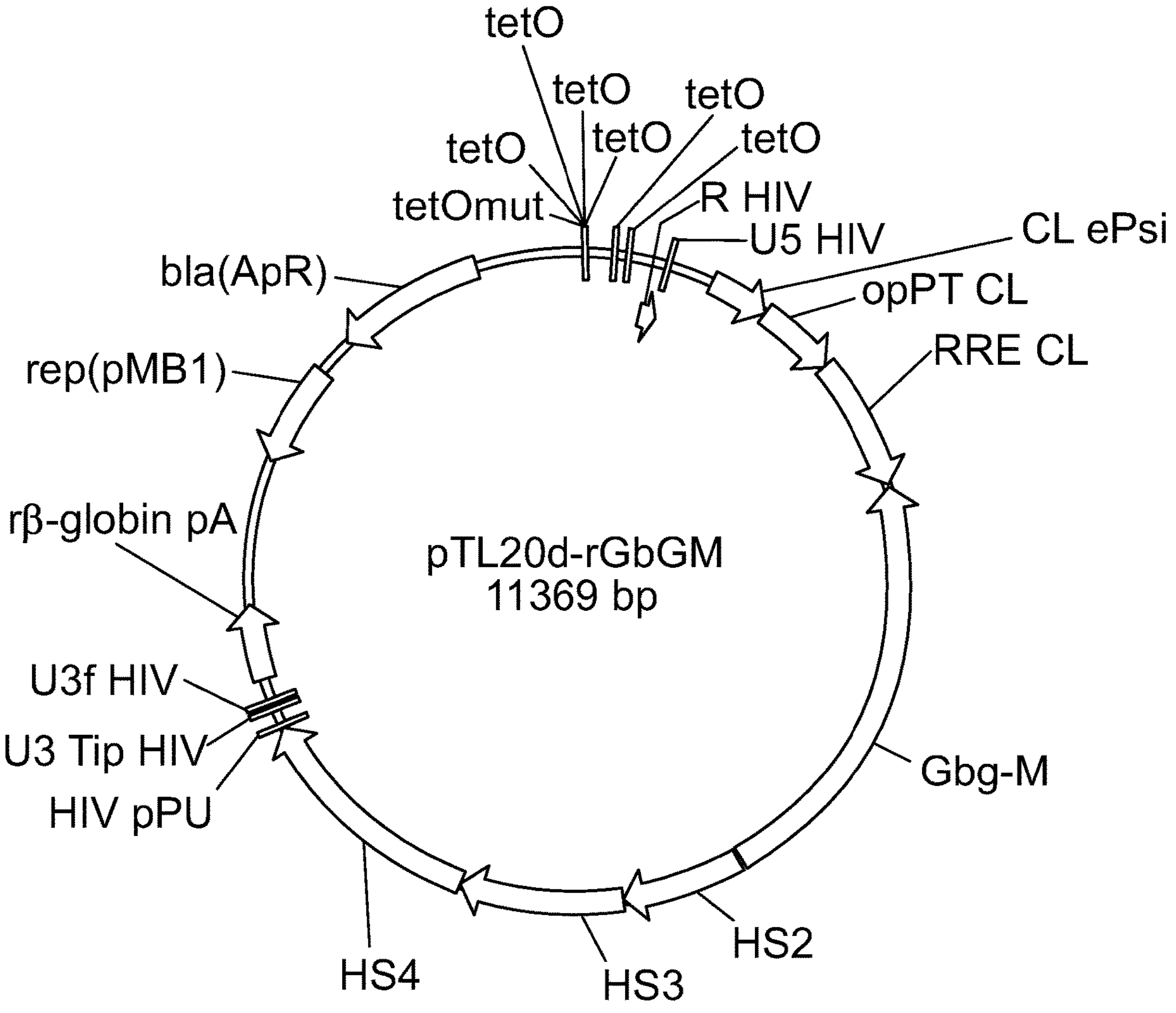
FIG. 19 provides a vector map of TL20d-rGbG$^{M}$.

In some embodiments, the vector has a nucleic acid sequence having at least 90% sequence identity to that of SEQ ID NO: 18 (TL20d-GbGM). In other embodiments, the vector has a nucleic acid sequence having at least 95% sequence identity to that of SEQ ID NO: 18. In yet other embodiments, the vector has a nucleic acid sequence having at least 98% sequence identity to that of SEQ ID NO: 18. In further other embodiments, the vector has the nucleic acid sequence of SEQ ID NO: 18 (see also FIG. 19).

Figure 20:
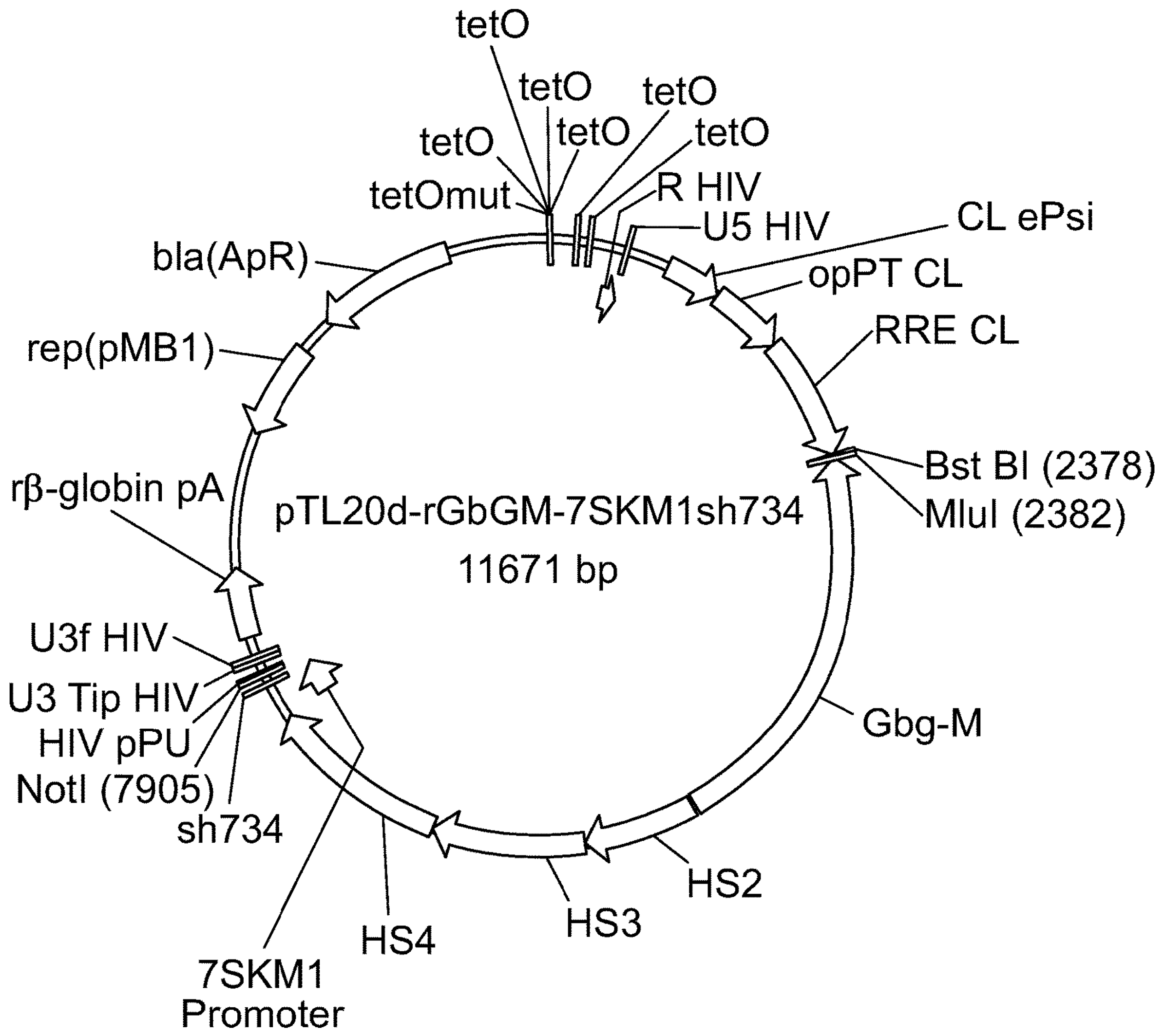
FIG. 20 provides a vector map of TL20d-rGbG$^{M}$-7SK$^{M1}$/sh734.

In some embodiments, the vector has a nucleic acid sequence having at least 90% sequence identity to that of SEQ ID NO: 19 (TL20d-rGbGM-7skM1/sh734). In other embodiments, the vector has a nucleic acid sequence having at least 95% sequence identity to that of SEQ ID NO: 19. In yet other embodiments, the vector has a nucleic acid sequence having at least 98% sequence identity to that of SEQ ID NO: 19. In further other embodiments, the vector has the nucleic acid sequence of SEQ ID NO: 19 (see also FIG. 20).

Figure 21:
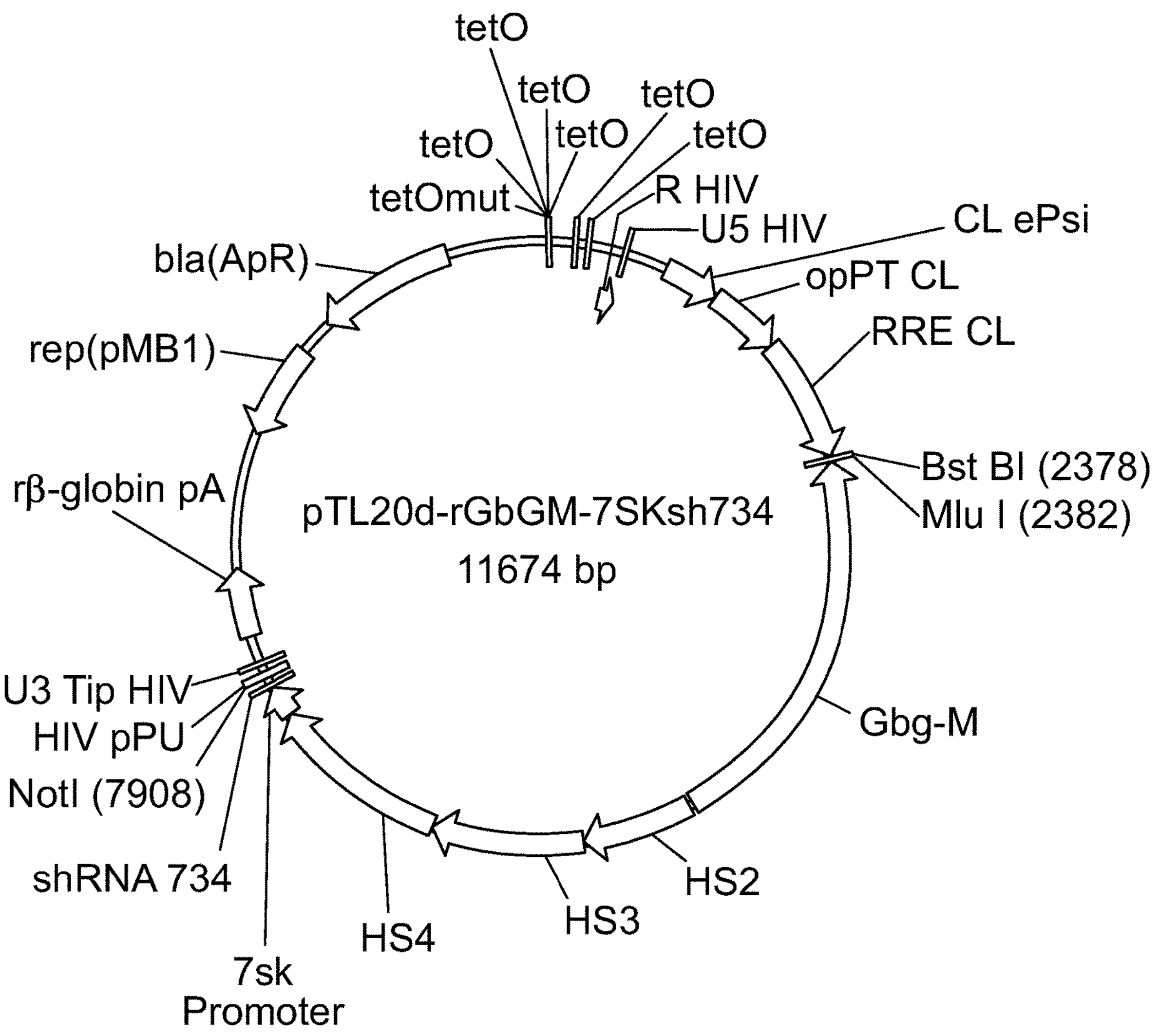
FIG. 21 provides a vector map of TL20d-GbG$^{M}$-7SK/sh734.

In some embodiments, the vector has a nucleic acid sequence having at least 90% sequence identity to that of SEQ ID NO: 20 (TL20d-GbGM-7sk/sh734). In other embodiments, the vector has a nucleic acid sequence having at least 95% sequence identity to that of SEQ ID NO: 20. In yet other embodiments, the vector has a nucleic acid sequence having at least 98% sequence identity to that of SEQ ID NO: 20. In further other embodiments, the vector has the nucleic acid sequence of SEQ ID NO: 20 (see also FIG. 21).

Figure 22:
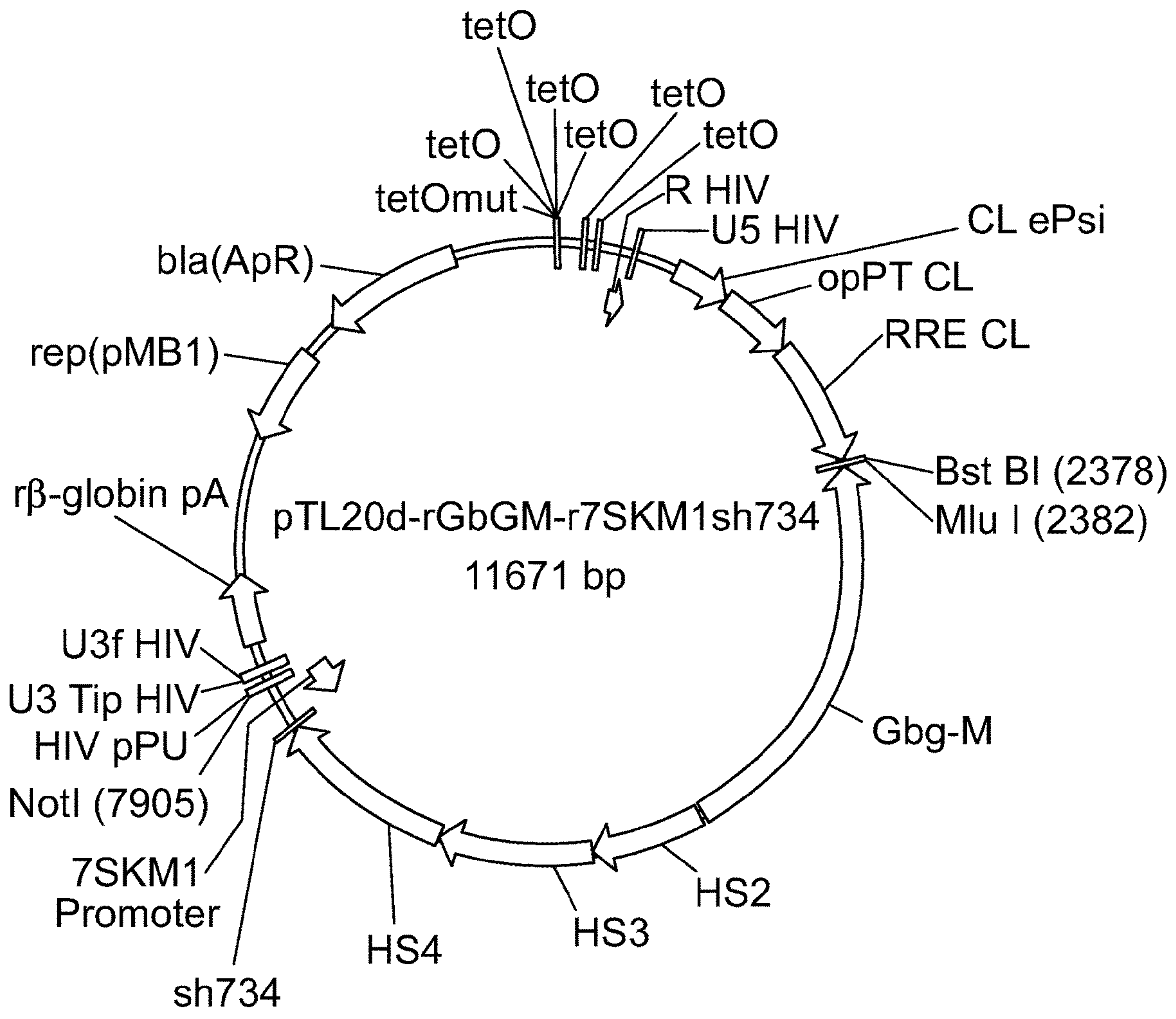
FIG. 22 provides a vector map of TL20d-rGbG$^{M}$_r7SK$^{M1}$/sh734.

In some embodiments, the vector has a nucleic acid sequence having at least 90% sequence identity to that of SEQ ID NO: 21 (TL20d-rGbGM-r7skM1/sh734). In other embodiments, the vector has a nucleic acid sequence having at least 95% sequence identity to that of SEQ ID NO: 21. In yet other embodiments, the vector has a nucleic acid sequence having at least 98% sequence identity to that of SEQ ID NO: 21. In further other embodiments, the vector has the nucleic acid sequence of SEQ ID NO: 21 (see also FIG. 22).

Figure 23:
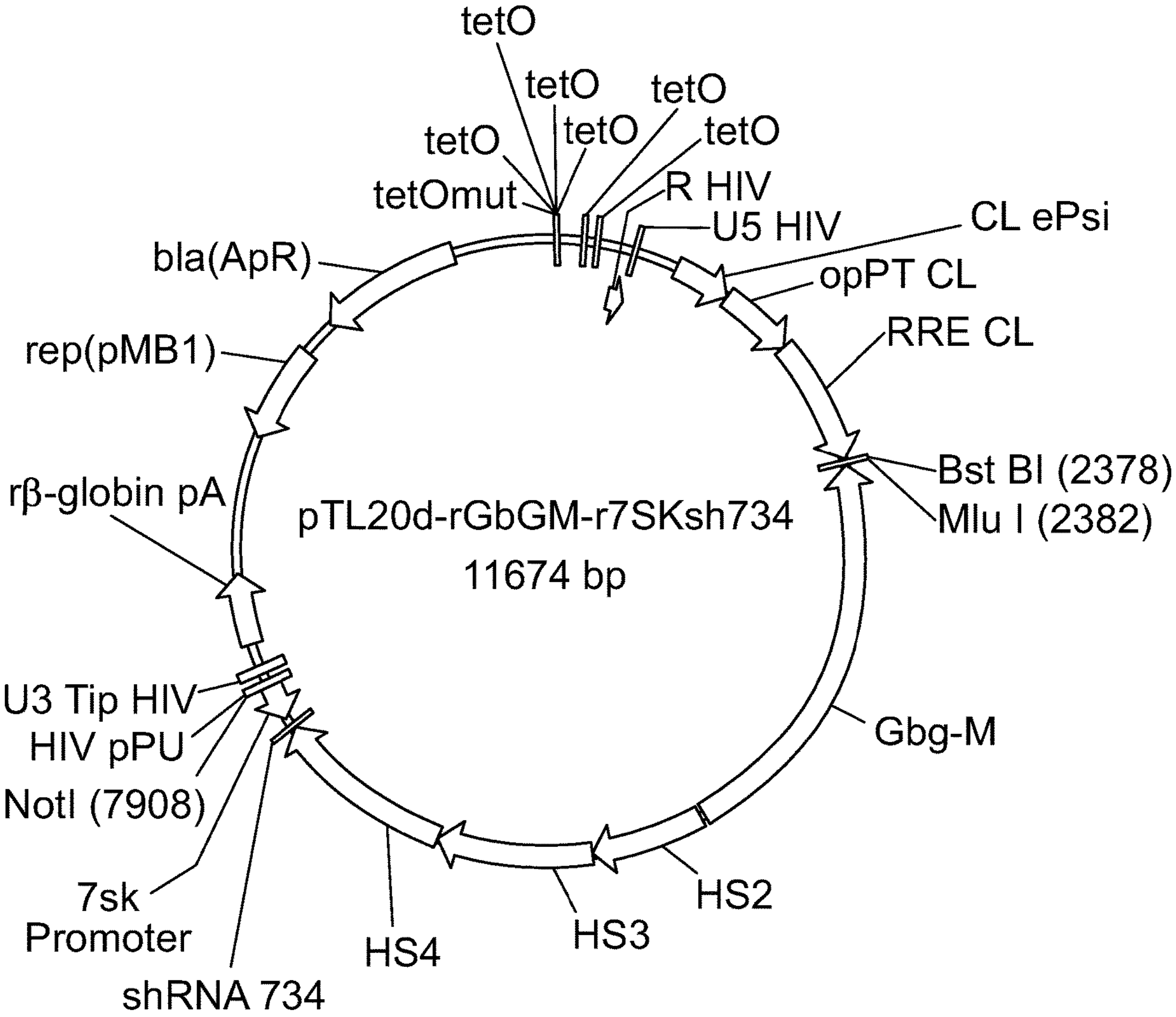
FIG. 23 provides a vector map of TL20d-rGbG$^{M}$_r7SK/sh734.

In some embodiments, the vector has a nucleic acid sequence having at least 90% sequence identity to that of SEQ ID NO: 22 (TL20d-rGbGM-r7sk/sh734). In other embodiments, the vector has a nucleic acid sequence having at least 95% sequence identity to that of SEQ ID NO: 22. In yet other embodiments, the vector has a nucleic acid sequence having at least 98% sequence identity to that of SEQ ID NO: 22. In further other embodiments, the vector has the nucleic acid sequence of SEQ ID NO: 22 (see also FIG. 23).

Production of Vectors

Figure 40A:
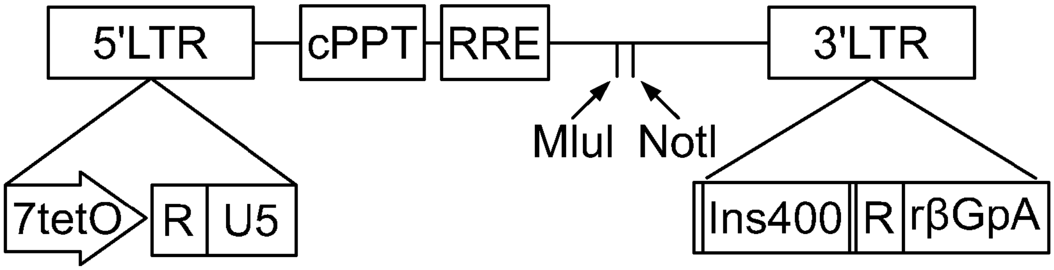
FIG. 40A provides a schematic representation of the components of the pTL20c vector.
Figure 40B:
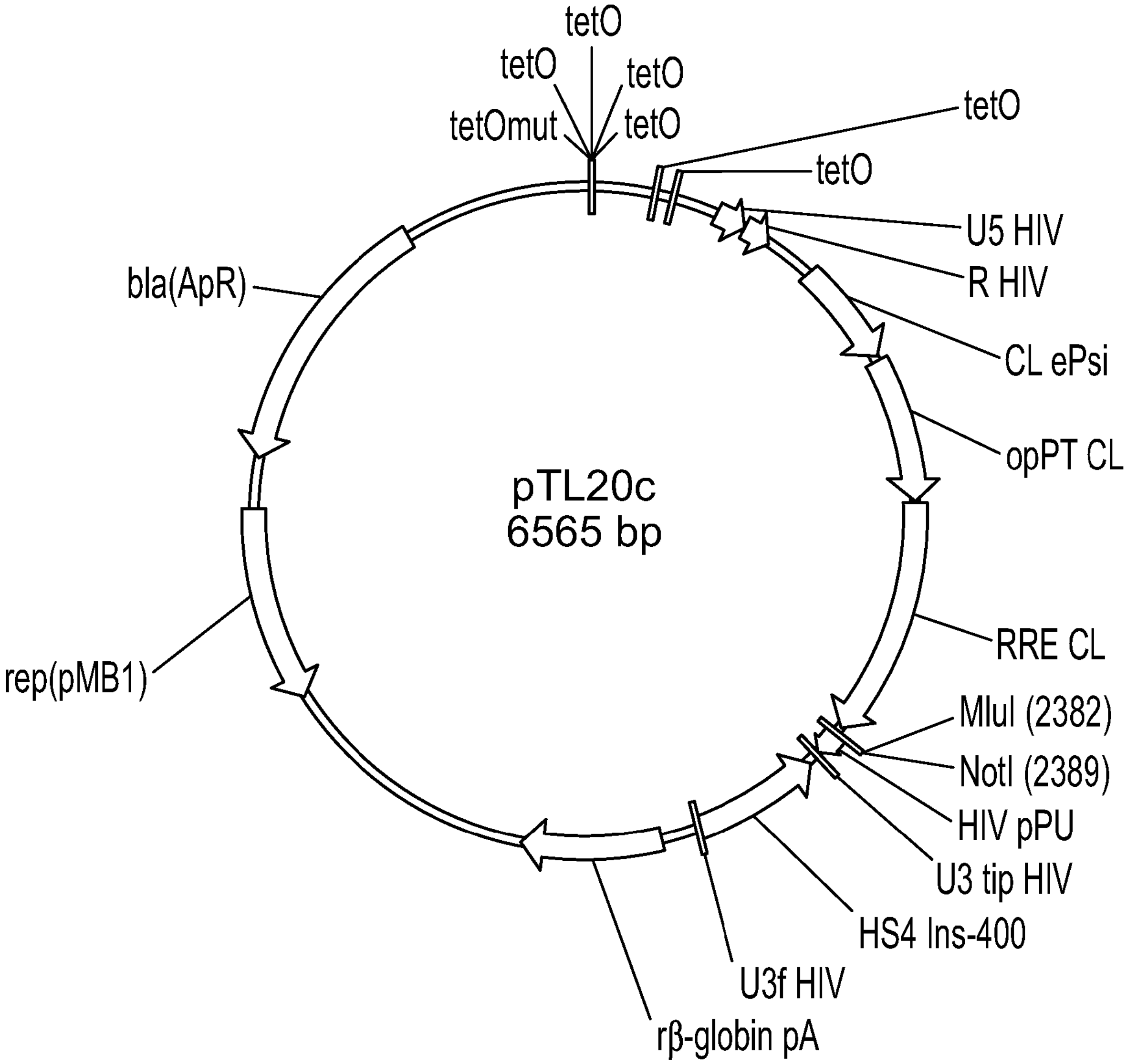
FIG. 40B illustrates a vector map for the pTL20c vector.

In some embodiments, an expression cassette, such as one having a particular transgene for expression, is inserted into expression vector, such as a lentiviral expression vector, to provide for a vector having at least one transgene for expression. For example, an expression cassette having a transgene for expression may be inserted into a pTL20c vector (SEQ ID NO: 47) (FIGS. 40A and 40B) or a pTL20d vector (i.e. PTL20c, but lacking the CHS4 insulator (SEQ ID NO: 49)) according to the methods described in in United States Patent Publication No. 2018/0112233, the disclosure of which is hereby incorporated by reference herein in its entirety. An example of inserting an expression cassette into the pTL20c vector is described at Example 1 herein.

Following insertion of the expression cassette into the expression vector, a second expression cassette is inserted into the vector having the at least one transgene for expression. For example, an expression cassette including a nucleic acid sequence to knockdown HPRT or otherwise decrease its expression may be inserted into the vector having the at least one transgene for expression. An example of inserting an expression cassette including an anti-HPRT shRNA into the vector having the at least one transgene for expression is described at Example 1 herein.

Non-Viral Delivery of Agents to Downregulate HPRT and/or to Introduce a Transgene In some embodiments, agents designed to knockdown the HPRT gene (including expression constructions including an RNAi) may be delivered through a nanocapsule other non-viral delivery vehicle. Delivery of such an agent through this method represents an alternative to effectuating downregulation of HPRT by means of an expressed RNAi or other agent from an expression vector. As described further herein, it is possible to deliver antisense RNA, oligonucleotides designed for exon skipping, or gene editing machinery by means of nanocapsules.

In general, a nanocapsule is a vesicular system that exhibits a typical core-shell structure in which active molecules are confined to a reservoir or cavity that is surrounded by a polymer membrane or coating. In some embodiments, the shell of a typical nanocapsule is made of a polymeric membrane or coating. In some embodiments, the nanocapsules are derived from a biodegradable or bioerodable polymeric material.

In some embodiments, the nanocapsule is an enzymatically degradable nanocapsule. In some embodiments, the nanocapsule consists of a single-protein core and a thin polymeric shell cross-linked by peptides. In some embodiments, a nanocapsule may be selected such that it is specifically recognizable and able to be cleaved by a protease. In some embodiments, the cleavable cross-linkers include a peptide sequence or structure that is a substrate of a protease or another enzyme.

Suitable nanocapsules includes those described in U.S. Pat. No. 9,782,357; those described in United States Patent Application Publication Nos. 2017/0354613, 2015/0071999 and 2015/035975; and those described in PCT Publication Nos. WO2016/085808, WO2017/06380, and WO2017/205541, the disclosures of which are hereby incorporated by reference herein in their entireties. Other suitable nanocapsules, their methods of synthesis, and/or methods of encapsulation, are further disclosed in United States Patent Publication No. 2011/0274682, the disclosure of which is hereby incorporated by reference herein in its entirety. Yet other suitable nanocapsules for the incorporation and delivery of agents designed to decrease expression of the HPRT gene are described in PCT Publication Nos. WO2013/138783, WO2013/033717, and WO2014/093966, the disclosures of which are hereby incorporated by reference herein in their entireties.

In some embodiments, the nanocapsules are adapted to target specific cell types (e.g. T cells, CD34 hematopoietic stem cells and progenitor cells) in vivo. For example, the nanocapsules may include one or more targeting moieties coupled to a polymer nanocapsule. In some embodiments, the targeting moiety delivers the polymer nanocapsules to a specific cell type, wherein the cell type is selected from the group comprising immune cells, blood cells, cardiac cells, lung cells, optic cells, liver cells, kidney cells, brain cells, cells of the central nervous system, cells of the peripheral nervous system, cancer cells, cells infected with viruses, stem cells, skin cells, intestinal cells, and/or auditory cells. In some embodiments, the targeting moieties are antibodies. Suitable payloads for such nanocapsules include synthetic oligonucleotides, shRNAs, miRNAs, and Ago-shRNAs targeting HPRT. In some embodiments, the payloads may be expressed in Pol III or Pol II driven promoter cassettes.

In other embodiments, agents for downregulating HPRT may be formulated within bio-nanocapsules, which are nano-size capsules produced by a genetically engineered microorganism. In some embodiments, a bio-nanocapsule is a virus protein-derived or modified virus protein-derived particle, such as a virus surface antigen particle (e.g., a hepatitis B virus surface antigen (HBsAg) particle). In other embodiments, a bio-nanocapsule is a nano-size capsule comprising a lipid bilayer membrane and a virus protein-derived or modified virus protein-derived particle such as a virus surface antigen particle. Such particles can be purified from eukaryotic cells, such as yeasts, insect cells, and mammalian cells. The size of a capsule may range from between about 10 nm to about. 500 nm. In other embodiments, the size of the capsule may range from between about 20 nm to about 250 nm. In yet other embodiments, the size of the capsule may range from between about 80 nm to about 150.

In some embodiments, a nanocapsule formulation is provided that both "corrects" a gene by "fixing" the original genetic mutation (such as by employing genome editing/engineering) and simultaneously delivering and inserting a transcription cassette encoding a mechanism to knock-down HPRT.

Antisense RNA

Antisense RNA (asRNA) is a single-stranded RNA that is complementary to a messenger RNA (mRNA) strand transcribed within a cell. Without wising to be bound by any particular theory, it is believed that antisense RNA may be introduced into a cell to inhibit translation of a complementary mRNA by base pairing to it and physically obstructing the translation machinery. Said another way, antisense RNAs are single-stranded RNA molecules that exhibit a complementary relationship to specific mRNAs.

Antisense RNAs may be utilized for gene regulation and specifically target mRNA molecules that are used for protein synthesis. The antisense RNA can physically pair and bind to the complementary mRNA, thus inhibiting the ability of the mRNA to be processed in the translation machinery. In addition to siRNA/shRNA LV delivered constructs, phosphorothioate-modified antisense oligonucleotides may be utilized to target sequences within the coding region of HPRT mRNA (see FIG. 37). These oligonucleotides can be delivered to specific cell populations and anatomic sites cells using targeted nanoparticles, as described above.

Exon Skipping

As noted herein, exon skipping may be utilized to create a defect within the HPRT gene that results in HPRT deficiency. In some embodiments, an oligonucleotide (including a modified oligonucleotide) may be delivered by means of a nanocapsule, the oligonucleotide designed to target unspliced HPRT mRNA and mediate either premature termination or skipping of an intron required for activity. An HPRT duplication mutation, e.g. e.g. a duplication mutation in Exon 4, (see Baba S, et al., "Novel mutation in HPRT1 causing a splicing error with multiple variations," Nucleosides Nucleotides Nucleic Acids. 2017 Jan. 2; 36(1):1-6) could be introduced to cause a splicing error and functional inactivation of the HPRT protein. Replacing HPRT with a modified mutated sequence by spliceosome trans-splicing is a potential therapeutic strategy to knockdown HPRT. It is believed that this requires (1) a mutated coding region to replace the coding sequence in target RNA, (2) a 5' or 3' splice site, and (3) a binding domain, e.g., an antisense oligonucleotide sequence, which is complementary to target RNA.

The oligonucleotides may be structurally modified such that they are nuclease resistant. In some embodiments, the oligonucleotides have modified backbones or non-natural inter-nucleoside linkages. Such oligonucleotides having modified backbones include those that retain a phosphorus atom in the backbone and those that do not have a phosphorus atom in the backbone. In some embodiments, modified oligonucleotides that do not have a phosphorus atom in their inter-nucleoside backbone can also be considered to be oligonucleotides. In other embodiments, the oligonucleotides are modified such that both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone. Modified oligonucleotides may also contain one or more substituted sugar moieties. Oligonucleotides may also include nucleobase (often referred to in the art simply as "base") modifications or substitutions. Certain nucleo-bases are particularly useful for increasing the binding affinity of the oligomeric compounds of the disclosure. These include, without limitation, 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Gene Editing Techniques

The present disclosure also provides compositions for the targeted insertion of a transgene (donor) including a protein-encoding sequence, for example a protein that is lacking or deficient in a subject with beta-thalassemia or sickle-cell disease. In certain embodiments, targeted integration of a corrective gene cassette into the genome of a cell is achieved using highly specific DNA binding proteins (e.g. meganucleases, ZFNs, TALENs, CRISPR/Cas systems). The gene cassettes integrated into the targeted gene may be carried on a viral or non-viral vector and/or may be integrated using one or more nucleases. Meganucleases are engineered versions of naturally occurring restriction enzymes that typically have extended DNA recognition sequences (e.g., 14-40 bp). ZFNs and TALENs are artificial fusion proteins composed of an engineered DNA binding domain fused to a nonspecific nuclease domain from the FokI restriction enzyme. Zinc finger and TALE repeat domains with customized specificities can be joined together into arrays that bind to extended DNA sequences.

In some embodiments, a CRISPR approach (described below) is utilized to knockout HPRT, combined with a "knock in" strategy to correct the SCD mutation or to convert an endogenous gamma globin promoter to beta-globin in order to, it is believed, prevent repression and allow the constitutive expression of fetal Hb in adult cells.

In some embodiments, a gene editing approach may be used to knockout HPRT. For example, isolated cells may be treated with a HPRT-targeted CRISPR/Cas9 RNP. A CRISPR/Cas system is designed to bind to a target site in a region of interest (e.g., a highly expressed gene, a disease associated gene or a safe harbor gene) in a genome, wherein the CRISPR/Cas system comprises a CRIPSR/Cas nuclease and an engineered crRNA/tracrRNA (or single guide RNA). In some embodiments, the CRISPR/Cas system recognizes a target in a HPRT gene. sgRNA candidates for knockdown of HPRT are shown in FIG. 38. Forward and reverse point accepted mutation ("PAM") sequences are listed including specificity and efficiency scores and HPRT chromosome coordinates targeted (where PAM refers to the replacement of a single amino acid in the primary structure of a protein with another single amino acid). In some embodiments, the Cas9 protein is complexed with guide RNA in a RNP (ribonucleoprotein) particle. In some embodiments, the particles further include a single-stranded DNA for targeted insertion in the disrupted HPRT locus.

Lesch-Nyhan syndrome is a rare genetic disorder of purine metabolism due to functional mutations in the HPRT gene. Mutations resulting in Lesch-Nyhan syndrome are highly heterogenous and provide functional targets for CRISPR/Cas9 and other gene editing approaches for ex vivo gene editing of T cells, Progenitor T cells, HSC and progenitor cells (Gasperini, M., G. M. Findlay, A. McKenna, J. H. Milbank, C. Lee, M. D. Zhang, D. A. Cusanovich, and J. Shendure. 2017. CRISPR/Cas9-Mediated Scanning for Regulatory Elements Required for HPRT1 Expression via Thousands of Large, Programmed Genomic Deletions. The American Journal of Human Genetics 101:192-205). A novel mutation has been identified in exon 4 of HPRT1 that is believed to cause aberrant splicing and loss of HPRT function. In some embodiments, the natural mutation could be exploited for reproducing the spicing error using a gene editing approach. (Baba, Shimpei Saito, Takashi Yamada, Yasukazu Takeshita, Eri Nomura, Noriko Yamada, Ken-ichiro Wakamatsu, Nobuaki Sasaki, Masayuki Nucleosides Nucleotides Nucleic Acids Nucleosides, Nucleotides & Nucleic Acids, 2017, Vol. 36(1), p. 1-6.

Nanocapsules targeting these specific cell-types can provide efficient in vivo delivery. Maeder M L et al. Genome-editing Technologies for Gene and Cell Therapy, Mol Ther. 2016 March; 24(3):430-46), describe various gene editing techniques, including CRISPR/Cas9 nuclease mediated methods, and these disclosures are hereby incorporated by reference herein in their entirety.

Other gene editing techniques using certain nucleases are described in U.S. Pat. Nos. 8,895,264, 9,616,090, 9,624,498, 9,650,648 and 9,22,105 and in PCT Application No. PCT/US12/61896, the disclosures of which are each hereby incorporated by reference herein in their entireties. In some embodiments, a zinc-finger protein (ZFP) that binds to a target site in an HPRT gene in a genome may be utilized, wherein the ZFP comprises one or more engineered zinc-finger binding domains. In some embodiments, ZFPs are used as a pair of zinc-finger nucleases (ZFNs) that dimerize and then cleave a target genomic region of interest, wherein the ZFNs comprise one or more engineered zinc-finger binding domains and a nuclease cleavage domain or cleavage half-domain. A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. In some embodiments, gene editing is performed using a fusion protein comprising a zinc finger protein that binds to an endogenous hypoxanthine-guanine HPRT gene and a cleavage domain, wherein the fusion protein modifies the endogenous HPRT gene. In some embodiments, a fusion protein comprising a ZFP may be incorporated into a nanocapsule for delivery, the ZFP binding capable of binding to a target site in a region of interest in a HPRT locus.

In some embodiments, a TALE protein (Transcription activator like effector) that binds to target site in an HPRT gene in a genome may be utilized, wherein the TALE comprises one or more engineered TALE DNA binding domains. In some embodiments, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains of ZFNs and/or TALENs can be obtained, for example, from various restriction endonucleases and/or homing endonucleases. In some embodiments, the cleavage half-domains are derived from a Type IIS restriction endonuclease (e.g., Fok I). Knockout efficiency of TAL, CRISPR/Cas9 gene editing methods and siRNA knockdown approaches resulting in loss of HPRT functional gene expression is determined by HPRT qPCR. Knockdown of HPRT expression using the miRNA211-3 g is shown in FIG. 27.

In other embodiments, a vector encoding a guide RNA targeting HPRT is utilized.

In yet other embodiments, a hybrid nuclease architecture that combines a TALE with the cleavage sequence specificity of a meganuclease cleavage domain, referred to herein as a "megaTAL." In some embodiments, the megaTAL is provided by fusing minimal TAL effector domains to the N-terminus of meganuclease derived from the LAGLIDADG homing endonuclease family. In some embodiments, a megaTAL is engineered to knockout HPRT. Methods of engineering a suitable megaTAL are described by "Boissel S, Jarjour J, Astrakhan A, et al. megaTALs: A Rare-Cleaving Nuclease Architecture for Therapeutic Genome Engineering. Nucleic Acids Research. 2014; 42(4):2591-2601," the disclosure of which is hereby incorporated by reference herein in its entirety.

The nucleases, polynucleotides encoding these nucleases, donor polynucleotides and compositions comprising the proteins and/or polynucleotides described herein may be delivered in vivo or ex vivo by any suitable means. For example, methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Host Cells

The present disclosure also provides a host cell comprising the novel expression vectors of the present disclosure. A "host cell" or "target cell" means a cell that is to be transformed using the methods and expression vectors of the present disclosure. In some embodiments, the host cells are mammalian cells in which the expression vector can be expressed. Suitable mammalian host cells include, but are not limited to, human cells, murine cells, non-human primate cells (e.g. rhesus monkey cells), human progenitor cells or stem cells, 293 cells, HeLa cells, D17 cells, MDCK cells, BHK cells, and Cf2Th cells. In certain embodiments, the host cell comprising an expression vector of the disclosure is a hematopoietic cell, such as hematopoietic progenitor/stem cell (e.g. CD34-positive hematopoietic progenitor/stem cell (HPSC)), a monocyte, a macrophage, a peripheral blood mononuclear cell, a CD4+T lymphocyte, a CD8+T lymphocyte, or a dendritic cell.

The hematopoietic cells (e.g. HPSC, CD4+T lymphocytes, CD8+T lymphocytes, and/or monocyte/macrophages) to be transduced with an expression vector of the disclosure can be allogeneic, autologous, or from a matched sibling. The HPSC are, in some embodiments, CD34-positive and can be isolated from the patient's bone marrow or peripheral blood. The isolated CD34-positive HPSC (and/or other hematopoietic cell described herein) is, in some embodiments, transduced with an expression vector as described herein.

In some embodiments, the host cells or transduced host cells are combined with a pharmaceutically acceptable carrier. In some embodiments, the host cells or transduced host cells are formulated with PLASMA-LYTE A (e.g. a sterile, nonpyrogenic isotonic solution for intravenous administration; where one liter of PLASMA-LYTE A has an ionic concentration of 140 mEq sodium, 5 mEq potassium, 3 mEq magnesium, 98 mEq chloride, 27 mEq acetate, and 23 mEq gluconate). In other embodiments, the host cells or transduced host cells are formulated in a solution of PLASMA-LYTE A, the solution comprising between about 8% and about 10% dimethyl sulfoxide (DMSO). In some embodiments, the less than about $2\times10^7$ host cells/transduced host cells are present per mL of a formulation including PLASMA-LYTE A and DMSO.

In some embodiments, the host cells are rendered substantially HPRT deficient after transduction with a vector according to the present disclosure, e.g. having at least a 50% reduction in HPRT expression. In some embodiments, the host cells include a nucleic acid molecule including at least one of SEQ ID NO: 1, SEQ ID NO: 2, or SEQ ID NO: 3.

Pharmaceutical Compositions

The present disclosure also provides for compositions, including pharmaceutical compositions, comprising one or more expression vectors and/or non-viral delivery vehicles (e.g. nanocapsules) as disclosed herein. In some embodiments, pharmaceutical compositions comprise an effective amount of at least one of the expression vectors and/or non-viral delivery vehicles as described herein and a pharmaceutically acceptable carrier. For instance, in certain embodiments, the pharmaceutical composition comprises an effective amount of an expression vector and a pharmaceutically acceptable carrier. An affective amount can be readily determined by those skilled in the art based on factors such as body size, body weight, age, health, sex of the subject, ethnicity, and viral titers.

The phrases "pharmaceutically acceptable" or "pharmacologically acceptable" refer to molecular entities and compositions that do not produce adverse, allergic, or other untoward reactions when administered to an animal or a human. For example, an expression vector may be formulated with a pharmaceutically acceptable carrier. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. Methods for the formulation of compounds with pharmaceutical carriers are known in the art and are described in, for example, in Remington's Pharmaceutical Science, (17th ed. Mack Publishing Company, Easton, Pa. 1985); and Goodman & Gillman's: The Pharmacological Basis of Therapeutics (11th Edition, McGraw-Hill Professional, 2005); the disclosures of each of which are hereby incorporated herein by reference in their entirety.

In some embodiments, the pharmaceutical compositions may comprise any of the expression vectors, nanocapsules, or compositions disclosed herein in any concentration that allows the silencing nucleic acid administered to achieve a concentration in the range of from about 0.1 mg/kg to about 1 mg/kg. In some embodiments, the pharmaceutical compositions may comprise the expression vector in an amount of from about 0.1% to about 99.9% by weight. Pharmaceutically acceptable carriers suitable for inclusion within any pharmaceutical composition include water, buffered water, saline solutions such as, for example, normal saline or balanced saline solutions such as Hank's or Earle's balanced solutions), glycine, hyaluronic acid etc. The pharmaceutical composition may be formulated for parenteral administration, such as intravenous, intramuscular or subcutaneous administration. Pharmaceutical compositions for parenteral administration may comprise pharmaceutically acceptable sterile aqueous or non-aqueous solutions, dispersions, suspensions or emulsions as well as sterile powders for reconstitution into sterile injectable solutions or dispersions. Examples of suitable aqueous and non-aqueous carriers, solvents, diluents or vehicles include water, ethanol, polyols (such as glycerol, propylene glycol, polyethylene glycol, etc.), carboxymethylcellulose and mixtures thereof, vegetable oils (such as olive oil), injectable organic esters (e.g. ethyl oleate).

The pharmaceutical composition may be formulated for oral administration. Solid dosage forms for oral administration may include, for example, tablets, dragees, capsules, pills, and granules. In such solid dosage forms, the composition may comprise at least one pharmaceutically acceptable carrier such as sodium citrate and/or dicalcium phosphate and/or fillers or extenders such as starches, lactose, sucrose, glucose, mannitol, and silicic acid; binders such as carboxylmethylcellulose, alginates, gelatin, polyvinylpyrrolidone, sucrose and acacia; humectants such as glycerol; disintegrating agents such as agar-agar, calcium carbonate, potato or tapioca starch, alginic acid, silicates, and sodium carbonate; wetting agents such as acetyl alcohol, glycerol monostearate; absorbants such as kaolin and bentonite clay; and/or lubricants such as talc, calcium stearate, magnesium stearate, solid polyethylene glycol, sodium lauryl sulfate, and mixtures thereof. Liquid dosage forms for oral administration may include, for example, pharmaceutically acceptable emulsions, solutions, suspensions, syrups and elixirs. Liquid dosages may include inert diluents such as water or other solvents, solubilizing agents and/or emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (such as, for example, cottonseed oil, corn oil, germ oil, castor oil, olive oil, sesame oil), glycerol, tetrahydrofurfuryl alcohol, polyethylene glycols and fatty acid esters of sorbitan, and mixtures thereof.

The pharmaceutical compositions may comprise penetration enhancers to enhance their delivery. Penetration enhancers may include fatty acids such as oleic acid, lauric acid, capric acid, myristic acid, palmitic acid, stearic acid, linoleic acid, linolenic acid, dicaprate, reclineate, monoolein, dilaurin, caprylic acid, arachidonic acid, glyceryl 1-monocaprate, mono and di-glycerides and physiologically acceptable salts thereof. The compositions may further include chelating agents such as, for example, ethylenediaminetetraacetic acid (EDTA), citric acid, salicylates (e.g. sodium salicylate, 5-methoxysalicylate, homovanilate).

The pharmaceutical compositions may comprise any of the expression vectors disclosed herein in an encapsulated form. For example, the expression vectors may be encapsulated by biodegradable polymers such as polylactide-polyglycolide, poly(orthoesters) and poly(anhydrides), or may be encapsulated in liposomes or dispersed within a microemulsion. Liposomes may be, for example, lipofectin or lipofectamine. In another example, a composition may comprise the expression vectors disclosed herein in or on a nucleated bacterial minicells (Giacalone et al, Cell Microbiology 2006, 8(10): 1624-33). The expression vectors disclosed herein may be combined with nanoparticles.

Kits

In some embodiments is a kit comprising an expression vector or a composition comprising an expression vector as described herein. The kit may include a container, where the container may be a bottle comprising the expression vector or composition in an oral or parenteral dosage form, each dosage form comprising a unit dose of the expression vector. The kit may comprise a label or the like, indicating treatment of a subject according to the methods described herein.

In some embodiments, the kit may include additional active agents. The additional active agents may be housed in a container separate from the container housing the vector or composition comprising the vector. For example, in some embodiments, the kit may comprise one or more doses of a purine analog (e.g. 6TG) and optionally instructions for dosing the purine analog for conditioning and/or chemoselection (as those steps are described further herein). In other embodiments, the kit may comprise one or more doses of MTX or MPA and optionally instructions for dosing the MTX or MPA for negative selection as described herein.

In yet other embodiments, the kit may include one or more internalizing immunotoxinss or antibody-drug conjugates, such as those described in US Patent Publication Nos. 2017/0360954 and 2018/0147294; and PCT Publication Nos. WO/2017/219025 and WO/2017/219029, the disclosures of which are each incorporated by reference herein in their entireties. In some embodiments, the kit may include an immunotoxin is selected from pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, Ricin-A or a variant thereof. In some embodiments, the kit may include saporin.

Methods of Treatment

The methods and compositions disclosed herein are for modifying expression of a protein or correcting an aberrant gene sequence that encodes a protein expressed in a genetic disease, such as a sickle cell disease or a thalassemia. In some embodiments, the therapeutic gene provided within the vectors of the present disclosure are used to treat immune deficiencies, hereditary diseases, blood diseases (e.g. hemophilia, hemoglobin disorders), lysosomal storage diseases, neurological diseases, angiogenic disorders, or cancer. While particular reference may be made to the genetic treatment of sickle cell anemia or β-thalassemia, the present disclosure is not limited to methods of treating only those diseases. As such, in some embodiments, the method of treating immune deficiencies, hereditary diseases, blood diseases (e.g. hemophilia, hemoglobin disorders), lysosomal storage diseases, neurological diseases, angiogenic disorders, or cancer comprises (i) transducing HSCs including, autologous HSCs, allogenic HSCs, sibling matched HSCs, etc. with a vector comprising at least two nucleic acid sequences, namely a nucleic acid sequence encoding an agent to decrease HPRT expression, and a nucleic acid sequence encoding a therapeutic gene, and (ii) administering the transduced HSCs to a mammalian subject.

By way of example, an expression vector including a nucleic acid sequence encoding a gamma-globin gene (such as described herein) may be administered so as to genetically correct sickle cell disease or β-thalassemia, or reduce symptoms thereof. In some embodiments, a population of host cells transduced with an expression vector including a nucleic acid sequence encoding a gamma-globin gene may be administered so as to genetically correct sickle cell disease or β-thalassemia, or reduce symptoms thereof. It is believed that the genetic correction of HSCs with a vector encoding the gamma globin gene would result in a continuous (i.e. permanent) production of the anti-sickling HbF, thereby preventing or mitigating red blood cell sickling for the life of the subject. It is believed that this method is advantageous over currently available therapies, including its availability to all patients, particularly those who do not have a matched sibling donor, and the fact that it would be a one-time treatment, resulting in lifelong correction. It is also believed that the method is advantageously devoid of any immune side effects, and if side effects did arise, the side-effects could be mitigated by administering MTX or MPA as noted herein. It is further believed that an effective gene therapy approach will revolutionize the way SCD is treated and improve the outcomes of patients with this devastating disorder.

As noted herein, in addition to the therapeutic gene, the expression vectors of the present disclosure include an agent designed to decrease HPRT expression (e.g. a shRNA to HPRT to effect knockdown of HPRT expression), and hence provide for an in vivo chemoselection strategy that exploits the essential role that HPRT plays in metabolizing purine analogs, e.g. 6TG, into myelotoxic agents. Because HPRT-deficiency does not impair hematopoietic cell development or function, it can be removed from hematopoietic cells used for transplantation. Conditioning and chemoselection with a purine analog is discussed further herein.

Figure 2:
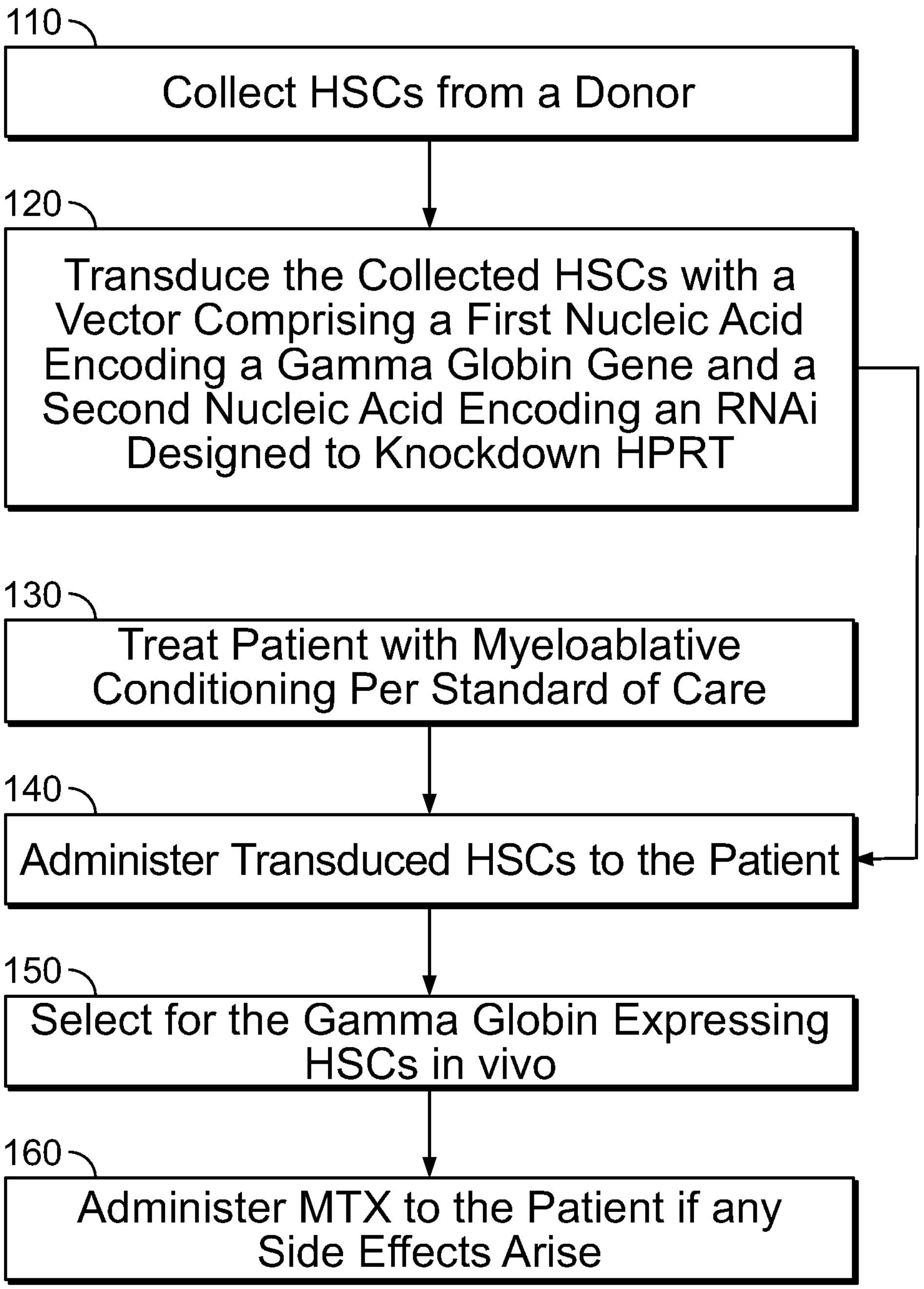
FIG. 2 sets forth a flowchart illustrating methods of treating a subject with transduced HSCs, including the steps of conditioning and chemoselection in accordance with certain embodiments of the present disclosure.
Figure 3:
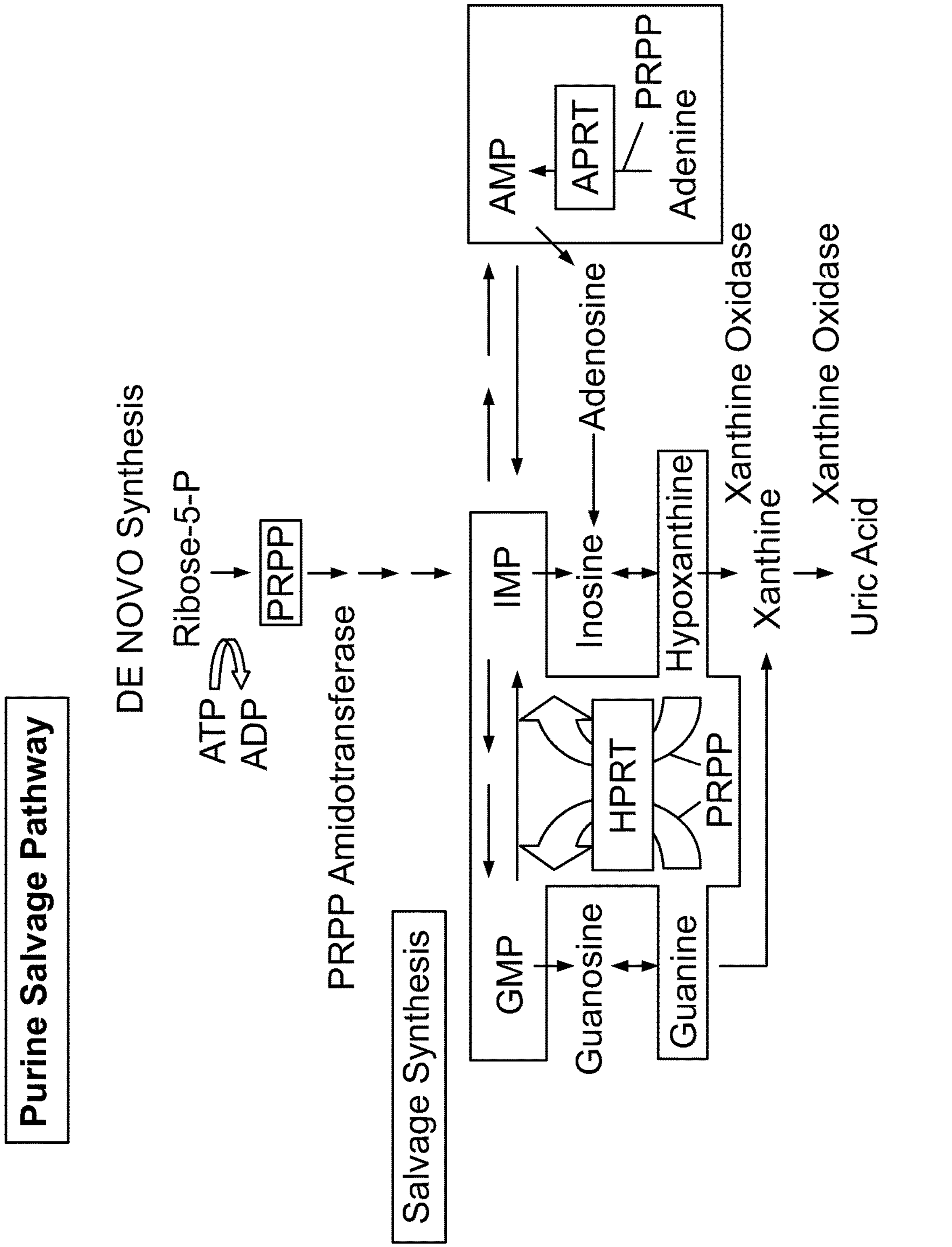
FIG. 3 illustrates the purine salvage pathway.
Figure 4:
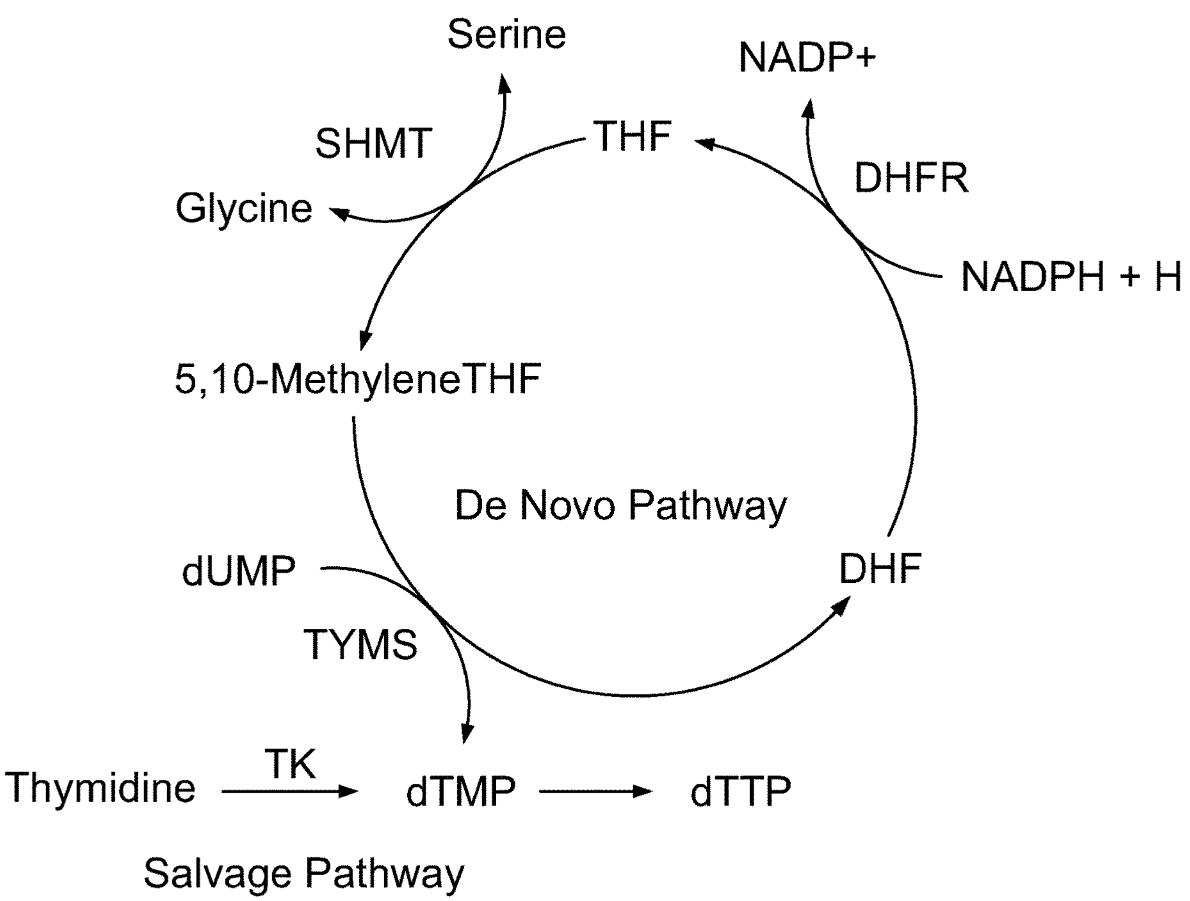
FIG. 4 illustrates the de novo path for the synthesis of dTTP.
Figure 5:
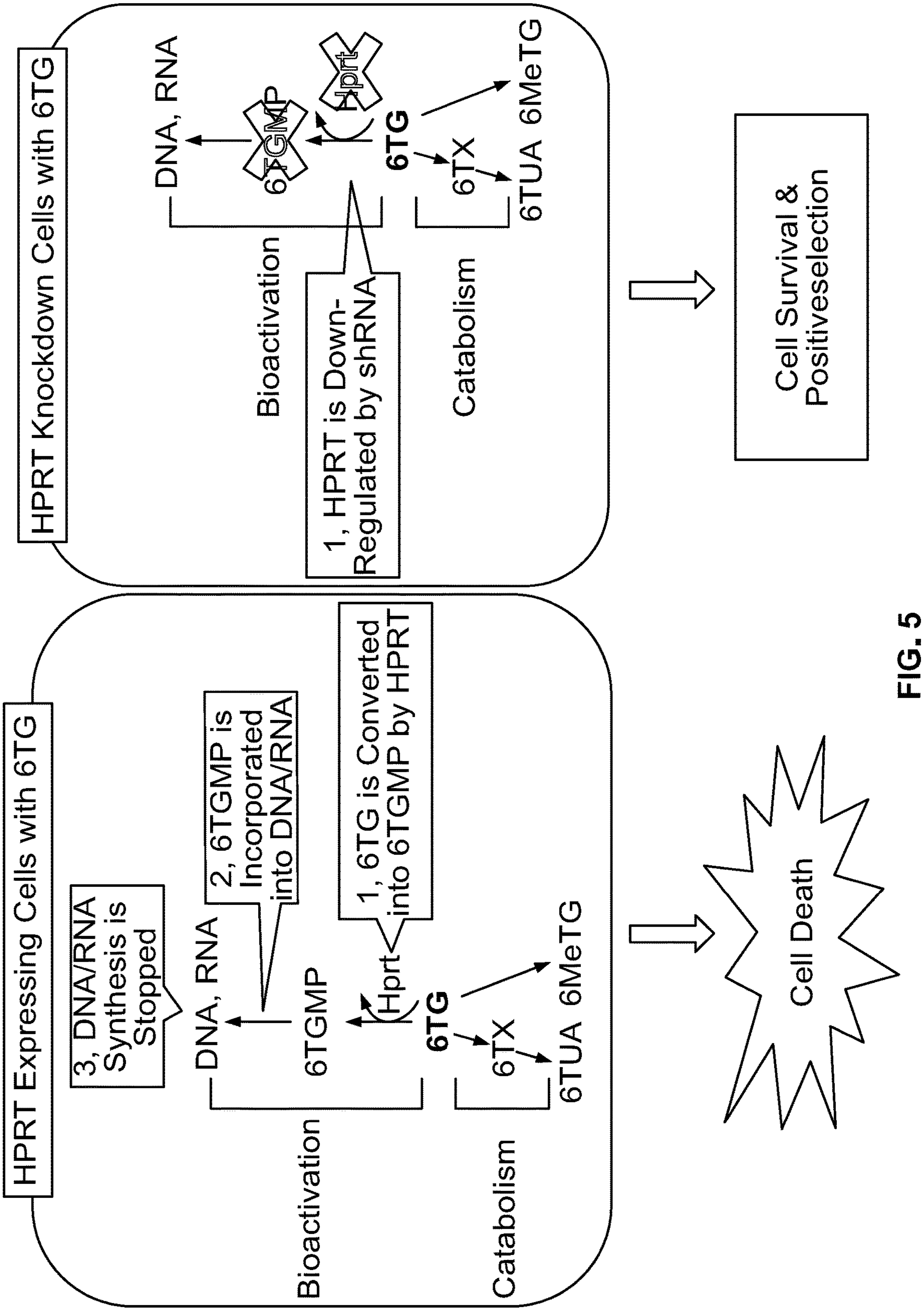
FIG. 5 illustrates a process for selecting of HPRT-deficient cells in the presence of 6TG.

In the context of the treatment of sickle cell disease or β-thalassemia (or reducing the symptoms of sickle cell disease or β-thalassemia), and with reference to FIG. 2, the treatment of a subject includes: identifying a subject in need of treatment thereof; transducing HSCs (e.g. autologous HSCs, allogenic HSCs, sibling matched HSCs) with an expression vector (e.g. a lentiviral vector) of the present disclosure (step 120); and transplanting or administering the transduced HSCs into the subject (step 140). In some embodiments, the subject in need of treatment thereof is one suffering from severe symptomatic SCD.

In some embodiments, the method of treating hemoglobinopathies comprises (i) transducing HSCs with a vector comprising at least two nucleic acid sequences, namely a nucleic acid sequence encoding a shRNA to knockdown the HPRT gene, and a nucleic acid sequence encoding a gamma globin gene, and (ii) administering the transduced HSCs to a mammalian subject. In some embodiments, the nucleic acid sequence encoding the shRNA comprises the sequence of SEQ ID NO: 30. In some embodiments, the nucleic acid sequence encoding the gamma globin gene comprises the sequence of SEQ ID NO: 55. In some embodiments, the method further comprises a step of myeloablative conditioning prior to the administration of the transduced HSCs (e.g. using a purine analog, chemotherapy, radiation therapy, treatment with one or more internalizing immunotoxins or antibody-drug conjugates, or any combination thereof). In some embodiments, the method further comprises the step of in vivo chemoselection utilizing a purine analog (e.g. 6TG) following administration of the transduced HSCs. In some embodiments, the method further comprises the step of negative selection utilizing MTX or MPA should side effects arise (e.g. GVHD).

In another aspect of the present disclosure is a method of treating hemoglobinopathies comprising administering an effective amount of a pharmaceutical composition to a mammalian subject (e.g. a human patient), wherein the pharmaceutical compositions includes an expression vector comprising at least two nucleic acid sequences, and a pharmaceutically acceptable carrier. In another aspect of the present disclosure is a method of treating hemoglobinopathies comprising administering an effective amount of a pharmaceutical composition to a mammalian subject (e.g. a human patient), wherein the pharmaceutical compositions includes a population of host cells transduced with an expression vector comprising at least two nucleic acid sequences, and a pharmaceutically acceptable carrier. In some embodiments, the expression vector is a lentiviral expression vector including a first nucleic acid encoding an RNAi to knockdown the HPRT gene; and a second nucleic acid encoding a therapeutic gene (e.g. a gamma globin gene). In some embodiments, the nucleic acid sequence encoding the gamma globin gene comprises the sequence of SEQ ID NO: 55. In some embodiments, the method further comprises a step of myeloablative conditioning prior to the administration of the transduced HSCs. In some embodiments, the method further comprises the step of in vivo chemoselection utilizing 6TG following administration of the transduced HSCs. In some embodiments, the method further comprises the step of negative selection utilizing MTX or MPA should side effects arise (e.g. GVHD).

In another aspect of the present disclosure is a method of treating severe symptomatic SCD, or reducing or ameliorating one or more symptoms of severe symptomatic SCD, comprising (i) transducing HSCs with a vector comprising at least two nucleic acid sequences, namely a nucleic acid sequence encoding a shRNA to knockdown the HPRT gene, and a nucleic acid sequence encoding a gamma globin gene, and (ii) administering the transduced HSCs to a mammalian subject. In some embodiments, the nucleic acid sequence encoding the shRNA comprises the sequence of SEQ ID NO: 30. In some embodiments, the nucleic acid sequence encoding the gamma globin gene comprises the sequence of SEQ ID NO: 55. In some embodiments, the method further comprises a step of myeloablative conditioning prior to the administration of the transduced HSCs (e.g. using a purine analog, chemotherapy, radiation therapy, treatment with one or more internalizing immunotoxins or antibody-drug conjugates, or any combination thereof). In some embodiments, the method further comprises the step of in vivo chemoselection utilizing a purine analog (e.g. 6TG) following administration of the transduced HSCs. In some embodiments, the method further comprises the step of negative selection utilizing MTX or MPA should side effects arise (e.g. GVHD). In some embodiments, treatment reduces or ameliorates at least one of acute chest syndrome, severe pain episodes, recurrent priapism, red-cell alloimmunization, and/or neurologic events.

In some embodiments, post-transplantation fetal hemoglobin exceeds at least 20%; F cells constitute at least ⅔ of the circulating red blood cells; fetal hemoglobin per F cells account for at least ⅓ of total hemoglobin in sickle red blood cells; and at least 20% gene-modified HSCs re-populate bone marrow of the subject. In some embodiments, post-transplantation fetal hemoglobin exceeds 25%, 30%, 35%, 40%, 45%, 50%, or greater. In some embodiments, post-transplantation fetal hemoglobin exceeds 55%, 60%, 65%, 70%, 75%, 80%, 85%, 90%, 95%, or greater. In some embodiments, F cells constitute at least 70%, 75%, 80%, 85%, 90%, 95%, or greater of the circulating red blood cells. In some embodiments, fetal hemoglobin per F cells account for at least ⅓ of total hemoglobin in sickle red blood cells. In some embodiments, fetal hemoglobin per F cells account for at least 40%, 45%, 50%, 55%, 60%, 65%, 70%, 75%, 80%, 85%, 90%, 95% or greater of total hemoglobin in sickle red blood cells. In some embodiments, 20%, 25%, 30%, 35%, 40%, 45%, 50%, 55%, 60%, 65%, 70%, 75%, 80%, 85%, 90%, 95%, or greater gene-modified HSCs re-populate bone marrow of the subject.

In another aspect of the present disclosure is a method of treating treat immune deficiencies, hereditary diseases, blood diseases (e.g. hemophilia, hemoglobin disorders), lysosomal storage diseases, neurological diseases, angiogenic disorders, or cancer comprising administering an effective amount of a vector to a mammalian subject, the vector comprising at least two nucleic acid sequences, namely a nucleic acid sequence encoding an RNAi to knockdown the HPRT gene, and a nucleic acid sequence encoding a therapeutic gene.

Conditioning and Chemoselection with a Purine Analog

In some embodiments, the method of treatment comprises the additional steps of (i) conditioning prior to HSC transplantation; and/or (ii) in vivo chemoselection. One or both steps may utilize a purine analog, In some embodiments, the purine analog is 6TG. It is believed that the engrafted gamma-globin gene-containing HSCs deficient in HPRT activity are highly resistant to the cytotoxic effects of the introduced purine analog. With a combined strategy of conditioning and chemoselection, efficient and high engraftment of HPRT-deficient, therapeutic gene (e.g. gamma globin gene) containing HSCs with low overall toxicity can be achieved. It is believed that resultant expression of the therapeutic gene (e.g. gamma globin gene), combined with the enhanced engraftment and chemoselection of gene-modified HSCs, can result in sufficient protein production to correct for immune deficiencies, hereditary diseases, blood diseases (e.g. hemophilia, hemoglobin disorders), lysosomal storage diseases, neurological diseases, angiogenic disorders, or cancer (and, in the case of the production of the gamma-globin protein, sufficient fetal hemoglobin formation to correct for SCD and/or beta thalassemia).

6TG is a purine analog having both anticancer and immune-suppressive activities. Thioguanine competes with hypoxanthine and guanine for the enzyme hypoxanthine-guanine phosphoribosyltransferase (HGPRTase) and is itself converted to 6-thioguanylic acid (TGMP). This nucleotide reaches high intracellular concentrations at therapeutic doses. TGMP interferes several points with the synthesis of guanine nucleotides. It inhibits de novo purine biosynthesis by pseudo-feedback inhibition of glutamine-5-phosphoribosylpyrophosphateamidotransferase—the first enzyme unique to the de novo pathway for purine ribonucleotide. TGMP also inhibits the conversion of inosinic acid (IMP) to xanthylic acid (XMP) by competition for the enzyme IMP dehydrogenase. At one-time TGMP was felt to be a significant inhibitor of ATP: GMP phosphotransferase (guanylate kinase), but recent results have shown this not to be so. Thioguanylic acid is further converted to the di- and triphosphates, thioguanosine diphosphate (TGDP) and thioguanosine triphosphate (TGTP) (as well as their 2'-deoxyribosyl analogues) by the same enzymes which metabolize guanine nucleotides.

As those of skill in the art will appreciate, given the inclusion of an agent designed to reduce HPRT expression, e.g. an RNAi agent to knockdown HPRT, in the vectors of the present disclosure, the resulting transduced HSCs are HPRT-deficient or substantially HPRT-deficient. As such, those HSCs that do express HPRT, i.e. HPRT wild-type cells, may be selectively depleted by administering one or more doses of 6TG. In some embodiments, 6TG may be administered for both myeloablative conditioning of HPRT-wild type recipients and for in vivo chemoselection process of donor cells. Hence, this strategy is believed to allow for the selection of gene-modified cells in vivo, i.e. for the selection of the gamma-globin containing gene-modified cells in vivo.

With reference to FIG. 2, in some embodiments, following the collection of HSCs from a donor (step 110), the HSCs are transduced with a vector according to the present disclosure (step 120). The resulting HSCs are HPRT-deficient and express the therapeutic gene, e.g. the gamma globin gene. In parallel, a patient to receive the HSCs is first treated with a myeloablative conditioning step (step 130). Following conditioning, the transduced HSCs are transplanted or administered to the patient (step 140). Therapeutic gene (e.g. gamma globin gene) containing HSCs may then be selected for (step 150) in vivo using 6TG, as discussed herein.

Myeloablative conditioning may be achieved using high-dose conditioning radiation, chemotherapy, and/or treatment with a purine analog (e.g. 6TG). In some embodiments, the HSCs are administered between about 24 and about 96 hours following treatment with the conditioning regimen. In other embodiments, the patient is treated with the HSC graft between about 24 and about 72 hours following treatment with the conditioning regimen. In yet other embodiments, the patient is treated with the HSC graft between about 24 and about 48 hours following treatment with the conditioning regimen. In some embodiments, the HSC graft comprises between about $2\times10^6$ cells/kg to about $15\times10^6$ cells/kg (body weight of patient). In some embodiments, the HSC graft comprises a minimum of $2\times10^6$ cells/kg, with a target of greater than $6\times10^6$ cells/kg. In some embodiments, at least 10% of the cells administered are transduced with a lentiviral vector as described herein. In some embodiments, at least 20% of the cells administered are transduced with a lentiviral vector as described herein. In some embodiments, at least 30% of the cells administered are transduced with a lentiviral vector as described herein. In some embodiments, at least 40% of the cells administered are transduced with a lentiviral vector as described herein. In some embodiments, at least 50% of the cells administered are transduced with a lentiviral vector as described herein.

In some embodiments, the therapeutic gene containing, HPRT-deficient HSCs are selected for in vivo using a low dose schedule of 6TG, which is believed to have minimal adverse effects on extra-hematopoietic tissues. In some embodiments, a dosage of 6TG for in vivo chemoselection ranging from between about 0.2 mg/kg/day to about 0.6 mg/kg/day is provided to a patient following introduction of the HSCs into the patient. In some embodiments, the dosage ranges from between about 0.3 mg/kg/day to about 1 mg/kg/day. In some embodiments, the dosage is up to about 2 mg/kg/day.

In some embodiments, the amount of 6TG administered per dose is based on a determination of a patient's HPRT enzyme activity. Those of ordinary skill in the art will appreciate that those presenting with higher levels of HPRT enzyme activity may be provided with doses having lower amounts of 6TG. The higher the level of HPRT the greater conversion of 6TG to toxic metabolites. Therefore, the lower dose you would need to administer to achieve the same goal.

Measurement of TPMT genotypes and/or TPMT enzyme activity before instituting 6TG conditioning may identify individuals with low or absent TPMT enzyme activity. As such, in other embodiments, the amount of 6TG administered is based on thiopurine S-methyltransferase (TPMT) levels or TPMT genotype.

In some embodiments, the dosage of 6TG for in vivo chemoselection is administered to the patient one to three times a week on a schedule with a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five weeks off; (vi) four weeks of therapy followed by one, two, three, four or five weeks off; (vii) five weeks of therapy followed by one, two, three, four or five weeks off; and (viii) monthly.

In some embodiments, between about 3 and about 10 dosages of 6TG are administered to the patient over an administration period ranging from 1 week to about 4 weeks. In some embodiments, 4 or 5 dosages of 6TG are administered to the patient over a 14-day period.

Negative Selection with MTX or MPA

In addition, HPRT-deficient cells can be negatively selected by using methotrexate (MTX) to inhibit the enzyme dihydrofolate reductase (DHFR) in the purine de novo synthetic pathway. This has been developed as a safety procedure to eliminate gene-modified HSCs in case of unexpected adverse effects observed. As such, and in reference to FIG. 2, should any adverse side effects arise, a patient may be treated with MTX or mycophenolic acid (MPA) (step 160). Adverse side effects include, for example, aberrant blood counts/clonal expansion indicating insertional mutagenesis in a particular clone of cells or cytokine storm.

It is believed that MTX or MPA competitively inhibits dihydrofolate reductase (DHFR), an enzyme that participates in tetrahydrofolate (THF) synthesis. DHFR catalyzes the conversion of dihydrofolate to active tetrahydrofolate. Folic acid is needed for the de novo synthesis of the nucleoside thymidine, required for DNA synthesis. Also, folate is essential for purine and pyrimidine base biosynthesis, so synthesis will be inhibited. MTX or MPA, therefore inhibits the synthesis of DNA, RNA, thymidylates, and proteins. MTX or MPA blocks the de novo pathway by inhibiting DHFR. In HPRT−/− cell, there is no salvage or de novo pathway functional, leading to no purine synthesis, and therefore the cells die. However, the HPRT wild type cells have a functional salvage pathway, their purine synthesis takes place and the cells survive.

Given the sensitivity of the modified HSCs produced according to the present disclosure, MTX or MPA may be used to selectively eliminate HPRT-deficient cells. In some embodiments, the MTX or MPA is administered as a single dose. In some embodiments, multiple doses of the MTX or MPA are administered.

In some embodiments, an amount of MTX administered ranges from about 2 $mg/m^2$/infusion to about 100 $mg/m^2$/infusion. In some embodiments, an amount of MTX administered ranges from about 2 $mg/m^2$/infusion to about 90 $mg/m^2$/infusion. In some embodiments, an amount of MTX administered ranges from about 2 $mg/m^2$/infusion to about 80 $mg/m^2$/infusion. In some embodiments, an amount of MTX administered ranges from about 2 $mg/m^2$/infusion to about 70 $mg/m^2$/infusion. In some embodiments, an amount of MTX administered ranges from about 2 $mg/m^2$/infusion to about 60 $mg/m^2$/infusion. In some embodiments, an amount of MTX administered ranges from about 2 $mg/m^2$/infusion to about 50 $mg/m^2$/infusion. In some embodiments, an amount of MTX administered ranges from about 2 $mg/m^2$/infusion to about 40 $mg/m^2$/infusion. In some embodiments, an amount of MTX administered ranges from about 2 $mg/m^2$/infusion to about 30 $mg/m^2$/infusion. In some embodiments, an amount of MTX administered ranges from about 20 $mg/m^2$/infusion to about 20 $mg/m^2$/infusion. In some embodiments, an amount of MTX administered ranges from about 2 $mg/m^2$/infusion to about 10 $mg/m^2$/infusion. In some embodiments, an amount of MTX administered ranges from about 2 $mg/m^2$/infusion to about 8 $mg/m^2$/infusion. In other embodiments, an amount of MTX administered ranges from about 2.5 $mg/m^2$/infusion to about 7.5 $mg/m^2$/infusion. In yet other embodiments, an amount of MTX administered is about 5 $mg/m^2$/infusion. In yet further embodiments, an amount of MTX administered is about 7.5 $mg/m^2$/infusion.

In some embodiments, between 2 and 6 infusions are made, and the infusions may each comprise the same dosage or different dosages (e.g. escalating dosages, decreasing dosages, etc.). In some embodiments, the administrations may be made on a weekly basis, or a bi-monthly basis.

In some embodiments, MPA is dosed in an amount of between about 500 mg to about 1500 mg per day. In some embodiments, the dose of MPA is administered in a single bolus. In some embodiments, the dose of MPA is divided into a plurality of individual doses totaling between about 500 mg to about 1500 mg per day.

In some embodiments, an analog or derivative of MTX or MPA may be substituted for MTX or MPA. Derivatives of MTX are described in U.S. Pat. No. 5,958,928 and in PCT Publication No. WO/2007/098089, the disclosures of which are hereby incorporated by reference herein in their entireties.

Combination Therapy

Hydroxyurea, a myelosuppressive agent, is believed to raise the level of HbF and hemoglobin levels in patients. Current evidence suggests that several potential mechanisms of action by hydroxyurea may be relevant for patients with SCD, which together lead not only to HbF induction but also to additional benefits. It is believed that hydroxyurea is a potent ribonucleotide reductase (RR) inhibitor that reduces intracellular deoxynucleotide triphosphate pools and acts as an S-phase-specific agent with inhibition of DNA synthesis and eventual cellular cytotoxicity. Hydroxyurea directly inhibits the RR M2 subunit, but spontaneous regeneration of the active enzyme occurs when hydroxyurea is removed. For this reason, the in vivo effects of hydroxyurea on RR are predictably transient, resulting from the rapid absorption, metabolism, and excretion of hydroxyurea in mammalian systems. Presumably with once-daily dosing in SCD, hydroxyurea causes intermittent cytotoxic suppression of erythroid progenitors and cell stress signaling, which then affects erythropoiesis kinetics and physiology and leads to recruitment of erythroid progenitors with increased HbF levels. A remarkable attribute of hydroxyurea is the observation that treatment has multiple potential benefits for patients with SCD. Beyond HbF induction, the cytotoxic effects of hydroxyurea also reduce marrow production of neutrophils, reticulocytes and also reduce no of platelets which is an important mediator of inflammation. Additional benefits of hydroxyurea treatment include salutary effects on the circulating erythrocytes.

In another aspect of the present disclosure is a combination therapy whereby hydroxyurea is administered prior to, during, or following the administration or transplantation of transduced HSCs (described above) into a patient in need of treatment thereof. In some embodiments, hydroxyurea may be administered following the administration or transplantation of transduced HSCs on an as-needed basis, such as during a pain crisis, at the onset of acute chest syndrome, at the onset of severe or symptomatic anemia (Hb<7 g/dL), etc. In some embodiments, hydroxyurea is administered in a dose ranging from about 10 mg/kg/day to about 15 mg/kg/day, and given as a single daily dose. In some embodiments, a dose of hydroxyurea may be escalated or reduced over time.

EXAMPLES

Example 1—Production of the TL20c-rGbG$^M$-7SK/Sh734 Vector

The pTL20c vector (SEQ ID NO: 47) (see FIG. 40) contains the 400 bp extended core element of the chicken hypersensitivity site 4 insulator (cHS4) (SEQ ID NO: 49) inserted in the 3'LTR in reverse orientation to the viral transcript. The cHS4 insulator contains both enhancer-blocking activity mediated by the core CTCF binding site and barrier activity mediated by VEZF1 binding sites. Additional details pertaining to the pTL20c vector, including its backbone (SEQ ID NO: 48), methods of producing producer cells lines therefrom, or harvesting viral titer are described in United States Patent Publication No. 2018/0112233, the disclosure of which is hereby incorporated by reference herein in its entirety.

Figure 41:
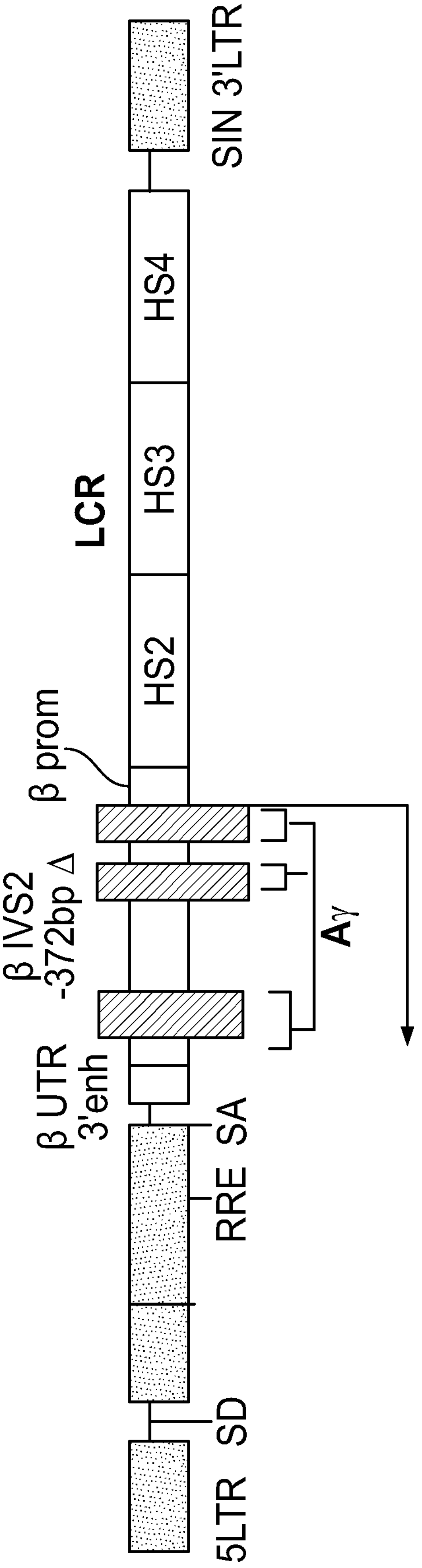
FIG. 41 illustrates the relevant transgene and regulatory sequences of the sGbG$^M$ lentivirus vector.

The 400 bp cHS4 insulator was placed in the reverse orientation within the LTR, and combined with a 46 bp deletion that removed the residual nef sequence, which was believed to reduce the frequency of polyadenylation read-through from a lentiviral LTR 3. In addition, the rabbit β-globin polyadenylation signal was inserted downstream of the 3'LTR to provide a stronger polyadenylation signal for the vector transcript and reduce transcriptional read-through.

sGbG$^M$ Lentivirus Vector—The Gamma Globin sSIN lentivirus vector—sGbG$^M$(SEQ ID NO: 50) with relevant transgene and regulatory sequences are illustrated in FIG. 41. Exons 1, 2, and 3 are set forth in SEQ ID NOS; 41, 52, and 53, respectively. The HIV lentivirus vector is a self-inactivating (SIN) design. The U3 region of the 5'LTR (HIVenhancer/promoter) was replaced by the CMV enhancer/promoter. The U3 region of the 3'LTR contained a 400 bp deletion of the promoter enhancer, to allow a SIN design, so that it contained no viral transcriptional elements upon integration into host cells. Downstream of the 3'LTR, a bovine growth hormone poly A signal as inserted to enhance vector polyadenylation. Besides the packaging region, the vector carried approximately 350 bp of a gag gene, 540 bp of env, including the splice acceptor and rev response element, followed by 150 bp of the central polypurine tract of the pol gene downstream of the 5' LTR. The transgene expression cassette consisted of 3.2 Kb of hypersensitive sites 2, 3 and 4, derived by PCR from the genome and a modified β-globin/γ-globin hybrid gene. The hybrid globin gene was further modified using PCR and site directed mutagenesis to change all codons to γ-globin codons.

The pTL20c-sGbGM vector (FIG. 42) was constructed by inserting the sGbGM modified β-globin/γ-globin hybrid gene expression cassette (SEQ ID NO: 50) (FIG. 41) into the lentiviral pTL20c (FIG. 40) vector between MluI and NotI sites. The sequences of the transgene expression cassette consisted of 3.2 Kb of hypersensitive sites 2, 3, and 4 and a modified β-globin/γ-globin hybrid gene. The β-globin promoter and modified β-globin/γ-globin hybrid gene was inserted in reverse orientation to the viral RNA transcript in the SIN lentiviral backbone.

Figure 42A:
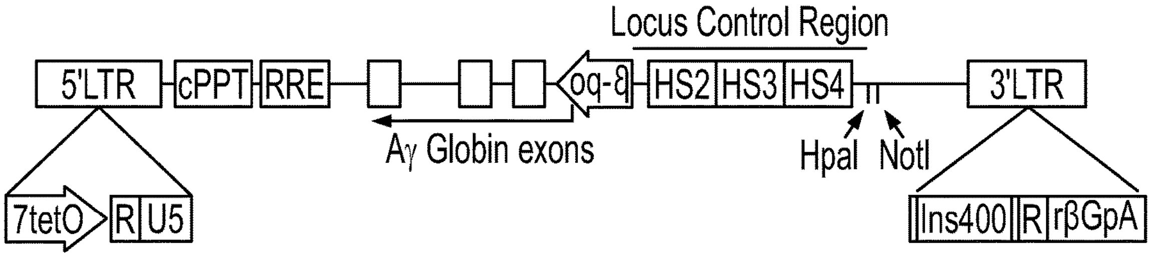
FIG. 42A provides a schematic representation of the pTL20c-sGbGM vector.
Figure 42B:
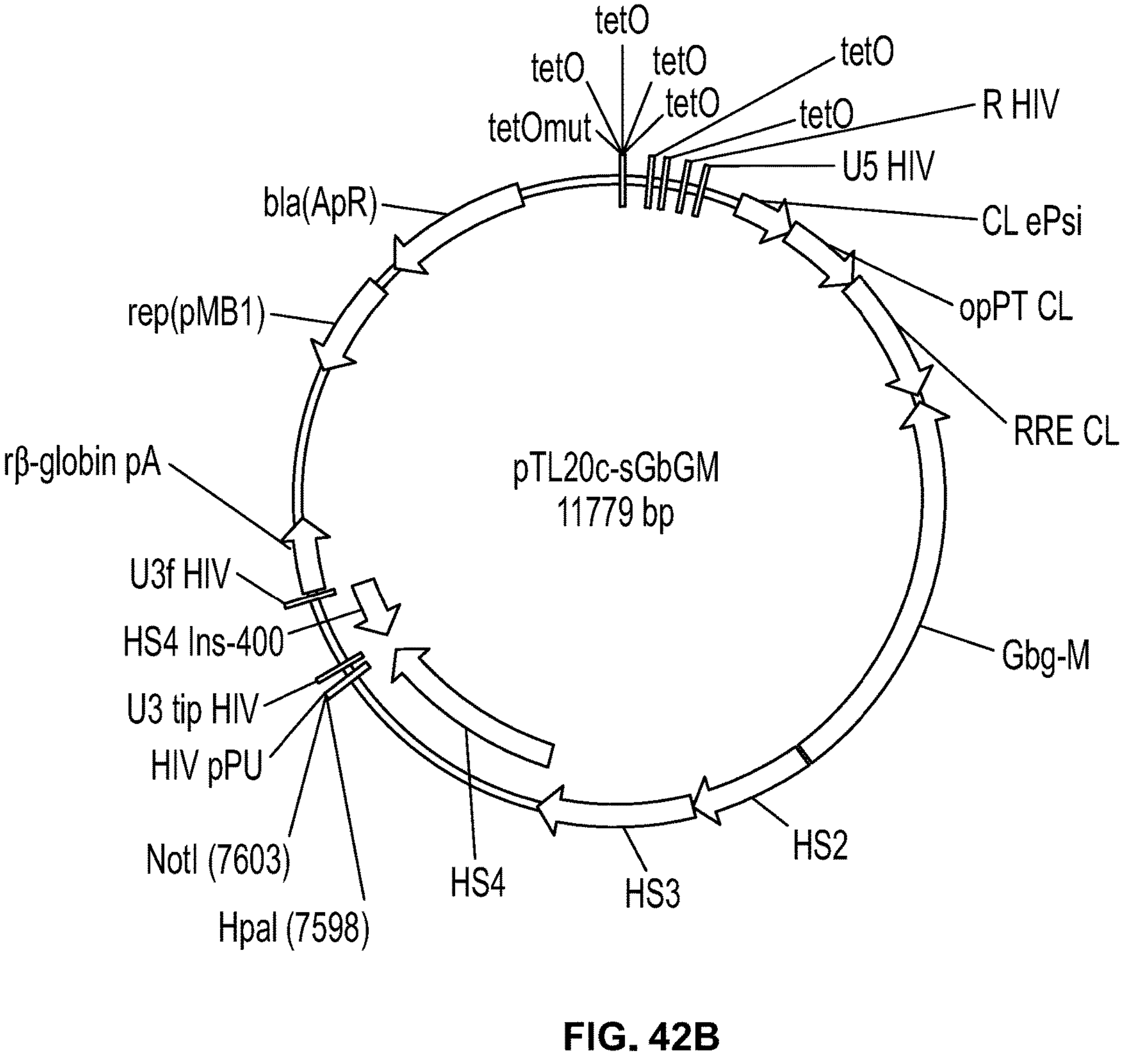
FIG. 42B illustrates a vector map for the pTL20c-sGbGM vector.
Figure 43A:
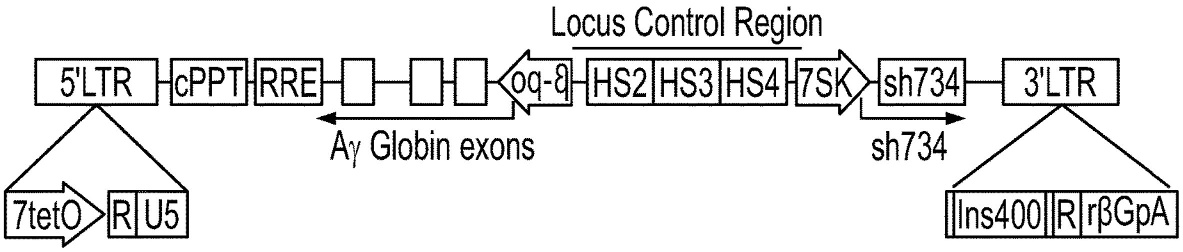
FIG. 43A provides a schematic representation of the TL20c-rGbGM-7SK/sh734 vector.
Figure 43B:
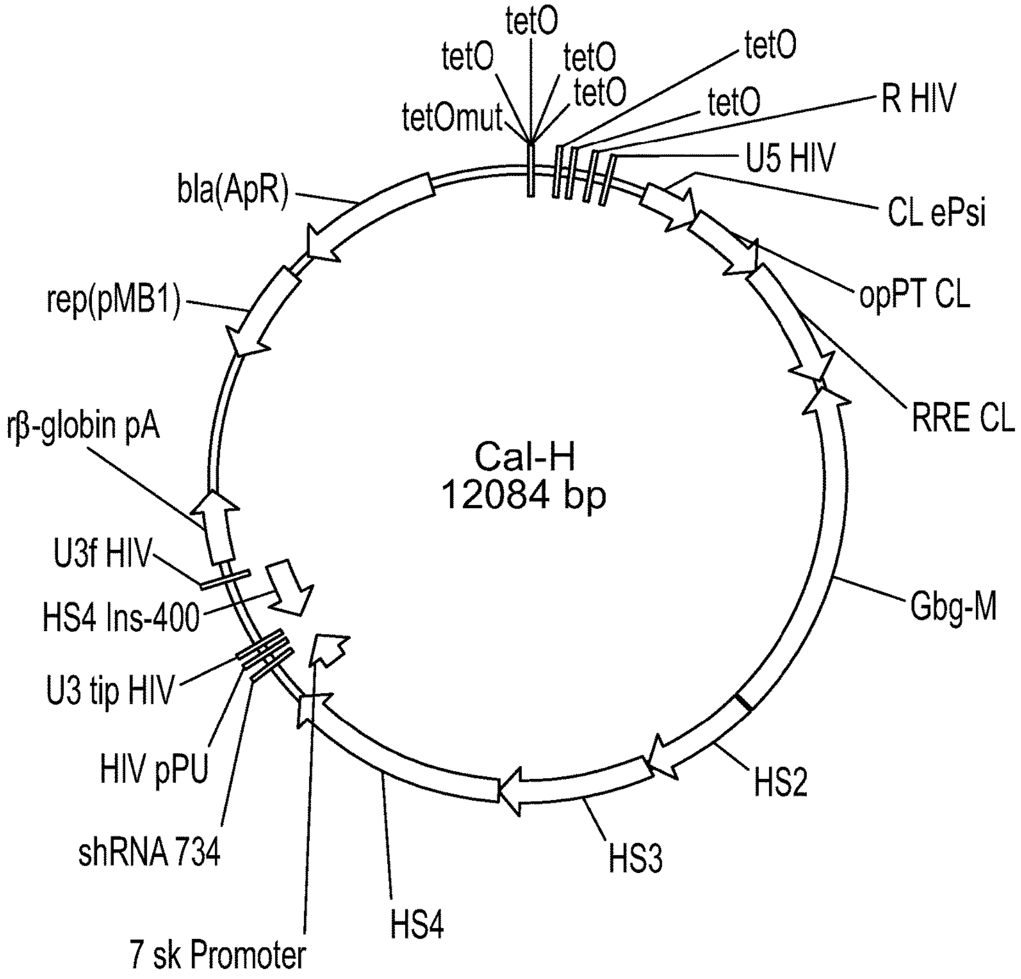
FIG. 43B illustrates a vector map for the TL20c-rGbGM-7SK/sh734 vector.

The TL20c-rGbG$^M$-7SK/sh734 (FIG. 43) vector was constructed by inserting the short hairpin RNA (shRNA734) expression cassette (SEQ ID NO: 54) into the lentiviral pTL20c-sGbGM vector between HpaI and NotI sites (see FIG. 42). The sequence of the short hairpin RNA (shRNA734) expression cassette included the human 7sk RNA Pol III promoter (SEQ ID NO: 32) and a short hairpin RNA (shRNA734) gene (SEQ ID NO: 30).

Example 2—Pre-Clinical Testing of the TL20c-rGbG$^M$-7SK/Sh734 Vector

Overview

The pTL20c-rGbG$^M$-7SK/sh734 dual therapeutic lentiviral vector construct was identified using a functional screen in K562 cells that compared the effect of position and orientation of the transgenes relative to each other on transgene expression and in vitro 6-TG selection. pTL20c-rGbG$^M$-7SK/sh734 transduced K562 cells selected in 6TG culture demonstrated long term stability and expression of the $\gamma^A$-globin transgene normalized to VCN equivalent to cells transduced with parental GbG$^M$ lentiviral vector or CAL-H that were not treated with 6TG. These findings indicated that functional expression of the sh734 and the corrective sGbG$^M$ gene driven by different promoters was mutually exclusive and that regulation of sGbG$^M$ was lineage dependent. Using an in vitro model of human erythroid differentiation, we showed that CD34+ HSCs transduced with the CAL-H lentiviral vector constitutively expressed sh734 in extended cultures at a sufficient level to knockdown the expression HPRT and confer selection of gene modified cells as determined by an increase in average vector copy number (VCN) and the frequency of transduced cells at day 14. When 6TG selected cultures were then transferred to erythroid differentiation culture conditions, the $^{A}\gamma$-Globin transgene was expressed in a lineage specific manner establishing proof of concept of sequential and coordinate regulation of transgene expression in transduced human CD34+ HSPCs. Results described herein support a clinical trial to evaluate an in vivo amplification protocol using 6TG to increase the long-term engraftment potential of CAL-H transduced CD34+ HSCs needed to achieve curative levels of total HbF and percentage of F cells for Sickle Cell Disease.

Experience to date with autologous gene therapy for thalassemia and sickle cell disease have suggested that the level of sub-myeloablative conditioning with bulsulfan doses of 12 mg/kg may be insufficient to achieve adequate donor chimerism necessary to cure disease, although estimates of mixed chimerism with gene engraftment of 30% gene modified cells might be curative. One approach to circumvent the lower efficiencies of engraftment is to apply in vivo amplification strategies. Since transduction efficiency of autologous CD34+ HSPCs can vary from 10% to 60% and an even smaller fraction of these cells are long term repopulating HSC/MPP stem cells in most cases the transduced stem cell dose is inadequate optimal. The lower efficiency is reflected in the vector copy number (VCN) that is seen in hematopoietic cell lineages after infusion. In most cases, the average VCN is significantly less than 1 per cell.

The goal of gene therapy is to offer the subject in need of treatment thereof a one-time ex-vivo correction of sickle cell HSCs with their autologous transplant and circumvent the immunological consequences such as graft rejection and graft versus host disease associated with allogeneic transplant.

Materials and Methods

HbF Infectious Titer in MEL Cells.

MEL cells were transduced by spinoculation with serial dilutions of CAL-H and sh7/GFP vector at MOI of 1 to 10 and plated at limiting dilution.

24-48 h determine % GFP positive cells

Expand and induce differentiation with 10 mM hemin and 3 mM HMBA for 3-4d.

Measure erythroblast differentiation by flow cytometry and viability/apoptosis by Annexin/7AAD staining Extract RNA. Measure sh7 and -globin expression and VCN by RT-PCR Plot fold increase-globin mRNA and -globin mRNA/VCN in transduced versus mock-transduced cells 6TG Selection and Long-term stability of CAL-H transduced K562 cells Assays to Measure Transduction Efficiency, VCN, Sh7 and γ-Globin Expression, Viability and Differentiation 1) K562 cells ($1\times10^5$ cells each condition) are transduced with 6 different vectors at 2 dilution factors at day 7.

2) The cells are reseeded into 6-well plate with additional 4 mL of fresh RPMI medium on Day 3.

3) Two cell pellets ($1\times10^6$ cells each) for DNA & RNA analysis for 13 samples including control K562 will be frozen down at day 0 (MY). Copy numbers of GbG and sh734 are analyzed.

4) $2\times10^5$ cells of control K562, 6 samples transduced at dilution factor 32 and 6 samples transduced at dilution factor 1 are reseeded in 6-well plate with 4 mL of RPMI without and with 300 nM of 6-thioguanine, respectively. $2.5\times10^6$ cells of 6 samples transduced at dilution factor 1 are made through mixing transduced and untransduced cells at ratio of 1:3. Two cell pellets ($1\times10^6$ cells each) for DNA & RNA analysis for these 6 samples will be frozen down. The medium is refreshed every 3-4 days. K562 transduced with TL20cw-7SK/sh734-GFP (dilution factor at 256 and 8) will be included as positive controls.

5) Two cell pellets ($1\times10^6$ cells each) for DNA & RNA analysis for 13 samples including control K562 will be frozen down at day 7/14/21 or even 28(MY). Copy numbers of GbG and sh734 are analyzed. The samples at day 21/28 are optional if the copy numbers of all samples are higher than 95% of expected value for day 14.

6) At day 14/21, seed 1×105 of cells of 12 samples under 6-TG selection into 12-well plate with 1 mL of RPMI without 6-TG. Run Annexin V and 7-AAD assay runs 3 days later. Use Camptothecin-treated cells and cells transduced with TL20cw-7SK/sh734-GFP (dilution factor 1) as positive control.

Objective

Given that high levels of erythroid-specific fetal-hemoglobin (gamma-globin) expression can be curative in SCD and beta-thalassemia, we assessed gene transfer efficiency (VCN), globin gene expression, erythroid differentiation, and total RBC Hb production. The K562 human erythroid leukemia cell line was used as a model of erythroid in vitro differentiation to provide evidence that (1) transferred γ-globin genes were correctly expressed and regulated as a consequence of erythroid differentiation (no expression in the undifferentiated state versus. abundant expression following differentiation); (2) that the sh734 against HPRT did not significantly alter the expression of γ-globin; and (3) that expression of the sh734 against HPRT did not significantly influenced by erythroid differentiation (high level expression in the undifferentiated state vs. similar or lower expression following differentiation).

Additional objectives for sh734 functionality/6TG selection:

Determine if comparable function of sh734±γ-globin;

Determine if comparable function of sh734±erythroid differentiation;

Determine selection and long-term stability of sh734 transduced cells; and

Determine whether sh734 does not affect cell viability or vector stability.

In Vitro Characterization

Figures 44A, 44B:
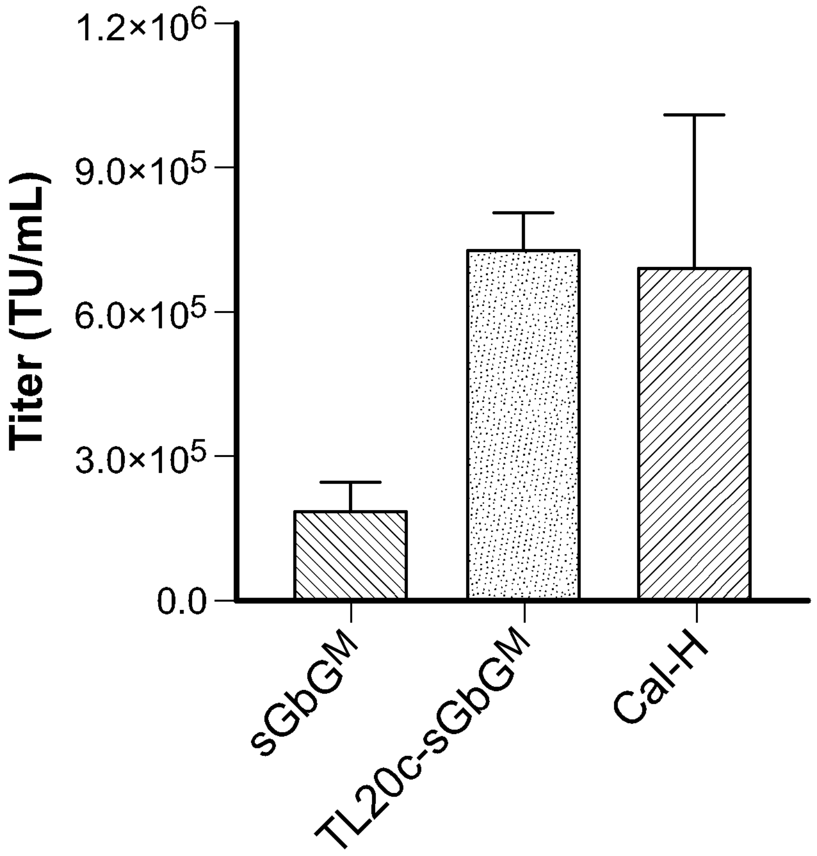
FIG. 44A illustrates that the TL20 backbone improved transduction efficiency of VSVg-pseudotyped SIN-lentivirus vectors.
FIG. 44B sets forth average titers obtained from the sGbG$^M$, pTL20c-sGbGM, and the TL20c-rGbGM-7SK/sh734 vectors.
Figure 45:
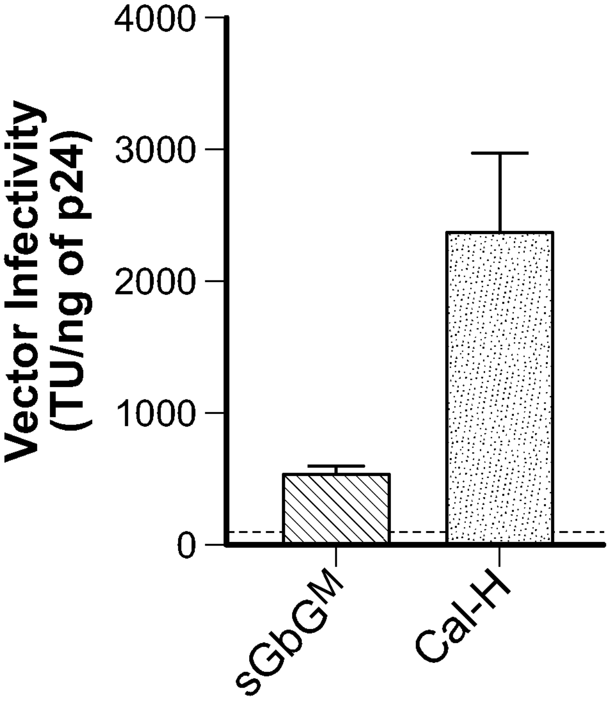
FIG. 45 sets forth the vector infectivity of the sGbG$^M$ and the sGbG$^M$-7SK/sh734 vectors.

It has been determined that the TL20c LV backbone significantly enhances the titer of the parental $sGbG^{M}$ lentiviral vector as illustrated in FIGS. 44A, 44B and 45. Comparable titers were obtained with the mono-vector expressing $sGbG^{M}$ and the dual therapeutic CAL-H vector suggesting that the expression of transgenes did not affect the titer measured as a percentage of HbF positive cells or hemoglobinization per cell as measured by the normalized MFI (data not shown). Importantly, inclusion of the 400 bp cHS4 insulator sequence in the TL20c backbone did not have an adverse effect on virus titer.

With reference to FIG. 44A, vector supernatant was generated by $CaPO_4$ mediated transient transfection of GPRG cells (see United States Patent Publication No. 2018/0112233) and stored at −80° C. All vectors were titered after 1 freeze thaw cycle. Titer (TU/mL)=% of HbF-positive cells/100)×dilution factor×number of cells/Volume (mL). Overall, the TL20 lentivirus vector backbone significantly improved the transduction efficiency of VSVg pseudotyped SIN-lentivirus vectors.

With regard to FIG. 45, vector stocks were produced by $CaPO_4$ transfection of GPRG cells and concentrated through a TFF system 700-fold. The vector titer was determined on MEL cells. The vector particle concentration was determined by an enzyme-linked immunosorbent assay (ELISA) specific for the HIV-1 p24 capsid protein. The values obtained were used to calculate average vector infectivity (introduction units [TU] per ng p24). Comparatively, the TL20c-rGbG$^M$-7SK/sh734 vector provided superior vector infectivity as compared with sGbG$^M$.

Equivalent Expression and Regulation of γ-Globin sGbG$^M$ Base Construct Compared to the Sh734-Containing Construct Since levels of sh7 expression correlated well with 6TG selection in the human K562 erythroid leukemia cell line, these cell models were used to provide evidence that (1) transferred γ-globin genes were correctly expressed and regulated as a consequence of erythroid differentiation (i.e. no expression in the undifferentiated state versus abundant expression following differentiation); (2) that sh734 did not significantly alter the expression of γ-globin; and (3) that expression of sh734 did not significantly influenced by erythroid differentiation (high level expression in the undifferentiated state vs. similar or lower expression following differentiation). Since the K562 cell constitutively expressed human fetal globin and did not express adult β-globin, this was believed to be a good system to validate the specificity of specific γ-globin transgene primers and probes.

Figure 46:
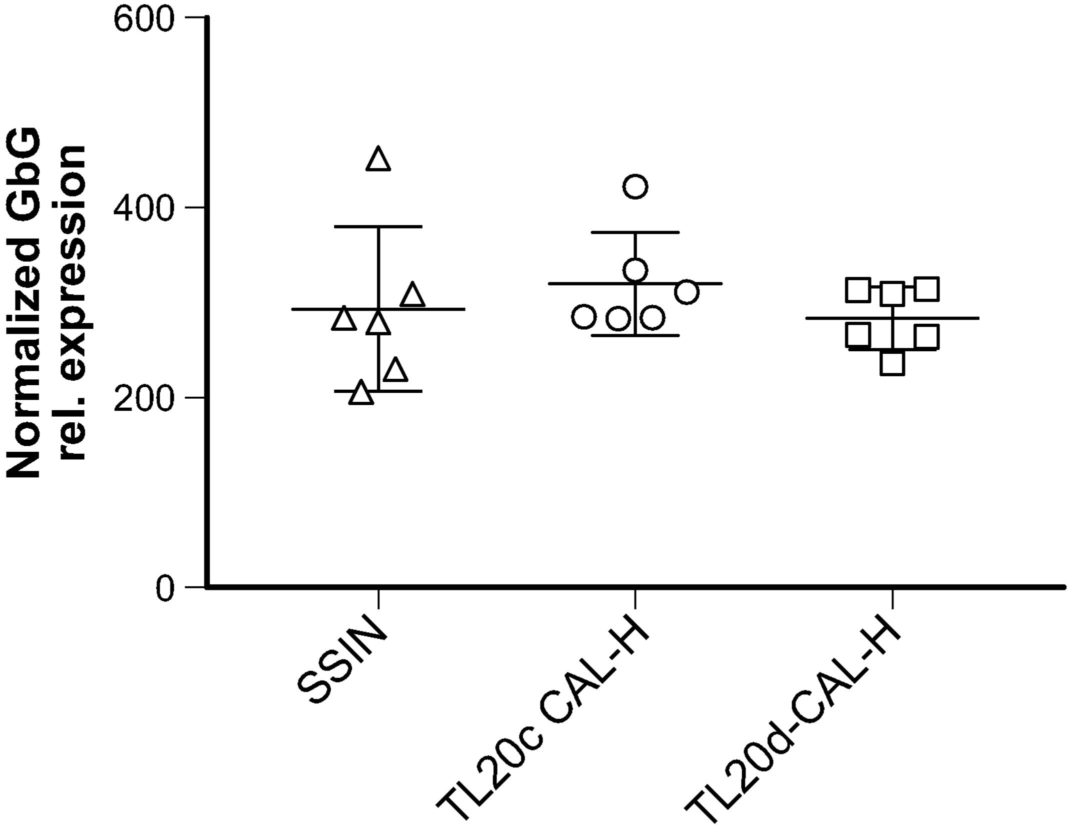
FIG. 46 illustrates the equivalent expression of sGbG$^M$ and between the monovector (pTL20c-sGbGM) and dual vector (pTL20c-sGbG$^M$-7SK/sh734).

As illustrated in FIG. 46, there was an equivalent expression of sGbG$^M$ between sGbG$^M$ (SSIN) monovector and the presently disclosed dual therapeutic TL20c-rGbG$^M$-7SK/sh734 vector construct. MEL cells were transduced with five two-fold dilutions (1:8-1:128) of LV VCM for 3d before treating the cells with 1 μM hemin and 3 mM HMBA in the standard induction protocol. Untransduced MEL cells and parallel, transduced uninduced cultures served as a negative control. Infectious virus titer HbF was determined at day 7 by measuring the % Hu-HbF positive cells by flow cytometry. RNA was extracted from cell pellets and g-globin expression was determined by RT-PCR normalized to expression of the housekeeping gene b2M. Relative expression of g-globin normalized to Infectious Virus Titer HbF (15-25%) is plotted for each vector. Values plotted represent all biological replicates from 3 separate experiments. There was no significant difference in expression of sGbGM between the different LV transduced cells. One way ANOVA, p=0.137 and Tukeys Multiple Comparison test p>0.05.

Figure 47:
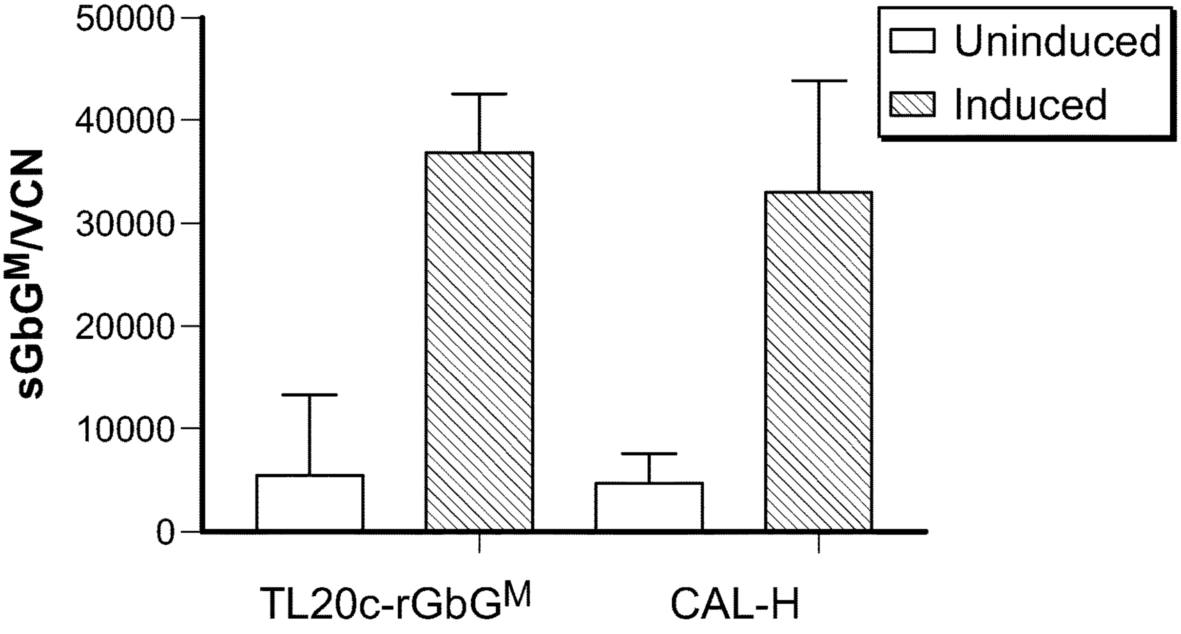
FIG. 47 illustrates the equivalent expression of the $^A$gamma-globin transgene in K562 cells transduced with the TL-20c-rGbG$^M$ vector or the TL20c-rGbGM-7SK/sh734 vector.

As shown in FIG. 47, there was a 12-fold increase in the expression of $^A$γ-globin mRNA levels in TL20c-rGbG$^M$ transduced K562 cells compared to a 7.9-fold increase in TL20c-rGbG$^M$-7SK/sh734 transduced cells. T test at p<0.05 was not significant. In addition, all specificity controls showed no cross-reactivity of our transgene-specific γ-globin primers with endogenous fetal Hb.

More specifically, K562 cells were transduced with TL20c GbGM or CAL-H for and passaged for 39 days. Cells were harvested and cultured in medium containing 1 μM hemin and 3 mM HMBA for 3-4 days. in a standard erythroid differentiation induction protocol. Relative expression of sGbGM was measured by RT-PCR and normalized to VCN to compare treatments. There was a 12-fold increase in the expression of Ag-globin mRNA levels in TL20crGbGM transduced K562 cells compared to a 7.9-fold increase in CAL-H transduced cells (T test, p<0.05 was not significant). No GbGM expression was detected in mock transduced cells uninduced or induced and no GbGM expression was detected in K562 cells transduced with the mono-vector rsh7-GFP uninduced or induced.

Figure 48:
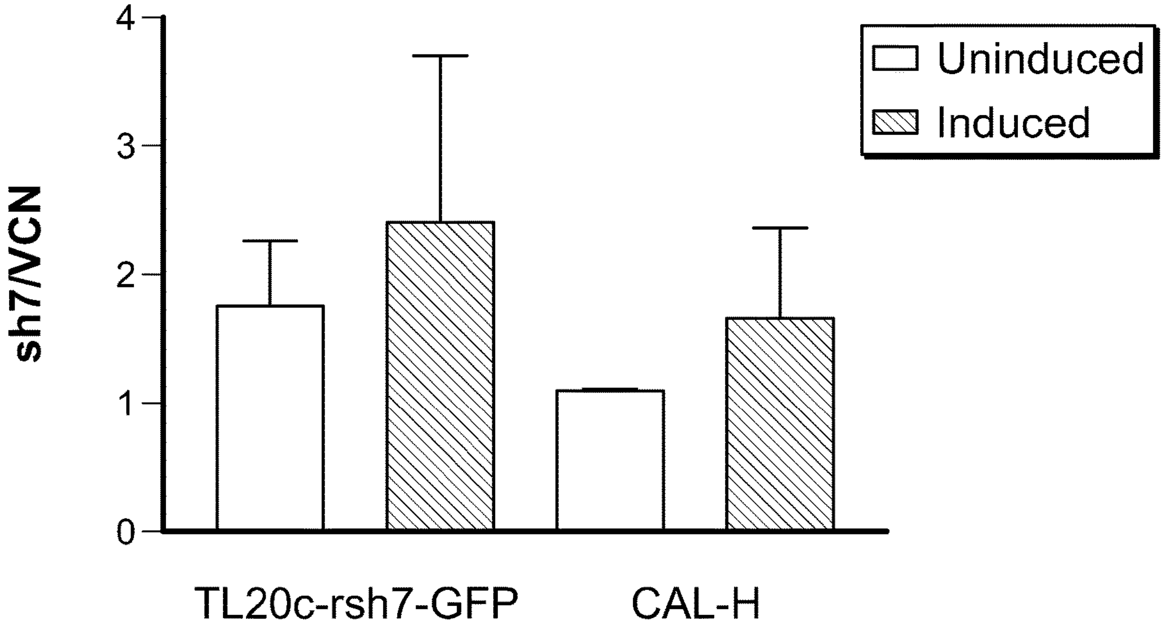
FIG. 48 illustrates that the expression of the sh7 transgene is unchanged in K562 cells during erythroid differentiation.

There is Little to No Transactivation of the Sh734 Promoter During Erythroid Differentiation Applicant has shown that the expression of the sh734 transgene remains unchanged in K562 Cells during erythroid differentiation (see FIG. 48). More specifically, K562 cells were transduced with TL20c GbGM or CAL-H for and passaged for 39d. Cells were harvested and cultured in medium containing 1 μM hemin and 3 mM HMBA for 3 to 4 days. in a standard erythroid differentiation induction protocol. Expression of sh734 was determined by RT-PCR relative to RNU38B and normalized to VCN to compare treatments. T-test was used to determine if differences in sh7 expression between groups reached significance. No significant differences were found at p<0.05. Control sh7GFP Induced and uninduced cultures p=0.69, CAL-H, p=0.226 and uninduced CAL-H vs rsh7-GFP, p=0.227. No sh734 expression was detected in the Mock and negative control TL20c-rGbGM groups.

Functional Screen of TL20 SIN LV Vectors in K562 Cells

Figure 9:
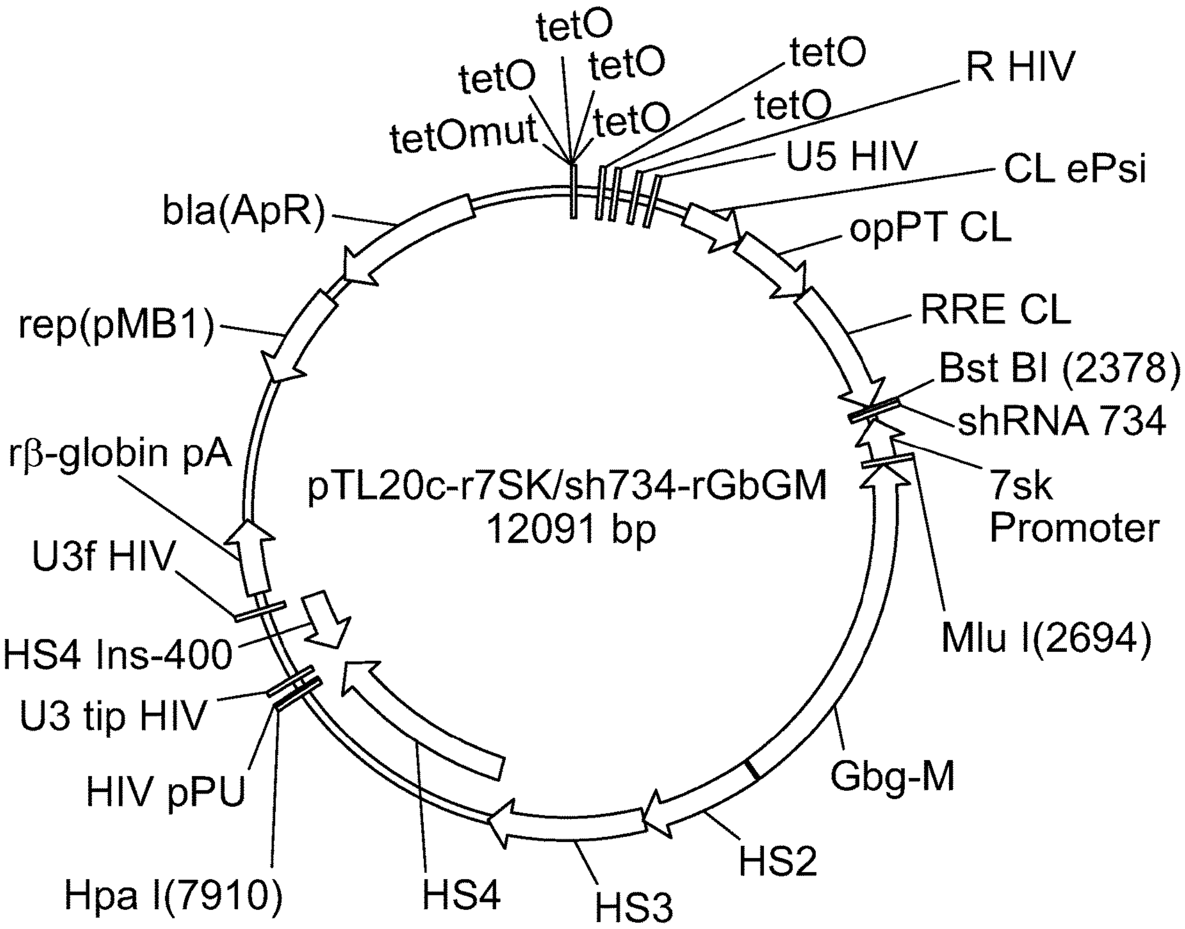
FIG. 9 provides a vector map of TL20c-r7SK/sh734-rGbG$^{M}$.

The TL20c-rGbGM-7SK/sh734 dual therapeutic lentiviral vector construct was identified using a functional screen in K562 cells that compared the effect of position and orientation of transgene relative to one other on transgene expression and in vitro 6-TG selection. Other dual transgene lentiviral vectors (see, e.g., SEQ ID NOS: 5 through 22) were constructed using the TL20c lentiviral vector backbone with the sh734 positioned either upstream or downstream to the GbGM cassette and in either a forward or revere orientation. TL20 self-inactivating lentiviral vectors with the cHS4 Ins-400 insulator tested included: TL20c-rGbGM-7SK/sh734 (FIG. 11), TL20c-rGbGM-r7SK/sh734 (FIG. 13), TL20c-7SK/sh734-rGbGM (FIG. 7), and TL20c-r7SK/sh734-rGbGM (FIG. 9). Other vectors tested included TL20d-rGbGM-7SK/sh734 without the cHS4 Ins-400 insulator (FIG. 21), a control sh7 reporter construct, TL20cw-7SK/sh734-UbC/GFP, and TL20c-rGbGM.

K562 cells were transduced with sh734 for 21 days before initiating 6TG treatment for 14 days (shaded areas). With reference to FIGS. 49A through 49G, vector copy number (VCN) was determined every two weeks from genomic DNA by multiplex RU5 qPCR and absolute quantitation from a standard curve using lentiviral vector (HIV-1-based LTR R-U5) target and human Apolipoprotein B (ApoB) reference sequences. Each data point represents the Mean±SD of three separate transductions (triplicate biological replicates).

TL20c-rGbGM-7SK/sh734 dual therapeutic lentiviral vector transduced K562 cells selected in 6TG culture demonstrated long term stability and expression of the gamma-globin transgene normalized to VCN equivalent to cells transduced with the parental GbGm LV vector or CAL-H transduced cells that were not treated with 6TG. These findings indicate that functional expression of the sh734 and the corrective sGbGM gene driven by separate Pol III and Pol II promoters, respectively, is mutually exclusive and that regulation of sGbGM is lineage dependent.

In this experiment, TL20c-rGbGM-r7SK/sh734, TL20c-7SK/sh734-rGbGM, and TL20c-r7SK/sh734-rGbGM lentiviral vector transduced K562 cells were only followed for two weeks post-6TG treatment. Interestingly, all dual construct vectors tested regardless of position or orientation of transgenes showed similar selection kinetics during 6TG treatment suggesting that transduced cells constitutively expressed a threshold level of sh7 that sustained HPRT knockdown allowing selection. We also observed a dose-response effect with the dual transgene self-inactivating lentiviral vectors where the VCN of 6TG treated cultures strongly correlates with sh7 expression and the dilution of virus used to transduce K562 cells (data not shown). All vectors tested showed similar expression levels of gamma-globin (relative expression GbGM/b2M) upon induction and viability (<0.5% Annexin V and 7-AAD double positive cells) (data not shown). The TL20c-rGbGM-7SK/sh734 LV vector proved most efficient in the expression of high levels of sh7, robust 6TG selection kinetics, and stability. These finding were consistent with results found in two previous experiments.

Figure 50:
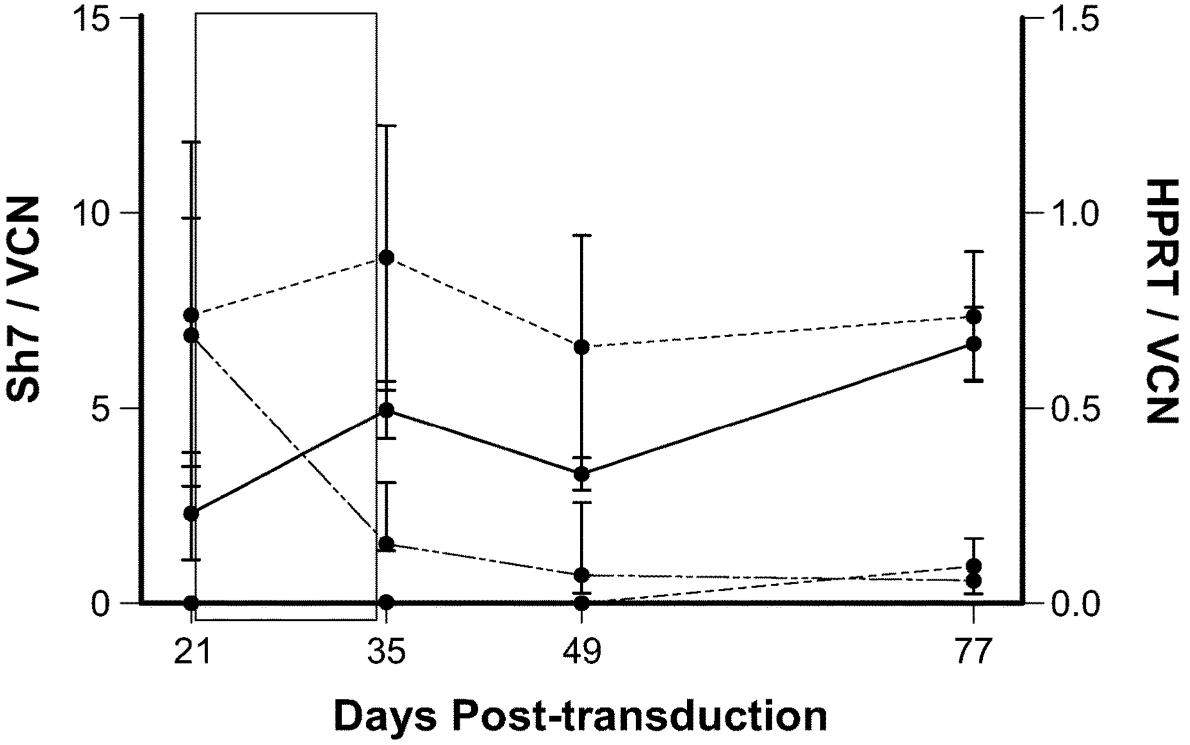
FIG. 50 illustrates that TL20c-rGbGM-7SK/sh734 transduced K562 cells expressing sh7 efficiently downregulate HPRT and confer long-term stability of 6-TG resistant cells.

With reference to FIG. 50, K562 cells were transduced with TL20c-rGbGM-7SK/sh734 or TL20c $GbG^{M}$21 days before initiating 6TG treatment. RNA was isolated and qRT-PCRT was performed to determine the number of copies of sh734 relative to RNU38B and normalized to VCN (relative expression/VCN). Relative expression levels of sh734 and HPRT were determined every two weeks post-transduction. The graph illustrated sh734 plotted on the left Y-axis and the percent of HPRT knockdown related to mock transduced cells (HPRT/mock×100) and normalized to VCN plotted on the right Y axis.

Figure 49A:
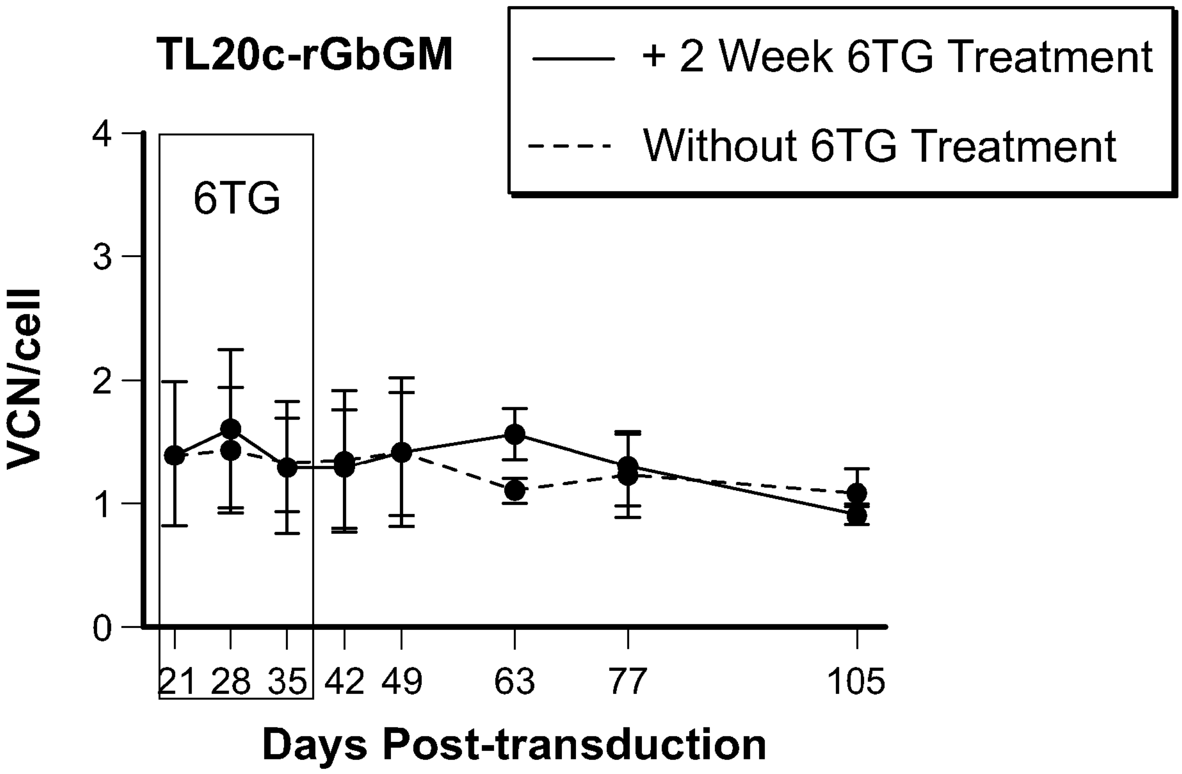
FIG. 49A sets forth a graph indicating that K562 cells transduced with the negative control GbGM mono-vector (TL20c-rGbGM) showed no increase in vector copy number during 6TG treatment.
Figure 49B:
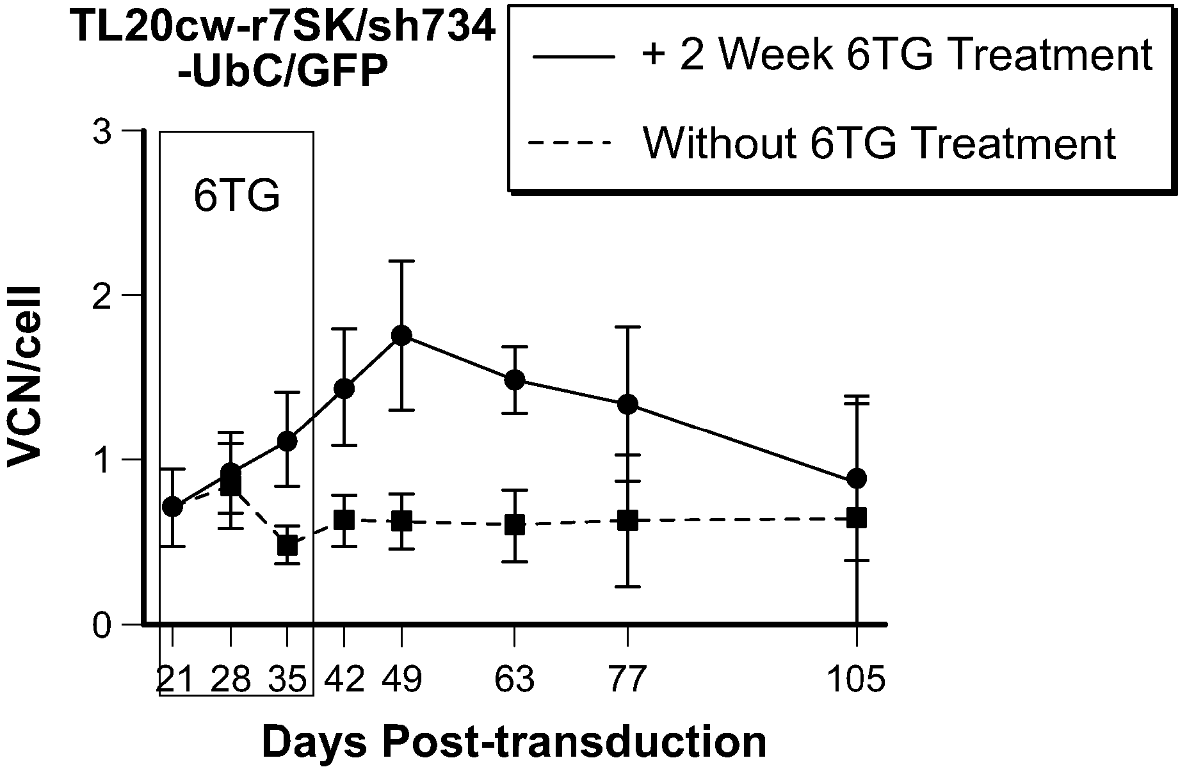
FIG. 49B sets forth a graph indicating that the control sh7 GFP reporter construct showed an increase in vector copy number during 6TG treatment which was associated with positive selection. A gradual decline in vector copy number over time was observed, despite the percentage of GFP positive cells being maintained in the culture.
Figure 49C:
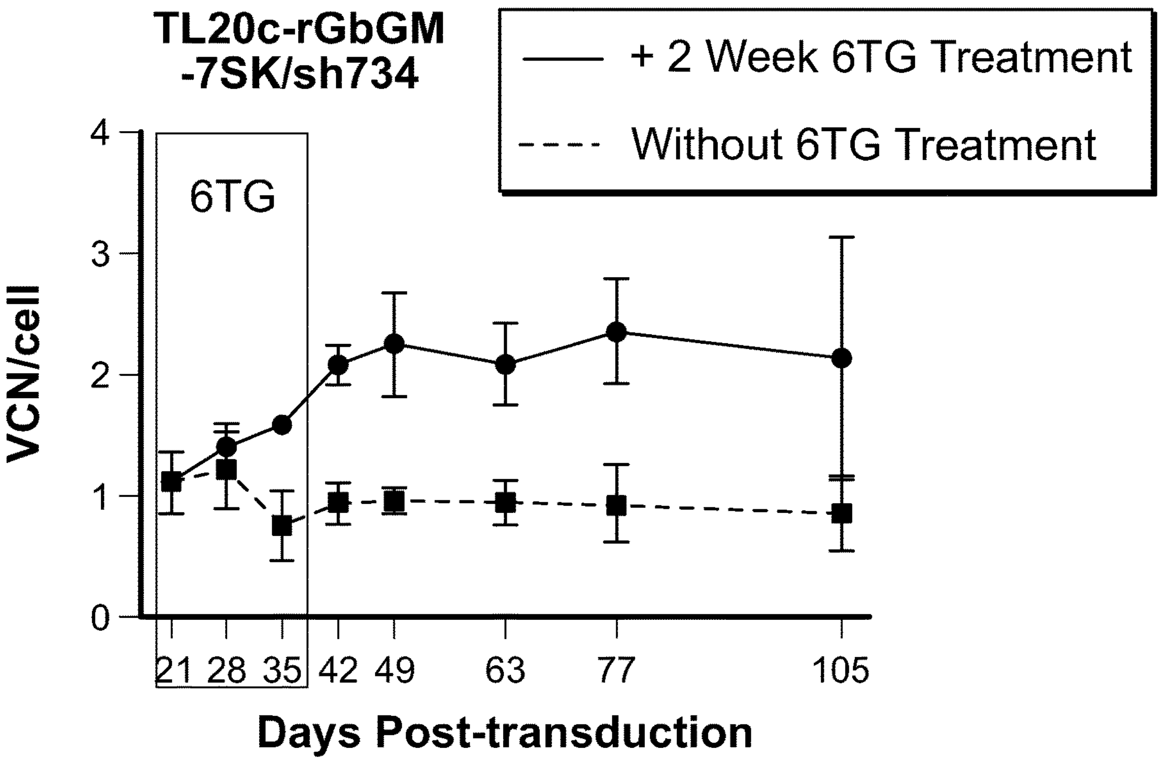
FIG. 49C provides a graph indicating the 6TG selection kinetics and stability of TL20c-rGbGM-7SK/sh734.
Figure 49D:
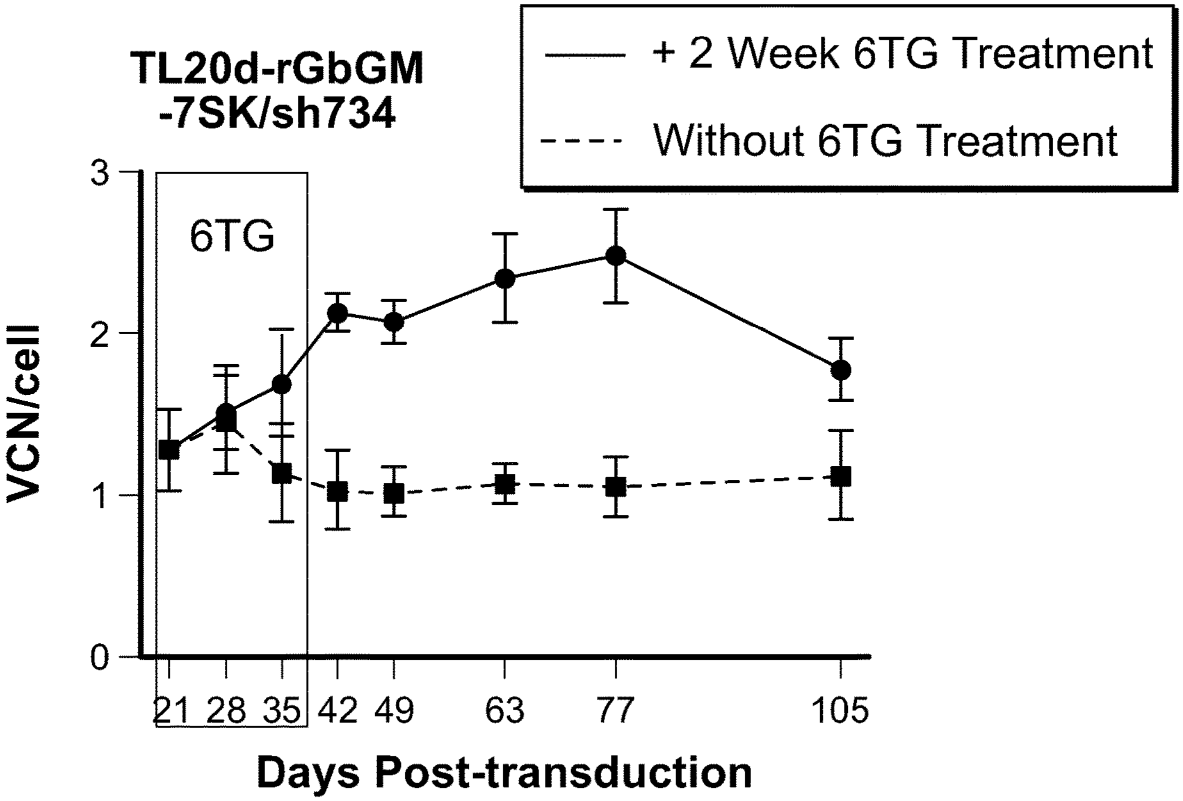
FIG. 49D provides a graph showing that removal of the cHS4 Ins-100 insulator from the TL20c-rGbGM-7SK/sh734 vector provides comparable 6TG selection kinetics and stability as compared with the TL20c-rGbGM-7SK/sh734 vector. This indicates that removal of the insulator does not adversely affect expression or result in silencing of the sh7 transgene in the lentiviral construct.
Figure 49E:
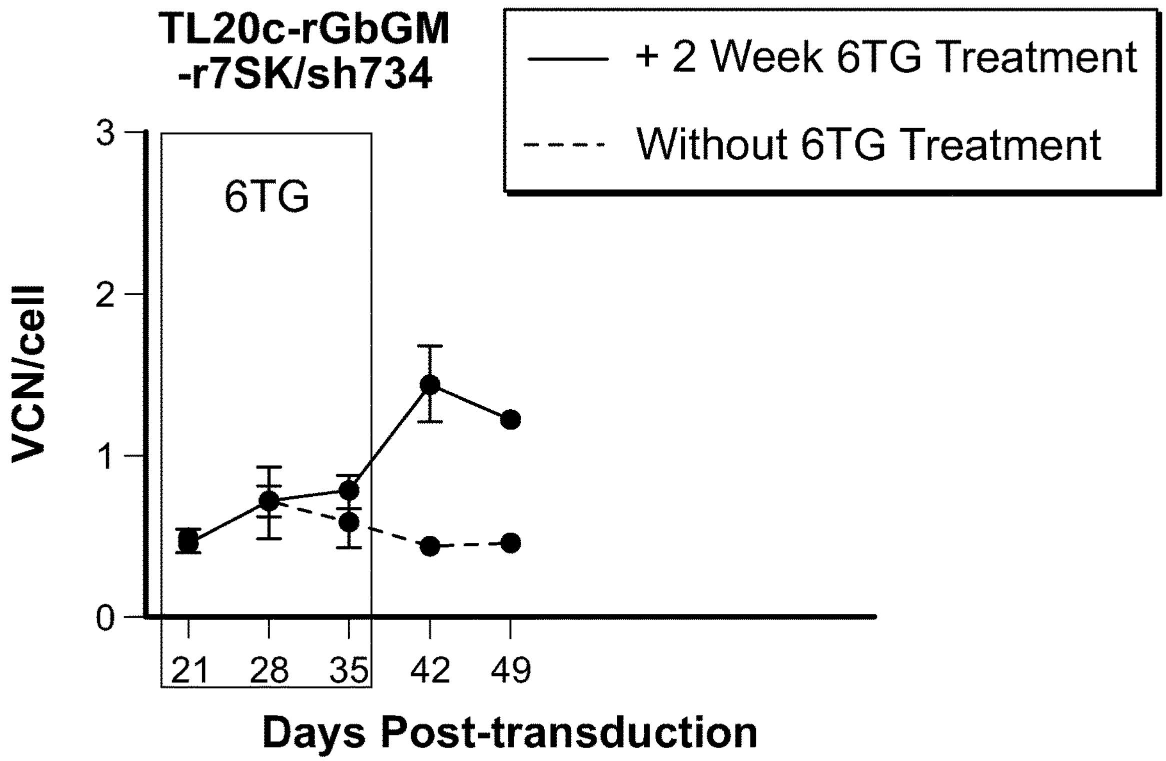
FIG. 49E provides a graph indicating the 6TG selection kinetics and stability of TL20c-rGbGM-r7SK/sh734.
Figure 49F:
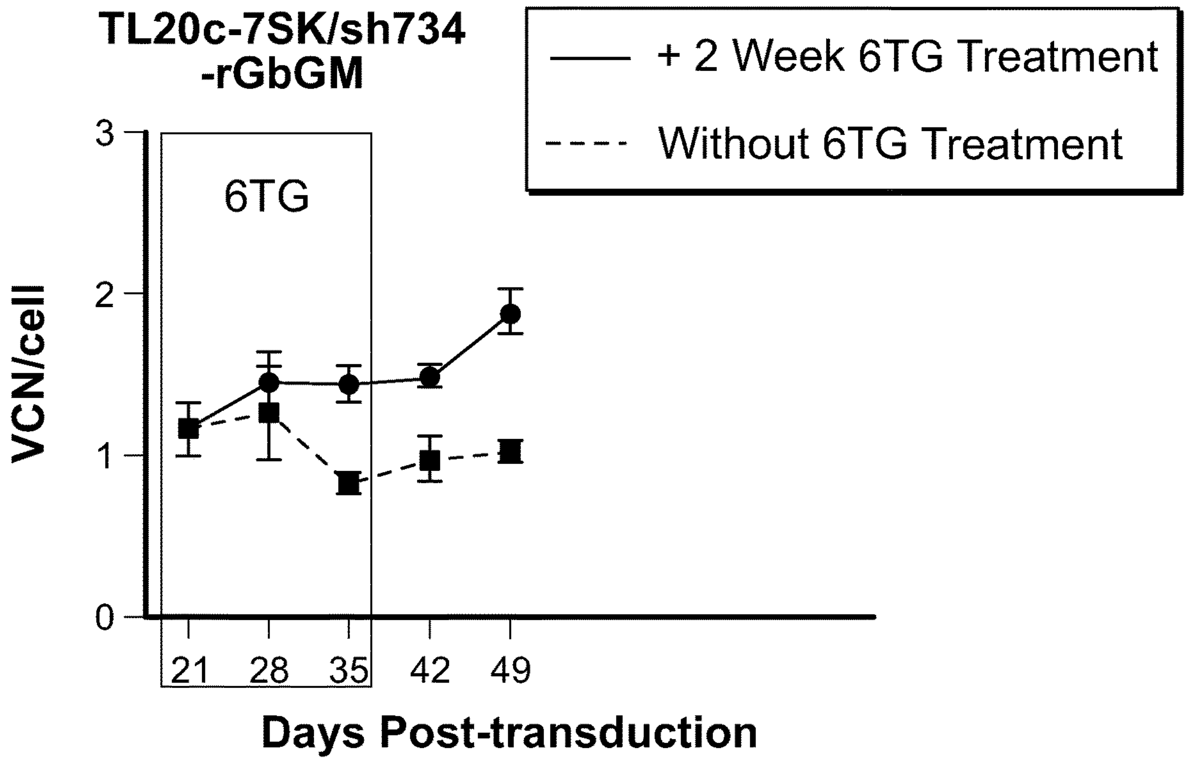
FIG. 49F provides a graph indicating the 6TG selection kinetics and stability of TL20c-rGbGM-r7SK/sh734.
Figure 49G:
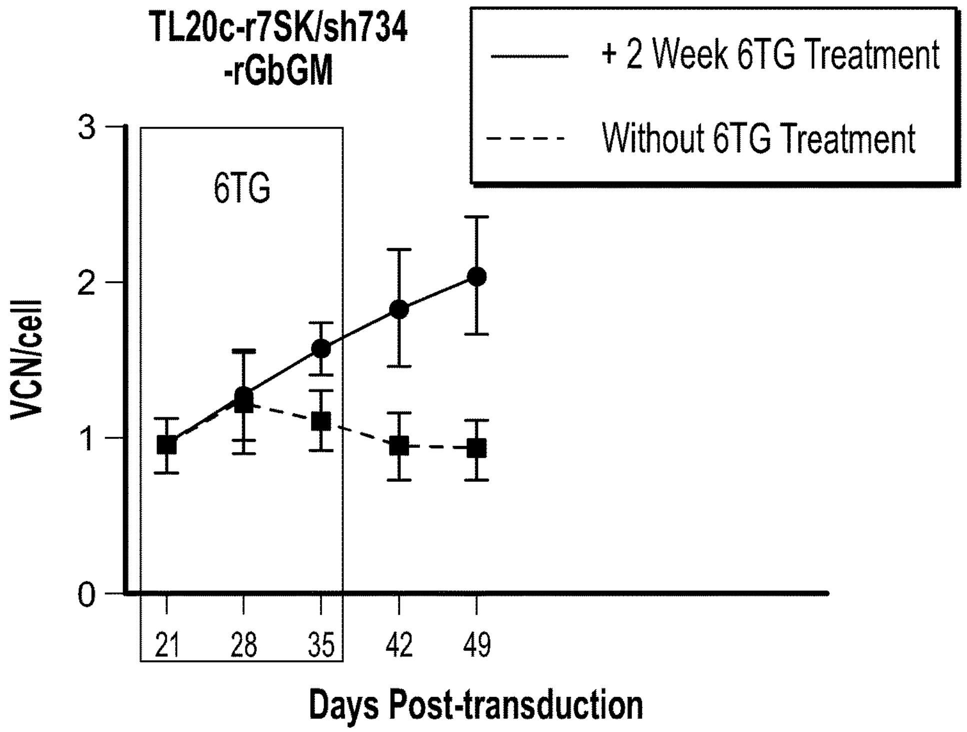
FIG. 49G provides a graph indicating the 6TG selection kinetics and stability of TL20c-r7SK/sh734-rGbGM.
Figure 49H:
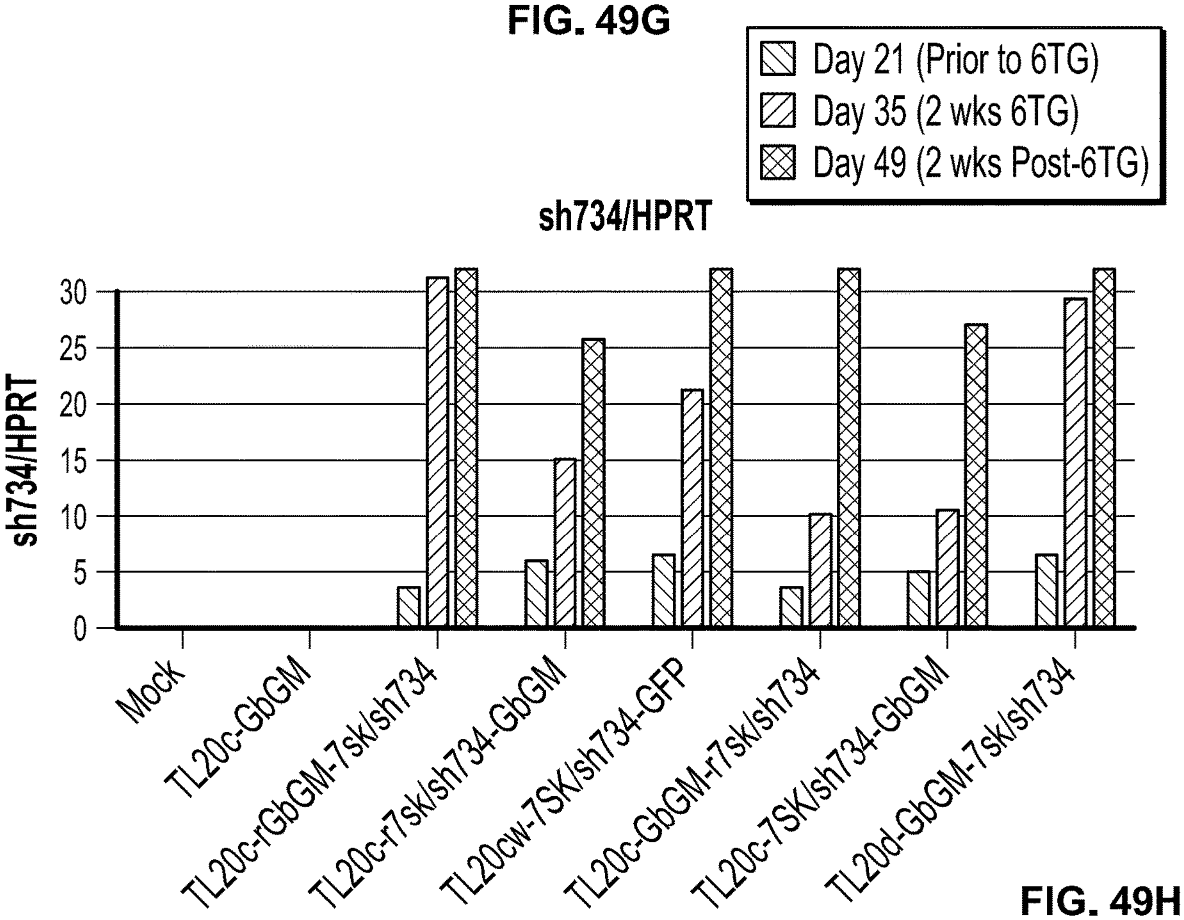
FIG. 49H shows the sh734/HPRT ratio as a measure of knockdown efficiency.
Figure 49I:
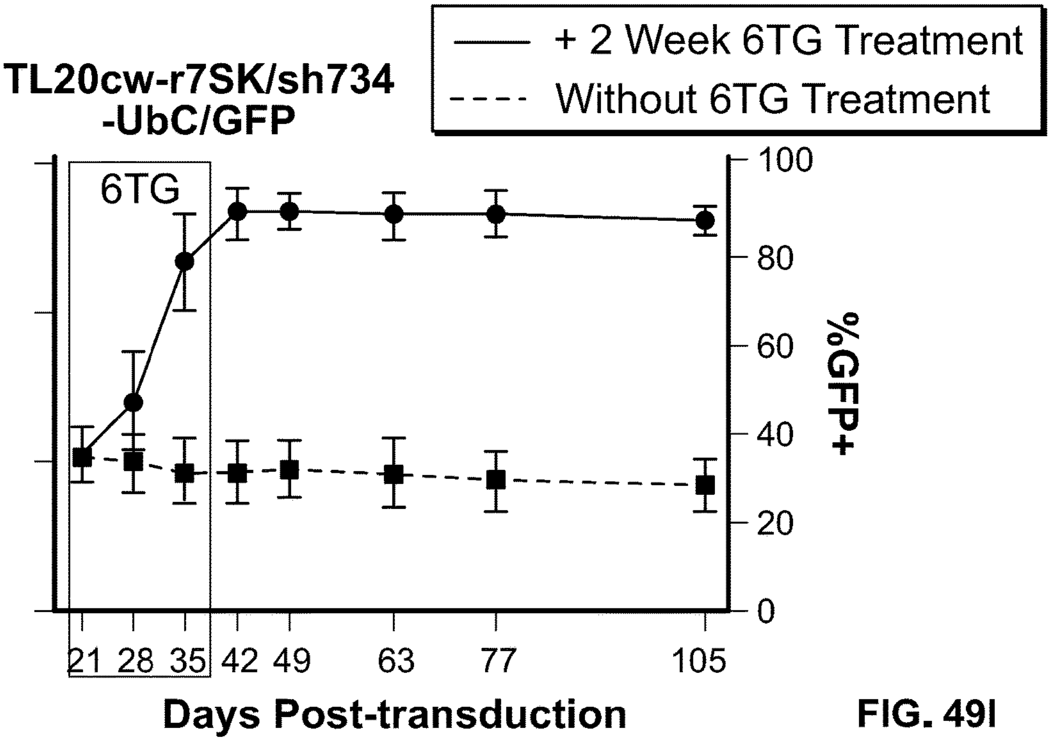
FIG. 49I illustrates that a control sh7 lentiviral vector expressing GFP showed a marked increase in sh7 gene-modified cells 14 days post 6TG treatment. At day 21, K562 cultures transduced with the sh7-GFP reporter construct were 35% GFP+ and increased to 88% GFP+ cells by day 42 following 6TG treatment. These findings suggest that sh7 is constitutively expressed in transduced K562 cells for greater than 3 months in culture at levels sufficient to maintain HPRT suppression and 6TG resistance without evidence of silencing or toxicity. Importantly, the selected cell population maintained long-term proliferative stability great than two months after discontinuation of 6TG selective pressure.
Figure 49J:
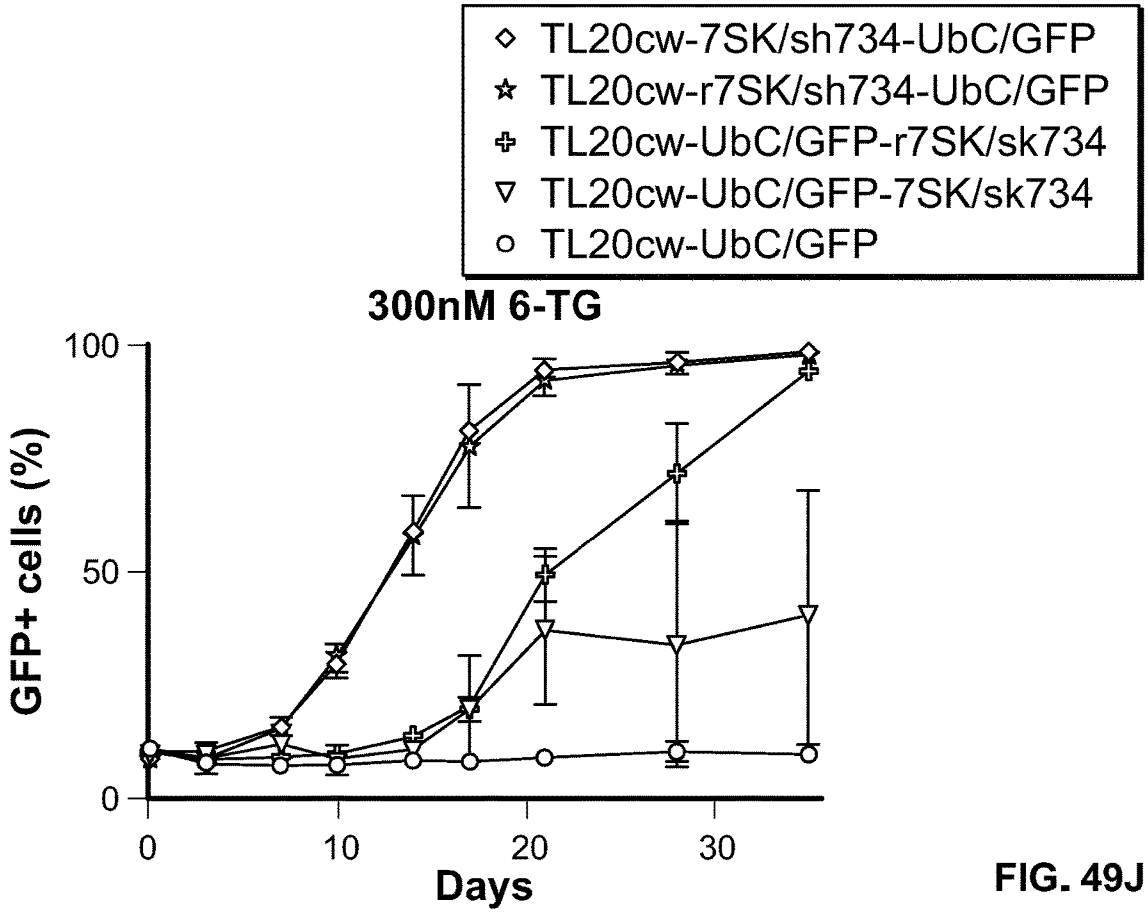
FIG. 49J illustrates the in vitro selection of K562 cells transduced with sh734-GFP reporter constructs. To establish proof of concept for LV transduced cells to express sh734 RNA and confer 6TG resistance, monitored the enrichment of gene-modified K562 GFP+ cells in cultures treated for 14d with 6TG (300 nM). The two vectors with sh734 positioned upstream of GFP in either orientation to the GFP reporter cassette in the sense orientation showed markedly faster time to enrichment of gene-modified cells compared to cultures transduced with vectors where sh734 was positioned downstream of GFP. In K562 cells, the relative level of expression of sh734/% GFP correlated with efficient knockdown of HPRT and rapid 6TG selection.
Figure 51A:
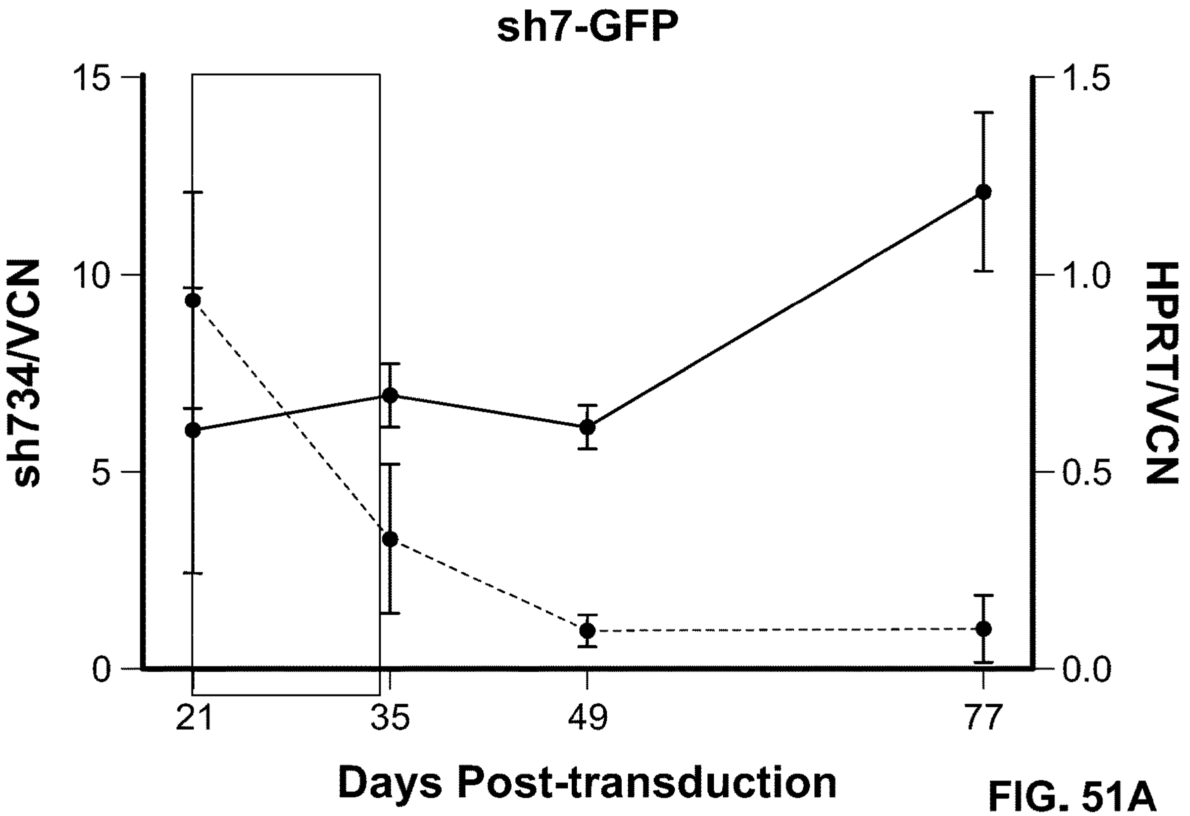
FIGS. 51A and 51B illustrate that K562 cells transduced with the TL20c-rGbGM-7SK/sh734 vector or a sh7-GFP mono-vector reporter construct exhibits similar levels of sh7 expression and kinetics of the HPRT knockdown and 6TG selection.
Figure 51B:
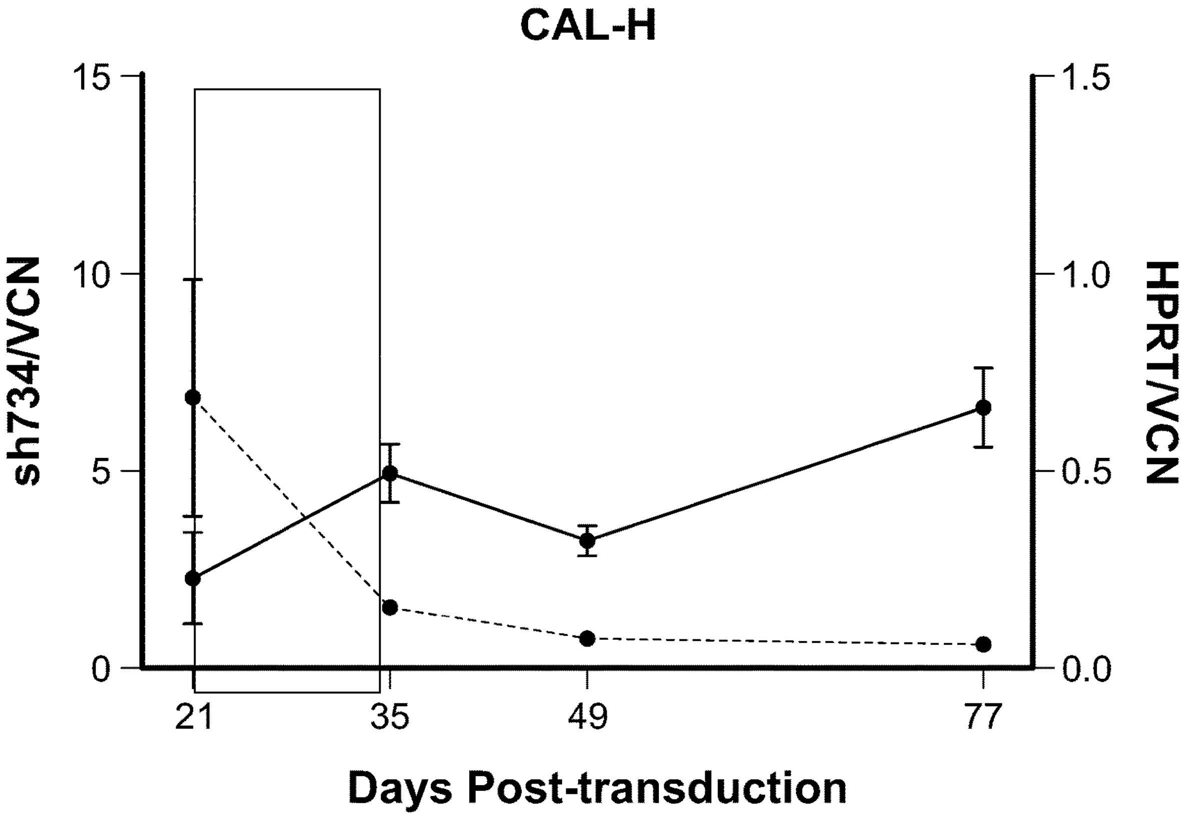

K562 cells were transduced with the sh7-GFP mono-vector reporter construct or CAL-H for 21 days before initiating 6TG. RNA was isolated, and qRT-PCR performed to determine the number of copies of sh734 relative to RNU38B and normalized to VCN (relative expression/VCN). FIGS. 51A and 51B illustrates the percent HPRT knockdown relative to mock transduced cells (HPRT/mock×100) normalized to VCN is plotted on the right Y axis. Overall, K562 cells transduced with the CAL-H or the sh7-GFP mono-vector reporter construct exhibited similar levels of sh734 expression and kinetics of HPRT knockdown and 6TG selection. Indeed, 6TG treatment resulted in a significant drop in HPRT levels (less than 10% of untreated cells) in cells expressing sh734. 14 days after selection, HPRT levels became undetectable in transduced cultures. 6TG selected K562 cells continued to grow and express sh734 after 3-months in culture (data not shown). These findings suggest that once resistance is established, sh734 transduced cells persist and there is little evidence of silencing in K562 cells. At day 21, K562 cultures transduced with the sh7-GFP reporter construct were 35% GFP+ and increased to 88% GFP+ cells by day 42 following 6TG treatment. With reference to FIG. 49H, the TL20c-rGbGM-7SK/sh734 LV and TL20d-rGbGM-7SK/sh734 LV vector showed rapid selection during the 2 week 6TG treatment (d35) compared to the other constructs tested.

Figures 52A, 52B, 52C:
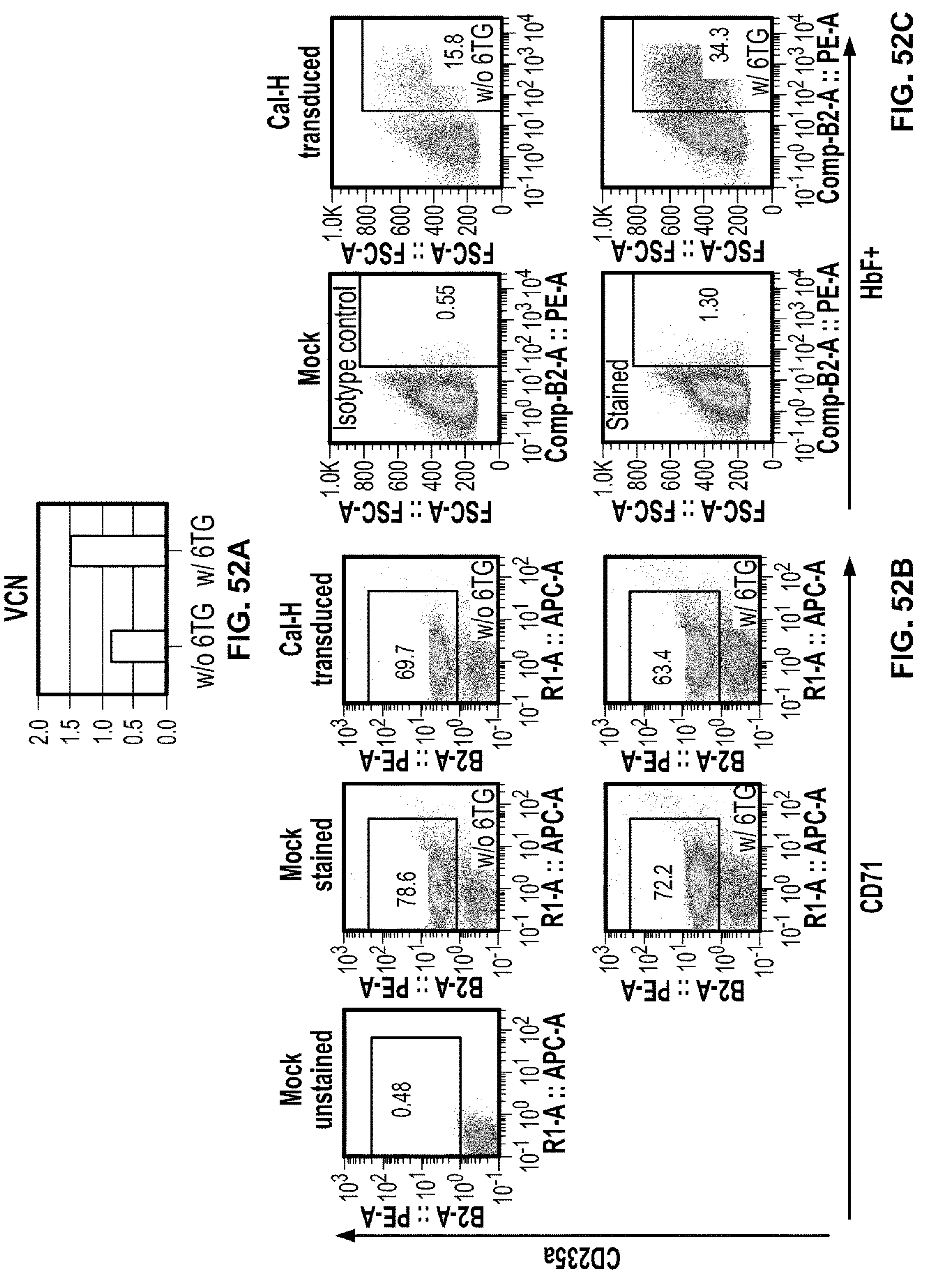
FIGS. 52A, 52B, and 52C illustrate a CD34+ extended culture under 6TG selection followed by erythroid differentiation.
Figure 53:
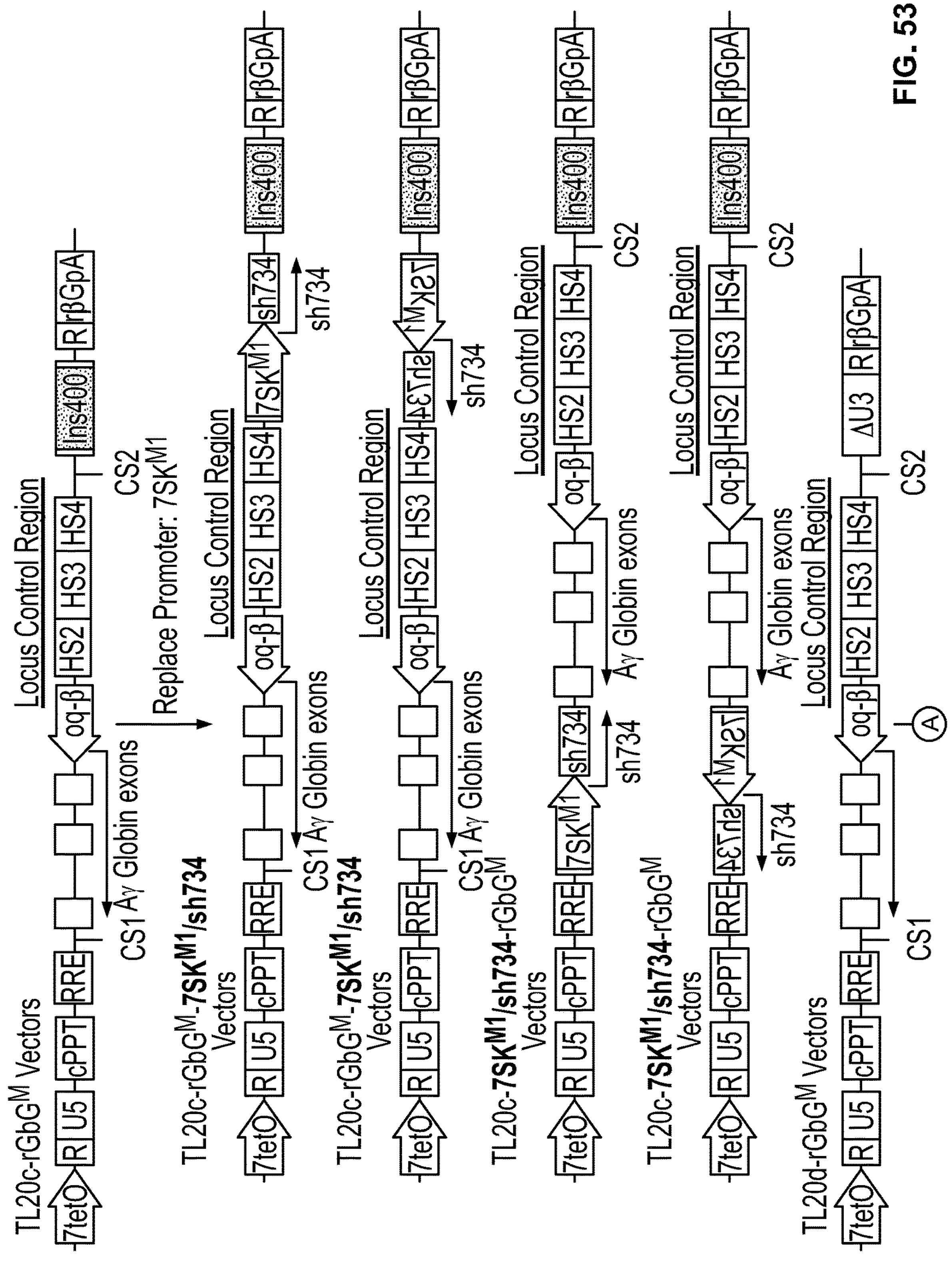
FIG. 53 illustrates constructs for a plurality of different vectors, comparatively illustrating the differences between the components of each of the vectors.

CD34+ cells were thawed and pre-stimulated by culturing overnight $2\times10^{4}$ cells in 0.1 mL of SFEM II medium supplemented with SCF/Flit-3/TPO/IL-3. Pre-stimulated cells were infected with Cal-H vector at MOI=20 with spinoculation (2500 rpm and 1.5 hrs) in the presence of polybrene (6 ug/ml). The cells were taken out of centrifuge and put back in incubator for 4 hrs before exchanging to the SFEM medium supplemented with StemSpan™ CD34+ Expansion Supplement (100×) and UM171(67 nM)/SR1 (750 nM). Cells were incubated at 37° C. and 5% CO2 for 4 days. Starting from day 4, 10 mM of 6-TG stock solution was added to CD34+ cells for a final concentration at 200 nM. Fresh extended culture medium with or without 6TG was refreshed every 3-4 days. (see FIG. 52A) At day 14, VCN assay was carried out for Cal-H-transduced cells cultured in the presence of 6-TG or in the absence of 6-TG. At day 15, CD34+ cells were washed and seeded in erythroid expansion medium as SFEM II medium supplemented with erythroid expansion supplement. Fresh erythroid expansion medium was added at day 2 and 4. From day 21, erythroid medium (SFEM II medium supplemented with 10U/mL of EPO was added every 3 days. At day 28, flow assay showed 60-80% of untransduced and transduced cells were CD235a+(see FIG. 52B) and HbF intracellular staining showed 34.3% of Cal-H transduced cells under 6-TG selection are HbF+ compared to 15.8% in the absence of 6-TG (see FIG. 52C).

This experiment provides proof of concept for the functional regulation of CAL-H transgene expression in primitive CD34+ HSPC. Functional regulation of sh7 and GbGm expression in CALH modified CD34+ HSPC is shown by an increase in the average VCN following 6TG selection and a >2-fold increase in the % of HbF cells following in vitro erythroid differentiation and maturation.

CONCLUSION

The TL20c-rGbGM-7SK/sh734 dual therapeutic LV construct was identified using a functional screen in K562 cells that compared the effect of position and orientation of the transgenes relative to each other on transgene expression, long term stability and function and in vitro 6-TG selection. Infectious titer HbF and expression of the $sGbG^{M}$ cassette was improved when inserted in the TL20c LV backbone with the 400 bp cHS4 insulator in reverse orientation. A high-level of sh734 expression and erythroid lineage-directed gene expression in the dual therapeutic TL20c-rGbGM-7SK/sh734 vector expression was observed suggesting mutually exclusive expression of transgenes and minimum interactions between the globin gene regulatory elements and Pol III promoter. Furthermore, TL20c-rGbGM-7SK/sh734 transduced K562 cultures selected with 6TG continued to express sh734 and maintain function for more than 3-months and could be induced to differentiate toward erythroid cells and upregulate the expression of the gamma-globin transgene about 8-fold. Since transgene silencing and variability are highly dependent on vector backbone and cell type, an investigation was conducted as to whether TL20c-rGbGM-7SK/sh734 would perom as well in CD34+ HSPC as it did in the K562 cell model. CD34+ HSCs were transduced with the TL20c-rGbGM-7SK/sh734 lentiviral vector and then cultured cells in medium supplemented with UM171 and SR1 to preserve the more primitive HSCs from differentiating in extended cultures treated with 6TG. After 2 weeks 6TG selected CD34 HSC cultures were transferred to erythroid differentiation medium for another 2 weeks and the percentage of HbF positive cells was measured by flow cytometry. 6TG selected cultures showed a 2-fold increase in HbF positive cells, suggesting that primitive HSCs transduced with the TL20c-rGbGM-7SK/sh734 lentiviral vector could undergo in vitro selection and express the gamma-globin in a lineage specific control.

Example 3—Design of Polymerase II (Pol-II)-Dependent shRNA for Knock Down of HPRT and its Applications for 6-TG Selection It has been well known that some polymerase III-dependent short-hairpin RNAs have overexpression issues and can induce acute cytotoxicity. Some pol III promoters, e.g. the U6, may lead to a much higher expression of short-hairpin RNAs (see Mol Ther. 2006 October; 14(4):494-504, which suggests the use of a pol II promoter driven shRNA to solve any toxicity issue), the disclosure of which is hereby incorporated by reference herein in its entirety). This is an important concern when considering the use of RNA interference (RNAi) as a potential therapeutic approach, especially in stem cell gene therapy. Here, polymerase II was used as alternative promoter to express microRNA so as to effectuate knockdown of the expression of HPRT. A CRISPR/Cas9 gene editing approach was utilized, and a Cas9 with a single guide RNA (Cas9 RNP) targeting CCR5, together with a single-stranded DNA oligonucleotide donor (ssODN) encoding an HPRT Pol II driven shRNA, was used to enable efficient replacement of the CCR5 locus with a functional HPRT miRNA. The ability to knock-in Pol II-driven shHPRT into a CCR5 region to knockdown HPRT and select for the cell line with a hairpin miroRNA expression gene under 6TG was demonstrated. For knock-in of sh211 and sh734, the obvious cytotoxicity in K562 cells was not observed.

Two types of microRNA-based shRNAs for knockdown of HPRT (Table 1) were designed. One type is a de novo design of artificial miroRNA shRNA (see Fang, W. & Bartel, David P. The Menu of Features that Define Primary MicroRNAs and Enable De Novo Design of MicroRNA Genes. Molecular Cell 60, 131-145). Two candidates for this design were employed, including miRNA734 (111nt) (SEQ ID NO: 23 or SEQ ID NO: 67) and miRNA211(111nt) (SEQ ID NO: 24 or SEQ ID NO: 68). Another type of microRNA-based shRNA was based on a third generation miRNA scaffold modified miRNA 16-2 (miRNA-3G) (see Watanabe, C., Cuellar, T. L. & Haley, B. Quantitative evaluation of first, second, and third generation hairpin systems reveals the limit of mammalian vector-based RNAi. RNA Biology 13, 25-33 (2016)). Two further candidates were employed, including sh734 and sh211, each embedded in a miRNA 3-G (165nt) (SEQ ID NO: 25 and SEQ ID NO: 25, respectively).

Figure 24:
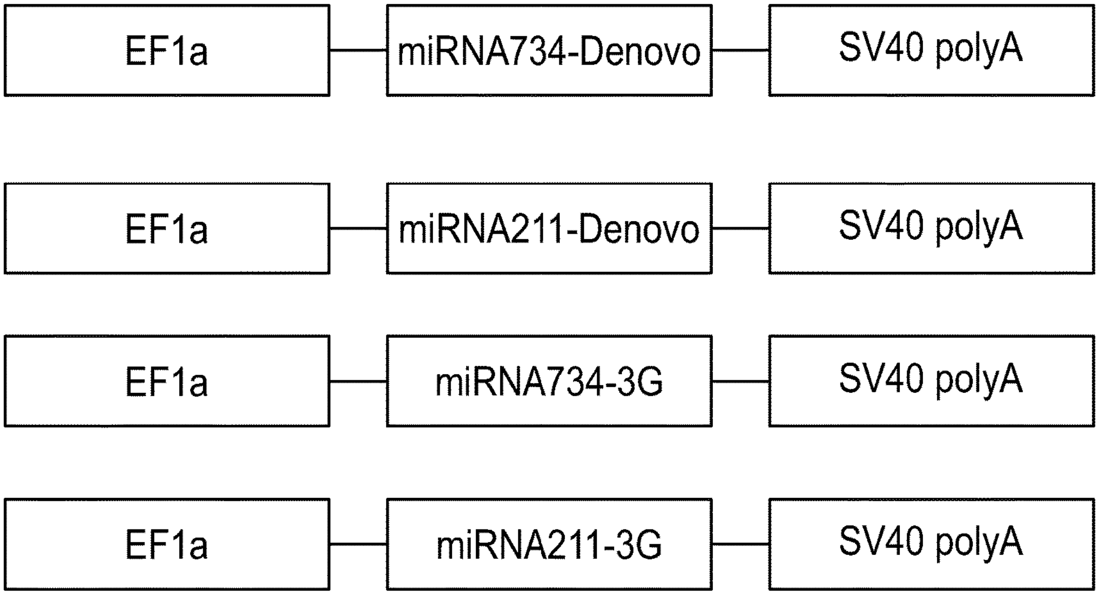
FIG. 24 provides a scheme for EF1a-driven microRNA-based shRNAs for knockdown of HPRT.
Figure 25A:
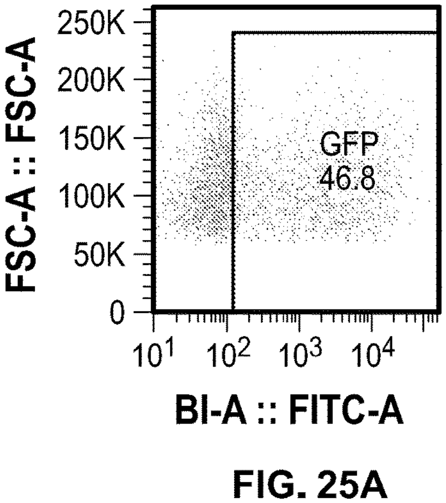
FIGS. 25A and 25B illustrate 6TG selection of K562 transiently transfected with sh734, miRNA RNA constructs delivered in nanocapsules. $1\times10^5$ of K562 cells were incubated with EF1a-GFP/EF1a-sh734-3G/EF1a-sh211-3G/7sk-sh734 nanocapsules (200 ng of DNA) for 4 hours. 6TG was added into the culture medium to the final concentration of 1 μM on day 2.
Figure 25B:
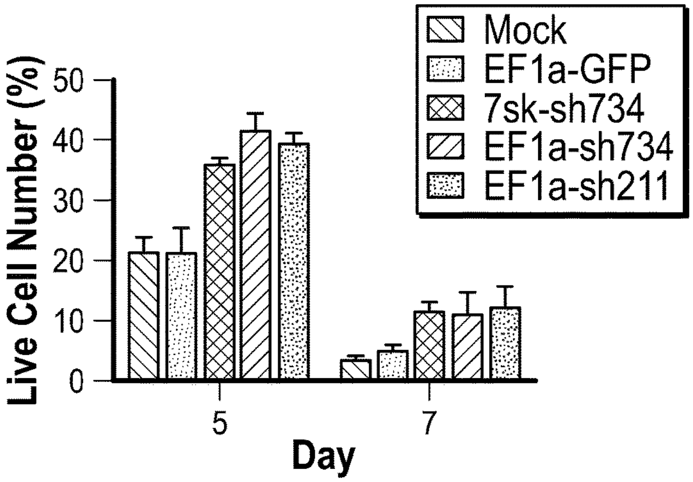

To demonstrate their biological functions, each of shRNAs having SEQ ID NOS: 23, 24, 25, and 26 were combined (each individually) with pol II promoters, namely with EF1a (SEQ ID NO: 64) and with SV40 polyA (SEQ ID NO: 65), and the corresponding DNA cassettes were synthesized to provide SEQ ID NO: 36, SEQ ID NO: 37, SEQ ID NO: 38, and SEQ ID NO:39 as set forth in Table 2 (see also FIG. 24). K562 cells were transiently transfected with nanocapsules incorporating each of the aforementioned shRNA DNA cassettes and incorporated into those cells under 6-TG selection. The cells transfected with shRNA showed resistance to 6-TG selection as demonstrated at least in FIGS. 25A and 25B. It is believed that the cells transfected with all shRNA DNA cassettes have higher survival cell number than control group under 6-TG treatment.

Figure 26:
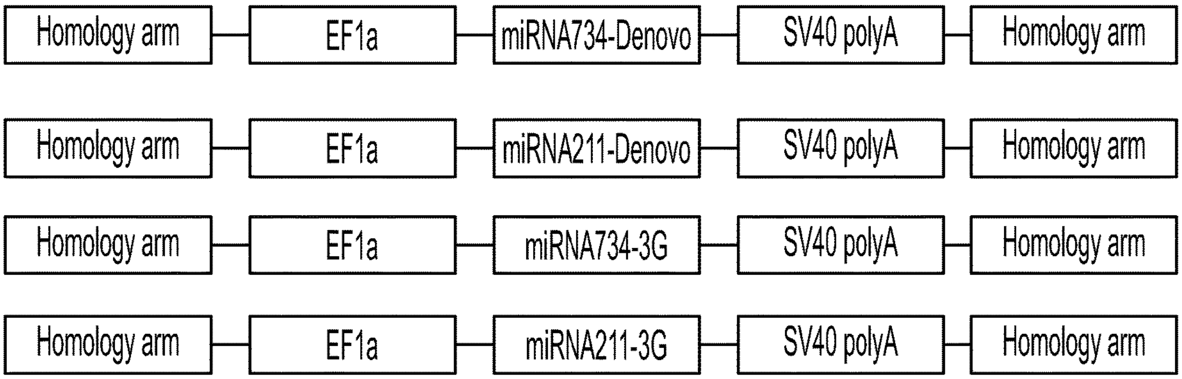
FIG. 26 provides a scheme of EF1a-driven microRNA-based shRNAs with homology arm for knock-in in CCR5 region.
Figure 27A:
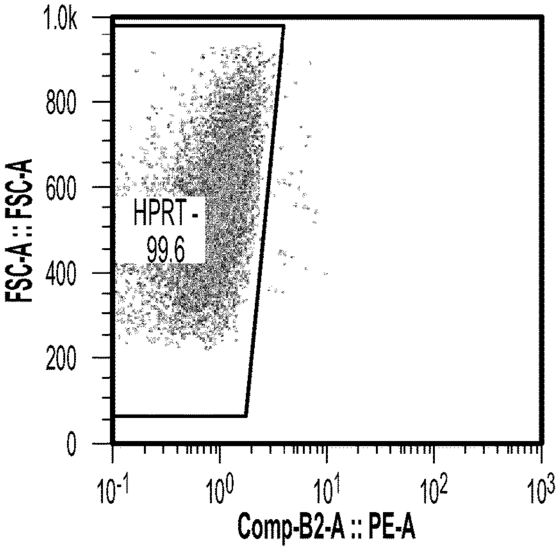
FIGS. 27A, 27B, and 27C illustrate FAC staining of control K562 cells for HPRT: Unstained (FIG. 27A), HPRT positive cells (FIG. 27B), and K562 cells with knock-in of EF1a-sh2l 1-3G at the CCR5 locus (FIG. 27C). Gates show frequencies of cells that are HPRT negative.
Figure 27B:
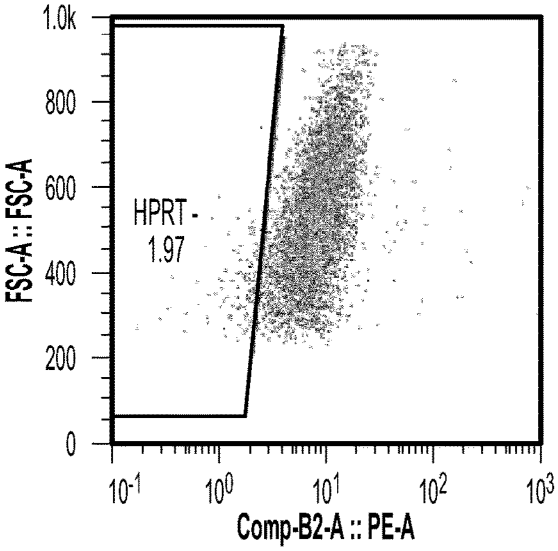
Figure 27C:
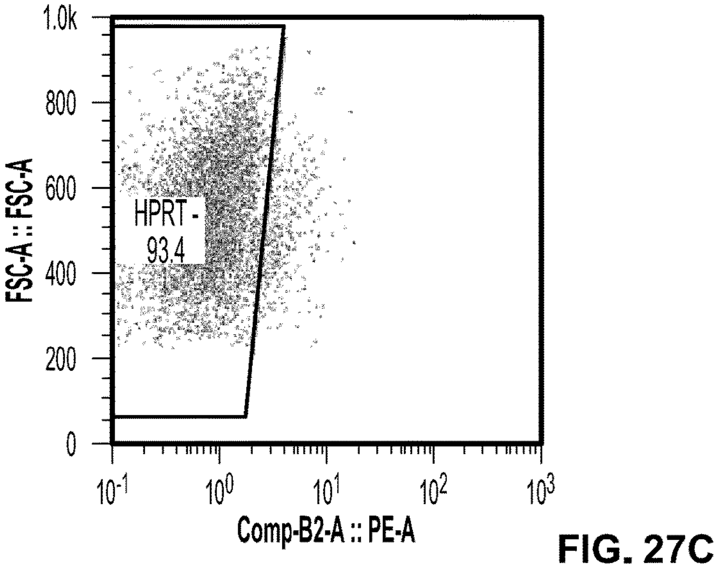

To investigate the long-term stability of the shRNAs, we also used CRIPSR technologies to knock-in shRNA-expressing cassettes into the CCR5 region to knockdown HPRT (see FIG. 26) and selected the cell line with a hairpin miroRNA expression gene under 6-TG (see also Table 3, SEQ ID NOS 40, 41, and 42; and also, SEQ ID NOS: 62 and 63). After three weeks of 6-TG selection, HPRT staining showed K562 cells with knock-iof Pol-II-driven sh211-3G had significantly lower HPRT levels (12%) as compared with that of the control (i.e. untransduced cells) (99%) (FIGS. 27A, 27B, and 27C).

TABLE 1

Pol II-driven microRNA-based shRNAs for knockdown of HPRT.

| Name | Length (nt) | SEQ ID NO: | Sequence |
|---|---|---|---|
| miRNA734-Denovo | 111 | 23 | acccgtacatatttttgtgtagctctagtttatagtcaagggcatatcc ttgtgtttttttgaaggatatgcccttgactataaactagcgctacac tttttcgtcttgt |
| miRNA211-Denovo | 111 | 24 | acccgtacatatttttgtgtagctctagttataaatcaaggtcataacc ttgtgtttttttgaaggttatgaccttgatttataactagcgctacact ttttcgtcttgt |
| miRNA734-3G | 166 | 26 | CCGGATCAACGCCCTAGGTTTATGTTTGGA TGAACTGACATACGCGTATCCGTCTTATAG TCAAGGGCATATCCTGTAGTGAAATATATA TTAAACAAGGATATGCCCTTGACTATAATA CGGTAACGCGGAATTCGCAACTATTTTATC AATTTTTTGCGTCGAC |
| miRNA211-3G | 166 | 25 | CCGGATCAACGCCCTAGGTTTATGTTTGGA TGAACTGACATACGCGTATCCGTCTTTTAA ATCAAGGTCATAACCGTAGTGAAATATAT ATTAAACAGGTTATGACCTTGATTTAAAAT ACGGTAACGCGGAATTCGCAACTATTTTAT CAATTTTTTGCGTCGAC |

TABLE 2

Sequences of EF1a-driven microRNA-based shRNAs for knockdown of HPRT.

| Name | Length (nt) | SEQ ID NO: | Sequence |
|---|---|---|---|
| EF1a-miRNA734-Denovo-SV40 polyA | 483 | 36 | ggatatcggctccggtgcccgtcagtgggcagagcgcacatcgcccacagtccccgagaagttg gggggaggggtcggcaattgaaccggtgcctagagaaggtggcgcggggtaaactgggaaag tgatgtcgtgtactggctccgcctttttcccgagggtgggggagaaccgtatataagtgcagtagtc gccgtgaacgttctttttcgcaacgggtttgccgccagaacacaggatgacccgtacatatttttgtgt agctctagttataaatcaaggtcataaccttgtgtttttttgaaggttatgaccttgatttataactagcg |

TABLE 2-continued

Sequences of EF1a-driven microRNA-based shRNAs for knockdown of HPRT.

| Name | Length (nt) | SEQ ID NO: | Sequence |
|---|---|---|---|
| | | | ctacactttttcgtcttgttagaacttgtttattgcagcttataatggttacaaataaagcaatagcatca<br>caaatttcacaaataaagcatttttttcactgcattctagttgtggtttgtccaaactcatcaatgtatctt<br>atcatct |
| EF1a-miRNA211-Denovo-SV40 polyA | 483 | 37 | ggatatcggctccggtgcccgtcagtgggcagagcgcacatcgcccacagtccccgagaagttg<br>gggggaggggtcggcaattgaaccggtgcctagagaaggtggcgcggggtaaactgggaaag<br>tgatgtcgtgtactggctccgcctttttcccgagggtgggggagaaccgtatataagtgcagtagtc<br>gccgtgaacgttctttttcgcaacgggtttgccgccagaacacaggatgacccgtacatatttttgtgt<br>agctctagtttatagtcaagggcatatccttgtgtttttttttgaaggatatgcccttgactataaactagc<br>gctacactttttcgtcttgttagaacttgtttattgcagcttataatggttacaaataaagcaatagcatc<br>acaaatttcacaaataaagcatttttttcactgcattctagttgtggtttgtccaaactcatcaatgtatct<br>tatcatct |
| EF1a-miRNA734-3G-SV40 polyA | 537 | 38 | ggatatcggctccggtgcccgtcagtgggcagagcgcacatcgcccacagtccccgagaagttg<br>gggggaggggtcggcaattgaaccggtgcctagagaaggtggcgcggggtaaactgggaaag<br>tgatgtcgtgtactggctccgcctttttcccgagggtgggggagaaccgtatataagtgcagtagtc<br>gccgtgaacgttctttttcgcaacgggtttgccgccagaacacaggatgccggatcaacgccctag<br>gtttatgtttggatgaactgacatacgcgtatccgtcttatagtcaagggcatatccagtagtgaaata<br>tatattaaactggatatgcccttgactataatacggtaacgcggaattcgcaactattttatcaatttttt<br>gcgtcgactagaacttgtttattgcagcttataatggttacaaataaagcaatagcatcacaaatttca<br>caaataaagcatttttttcactgcattctagttgtggtttgtccaaactcatcaatgtatcttatcatct |
| EF1a-miRNA211-3G-SV40 polyA | 537 | 39 | ggatatcggctccggtgcccgtcagtgggcagagcgcacatcgcccacagtccccgagaagttg<br>gggggaggggtcggcaattgaaccggtgcctagagaaggtggcgcggggtaaactgggaaag<br>tgatgtcgtgtactggctccgcctttttcccgagggtgggggagaaccgtatataagtgcagtagtc<br>gccgtgaacgttctttttcgcaacgggtttgccgccagaacacaggccggatcaacgccctaggttt<br>atgtttggatgaactgacatacgcgtatccgtctataaatcaaggtcataacctgtagtgaaatatata<br>ttaaacaaggttatgaccttgatttattacggtaacgcggaattcgcaactattttatcaatttttgcgt<br>cgacccggatcaacgccctaggtttatgtttggatgaactgacatacgcgtatccgtctataaatca<br>aggtcataacctgtagtgaaatatatattaaacaaggttatgaccttgatttattacggtaacgcggaa<br>ttcgcaactattttatcaatttttgcgtcgacaacttgtttattgcagcttataatggttacaaataaagc<br>aatagcatcacaaatttcacaaataaagcatttttttcactgcattctagttgtggtttgtccaaactcat<br>caatgtatcttatcatct |

TABLE 3 of EF1a-driven microRNA-based shRNAs with homology arm for knock-in in CCR5 region.

| Name | Length (nt) | SEQ ID NO: | Sequence |
|---|---|---|---|
| Left Arm 150-EF1a-miRNA734-Denovo-SV40 polyA-Right Arm 150 | 809 | 40 | gcttcttctctggaatcttcttcatcatcctcctgacaatcgataggtacctggctgtcgtccat<br>gctgtgtttgctttaaaagccaggacggtcacctttggggtggtgacaagtgtgatcacttg<br>ggtggtggctgtgtttgcgtctcaagcttttcgaagcggccgcggatatcggctccggtgc<br>ccgtcagtgggcagagcgcacatcgcccacagtccccgagaagttggggggaggggt<br>cggcaattgaaccggtgcctagagaaggtggcgcggggtaaactgggaaagtgatgtc<br>gtgtactggctccgcctttttcccgagggtgggggagaaccgtatataagtgcagtagtcg<br>ccgtgaacgttctttttcgcaacgggtttgccgccagaacacaggatgacccgtacatatttt<br>tgtgtagctctagttataaatcaaggtcataaccttgtgtttttttttgaaggttatgaccttgattt<br>ataactagcgctacactttttcgtcttgttagaacttgtttattgcagcttataatggttacaaat<br>aaagcaatagcatcacaaatttcacaaataaagcatttttttcactgcattctagttgtggtttg<br>tccaaactcatcaatgtatcttatcatctacgcgtccaggaatcatctttaccagatctcaaaa<br>agaaggtcttcattacacctgcagctctcattttccatacagtcagtatcaattctggaagaat<br>ttccagacattaaagatagtcatcttggggctggtcctgccgctgcttgtcatggtc |
| miRNA211-Denovo | 809 | 41 | gcttcttctctggaatcttcttcatcatcctcctgacaatcgataggtacctggctgtcgtccat<br>gctgtgtttgctttaaaagccaggacggtcacctttggggtggtgacaagtgtgatcacttg<br>ggtggtggctgtgtttgcgtctcaagcttttcgaagcggccgcggatatcggctccggtgc<br>ccgtcagtgggcagagcgcacatcgcccacagtccccgagaagttggggggaggggt<br>cggcaattgaaccggtgcctagagaaggtggcgcggggtaaactgggaaagtgatgtc<br>gtgtactggctccgcctttttcccgagggtgggggagaaccgtatataagtgcagtagtcg<br>ccgtgaacgttctttttcgcaacgggtttgccgccagaacacaggatgacccgtacatatttt<br>tgtgtagctctagtttatagtcaagggcatatccttgtgtttttttttgaaggatatgcccttgact<br>ataaactagcgctacactttttcgtcttgttagaacttgtttattgcagcttataatggttacaaa<br>taaagcaatagcatcacaaatttcacaaataaagcatttttttcactgcattctagttgtggttt<br>gtccaaactcatcaatgtatcttatcatctacgcgtccaggaatcatctttaccagatctcaaa<br>aagaaggtcttcattacacctgcagctctcattttccatacagtcagtatcaattctggaaga<br>atttccagacattaaagatagtcatcttggggctggtcctgccgctgcttgtcatggtc |

TABLE 3-continued of EF1a-driven microRNA-based shRNAs with homology arm for knock-in in CCR5 region.

| Name | Length (nt) | SEQ ID NO: | Sequence |
|---|---|---|---|
| miRNA734-3G | 863 | 42 | gcttcttctctggaatcttcttcatcatcctcctgacaatcgataggtacctggctgtcgtccat gctgtgtttgctttaaaagccaggacggtcacctttggggtggtgacaagtgtgatcacttg ggtggtggctgtgtttgcgtctcaagcttttcgaagcggccgcggatatcggctccggtgc ccgtcagtgggcagagcgcacatcgcccacagtccccgagaagttggggggaggggt cggcaattgaaccggtgcctagagaaggtggcgcggggtaaactgggaaagtgatgtc gtgtactggctccgcctttttcccgagggtgggggagaaccgtatataagtgcagtagtcg ccgtgaacgttctttttcgcaacgggtttgccgccagaacacaggatgccggatcaacgcc ctaggtttatgtttggatgaactgacatacgcgtatccgtcttatagtcaagggcatatccag tagtgaaatatatattaaactggatatgcccttgactataatacggtaacgcggaattcgcaa ctattttatcaatttttgcgtcgactagaacttgtttattgcagcttataatggttacaaataaag caatagcatcacaaatttcacaaataaagcatttttttcactgcattctagttgtggtttgtcca aactcatcaatgtatcttatcatctacgcgtccaggaatcatctttaccagatctcaaaaaga aggtcttcattacacctgcagctctcattttccatacagtcagtatcaattctggaagaatttcc agacattaaagatagtcatcttggggctggtcctgccgctgcttgtcatggtc |
| miRNA211-3G | 863 | 43 | gcttcttctctggaatcttcttcatcatcctcctgacaatcgataggtacctggctgtcgtccat gctgtgtttgctttaaaagccaggacggtcacctttggggtggtgacaagtgtgatcacttg ggtggtggctgtgtttgcgtctcaagcttttcgaagcggccgcggatatcggctccggtgc ccgtcagtgggcagagcgcacatcgcccacagtccccgagaagttggggggaggggt cggcaattgaaccggtgcctagagaaggtggcgcggggtaaactgggaaagtgatgtc gtgtactggctccgcctttttcccgagggtgggggagaaccgtatataagtgcagtagtcg ccgtgaacgttctttttcgcaacgggtttgccgccagaacacaggccggatcaacgcccta ggtttatgtttggatgaactgacatacgcgtatccgtctataaatcaaggtcataacctgtagt gaaatatatattaaacaaggttatgaccttgatttattacggtaacgcggaattcgcaactatt ttatcaatttttgcgtcgacccggatcaacgccctaggtttatgtttggatgaactgacatac gcgtatccgtctataaatcaaggtcataacctgtagtgaaatatatattaaacaaggttatga ccttgatttattacggtaacgcggaattcgcaactattttatcaatttttgcgtcgacaacttgt ttattgcagcttataatggttacaaataaagcaatagcatcacaaatttcacaaataaagcatt tttttcactgcattctagttgtggtttgtccaaactcatcaatgtatcttatcatctacgcgtcca ggaatcatctttaccagatctcaaaaagaaggtcttcattacacctgcagctctcattttccat acagtcagtatcaattctggaagaatttccagacattaaagatagtcatcttggggctggtc ctgccgctgcttgtcatggtc |

Example 4—Conditioning Prior to Hematopoietic Stem Cell Transplantation

Hematopoietic stem cell transplantation (HSCT) is widely used to treat hematological malignancies and also offers curative therapy for patients with hemoglobinopathies, congenital immunodeficiencies, and other conditions, including infectious diseases such as HIV/AIDS. However, the ability of HSCT to cure this broad range of non-malignant diseases is severely underutilized. The obstacles to using allogeneic HSCT in these diverse conditions relate primarily to the frequency of life-threatening graft-versus-host disease (GVHD), of acute complications that result from the cytotoxic effects of conditioning, such as mucositis and infections, and of long-term, irreversible complications that arise from the genotoxic effects of conditioning, such as infertility. Autologous HSCT using genetically corrected cells would avoid the risk of GVHD, but the genotoxicity of conditioning remains a substantial barrier to the development of this approach.

A promising avenue for improving the safety of conditioning is the use of drugs, such as antibodies, that are specifically targeted to HSCs and other hematopoietic cells in the bone marrow niche and that are believed to spare non-hematopoietic cells. Certain internalizing immunotoxins (also known as antibody-drug conjugates or ADCs) targeting the hematopoietic-cell-restricted CD45 receptor or the more HSC specific CD117 (c-Kit) may be used for this purpose (see, for example, US Patent Publication Nos. 2017/0360954 and 2018/0147294; and PCT Publication Nos. WO/2017/219025 and WO/2017/219029, the disclosures of which are each incorporated by reference herein in their entireties). In some embodiments, the immunotoxin is selected from *pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, Ricin-A or a variant thereof. In some embodiments, the immunotoxin is saporin, a catalytic N-glycosidase ribosome-inactivating protein that halts protein synthesis. Unlike other ricin family members, it is believed to lack a general cell entry domain and is non-toxic unless conjugated to a targeting antibody or ligand capable of receptor-mediated internalization.

In pre-clinical testing, a single dose of the immunotoxin, CD45-SAP (saporin conjugated to a CD45-targeting antibody), enabled efficient (>90%) engraftment of donor cells and full correction of a sickle-cell anemia mouse model. In contrast to irradiation, CD45-SAP completely avoided neutropenia and anemia, spared bone marrow and thymic niches, enabling rapid recovery of T and B cells, preserved anti-fungal immunity, and had minimal overall toxicity. Humanized NSG mice treated with a single dose of CD117-SAP had greater than 90% depletion of HSPCs in the bone marrow after a single administration of the ADC. These non-genotoxic conditioning methods may provide an attractive alternative to current conditioning regimens for HSCT in the treatment of non-malignant blood diseases. The improved safety of these targeted conditioning agents may extend the use of curative bone marrow transplant to patients who cannot tolerate current conditioning methods and in patients where bone marrow transplant is currently thought to be too dangerous.

In the context of the present disclosure, patients are conditioned to remove existing stem cells in the bone marrow and diseased cells, and to prevent rejection of the incoming stem cells. This process currently uses toxic agents originally developed to treat cancer, and procedures such as radiation that kill cells in a non-specific manner. To combat this harsh procedure, Applicants have developed a procedure whereby patients are treated with a combination of reduced intensity conditioning (e.g. busulfan or melphalan—both non-specific alkylating anti-cancer agents) followed by post-infusion selection of gene-modified cells, with the goal to provide HSCT as an out-patient procedure, with dramatically reduced adverse events related to the conditioning. Still, some level of non-specific chemotherapy is necessary to make space in the bone-marrow for the gene-modified cell population.

As an alternative to reduced intensity conditioning using busulfan or melphalan, antibody-drug conjugates (described above) may be used as an alternative method of conditioning, allowing for non-genotoxic bone marrow conditioning in patients prior to receiving gene therapy according to the methods described herein. Specifically, sickle cells disease or β-thalassemia patients are infused with either an anti-CD45-SAP or an anti-CD117/c-kit-SAP (or a combination of both antibodies) to "make space" in the bone marrow, followed by infusion of a modified HSC according to the methods described herein. Dosing post-infusion with 6TG could then increase the chimerism of the gene-modified cells to correct the disease. It is believed that this could potentially be done with minimal overall toxicity or adverse events to the patient.

Additional Embodiments

In another aspect of the present disclosure is a vector comprising (i) a nucleic acid sequence encoding a shRNA targeting a HPRT gene; and (ii) a nucleic acid sequence encoding a therapeutic gene. In some embodiments, the nucleic acid sequence encoding the shRNA targeting the HPRT gene has a sequence having at least 80% identity to that of SEQ ID NO: 30. In some embodiments, the nucleic acid sequence encoding the shRNA targeting the HPRT gene has a sequence having at least 90% identity to that of SEQ ID NO: 30. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 80% identity to that of SEQ ID NO: 55. In some embodiments, the nucleic acid sequence encoding the therapeutic gene has a sequence having at least 90% identity to that of SEQ ID NO: 55. In some embodiments, the nucleic acid sequence encoding the therapeutic gene has a sequence having at least 95% identity to that of SEQ ID NO: 55. In some embodiments, the nucleic acid sequence encoding the therapeutic gene has the sequence of SEQ ID NO: 55. In some embodiments, the nucleic acid sequence encoding the shRNA targeting the HPRT gene is operably linked to a Pol III promoter. In some embodiments, the Pol III promoter is 7sk, or a 7sk promoter having at least one mutation or deletion. In some embodiments, the nucleic acid sequence encoding the therapeutic gene is operably linked to a Pol II promoter. In some embodiments, the nucleic acid sequence encoding the therapeutic gene is operably linked to a beta globin promoter. In some embodiments, the vector further comprises an expression control sequence having a 5' long terminal repeat upstream of the nucleic acid encoding the shRNA targeting the HPRT gene, and a 3' long terminal repeat downstream of the nucleic acid encoding the gamma-globin gene.

In another aspect of the present disclosure is a vector comprising a first nucleic acid sequence having at least 90% identity to that of SEQ ID NO: 30, and a second nucleic acid sequence having at least 90% identity to that of SEQ ID NO: 55. In some embodiments, the vector is a lentiviral vector.

In another aspect of the present disclosure is a vector comprising a first nucleic acid sequence having at least 95% identity to that of SEQ ID NO: 30, and a second nucleic acid sequence having at least 95% identity to that of SEQ ID NO: 55. In some embodiments, the vector is a lentiviral vector.

In another aspect of the present disclosure is a vector comprising a first nucleic acid sequence having at least 96% identity to that of SEQ ID NO: 30, and a second nucleic acid sequence having at least 96% identity to that of SEQ ID NO: 55. In some embodiments, the vector is a lentiviral vector.

In another aspect of the present disclosure is a vector comprising a first nucleic acid sequence having at least 97% identity to that of SEQ ID NO: 30, and a second nucleic acid sequence having at least 97% identity to that of SEQ ID NO: 55. In some embodiments, the vector is a lentiviral vector.

In another aspect of the present disclosure is a vector comprising a first nucleic acid sequence having at least 98% identity to that of SEQ ID NO: 30, and a second nucleic acid sequence having at least 98% identity to that of SEQ ID NO: 55. In some embodiments, the vector is a lentiviral vector.

In another aspect of the present disclosure is a vector comprising a first nucleic acid sequence having at least 99% identity to that of SEQ ID NO: 30, and a second nucleic acid sequence having at least 99% identity to that of SEQ ID NO: 55. In some embodiments, the vector is a lentiviral vector.

In another aspect of the present disclosure is a vector comprising a first nucleic acid sequence having SEQ ID NO: 30, and a second nucleic acid sequence having SEQ ID NO: 55. In some embodiments, the vector is a lentiviral vector.

In another aspect of the present disclosure is a composition comprising a vector comprising (i) a nucleic acid sequence encoding a shRNA targeting a HPRT gene; and (ii) a nucleic acid sequence encoding a therapeutic gene. In some embodiments, the composition further comprises a pharmaceutically acceptable carrier. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 95% identity to that of SEQ ID NO: 55. In some embodiments, the nucleic acid sequence encoding the therapeutic gene has a sequence of SEQ ID NO: 55. In some embodiments, the nucleic acid sequence encoding the shRNA targeting the HPRT gene is operably linked to a Pol III promoter. In some embodiments, the nucleic acid sequence encoding the therapeutic gene is operably linked to a beta globin promoter. In some embodiments, the composition is formulated as an emulsion. In some embodiments, the composition is formulated within micelles. In some embodiments, the composition is encapsulated within a polymer. In some embodiments, the compositions are encapsulated within liposomes. In some embodiments, the compositions are encapsulated within minicells or nanocapsules.

In another aspect of the present disclosure is a cell comprising a vector comprising (i) a nucleic acid sequence encoding a shRNA targeting a HPRT gene; and (ii) a nucleic acid sequence encoding a therapeutic gene. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 95% identity to that of SEQ ID NO: 55. In some embodiments, the nucleic acid sequence encoding the therapeutic gene has a sequence of SEQ ID NO: 55. In some embodiments, the nucleic acid sequence encoding the shRNA targeting the HPRT gene is operably linked to a Pol III promoter. In some embodiments, the nucleic acid sequence encoding the therapeutic gene is operably linked to a beta globin promoter.

In another aspect of the present disclosure is a cell transduced by a vector comprising (i) a nucleic acid sequence encoding a shRNA targeting a HPRT gene; and (ii) a nucleic acid sequence encoding a therapeutic gene. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 95% identity to that of SEQ ID NO: 55. In some embodiments, the nucleic acid sequence encoding the therapeutic gene has a sequence of SEQ ID NO: 55. In some embodiments, the nucleic acid sequence encoding the shRNA targeting the HPRT gene is operably linked to a Pol III promoter. In some embodiments, the nucleic acid sequence encoding the therapeutic gene is operably linked to a beta globin promoter. In some embodiments, the cell is an HSC.

In another aspect of the present disclosure is a polynucleotide having at least 90% sequence identity to that of SEQ ID NO: 5.

In another aspect of the present disclosure is a recombinant plasmid comprising between about 11200 nucleotides and about 12300 nucleotides, and wherein the plasmid comprises a first nucleic acid sequence having at least 95% identity to that of SEQ ID NO: 30, and a second nucleic acid sequence having at least 95% identity to that of SEQ ID NO: 55. In some embodiments, the plasmid comprises between about 11600 nucleotides and about 12200 nucleotides. In some embodiments, the plasmid comprises between about 11600 nucleotides and about 11700 nucleotides. In some embodiments, the plasmid comprises between about 12000 nucleotides and about 12100 nucleotides.

In another aspect of the present disclosure is a lentiviral vector comprising (a) a lentiviral backbone comprising essential lentiviral sequences for integration into a target cell genome; (b) a first nucleic acid sequence having at least 95% identity to that of SEQ ID NO: 30; (c) a second nucleic acid sequence having at least 95% identity to that of SEQ ID NO: 55; (d) a first expression control element that regulates expression of the first nucleic acid; and (e) a second expression control element that regulates expression of the second nucleic acid.

In another aspect of the present disclosure is a lentiviral expression vector comprising a first nucleic acid sequence having at least 95% identity to any of SEQ ID NOS: 23-31, and a second nucleic acid sequence having SEQ ID NO: 55.

In another aspect of the present disclosure is a modified sh734 shRNA having at least one of: (i) an incorporation of an hsa-miR-22 loop sequence; (ii) an addition of a 3'-5' spacer; (iii) a 5' start modification; and/or (iv) an addition of two nucleotides 5' and 3' to the stem and loop.

In another aspect of the present disclosure is a method of co-delivering into a cell both a therapeutic gene and an interfering RNA, the interfering RNA targeting HPRT. In some embodiments, the therapeutic gene therapeutic gene encodes a gene to treat immune deficiencies, hereditary diseases, blood diseases (e.g. hemophilia, hemoglobin disorders), lysosomal storage diseases, neurological diseases, angiogenic disorders, or cancer.

In another aspect of the present disclosure is a vector comprising a first expression control sequence operably linked to a first nucleic acid sequence, the first nucleic acid sequence encoding an RNAi to knockdown HPRT; and a second expression control sequence operably linked to a second nucleic acid sequence, the second nucleic acid sequence encoding a gamma-globin gene. In some embodiments, the RNAi is an shRNA. In some embodiments, the shRNA comprises a hairpin loop sequence of SEQ ID NO: 35. In some embodiments, shRNA has at least 95% sequence identity to that of SEQ ID NO: 30. In some embodiments, the shRNA has the sequence of SEQ ID NO: 30. In some embodiments, the shRNA has at least 95% sequence identity to a nucleic acid sequence selected from the group consist of SEQ ID NO: 27, SEQ ID NO: 28, and SEQ ID NO: 29. In some embodiments, the shRNA has at least 95% sequence identity to a nucleic acid sequence selected from the group consist of SEQ ID NO: 67 and SEQ ID NO: 68. In some embodiments, the shRNA has at least 95% sequence identity to a nucleic acid sequence selected from the group consist of SEQ ID NO: 26 and SEQ ID NO: 27. In some embodiments, the shRNA has at least 95% sequence identity to that of SEQ ID NO: 59. In some embodiments, the first expression control sequence is a Pol III promoter. In some embodiments, the Pol III promoter is 7sk. In some embodiments, the 7sk promoter has at least 95% sequence identity to that of SEQ ID NO: 32. In some embodiments, 7sk promoter has the sequence of SEQ ID NO: 32. In some embodiments, 7sk promoter has the sequence of SEQ ID NO: 33. In some embodiments, the second nucleic acid encoding the gamma-globin gene has at least 95% sequence identity to that of SEQ ID NO: 55. In some embodiments, the second nucleic acid encoding the gamma-globin gene has SEQ ID NO: 55. In some embodiments, the second expression control sequence is a pol II promoter. In some embodiments, the pol II promoter is a beta-globin promoter. In some embodiments, the beta-globin promoter has at least 95% identity to that of SEQ ID NO: 66. In some embodiments, the first nucleic acid encodes a nucleic acid molecule having SEQ ID NO: 1 or SEQ ID NO: 2. In some embodiments, the second nucleic acid encodes a nucleic acid molecule having SEQ ID NO: 3. In some embodiments, the second nucleic acid encodes the amino acid sequence of SEQ ID NO: 4. In some embodiments, the vector is a self-inactivating lentiviral vector. In some embodiments, the vector has at least 95% sequence identity to any one of SEQ ID NOS: 5 to 22. In some embodiments, the vector encodes for the amino acid sequence of SEQ ID NO: 4; and encodes a nucleic acid molecule having SEQ ID NO: 1 or SEQ ID NO: 2.

In another aspect of the present disclosure is an isolated host cell include the aforementioned vector.

1. A vector comprising a first expression control sequence operably linked to a first nucleic acid sequence, the first nucleic acid sequence encoding an RNAi to knockdown HPRT; and a second expression control sequence operably linked to a second nucleic acid sequence, the second nucleic acid sequence encoding a gamma-globin gene.

2. The vector of embodiment 1, wherein the RNAi is an shRNA.

3. The vector of embodiment 2, wherein the shRNA comprises a hairpin loop sequence of SEQ ID NO: 35.

4. The vector of embodiment 2, wherein the shRNA has at least 95% sequence identity to that of SEQ ID NO: 30.

5. The vector of embodiment 4, wherein the shRNA has the sequence of SEQ ID NO: 30.

6. The vector of embodiment 2, wherein the shRNA has at least 95% sequence identity to a nucleic acid sequence selected from the group consist of SEQ ID NO: 27, SEQ ID NO: 28, and SEQ ID NO: 29.

7. The vector of embodiment 2, wherein the shRNA has at least 95% sequence identity to a nucleic acid sequence selected from the group consist of SEQ ID NO: 67 and SEQ ID NO: 68.

8. The vector of embodiment 2, wherein the shRNA has at least 95% sequence identity to a nucleic acid sequence selected from the group consist of SEQ ID NO: 26 and SEQ ID NO: 27.

9. The vector of embodiment 2, wherein the shRNA has at least 95% sequence identity to that of SEQ ID NO: 59.

10. The vector of any of the preceding embodiments, wherein the first expression control sequence is a Pol III promoter.

11. The vector of embodiment 10, wherein the Pol III promoter is 7sk.

12. The vector of embodiment 11, wherein the 7sk promoter has at least 95% sequence identity to that of SEQ ID NO: 32.

13. The vector of embodiment 12, wherein the 7sk promoter has the sequence of SEQ ID NO: 32.

14. The vector of embodiment 11, wherein the 7sk promoter has the sequence of SEQ ID NO: 33.

15. The vector of any of the preceding embodiments, wherein the second nucleic acid encoding the gamma-globin gene has at least 95% sequence identity to that of SEQ ID NO: 55.

16. The vector of any of the preceding embodiments, wherein the second nucleic acid encoding the gamma-globin gene has SEQ ID NO: 55.

17. The vector of any of the preceding embodiments, wherein the second expression control sequence is a pol II promoter.

18. The vector of embodiment 17, wherein the pol II promoter is a beta-globin promoter.

19. The vector of embodiment 18, wherein the beta-globin promoter has at least 95% identity to that of SEQ ID NO: 66.

20. The vector of any of the preceding embodiments, wherein the first nucleic acid encodes a nucleic acid molecule having SEQ ID NO: 1 or SEQ ID NO: 2.

21. The vector of any of the preceding embodiments, wherein the second nucleic acid encodes a nucleic acid molecule having SEQ ID NO: 3.

22. The vector of any of the preceding embodiments, wherein the second nucleic acid encodes a polypeptide having at least 95% identity to that of SEQ ID NO: 4.

23. The vector of any of the preceding embodiments, wherein the vector is a self-inactivating lentiviral vector.

24. The vector of any of the preceding embodiments, further comprising a cSH4 insulator.

25. The vector of embodiment 1, having at least 95% sequence identity to any one of SEQ ID NOS: 5 to 22.

26. The vector embodiment 1, wherein the second nucleic acid sequence encodes a polypeptide having at least 98% identity to that of SEQ ID NO: 4; and the first nucleic acid sequence encodes a nucleic acid molecule having at least 98% identity to of SEQ ID NO: 1 or its complement thereof.

27. A pharmaceutical composition comprising the vector of any one of embodiments 1 to 26 and a pharmaceutically acceptable carrier.

28. An isolated cell comprising the vector of any one of embodiments 1 to 26.

29. A host cell transduced with the vector according to any one of embodiments 1 to 26, wherein the host cell is substantially HPRT deficient.

30. The host cell of embodiment 29, wherein the host cell expresses the gamma-globin gene.

31. The host cell of embodiment 29, wherein the host cell is formulated with a pharmaceutically acceptable carrier.

32. The host cell of any of embodiments 29 to 31 for use in the treatment of sickle cell disease or to reduce the symptoms of sickle cell disease.

33. A method of selecting transduced cells comprising: transducing a population of cells with the vector according to any one of embodiments 1 to 26; and enriching the population of transduced cells by selecting for transduced cells with a purine analog.

34. The method of embodiment 33, wherein the purine analog is selected from the group consisting of 6TG and 6-mercaptopurin.

35. The method of 33, wherein the transduced cells are HSCs.

36. The method of 33, wherein the HSCs are allogenic HSCs.

37. The method of 33, wherein the HSCs are autologous HSCs.

38. The method of 33, wherein the HSCs are sibling matched HSCs.

39. A host cell prepared by transducing a hematopoietic stem cell with a lentiviral expression vector, the lentiviral expression vector comprising a first nucleic acid sequence encoding an anti-HPRT shRNA, and a second nucleic acid sequence encoding a gamma-globin gene.

40. The host cell of embodiment 39, wherein the lentiviral expression vector has a sequence having at least 95% identity to any of SEQ ID NOS: 5 to 22.

41. A pharmaceutical composition comprising the host cell of any of embodiments 39 and 40 and a pharmaceutically acceptable carrier.

42. A host cell comprising: (i) a nucleic acid molecule having either SEQ ID NO: 1 or SEQ ID NO: 2; and (ii) a nucleic acid molecule having SEQ ID NO: 3.

43. A method of treating sickle cell disease comprising administering the host cells of any one of embodiments 29, 30, 39, and 40 to a patient in need of treatment thereof.

44. A method of reducing the symptoms of sickle cell disease comprising administering the host cells of any one of embodiments 29, 30, 39, and 40 to a patient in need of treatment thereof.

45. A method of reducing the symptoms of severe sickle cell disease comprising administering the host cells of any one of embodiments 29, 30, 39, and 40 to a patient in need of treatment thereof.

46. A method of treating a hemoglobinopathy comprising administering the host cells of any one of embodiments 29, 30, 39, and 40 to a patient in need of treatment thereof.

47. A method of treating beta-thalassemia comprising administering the host cells of any one of embodiments 29, 30, 39, and 40 to a patient in need of treatment thereof.

48. A method of treating sickle cell disease or reducing at least one symptom of sickle cell disease in a human patient comprising: (a) transducing hematopoietic cells with a lentiviral expression vector, wherein the lentiviral expression vector comprises a first nucleic acid sequence encoding an anti-HPRT shRNA, and a second nucleic acid sequence encoding a gamma-globin gene; and (b) introducing the transduced hematopoietic cells to the human patient.

49. The method of embodiment 48, further comprising conditioning the patient prior to introducing the transduced hematopoietic cells, wherein the conditioning comprises administering chemotherapy, radiation therapy, or treatment with one or more antibody-drug conjugates.

50. The method of embodiment 48, wherein the treatment further comprises administering one or more doses of hydroxyurea following transplantation.

51. A method of increasing fetal hemoglobin levels comprising administering the host cells of any one of embodiments 29, 30, 39, and 40 to a patient in need of treatment thereof.

52. A host cell which is HPRT deficient and which expresses a polypeptide having SEQ ID NO: 4, wherein the host cell is prepared by transducing an HSC with the vector of any one of embodiments 1 to 26.

53. A host cell comprising: (i) at least one of a nucleic acid molecule having SEQ ID NO: 3 or a polypeptide having SEQ ID NO: 4; and (ii) at least one of a nucleic acid molecule having SEQ ID NO: 1 or a nucleic acid molecule having SEQ ID NO: 2.

54. The host cell of embodiment 53, wherein the host cell is prepared by contacting an HSC with the vector of any of one embodiments 1 to 26.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A vector comprising a first expression control sequence operably linked to a first nucleic acid sequence, the first nucleic acid sequence encoding a shRNA targeting hypoxanthine guanine phosphoribosyitransferase (HPRT), the shRNA comprising the sequence of SEQ ID NO: 30; and a second expression control sequence operably linked to a second nucleic acid sequence, the second nucleic acid sequence encoding a gamma-globin gene.

2. The vector of claim 1, wherein the first expression control sequence comprises a Pol III promoter.

3. The vector of claim 2, wherein the Pol III promoter comprises 7sk.

4. The vector of claim 3, wherein the 7sk promoter has at least 95% sequence identity to that of SEQ ID NO: 32.

5. The vector of claim 3, wherein the 7sk promoter comprises the sequence of SEQ ID NO: 32.

6. The vector of claim 3, wherein the 7sk promoter comprises the sequence of SEQ ID NO: 33.

7. The vector of claim 1, wherein the gamma-globin gene has at least 80% sequence identity to that of SEQ ID NO: 55.

8. The vector of claim 1, wherein the gamma-globin gene has at least 85% sequence identity to that of SEQ ID NO: 55.

9. The vector of claim 1, wherein the gamma-globin gene has at least 90% sequence identity to that of SEQ ID NO: 55.

10. The vector of claim 1, wherein the gamma-globin gene has at least 95% sequence identity to that of SEQ ID NO: 55.

11. The vector of claim 1, wherein the gamma-globin gene comprises the sequence of SEQ ID NO: 55.

12. The vector of claim 1, wherein the gamma-globin gene encodes an amino acid sequence having at least 90% identity to that of SEQ ID NO: 4.

13. The vector of claim 1, wherein the gamma-globin gene encodes an amino acid sequence having at least 95% identity to that of SEQ ID NO: 4.

14. The vector of claim 1, wherein the second expression control sequence comprises a pol II promoter.

15. The vector of claim 14, wherein the pol II promoter comprises a beta-globin promoter.

16. The vector of claim 15, wherein the beta-globin promoter has at least 95% identity to that of SEQ ID NO: 66.

17. A host cell which is hypoxanthine guanine phosphoribosyitransferase (HPRT) deficient and which expresses a gamma-globin gene, wherein the host cell is prepared by transducing an hematopoietic stem cell (HSC) with a vector comprising a first expression control sequence operably linked to a first nucleic acid sequence, the first nucleic acid sequence encoding a shRNA targeting HPRT, the shRNA comprising the sequence of SEQ ID NO: 30; and a second expression control sequence operably linked to a second nucleic acid sequence, the second nucleic acid sequence encoding the gamma-globin gene.

18. The host cell of claim 17, wherein the gamma-globin gene has at least 80% sequence identity to that of SEQ ID NO: 55.

19. The host cell of claim 17, wherein the first expression control sequence comprises a Pol III promoter.

20. The host cell of claim 17, wherein the second expression control sequence comprises a Pol II promoter.

21. A composition comprising: (a) a hematopoietic stem cell; and (ii) a vector comprising a first expression control sequence operably linked to a first nucleic acid sequence, the first nucleic acid sequence encoding a shRNA targeting hypoxanthine guanine phosphoribosyitransferase (HPRT), the shRNA comprising the sequence of SEQ ID NO: 30; and a second expression control sequence operably linked to a second nucleic acid sequence, the second nucleic acid sequence encoding a gamma-globin gene.

* * * * *